United States Patent
Manning et al.

(10) Patent No.: US 11,692,035 B2
(45) Date of Patent: *Jul. 4, 2023

(54) THERAPEUTIC CD47 ANTIBODIES

(71) Applicant: Arch Oncology, Inc., St. Louis, MO (US)

(72) Inventors: Pamela T. Manning, Chesterfield, MO (US); Robyn Puro, St. Louis, MO (US); Juan C. Almagro, Cambridge, MA (US); Robert W. Karr, Frontenac, MO (US)

(73) Assignee: Arch Oncology, Inc., Brisbane, CA (US)

( * ) Notice: Subject to any disclaimer, the term of this patent is extended or adjusted under 35 U.S.C. 154(b) by 481 days.

This patent is subject to a terminal disclaimer.

(21) Appl. No.: 16/703,484

(22) Filed: Dec. 4, 2019

(65) Prior Publication Data
US 2020/0095318 A1 Mar. 26, 2020

Related U.S. Application Data

(63) Continuation of application No. 16/223,009, filed on Dec. 17, 2018, now abandoned, which is a continuation of application No. 15/871,802, filed on Jan. 15, 2018, now abandoned, which is a continuation of application No. PCT/US2017/057716, filed on Oct. 20, 2017.

(60) Provisional application No. 62/475,032, filed on Mar. 22, 2017, provisional application No. 62/411,319, filed on Oct. 21, 2016.

(51) Int. Cl.
| | |
|---|---|
| A61P 35/00 | (2006.01) |
| A61P 35/02 | (2006.01) |
| A61K 39/00 | (2006.01) |
| C07K 16/28 | (2006.01) |
| A61P 9/00 | (2006.01) |
| A61P 19/02 | (2006.01) |
| A61P 25/28 | (2006.01) |
| A61P 17/06 | (2006.01) |
| A61P 1/00 | (2006.01) |
| A61P 37/02 | (2006.01) |
| A61P 5/38 | (2006.01) |
| A61P 21/04 | (2006.01) |
| A61P 7/06 | (2006.01) |
| A61P 3/10 | (2006.01) |
| A61P 9/10 | (2006.01) |

(52) U.S. Cl.
CPC ............ *C07K 16/2803* (2013.01); *A61P 1/00* (2018.01); *A61P 3/10* (2018.01); *A61P 5/38* (2018.01); *A61P 7/06* (2018.01); *A61P 9/00* (2018.01); *A61P 9/10* (2018.01); *A61P 17/06* (2018.01); *A61P 19/02* (2018.01); *A61P 21/04* (2018.01); *A61P 25/28* (2018.01); *A61P 35/00* (2018.01); *A61P 35/02* (2018.01); *A61P 37/02* (2018.01); *A61K 2039/505* (2013.01); *C07K 2317/24* (2013.01); *C07K 2317/33* (2013.01); *C07K 2317/56* (2013.01); *C07K 2317/565* (2013.01); *C07K 2317/73* (2013.01); *C07K 2317/732* (2013.01); *C07K 2317/734* (2013.01); *C07K 2317/76* (2013.01); *C07K 2317/92* (2013.01)

(58) Field of Classification Search
CPC ............ C07K 16/2803; C07K 16/2896; C07K 2317/33
See application file for complete search history.

(56) References Cited

U.S. PATENT DOCUMENTS

| | | |
|---|---|---|
| 6,261,839 B1 | 7/2001 | Multhoff et al. |
| 7,282,556 B2 | 10/2007 | Parkos |
| 7,514,229 B2 | 4/2009 | Jamieson et al. |
| 7,531,643 B2 | 5/2009 | Fukushima et al. |
| 7,696,325 B2 | 4/2010 | Fukushima et al. |
| 8,101,719 B2 | 1/2012 | Kikuchi et al. |
| 8,236,313 B2 | 8/2012 | Isenberg et al. |
| 8,562,997 B2 | 10/2013 | Jaiswal et al. |
| 8,728,476 B2 | 5/2014 | Van Den Berg |
| 8,758,750 B2 | 6/2014 | Weissman et al. |
| 8,759,495 B2 | 6/2014 | Boghaert et al. |
| 8,951,527 B2 | 2/2015 | Isenberg et al. |
| 9,017,675 B2 | 4/2015 | Liu et al. |
| 9,045,541 B2 | 6/2015 | Eckelman et al. |
| 9,221,908 B2 | 12/2015 | Frazier et al. |
| 9,382,320 B2 | 7/2016 | Liu et al. |
| 9,518,116 B2 | 12/2016 | Frazier et al. |

(Continued)

FOREIGN PATENT DOCUMENTS

| | | |
|---|---|---|
| AU | 2014201010 A1 | 3/2014 |
| BY | BY6782 C1 | 3/2005 |

(Continued)

OTHER PUBLICATIONS

Subramanian et al., J Biol Chem, 282:1805-18 (Year: 2007).*

(Continued)

*Primary Examiner* — Jessica H Roark
(74) *Attorney, Agent, or Firm* — Cooley LLP

(57) ABSTRACT

Provided are anti-CD47 monoclonal antibodies (anti-CD47 mAbs) with distinct functional profiles as described herein, methods to generate anti-CD47 mAbs, and to methods of using these anti-CD47 mAbs as therapeutics for the prevention and treatment of solid and hematological cancers, ischemia-reperfusion injury, cardiovascular diseases, autoimmune diseases, inflammatory diseases or as diagnostics for determining the level of CD47 in tissue samples.

17 Claims, 42 Drawing Sheets

Specification includes a Sequence Listing.

(56) References Cited

U.S. PATENT DOCUMENTS

| | | |
|---|---|---|
| 9,518,117 B2 | 12/2016 | Frazier et al. |
| 9,650,441 B2 | 5/2017 | Grosveld et al. |
| 10,239,945 B2 * | 3/2019 | Manning .................. A61P 37/06 |
| 10,259,873 B2 | 4/2019 | Frazier et al. |
| 10,669,336 B2 | 6/2020 | Frazier et al. |
| 10,676,524 B2 | 6/2020 | Frazier et al. |
| 10,844,124 B2 * | 11/2020 | Manning .................. A61P 17/06 |
| 2001/0041670 A1 | 11/2001 | Simantov et al. |
| 2003/0108546 A1 | 6/2003 | Fukushima et al. |
| 2004/0073013 A1 | 4/2004 | Fukushima et al. |
| 2004/0213792 A1 | 10/2004 | Clemmons et al. |
| 2005/0009753 A1 | 1/2005 | Sattin et al. |
| 2006/0088522 A1 | 4/2006 | Boghaert et al. |
| 2007/0111238 A1 | 5/2007 | Jamieson et al. |
| 2010/0173382 A1 | 7/2010 | Boghaert et al. |
| 2010/0203559 A1 | 8/2010 | Ester et al. |
| 2011/0117085 A1 | 5/2011 | Rotem-Yehudar et al. |
| 2011/0177064 A1 | 7/2011 | Whiteman et al. |
| 2013/0142786 A1 | 6/2013 | Liu et al. |
| 2013/0224188 A1 | 8/2013 | Eckelman et al. |
| 2014/0065169 A1 | 3/2014 | Jaiswal et al. |
| 2014/0140989 A1 * | 5/2014 | Eckelman .......... C07K 16/2803 424/139.1 |
| 2014/0161799 A1 | 6/2014 | Frazier et al. |
| 2014/0161825 A1 | 6/2014 | Jaiswal et al. |
| 2014/0199308 A1 | 7/2014 | Van Den Berg |
| 2014/0294765 A1 | 10/2014 | Cojocaru et al. |
| 2014/0303354 A1 | 10/2014 | Masternak et al. |
| 2014/0363442 A1 | 12/2014 | Frazier et al. |
| 2014/0369924 A1 | 12/2014 | Weissman et al. |
| 2015/0030600 A1 | 1/2015 | Marks et al. |
| 2015/0274826 A1 | 10/2015 | Frazier et al. |
| 2016/0130336 A1 | 5/2016 | Lai et al. |
| 2016/0137733 A1 | 5/2016 | Frazier et al. |
| 2016/0137734 A1 | 5/2016 | Frazier et al. |
| 2016/0289326 A1 | 10/2016 | Chao et al. |
| 2017/0081407 A1 | 3/2017 | Grosveld et al. |
| 2017/0151282 A1 | 6/2017 | Discher et al. |
| 2017/0166645 A1 | 6/2017 | Weissman et al. |
| 2018/0142019 A1 | 5/2018 | Manning et al. |
| 2018/0171014 A1 | 6/2018 | Manning et al. |
| 2018/0355585 A1 | 12/2018 | Ohiwa et al. |
| 2019/0112373 A1 | 4/2019 | Manning et al. |
| 2019/0248892 A1 | 8/2019 | Frazier et al. |
| 2019/0248915 A1 | 8/2019 | Chao et al. |
| 2019/0300611 A1 | 10/2019 | Manning et al. |
| 2019/0309066 A1 * | 10/2019 | Manning .................. A61P 3/10 |
| 2021/0070865 A1 * | 3/2021 | Manning .................. A61P 9/00 |
| 2021/0079091 A1 * | 3/2021 | Manning .................. A61P 1/00 |
| 2022/0185886 A1 | 6/2022 | Pereira et al. |
| 2022/0313819 A1 | 10/2022 | Donio et al. |

FOREIGN PATENT DOCUMENTS

| | | |
|---|---|---|
| CN | 101133083 A | 2/2008 |
| CN | 103665165 A | 3/2014 |
| CN | 104271757 A | 1/2015 |
| EP | 0256654 A2 | 2/1988 |
| EP | 1035132 A1 | 9/2000 |
| EP | 1693385 A1 | 8/2006 |
| EP | 2111869 A1 | 10/2009 |
| EP | 2242512 B1 | 4/2016 |
| JP | 2007008895 A | 1/2007 |
| JP | 2015508072 A | 3/2015 |
| JP | 2016507555 A | 3/2016 |
| WO | WO-9912973 A1 | 3/1999 |
| WO | WO-9940940 A1 | 8/1999 |
| WO | WO-0105968 A1 | 1/2001 |
| WO | WO-03050295 A2 | 6/2003 |
| WO | WO-2004096133 A2 | 11/2004 |
| WO | WO-2008043072 A2 | 4/2008 |
| WO | WO-2008060785 A2 | 5/2008 |
| WO | WO-2009091547 A1 | 7/2009 |
| WO | WO-2009091601 A1 | 7/2009 |
| WO | WO-2009114748 A1 | 9/2009 |
| WO | WO-2009131453 A1 | 10/2009 |
| WO | WO-2011083140 A1 | 7/2011 |
| WO | WO-2011143624 A2 | 11/2011 |
| WO | WO-2013119714 A1 | 8/2013 |
| WO | WO-2014087248 A2 | 6/2014 |
| WO | WO-2014093678 A2 | 6/2014 |
| WO | WO-2014123580 A1 | 8/2014 |
| WO | WO-2014149477 A1 | 9/2014 |
| WO | WO-2014093678 A3 | 11/2014 |
| WO | WO-2014123580 A8 | 10/2015 |
| WO | WO-2015191861 A1 | 12/2015 |
| WO | WO-2017049251 A2 | 3/2017 |
| WO | WO-2018075960 A1 | 4/2018 |
| WO | WO-2018175790 A1 | 9/2018 |
| WO | WO-2020097564 A1 | 5/2020 |
| WO | WO-2020198370 A2 | 10/2020 |
| WO | WO-2021046216 A1 | 3/2021 |
| WO | WO-2021080920 A2 | 4/2021 |
| WO | WO-2021263085 A2 | 12/2021 |

OTHER PUBLICATIONS

Sick et al., Br. J. Pharmacol. 167:1415-30 (Year: 2012).*
Almagro et al., Front. Immunol., 8:1751, doi: 10.3389/fimmu.2017.01751 (Year: 2018).*
PJ Carter, Nat Rev Immunol, 6:343-357 (Year: 2006).*
Finlay & Almagro, Front. Immunol., 3:342, doi: 10.3389/fimmu.2012.00342 (Year: 2012).*
Ahmed, F. et al., "Targeting CD47 as an Apoptotic Trigger of Human Lung Carcinoma Tumors", Am Ins Chem Eng., 2005 Annual Meeting, Abstract #457d, (2005).
Akewanlop, C. et al., "Phagocytosis of Breast Cancer Cells Mediated by Anti-Muc-1 Monoclonal Antibody, DF3, and its Bispecific Antibody", Cancer Res., 61(10):4061-5, (2001).
Almagro, J. C. et al., "Humanization of antibodies," Frontiers in Bioscience, Jan. 2008, 13:1619-1633.
Almagro, J. et al., "Progress and Challenges in the Design and Clinical Development of Antibodies for Cancer Therapy", Front Immunol., 8:1751, (2018).
Anonymous, "Anti-CD47 antibody [EPR 4150(2)] ab108415", retreived online at https://www.abcam.com/cd47-antibody-epr41502-ab108415.html on Jul. 20, 2015; 3 pages.
Anonymous, "Cancer Classification", National Cancer Institute, retreived from https://training.seer.cancer.gov/disease/catagories/classification.html on Jan. 3, 2017; 3 pages.
Anonymous, "Cancer Immunotherapy", Wikipedia, retreived online at https://en.wikipedia.org/w/index.php?title=Cancer_immunotherapy&oldid=171802591 on Jan. 8, 2017; 5 pages, (2017).
Anonymous, "Monoclonal Antibody", Wikipedia, retreived online https://en.wikipedia.org/w/index.php?title=Moloclonal antibody&oldid=175487212 on Jan. 8, 2017; 5 pages, (2017).
Anonymous, "Tumor-Toxic CD47 mAb Therapy for Leukemia: A Proof of Concept Study", retreived online at https://www.sbir.gov/print/sbirsearch/detail/677077 on Oct. 1, 2017; 3 pages, (2013).
Avent, N. et al., "Monoclonal Antibodies that Recognize Different Membrane Proteins that are Deficient in Rhnull Human Erythrocytes. One Group of Antibodies Reacts with a Variety of Cells and Tissues Wheras the Other Group is Erythroid-Specific", Biochem J., 251(2):499-505, (1988).
Baker, M., "Cancer and Stem Cells: Beckman Conference", Nature Reports Stem Cells, (2008).
Blazar, B. et al., "CD47 (Integrin-Associated Protein) Engagement of Dendritic Cell and Macrophage Counterreceptors is Required to Prevent the Clearance of Donor Lymphohematopoietic Cells", J Exp Med., 194(4):541-9, (2001).
Brown, E. et al., "Integrin-Associated Protein: A 50-kD Plasma Membrane Antigen Physically and Functionally Associated with Integrins", J Cell Biol., 111(6 Pt 1):2785-94, (1990).
Brown, E. et al., "Integrin-Associated Protein (CD47) and it's Ligands", Trends Cell Biol., 11 (3):130-5, (2001).
Cameron, C. et al., "Myxoma Virus M128L is Expressed as a Cell Surface CD47-Like Virulence Factor that Contributes to the Downregulation of Macrophage Activation In Vivo", Virology, 337(1):55-67, (2005).

(56) References Cited

OTHER PUBLICATIONS

Campbell, I. et al., "An Ovarian Tumor Marker with Homology to Vaccinia Virus Contains an IgV-like Region and Multiple Transmembrane Domains", Cancer Res., 52(19):5416-20, (1992).
Carter, P., "Potent Antibody Therapeutics by Design", Nat Rev Immunol., 6(5):343-57, (2006).
Chao, M. et al., "Anti-CD47 Antibody Synergizes with Rituximab to Promote Phagocytosis and Eradicate Non-Hodgkin Lymphoma", Cell, 142(5):699-713, S1-15, (2010).
Chao, M. et al., "Targeting CD47 Eliminates Human Acute Myeloid Leu-Kemia Stem Cells", Ins Cell Stem Biol Regen Med., 25th Ann Standford Med Student Res Symposium 2017, (2008).
Chao, M. et al., "The CD47-SIRP Alpha Pathway in Cancer Immune Evasion and Potential Therapeutic Implications", Curr Opin Immunol., 24(2):225-32, (2012).
Chao, M. et al., "Therapeutic Antibody Targeting of CD47 Eliminates Human Acute Lymphoblastic Leukemia", Cancer Res., 71(4):1374-84, (2011).
Chen, T. et al., "Expression and Activation of Signal Regulatory Protein Alpha on Astrocytomas", Cancer Res., 64(1):117-27, (2004).
Cioffi, M. et al., "Inhibition of CD47 Effectively Targets Pancreatic Cancer Stem Cells via Dual Mechanisms", Clin Cancer Res., 21(10):2325-37, (2015).
Cooper, G. et al., "The Development and Causes of Cancer", The Cell: A Molecular Approach, 4(Pt 4):720-8, (2000).
Edris, B. et al., "Antibody Therapy Targeting the CD47 Protein is Effective in a Model of Aggressive Metastatic Leiomyosarcoma", Proc Natl Acad Sci USA, 109(17):6656-61,(2012).
Epenetos, A. et al., "Monoclonal Antibodies for Imaging and Therapy", Br J Cancer, 59(2):152-5, (1989).
European Patent Application No. 2240780; Register Extract, date of retrieval Nov. 26, 2016; 3 pages.
European Patent Application No. 2282772; Register Extract, date of retrieval Jan. 25, 2017; 2 pages.
European Patent No. 2242512; Written Submission of Opposition Following Preliminary Opinion on Behalf of James Roger Wilding, dated Jun. 27, 2018; 13 pages.
European Patent No. 2242512; Written Submission of Opposition Following Preliminary Opinion on Behalf of Opponent Avidity IP Ltd, dated Jun. 27, 2018; 29 pages.
European Patent No. 2242512; Written Submission of Opposition Following Preliminary Opinion on Behalf of Surface Oncology, Inc., dated Jun. 27, 2018; 21 pages.
European Patent No. 2242512; Written Submission of Opposition Following Preliminary Opinion on Behalf of the Board of Trustees of the Leland Stanford Junior University, dated Jun. 27, 2018; 16 pages.
European Patent No. 2242512; Written Submission of Opposition Following Preliminary Opinion on Behalf of Tioma Therapeutics, Inc., dated Jun. 27, 2018; 21 pages.
European Patent No. 2282772; Observations under 115 EPC, dated Dec. 22, 2016; 2 pages.
Finlay, W. et al., "Natural and Man-Made V-Gene Repertoires for Antibody Discovery", Front Immunol., 3:342, (2012).
Florian, S. et al., "Evaluation of Normal and Neoplastic Human Mast Cells for Expression of CD172a (SIRPalpha), CD47, and SHP-1", J Leukoc Biol., 77(6):984-92, (2005).
Galluzzi, L. et al., "Immunogenic Cell Death in Cancer and Infectious Disease", Nat Rev Immunol., 17(2):97-111, (2017).
Gardai, S. et al., "Cell-Surface Calreticulin Initiates Clearance of Viable or Apoptotic Cells through Trans-Activation of LRP on the Phagocyte", Cell, 123(2):321-34, (2005).
Giusti, A. et al., "Somatic Diversification of S107 from an Antiphosphocholine to an Anti-DNA Autoantibody is Due to a Single Base Change in its Heavy Chain Variable Region", Proc Natl Acad Sci USA, 84(9):2926-30, (1987).
Gresham, H. et al., "A Novel Member of the Integrin Receptor Family Mediates Arg-Gly-Asp-stimulated Neutrophil Phagocytosis", J Cell Biol., 108(5):1935-43, (1989).
Han, X. et al., "CD47, a Ligand for the Macrophage Fusion Receptor, Participates in Macrophage Multinucleation", J Biol Chem., 275(48):37984-92, (2000).
Hanahan, D. et al. (2000) "The Hallmarks of Cancer" Cell, 100:57-70.
Head, D. et al., "Ligation of CD47 Mediates Phosphatidylserine Expression on Erythrocytes and a Concomitant Loss of Viability in Vitro", Br J Haematol., 130(5):788-90, (2005).
Henson, P. et al., "Apoptotic Cell Removal", Curr Biol., 11(19):R795-805, (2011).
International Application No. PCT/US2013/074766; International Preliminary Report on Patentability, date of issuance Jun. 16, 2015; 8 pages.
International Application No. PCT/US2013/074766; International Search Report and Written Opinion of the International Searching Authority, dated Oct. 10, 2014; 6 pages.
International Application No. PCT/US2015/035345; International Preliminary Report on Patentability, date of issuance Dec. 15, 2016; 4 pages.
International Application No. PCT/US2015/035345; International Search Report and Written Opinion of the International Searching Authority, dated Oct. 15, 2015; 6 pages.
International Application No. PCT/US2016/052383; International Preliminary Report on Patentability, date of issuance Mar. 20, 2018; 11 pages.
International Application No. PCT/US2016/052383; International Search Report and Written Opinion of the International Searching Authority, dated Mar. 1, 2017; 16 pages.
International Application No. PCT/US2017/057716; International Preliminary Report on Patentability, date of issuance Apr. 23, 2019; 16 pages.
International Application No. PCT/US2017/057716; International Search Report and Written Opinion of the International Searching Authority, dated Feb. 21, 2018; 22 pages.
International Application No. PCT/US2018/023860; International Preliminary Report on Patentability, date of issuance Oct. 3, 2019; 10 pages.
International Application No. PCT/US2018/023860; International Search Report and Written Opinion of the International Searching Authority, dated Jun. 20, 2018; 14 pages.
International Application No. PCT/US2020/024730; International Search Report and Written Opinion of the International Searching Authority, dated Oct. 1, 2020; 15 pages.
International Application No. PCT/US2020/049195; International Search Report and Written Opinion of the International Searching Authority, dated Feb. 9, 2021; 15 pages.
International Application No. PCT/US2020/056339; International Search Report and Written Opinion of the International Searching Authority, dated Apr. 29, 2021, 15 pages.
International Preliminary Report on Patentability for Application No. PCT/US2020/024730, dated Sep. 28, 2021, 11 Pages.
Isenberg, J. et al., "CD47 is Necessary for Inhibition of Nitric Oxide-Stimulated Vascular Cell Responses by Thrombospondin-1", J Biol Chem., 281(36):26069-80, (2006).
Isenberg, J. et al., "Differential Interactions of Thrombospondin-1, -2 and -4 with CD47 and Effects on cGMP Signaling and Ischemic Injury Response", J Biol Chem., 284(2):1116-25, (2009).
Isenberg, J. et al., "Treatment of Liver Ischemia/Reperfusion Injury by Limiting Thrombospondin-1/CD47 Signaling", Surgery, 144(5):752-61, (2008).
Jaiswal, S. et al., "CD47 is Upregulated on Circulating Hematopoietic Stem Cells and Leukemia Cells to Avoid Phagocytosis", Cell, 138(2):271-85, (2009).
Jamieson, C. et al., "Increased Expression of CD47 is a Constant Marker in Mouse and Human Myeloid Leukemias", Blood, 106(11):3260 (Abstract), (2005).
Jiang, P. et al., "Integrin-Associated Protein Is a Ligand for the P84 Neural Adhesion Molecule", J Biol Chem., 274(2):559-62, (1999).
Johnstone, R. et al., "Apoptosis: A Link between Cancer Genetics and Chemotherapy", Cell, 108(2):153-64, (2002).
Kaiser, U. et al., "Expression of Insulin-Like Growth Factor Receptors I and II in Normal Human Lung and in Lung Cancer", J Cancer Res Clin Oncol., 119(11):665-8, (1993).

(56) References Cited

OTHER PUBLICATIONS

Karr, R., "Experimental Data on Anti-CD47 Antibodies", Opposition Proceedings Relating to European Patent EP2242512, retrieved from the internet: URL:https://register.epo.org/application?number=EP09701993&Ing=en&tab=doclist, (retrieved on May 6, 2020).
Kathawala, R. et al., "Abstract 4001: The anti-CD47 antibody Hu5F9-G4 activates macrophages and inhibits ovarian cancer xenografts, alone and in combination with chemotherapy or immunotherapy", Cancer Res. AACR 107th Annual Meeting 2016, 76(14):5 pages, (2016).
Kenemans, P., "CA 125 and OA 3 as Target Antigens for Immunodiagnosis and Immunotherapy in Ovarian Cancer", Eur J Obstet Gynecol Reprod Biol., 36(3):221-8, (1990).
Kikuchi, Y. et al., "A Bivalent Single-Chain Fv Fragment Against CD47 Induces Apoptosis for Leukemic Cells", Biochem Biophys Res Commun., 315(4):912-8, (2004).
Kikuchi, Y. et al., "Apoptosis Inducing Bivalent Single-Chain Antibody Fragments Against CD47 Showed Antitumor Potency for Multiple Myeloma", Leuk Res., 29(4):445-50, (2005).
Kim, M. et al., "Association of CD47 with Natural Killer Cell-Mediated Cytotoxicty of Head-and-Neck Squamous Cell Carcinoma Lines", Tumour Biol., 29(1):28-34, (2008).
Knapp, W. et al., "CD Antigens 1989", Blood, 74(4):1448-50, (1989).
Kroemer, G. et al., "Classification of Cell Death: Recommendations of the Nomenclature Committee on Cell Death 2009", Cell Death Differ., 16(1):3-11, (2009).
Lamy, L. et al., "CD47 and the 19 kDa Interacting Protein-3 (BNIP3) in T Cell Apoptosis", J Biol Chem., 278(26):23915-21, (2003).
Latour, S. et al., "Bidirectional Negative Regulation of Human T and Dendritic Cells by CD47 and Its Cognate Receptor Signal-Regulator Protein-alpha: Down-Regulation of IL-12 Responsiveness and Inhibition of Dendritic Cell Activation", J Immunol., 167(5):2547-54, (2001).
Legrand, N. et al., "Functional CD47/Signal Regulatory Protein Alpha (SIRP(alpha)) Interaction is Required for Optimal Human T- and Natural Killer- (NK) Cell Homeostasis in Vivo", Proc Natl Acad Sci USA, 108(32):13224-9, (2001).
L'Esperance, S. et al., "Gene Expression Profiling of Paired Ovarian Tumors Obtained Prior to and Following Adjuvant Chemotherapy: Molecular Signatures of Chemoresistant Tumors", Int J Oncol., 29(1):5-24, (2006).
Lindberg, F. et al., "Decreased Resistance to Bacterial Infection and Granulocyte Defects in IAP-Deficient Mice", Science, 274(5288):795-8, (1996).
Lindberg, F. et al., "Molecular Cloning of Integrin-Associated Protein: An Immunoglobulin Family Member with Multiple Membrane-Spanning Domains Implicated in CvB3-dependent Ligand Binding", J Cell Biol., 123(2):485-96, (1993).
Lindberg, F. et al., "Rh-Related Antigen CD47 Is the Signal-Transducer Integrin-Associated Protein", J Biol Chem., 269(3):1567-70, (1994).
Liu, A., "Differential Expression of Cell Surface Molecules in Prostate Cancer Cells", Cancer Res., 60(13):3429-34, (2000).
Liu, J. et al., "Pre-Clinical Development of a Humanized Anti-CD47 Antibody with Anti-Cancer Therapeutic Potential", PLoS One, 10(9):e0137345, (2015).
Liu, X. et al., "CD47 Blockade Triggers T Cell-Mediated Destruction of Immunogenic Tumors", Nat Med., 21(10):1209-15, (2015).
Liu, Y. et al., "Signal Regulatory Protein (SIRP-alpha), a Cellular Ligand for CD47, Regulates Neutrophil Transmigration", J Biol Chem., 277(12):10028-36, (2002).
Lo J., et al., "Anti-CD47 Antibody Suppresses Tumour Growth and Augments the Effect of Chemotherapy Treatment in Hepatocellular Carcinoma," Liver International, 2016, vol. 36(5), pp. 737-745.
Majeti, R. et al., "Acute Myeloid Leukemia—Therapy, Excluding Transplantation", Blood, 112(11):284 (Abstract 766), (2008).

Majeti, R., et al., "CD47 is an Adverse Prognostic Factor and Therapeutic Antibody Target on Human Acute Myeloid Leukemia Stem Cells," Cell, 2009, vol. 138(2), pp. 286-299.
Majeti, R. et al., "CD47 is an Independent Prognostic Factor and Therapeutic Antibody Target on Human Acute Myeloid Leukemia Stem Cells", Blood, vol. 112(11):284 (Abstract 766), (2008).
Majeti, R., "Monoclonal Antibody Therapy Directed Against Human Acute Myeloid Leukemia Stem Cells", Oncogene., 30(9):1009-19, (2011).
Manna, P. et al., "CD47 Mediates Killing of Breast Tumor Cells via Gi-Dependent Inhibition of Protein Kinase A", Cancer Res., 64(3):1026-36, (2004).
Manna, P. et al., "The Mechanism of CD47-Dependent Killing of T Cells: Heterotrimeric Gi-Dependent Inhibition of Protein Kinase A", J Immunol., 170(7):3544-53, (2003).
Mariuzza, et al., "The Structural Basis of Antigen-antibody Recognition," Annual Review of Biophysics and Biophysical Chemistry, 1987, vol. 16.1: 139-159.
Martinez-Torres, A. et al., "CD47 Agonist Peptides Induce Programmed Cell Death in Refractory Chronic Lymphocytic Leukemia B Cells via PLCγl Activation: Evidence From Mice and Humans", PloS Med., 12(3):e1001796, (2015).
Mateo, V. et al., "CD47 Ligation Induces Caspase-Independent Cell Death in Chronic Lymphocytic Leukemia", Nat Med., 5(11):1277-84, (1999).
Mawby, W. et al., "Isolation and Characterization of CD47 Glycoprotein: A Multispanning Membrane Protein Which is the Same as Integrin-Associated Protein (IAP) and the Ovarian Tumour Marker OA3", Biochem J., 304(Pt 2):525-30, (1994).
McKenzie, S. et al., "Apoptosis Evasion: The Role of Survival Pathways in Prostate Cancer Progression and Therapeutic Resistance", J Cell Biochem., 97(1):18-32, (2006).
Morse, M. et al., "Handbook of Cancer Vaccines", Humana Press Inc., (2004).
Motegi, S. et al., "Role of CD47-SHPS-1 System in Regulation of Cell Migration", EMBO J., 22(11):2634-44, (2003).
Mughal, T. et al., "Understanding Leukemias, Lymphomas and Myelomas", Taylor & Francis, 1st ed:47-8 & 53, (2006).
Munn, D. et al., "Phagocytosis of Tumor Cells by Human Monocytes Cultured in Recombinant Macrophage Colony-Stimulating Factor", J Exp Med., 172(1):231-7, (1990).
NCBI, Genbank Accession No. 1A4J_L, "Chain L, Diels Alder Catalytic Antibody Germline Precursor", Database Protein, (2012).
NCBI, Genbank Accession No. ACN 59874.1, "Chimeric Anti-Human Type VII Collagen Immunoglobulin G1 [Synthetic Construct]", Database Protein, (2009).
Nishiyama, Y. et al., "Overexpression of Integrin-Associated Protein (CD47) in Rat Kidney Treated with a Renal Carcinogen, Ferric Nitrilotriacetate", Jpn J Cancer Res., 88(2):120-8, (1997).
Obeid, M. et al., "Ecto-Calreticulin in Immunogenic Chemotherapy", Immunol Rev., 220:22-34, (2007).
Oldenborg, P., "CD47: A Cell Surface Glycoprotein Which Regulates Multiple Functions of Hematopoietic Cells in Health and Disease", ISRN Hematol., 2013:614619, (2013).
Oldenborg, P. et al., CD47-Signal Regulatory Protein Alpha (SIRPa) Regulates Fc Gamma and Complement Receptor-Mediated Phagocytosis, J Exp Med., 193(7):855-61,(2001).
Oldenborg, P. et al., "Role of CD47 as a Marker of Self on Red Blood Cells", Science, 288(5473):2051-4, (2000).
Oldenborg, P., "Role of CD47 in Erythroid Cells and in Autoimmunity", Leuk Lymphoma, 45(7):1319-27, (2004).
Olsson, M. et al., "Platelet Homeostasis is Regulated by Platelet Expression of CD47 Under Normal Conditions and in Passive Immune Thromocytopenia", Blood, 105(9):3577-82, (2005).
Pettersen, R. et al., "CD47 Signals T Cell Death", J Immunol., 162(12):7031-40, (1999).
Pettersen, R. et al., "CD99 Signals Caspase-Independent T Cell Death", J Immunol., 166(8):4931-42, (2001).
Pietsch, E. et al., "Anti-Leukemic Activity and Tolerability of Anti-Human CD47 Monoclonal Antibodies", Am Assoc Cancer Res., Abstract 2470, (2017).

(56) References Cited

OTHER PUBLICATIONS

Pietsch EC et al., Anti-leukemic activity and tolerability of anti-human CD47 monoclonal antibodies, Blood Cancer Journal, Feb. 24, 2017;7(2): e536, 8 pages.
Poels, L. et al., "Monoclonal Antibody Against Human Ovarian Tumor-Associated Antigens", J Natl Cancer Inst., 76(5)781-91, (1986).
Puro RJ et al., Development of AO-176, a Next-Generation Humanized Anti-CD47 Antibody with Novel Anticancer Properties and Negligible Red Blood Cell Binding, Molecular Cancer Therapeutics Mar. 2020; 19(3): pp. 835-846.
Raetz, E. et al., "Gene Expression Profiling Reveals Intrinsic Differences Between T-Cell Acute Lymphoblastic Leukemia and T-Cell Lymphoblastic Lymphoma", Pediatr Blood Cancer, 47(2):130-40, (2006).
Rebres, R. et al., "Novel CD47-Dependent Intercellular Adhesion Modulates Cell Migration", J Cell Physiol., 205(2):182-93, (2005).
Reichert, J., "Marketed Therapeutic Antibodies Compendium", MAbs, 4(3):413-5, (2012).
Rendtlew Danielsen, J. et al., "Dysregulation of CD47 and the Ligands Thrombospondin 1 and 2 in Multiple Myeloma", Br J Haematol., 138(6):756-60, (2007).
Roberts, D. et al., "The Matricellular Protein Thrombospondin-1 Globally Regulates Cardiovascular Function and Responses to Stress via CD47", Matrix Biol., 31(3):162-9, (2012).
Roitt, I., et al., "Immunology" Moscow, "Mir", 2000, Chapter 6, pp. 110-111, and English translation.
Rudikoff, S. et al., "Single amino acid substitution altering antigen-binding specificity," Proc. Natl. Acad. Sci. USA, 79:1979-1983 (Mar. 1, 1982).
Sagawa, M. et al., "A New Disulfide-Linked Dimer of a Single-Chain Antibody Fragment Against Human CD47 Induces Apoptosis in Lymphoid Malignant Cells via the Hypoxia Inducible Factor-1 alpha Pathway", Cancer Sci., 102(6):1208-15, (2011).
Samani, A. et al., "The Role of the IGF System in Cancer Growth and Metastasis: Overview and Recent Insights", Endoc Rev., 28(1):20-47, (2007).
Seiffert, M. et al., "Human Signal-Regulatory Protein Is Expressed on Normal, but Not on Subsets of Leukemic Myeloid Cells and Mediates Cellular Adhesion Involving Its Counterreceptor CD47", Blood, 94(11):3633-43, (1999).
Sick, E. et al., "CD47 Update: A Multifaceted Actor in the Tumour Microenvironment of Potential Therapeutic Interest", Br J Pharmacol., 167(7):1415-30, (2012).
Singer, M. et al. (1998). "Genes and Genomes", Moscow, MIR, vol. 1, pp. 63-64 (with English machine translation).
Sonderegger, S. et al., "Interleukin (IL)11 Mediates Protein Secretion and Modification in Human Extravillous Trophoblasts", Hum Reprod., 26(10):2841-9, (2011).
Soto-Pantoja, D. et al., "Inhibitory Signaling Through Signal Regulatory Protein-A is Not Sufficient to Explain the Antitumor Activities of CD47 Antibodies", Proc Natl Acad Sci USA, 109(42):E2842, (2012).
Soto-Pantoja, D. et al., "Therapeutic Opportunities for Targeting the Ubiquitous Cell Surface Receptor CD47", Expert OpinTher Targets, 17(1):89-103, (2013).
Strome, et al., "A Mechanistic Perspective of Monoclonal Antibodies in Cancer Therapy Beyond Target-Related Effects". The Oncologist (Sep. 2007); 12(9): 1084-1095.
Subramanian, S. et al., "Species- and Cell Type-Specific Interactions Between CD47 and Human SIRPalpha", Blood, 107(6):2548-56, (2006).
Subramanian, S. et al., Phylogenetic Divergence of CD47 Interactions with Human Signal Regulatory Protein Alpha Reveals Locus of Species Specificity. Implications for the Binding Site, J Biol Chem., 282(3):1805-18, (2007).
Takizawa, H. et al., "Macrophage Tolerance: CD47-SIRP-Alpha-Mediated Signals Matter", Nat Immunol., 8(12):1287-9, (2007).

Tamoto, E. et al., "Gene-Expression Profile Changes Correlated with Tumor Progression and Lymph Node Metastasis in Esophageal Cancer", Clin Cancer Res., 10(11):3629-38, (2004).
Ticchioni, M. et al., "Integrin-Associated Protein (CD47) Is a Comitogenic Molecule on CD3-Activated Human T Cells", J Immunol., 158(2):677-84, (1997).
Trounson, A., "Stem Cells, Plasticity and Cancer—Uncomfortable Bed Fellows", Development, 131(12):2763-8, (2004).
Uno, S. et al., "Antitumor Activity of a Monoclonal Antibody Against CD47 in Xenograft Models of Human Leukemia", Oncol Rep., 17(5):1189-94, (2007).
Van Beek, E. et al., "Signal Regulatory Proteins in the Immune System", J Immunol., 175(12):7781-7, (2005).
Van Den Berg, T. et al., "Innate Immune 'Self' Recognition: A Role for CD47-SIRPa Interactions in Hemotopoietic Stem Transplantation", Trends Immunol., 29(5):203-6, (2008).
Van Ravenswaay, C. et al., "Analysis of Production, Purification, and Cytolytic Potential of Bi-Specific Antibodies Reactive With Ovarian-Carcinoma-Associated Antigens and the T-Cell Antigen CD3", Int J Cancer, 55(1):128-36, (1993).
Vermeer, D. et al., "Radiation-Induced Loss of Cell Surface CD47 Enhances Immune-Mediated Clearance of Human Papillomavirus-Positive Cancer", Int J Cancer, 133(1):120-9, (2013).
Vernon-Wilson, E. et al., "CD47 is a Ligand for Rat Macrophage Membrane Signal Regulatory Protein SIRP (0X41) and Human SIRPalpha 1", Eur J Immunol. 30(8):2130-7, (2000).
Wang, H. et al., "Attenuation of Phagocytosis of Xenogeneic Cells by Manipulating CD47", Blood, 109(2):836-42, (2007).
Washington University School of Medicine, "Scientists Discover New Way to Distinguish Self from Other", Science Daily, retreived online from https://sciencedaily.com/releases/2000/06/000619073418.htm on Jan. 22, 2017, (2000).
Weiskopf, K. et al., "CD47-Blocking Immunotherapies Stimulate Macrophage-Mediated Destruction of Small-Cell Lung Cancer", J Clin Invest., 126(7):2610-20, (2016).
Weiskopf, K. et al., "Engineered SIRPa Variants as Immunotherapeutic Adjuvants to Anticancer Antibodies", Science, 341(6141):88-91, (2013).
Weiskopf, K. et al., "Macrophages are Critical Effectors of Antibody Therapies for Cancer", MAbs, 7(2):303-10, (2015).
Weissman, I. et al., "The E. Donnall Thomas Lecture; Normal and Neoplastic Stem Cells", Biol Blood Marrow Transplant, 14(8):849-58, (2008).
Willingham, S. et al., "The CD47-Signal Regulatory Protein alpha (SIRPa) Interaction is a Therapeutic Target for Human Solid Tumors", Proc Natl Acad Sci USA, 109(17):6662-7, (2012).
Winkler et al., "Changing the Antigen Binding Specificity by Single PointMutations of an Anti-p24 (HIV-1) Antibody", The Journal of Immunology, 165: 4505-4514 (2000).
Yamao, T. et al., "Negative Regulation of Platelet Clearance and of the Macrophage Phagocytic Response by the Transmembrane Glycoprotein SHPS-1", J Biol Chem., 277(42):39833-9, (2002).
Yang, Y. et al., "Wogonin Induced Calreticulin/Annexin A1 Exposure Dictates the Immunogenicity of Cancer Cells in a PERK/AKT Dependent Manner", PLoS One, 7(12):e50811, (2012).
Yarilin, Immunology, 1999, p. 171-3.
Zhan, F. et al., "Global Gene Expression Profiling of Multiple Myeloma, Monoclonal Gammopathy of Undetermined Significance, and Normal Bone Marrow Plasma Cells", Blood, 99(5):1745-57, (2002).
Zhao, X. et al., "Is Targeting of CD47-SIRPa Enough for Treating Hematopoietic Malignancy", Blood, 119(18):4333-4, (2012).
Zhao, X.W., et al., "CD47-Signal Regulatory Protein-α (SIRPα) Interactions Form a Barrier for Antibody-Mediated Tumor Cell Destruction", Proceedings of the National Academy of Sciences, 2011, vol. 108(45), pp. 18342-18347.
Zipin-Roitman, A. et al., "CXCL10 Promotes Invasion-Related Properties in Human Colorectal Carcinoma Cells", Cancer Res., 67(7):3396-405, (2007).
Brown, M. et al., "Tolerance to Single, but Not Multiple, Amino Acid Replacements in Antibody VH CDR2: A Means of Minimizing B Cell Wastage from Somatic Hypermutation", The Journal of Immunology (1996); 156(9): 3285-3291.

(56) References Cited

OTHER PUBLICATIONS

European Patent Application No. 16847511.9, Extended European Search Report, dated Feb. 27, 2019; 12 pages.
European Patent Application No. 17862758.4, Extended European Search Report, dated May 18, 2020; 11 pages.
European Patent Application No. 18771103.1, Extended European Search Report, dated Nov. 25, 2020; 12 pages.
Garg, A. et al., "Immunogenic Cell Death, DAMPs and Anticancer Therapeutics: An Emerging Amalgamation", Biochimica et Biophysica Acta (2009); 1805(1): 53-71.
International Application No. PCT/US2016/052383; Invitation to Pay Additional Fees, dated Dec. 1, 2016, 3 pages.
International Application No. PCT/US2017/057716; Invitation to pay additional fees, dated Dec. 19, 2017, 4 pages.
International Application No. PCT/US2020/024730; Invitation to pay additional fees, dated Aug. 3, 2020, 3 pages.
International Application No. PCT/US2020/049195; Invitation to pay additional fees, dated Dec. 2, 2020; 3 pages.
International Application No. PCT/US2020/056339; Invitation to pay additional fees, dated Mar. 9, 2021; 4 pages.
International Preliminary Report on Patentability for Application No. PCT/US2020/049195, dated Mar. 8, 2022, 10 Pages.
International Preliminary Report on Patentability for Application No. PCT/US2020/056339; dated Apr. 26, 2022, 9 Pages.
Ju, B., et al., "In vitro application of anti-CD47 monoclonal antibody for targeted therapy of ovarian cancer", Chinese Journal of Clinical Oncology (2013); 40(8): 440-441.
Kepp, O. et al., "Molecular Determinants of Immunogenic Cell Death Elicited by Anticancer Chemotherapy", Cancer Metastasis Rev. (2011); 30(1): 61-69.
Kroemer, G. et al., "Immunogenic Cell Death in Cancer Therapy", Annu. Rev. Immunol. (2013); 31: 51-72.
Krysco, D. et al., "Immunogenic Cell Death and DAMPs in Cancer Therapy", Nat Rev Cancer (2012); 12(12): 860-875.
Li, L. et al., "Research Progress on Correlation Between CD47 and Tumor Immunity", Guangdong Medical Journal (Sep. 2011); 32(18): 2480-2481.
Bauer, Philip M., et al. "Activated CD47 promotes pulmonary arterial hypertension through targeting caveolin-1." Cardiovascular research (2012); 93(4): 682-693.
Bonvin, Pauline, et al., "De novo isolation of antibodies with pH-dependent binding properties", Mabs (2015); 7(2): 294-302.
De Oliveira, S., et al., "Integrin-associated protein (CD47) is a putative mediator for soluble fibrinogen interaction with human red blood cells membrane", Biochimica et Biophysica Acta (BBA)-Biomembranes (2012); 1818(3): 481-490.
Igawa, T., et al., "pH-dependent antigen-binding antibodies as a novel therapeutic modality", Biochimica et Biophysica Acta (BBA)-Proteins and Proteomics (2014); 1844(11): 1943-1950.
International Preliminary Report on Patentability for International Application No. PCT/US2021/039059 dated Jan. 5, 2023, 5 pages.
Isenberg, Jeff S., et al., "Blockade of thrombospondin-1-CD47 interactions prevents necrosis of full thickness skin grafts", Annals of Surgery (2008); 247(1): 180-190.
Isenberg, Jeff S., et al., "Blocking thrombospondin-1/CD47 signaling alleviates deleterious effects of aging on tissue responses to ischemia", Arteriosclerosis, Thrombosis, and Vascular Biology (2007); 27(12): 2582-2588.
Isenberg, Jeff S., et al., "Enhancing cardiovascular dynamics by inhibition of thrombospondin-1/CD47 signaling", Current Drug Targets (2008); 9(10): 833-841.
Kim, D., et al. "Anti-CD47 antibodies promote phagocytosis and inhibit the growth of human myeloma cells", Leukemia (2012); 26(12): 2538-2545.
Kojima, Yoko, et al., "CD47-blocking antibodies restore phagocytosis and prevent atherosclerosis", Nature (2016); 536(7614): 86-90.
Lin, Yiing, et al., "CD47 Blockade Reduces Ischemia Reperfusion Injury and Improves Outcomes in a Rat Kidney Transplant Model", Transplantation (2014); 98(4): 394-401.
Masternak, Krzysztof, et al., "Neutralizing CD47 in cancer cells with dual targeting kappa/lambda bodies", Cancer Research (2015); 75(15_Supplement): 2482-2482.
Maxhimer, Justin B., et al., "Thrombospondin-1/CD47 blockade following ischemiareperfusion injury is tissue protective", Plastic and Reconstructive Surgery (2009); 124(6): 1880-1889.
Miller, Thomas W., et al., "Thrombospondin-1 is an inhibitor of pharmacological activation of soluble guanylate cyclase", British Journal of Pharmacology (2010); 159(7): 1542-1547.
Mounho-Zamora, B., et al., "Nonclinical Safety Assessment of a Monoclonal Antibody against CD47", The Toxicologist Supplement to Toxicological Sciences (2015); 144(1): Abstract 596: p. 127.
Narla, Rama Krishna, et al., "Abstract 4694: The humanized anti-CD47 monclonal antibody, CC-90002, has antitumor activity in vitro and in vivo", Cancer Research (2017); 77(13_Supplement): 4694-4694.
Petrova, Penka S., et al., "TTI-621 (SIRPαFc): A CD47-Blocking Innate Immune Checkpoint Inhibitor with Broad Antitumor Activity and Minimal Erythrocyte Binding TTI-621 Is a Novel Antitumor Immune Checkpoint Inhibitor", Clinical Cancer Research (2017); 23(4): 1068-1079.
Petrova, Penka S., et al., "Lack of CD47 membrane mobility contributes to the poor erythrocyte binding of SIRPαFc, a novel CD47-blocking cancer immunotherapeutic", Cancer Research (2015); 75(15_Supplement): 4271-4271.
Pietsch, E. Christine, et al., "Anti-leukemic activity and tolerability of anti-human CD47 monoclonal antibodies", Cancer Research (2015); 75(15_Supplement): 2470.
Rogers, Natasha M., et al., "Activation of parenchymal CD47 promotes renal ischemia-reperfusion injury", Journal of the American Society of Nephrology (2012); 23(9): 1538-1550.
Rogers, Natasha M., et al., "CD47 regulates renal tubular epithelial cell self-renewal and proliferation following renal ischemia reperfusion", Kidney international (2016); 90(2): 334-347.
Sharifi-Sanjani, Maryam, et al., "Cardiac CD47 Drives Left Ventricular Heart Failure Through Ca2+-CaMKII-Regulated Induction of HDAC3", Journal of the American Heart Association (2014); 3(3): 1-21.
Sikic, Branimir I., et al., "A first-in-human, first-in-class phase I trial of the anti-CD47 antibody Hu5F9-G4 in patients with advanced cancers", Journal of Clinical Oncology (2016); 3019.
Soto-Pantoja, David R., et al. "CD47 in the tumor microenvironment limits cooperation between antitumor T-cell immunity and radiotherapy." Cancer research 74.23 (2014): 6771-6783.
Tseng, Diane, et al. "Anti-CD47 antibody-mediated phagocytosis of cancer by macrophages primes an effective antitumor T-cell response." Proceedings of the National Academy of Sciences 110.27 (2013): 11103-11108.
Uger, Robert A., et al., "Blockade ofCD47 using SIRPαFc: role of the Fc region in anti-leukemic activity and tolerability", Blood (2013); 122(21): 3935.
Uger, Robert A., et al., "Cancer immunotherapy targeting CD47: Wild type SIRPaFc is the ideal CD47-blocking agent to minimize unwanted erythrocyte binding", Cancer Research (2014); 74(19_Supplement): 5011.
Xiao, Zhenyu, et al., "Antibody mediated therapy targeting CD47 inhibits tumor progression of hepatocellular carcinoma", Cancer Letters (2015); 360(2): 302-309.
Xiao, Zhenyu, et al., "Attenuation of ischemia-reperfusion injury and improvement of survival in recipients of steatotic rat livers using CD47 monoclonal antibody." Transplantation (2016); 100(7): 1480-1489.
Xiao, Zhen-Yu, et al., "CD47 blockade reduces ischemia/reperfusion injury and improves survival in a rat liver transplantation model", Liver Transplantation (2015); 21(4): 468-477.
Xu, Meng Michelle, et al., "Dendritic cells but not macrophages sense tumor mitochondrial DNA for cross-priming through signal regulatory protein a signaling", Immunity (2017); 47(2): 363-373.

* cited by examiner

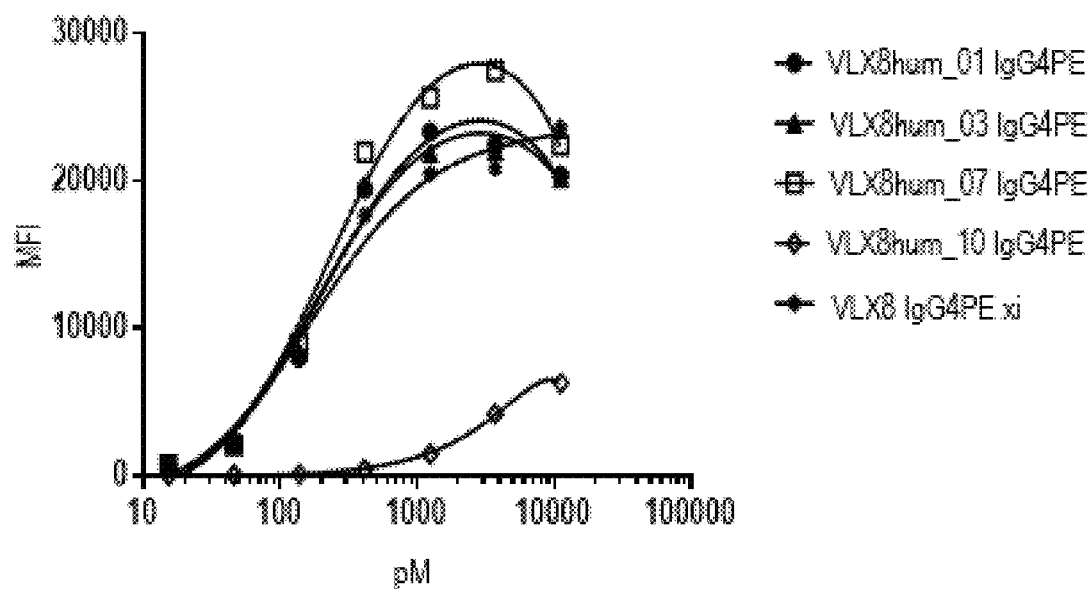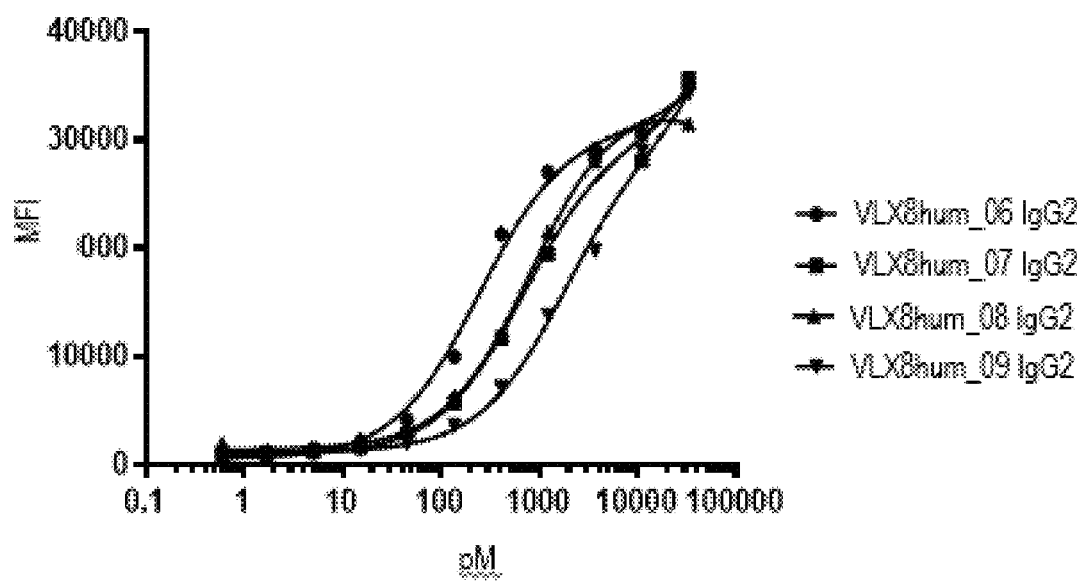

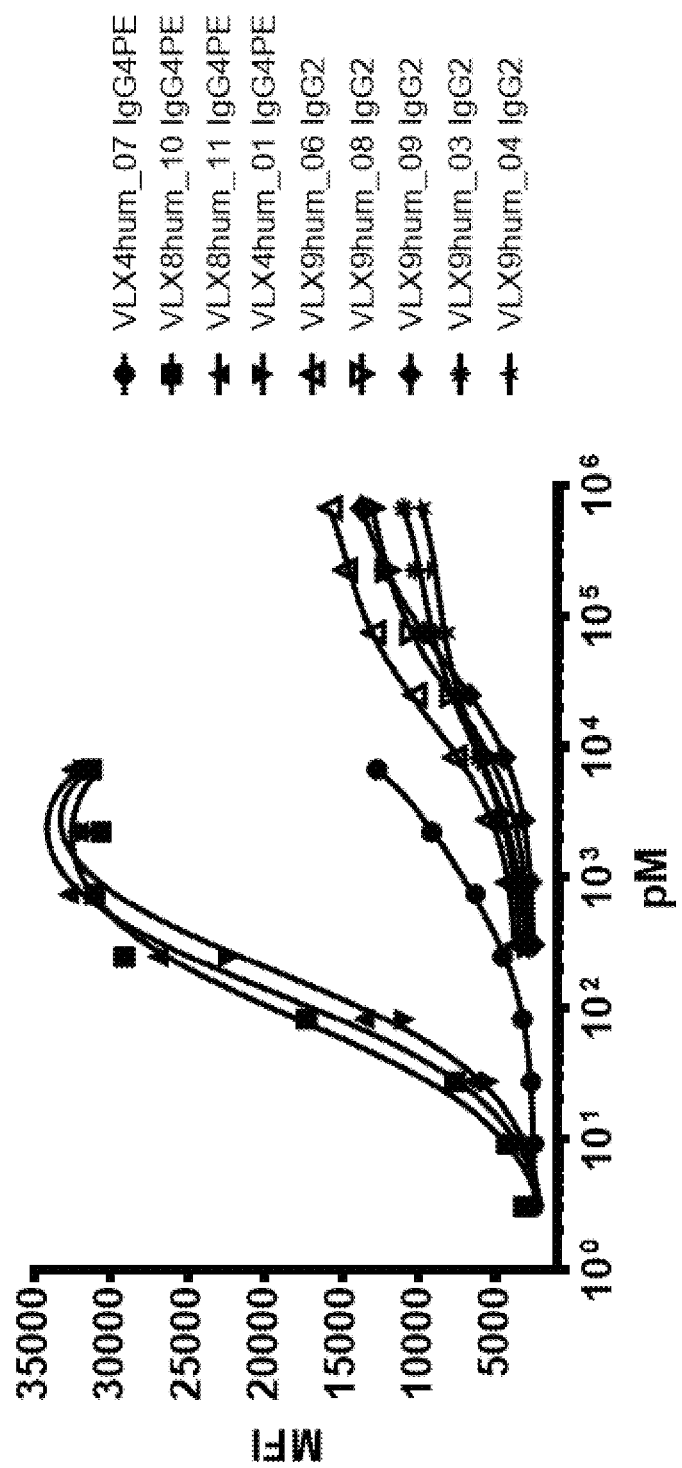

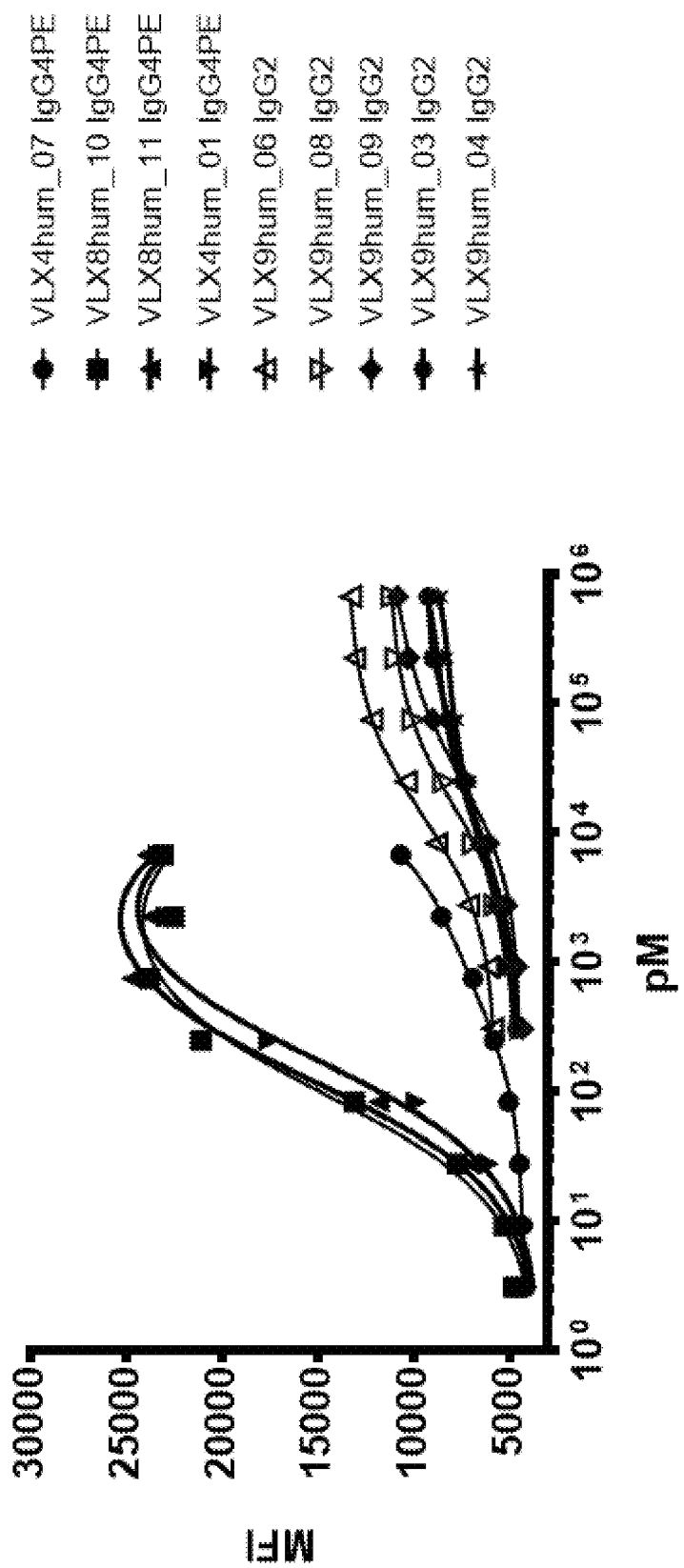

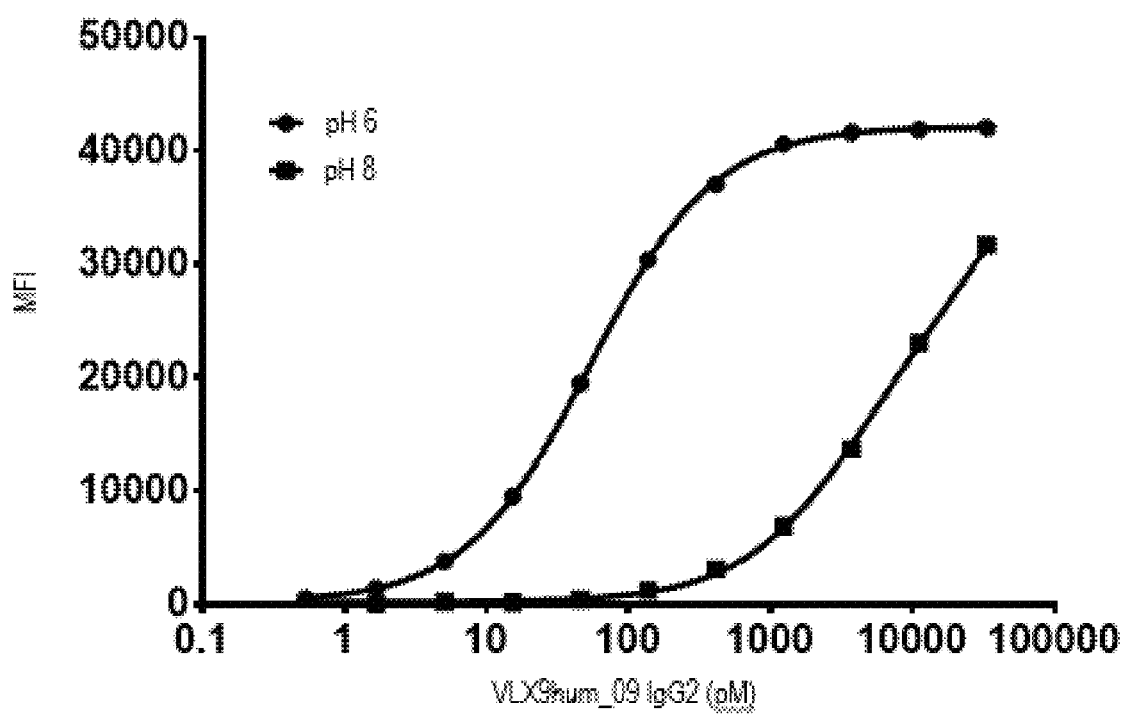

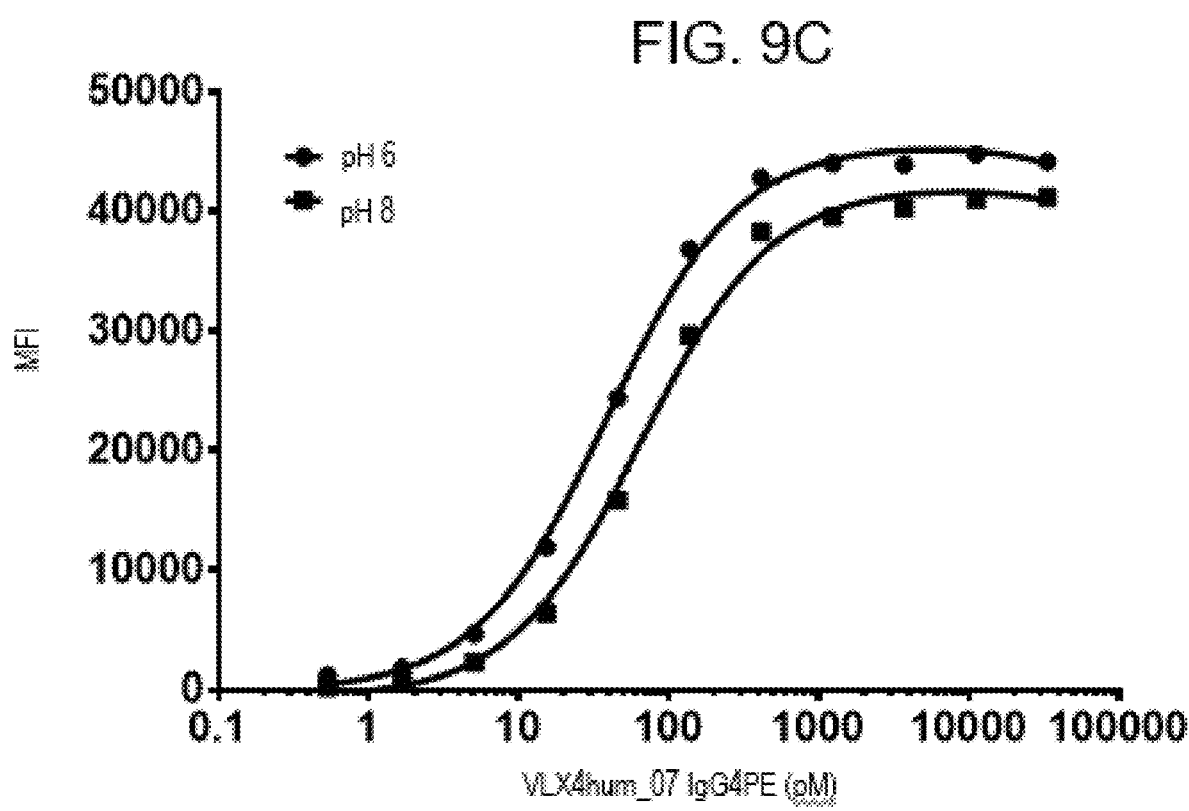

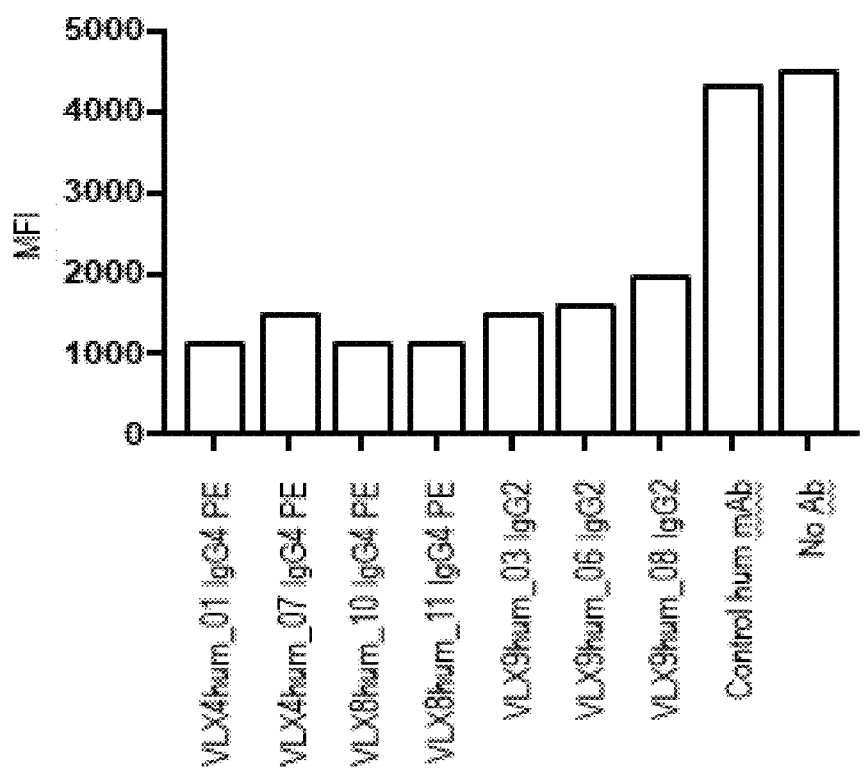

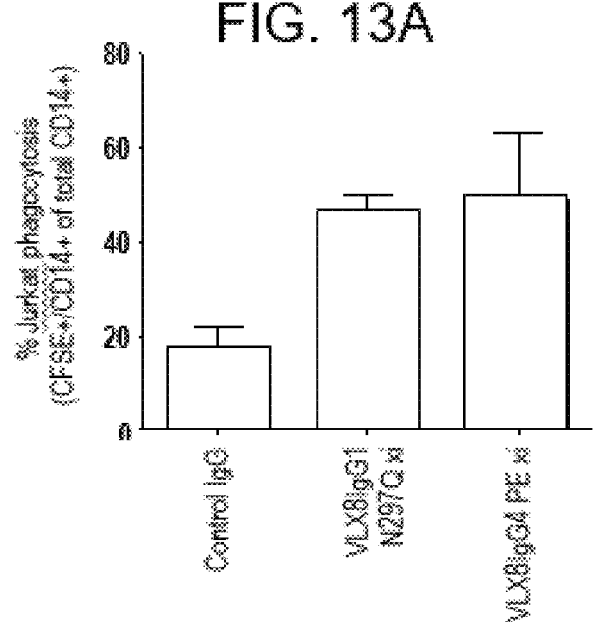
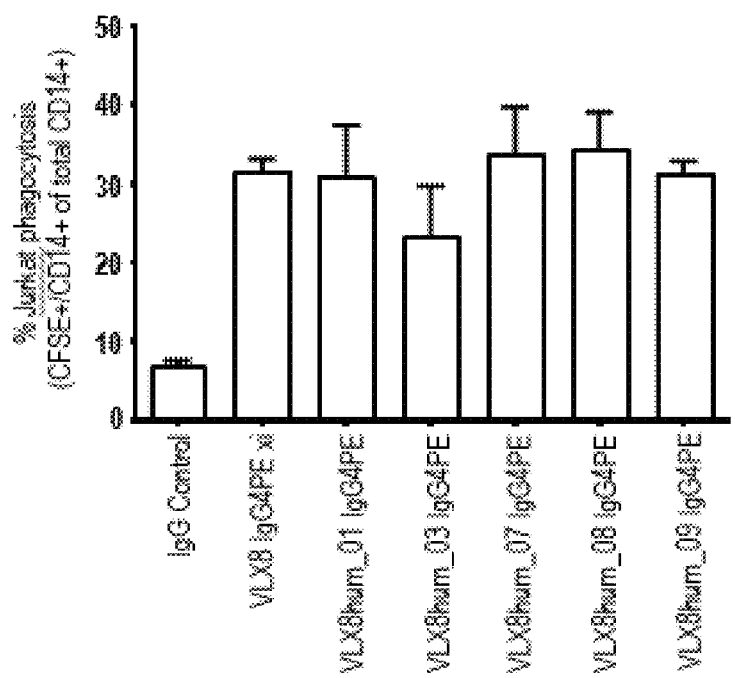

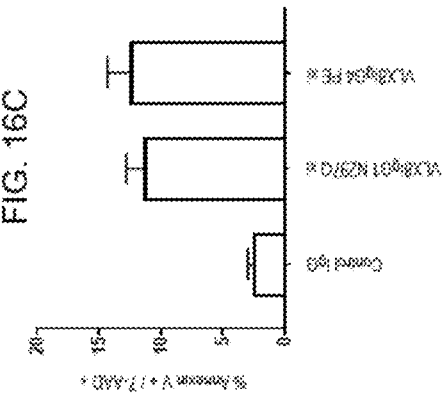
FIG. 16A
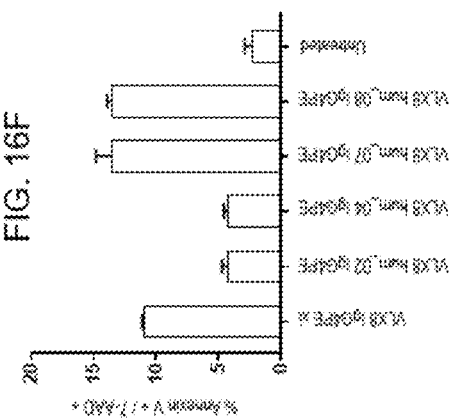
FIG. 16B
FIG. 16C
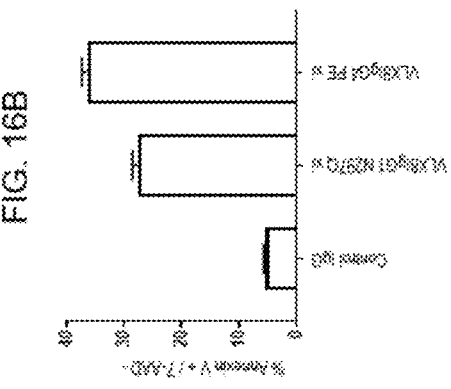
FIG. 16D
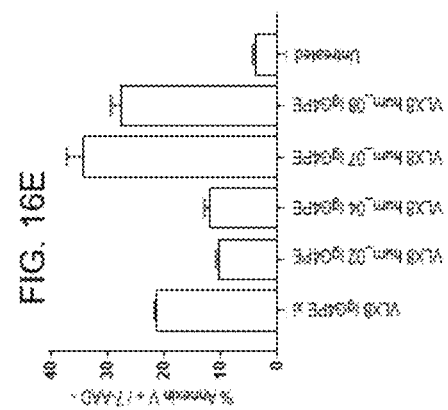
FIG. 16E
FIG. 16F
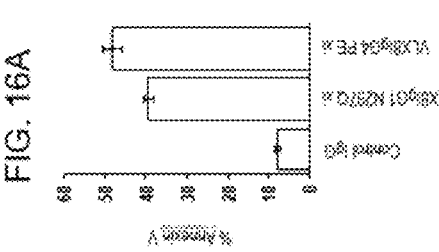
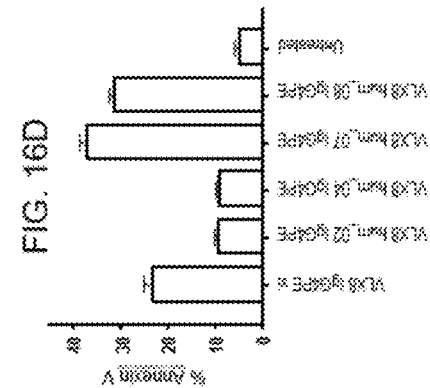

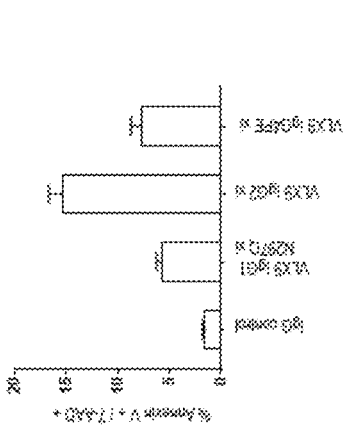
FIG. 17A
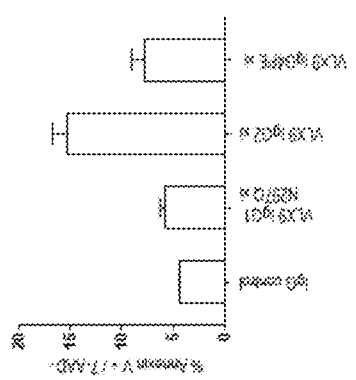
FIG. 17B
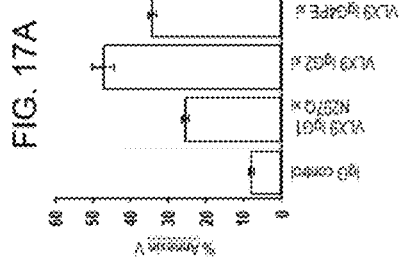
FIG. 17C
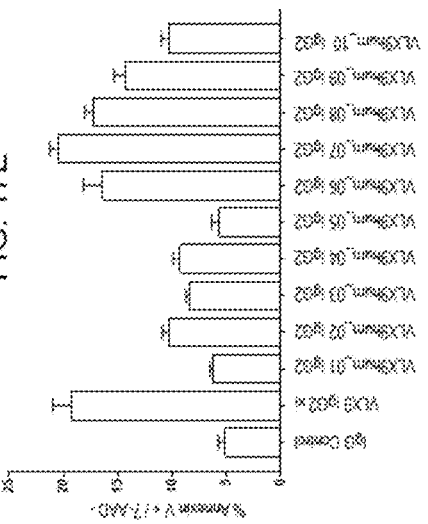
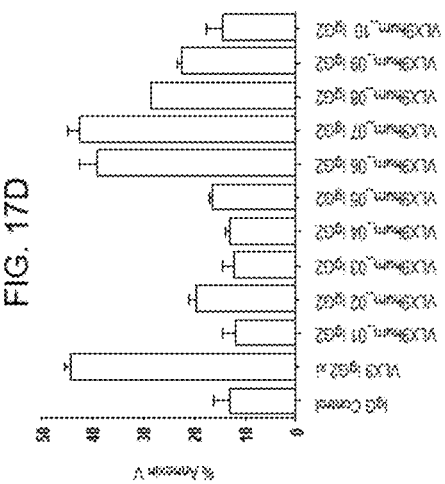

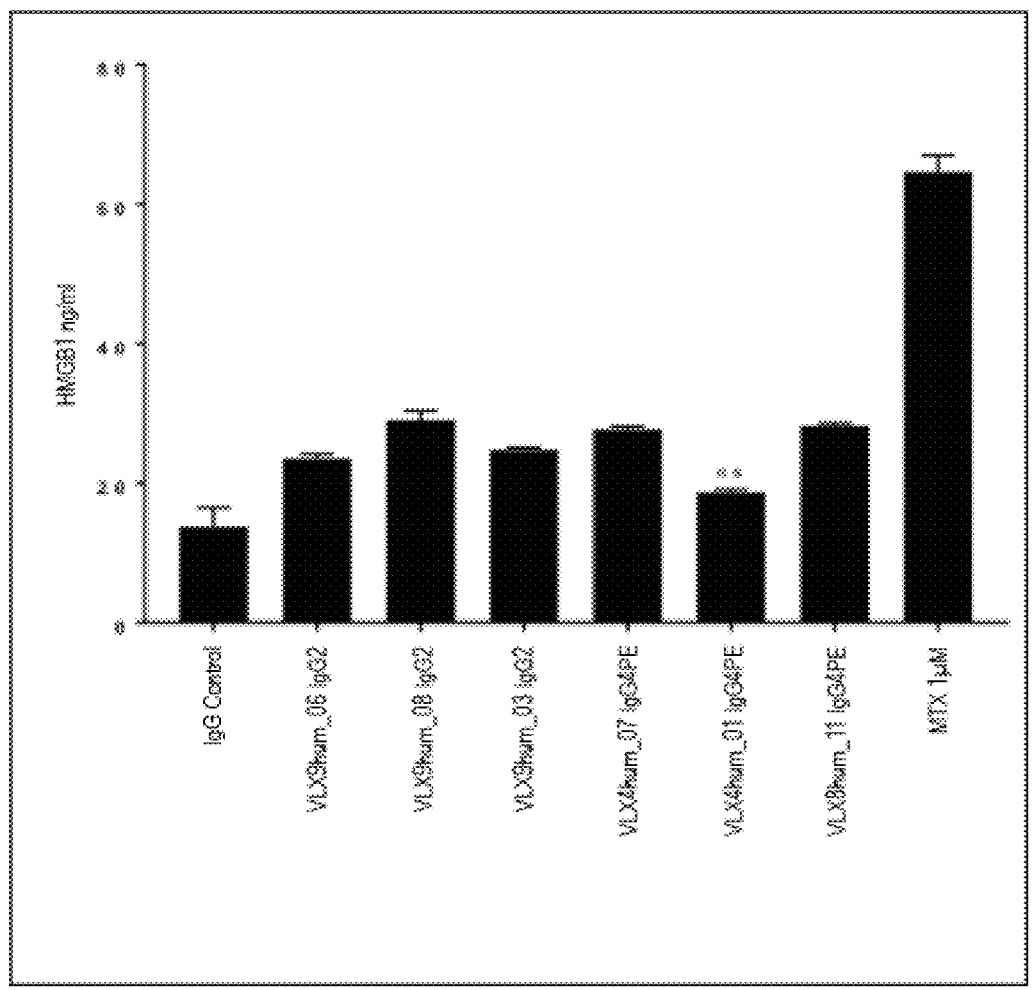

THERAPEUTIC CD47 ANTIBODIES

CROSS REFERENCE TO RELATED APPLICATIONS

This application is a continuation of U.S. application Ser. No. 16/223,009, filed Dec. 17, 2018, which is a continuation of U.S. application Ser. No. 15/871,802, filed Jan. 15, 2018, which is a continuation of International Application No. PCT/US2017/057716, filed Oct. 20, 2017, which claims the benefit of U.S. Provisional Application No. 62/411,319, filed Oct. 21, 2016, and U.S. Provisional Application No. 62/475,032, filed Mar. 22, 2017, the disclosures of which are incorporated herein in their entireties.

The instant application contains a Sequence Listing which has been submitted in ASCII format via EFS-Web and is hereby incorporated by reference in its entirety. Said ASCII copy, created on Nov. 3, 2021 is named "20191204_Sequence_Listing.txt" and is 179 kilobytes in size.

FIELD OF THE DISCLOSURE

This disclosure is related generally to anti-CD47 monoclonal antibodies (anti-CD47 mAbs) with distinct functional profiles as described herein, methods to generate anti-CD47 mAbs, and methods of using these anti-CD47 mAbs as therapeutics for the prevention and treatment of solid and hematological cancers, ischemia-reperfusion injury, cardiovascular diseases, autoimmune diseases, or inflammatory diseases, or as diagnostics for determining the level of CD47 in tissue samples.

BACKGROUND OF THE DISCLOSURE

CD47 is a cell surface receptor comprised of an extracellular IgV set domain, a 5 transmembrane domain, and a cytoplasmic tail that is alternatively spliced. Two ligands bind CD47: signal inhibitory receptor protein α (SIRPα) and thrombospondin-1 (TSP1). CD47 expression and/or activity has been implicated in a number of diseases and disorders. Accordingly, there exists a need for therapeutic compositions and methods for treating diseases and conditions associated with CD47 in humans and animals, including the prevention and treatment of solid and hematological cancers, ischemia-reperfusion injury (IRI), cardiovascular diseases, or an autoimmune or inflammatory disease.

SUMMARY OF THE DISCLOSURE

The present disclosure describes anti-CD47 mAbs with distinct functional profiles. These antibodies possess distinct combinations of properties selected from the following: 1) exhibit cross-reactivity with one or more species homologs of CD47; 2) block the interaction between CD47 and its ligand SIRPα; 3) increase phagocytosis of human tumor cells; 4) induce death of susceptible human tumor cells; 5) do not induce cell death of human tumor cells; 6) do not have reduced or minimal binding to human red blood cells (hRBCs); 7) have reduced binding to hRBCs; 8) have minimal binding to hRBCs; 9) cause reduced agglutination of hRBCs; 10) cause no detectable agglutination of hRBCs; 11) reverse TSP1 inhibition of the nitric oxide (NO) pathway; 12) do not reverse TSP1 inhibition of the NO pathway; 13) cause loss of mitochondrial membrane potential; 14) do not cause cause loss of mitochondrial membrane potential; 15) cause an increase in cell surface calreticulin expression on human tumor cells; 16) do not cause an increase in cell surface calreticulin expression on human tumor cells; 17) cause an increase in adenosine triphosphate (ATP) release by human tumor cells; 18) do not cause an increase in adenosine triphosphate (ATP) release by human tumor cells; 19) cause an increase in high mobility group box 1 (HMGB1) release by human tumor cells; 20) do not cause an increase in high mobility group box 1 (HMGB1) release by human tumor cells; 21) cause an increase in type I interferon release by human tumor cells; 22) do not cause an increase in type I interferon release by human tumor cells; 23) cause an increase in C-X-C Motif Chemokine Ligand 10 (CXCL10) release by human tumor cells; 24) do not cause an increase in C-X-C Motif Chemokine Ligand 10 (CXCL10) release by human tumor cells; 25) cause an increase in cell surface protein disulfide-isomerase A3 (PDIA3) expression on human tumor cells; 26) do not cause an increase in cell surface protein disulfide-isomerase A3 (PDIA3) expression on human tumor cells; 27) cause an increase in cell surface heat shock protein 70 (HSP70) expression on human tumor cells; 28) do not cause an increase in cell surface heat shock protein 70 (HSP70) expression on human tumor cells; 29) cause an increase in cell surface heat shock protein 90 (HSP90) expression on human tumor cells; 30) do not cause an increase in cell surface heat shock protein 90 (HSP90) expression on human tumor cells; 31) have reduced binding to normal human cells, which includes, but is not limited to, endothelial cells, skeletal muscle cells, epithelial cells, and peripheral blood mononuclear cells (e.g., human aortic endothelial cells, human skeletal muscle cells, human microvascular endothelial cells, human renal tubular epithelial cells, human peripherial blood CD3+ cells, and human peripheral blood mononuclear cells); 32) do not have reduced binding to normal human cells, which includes, but is not limited to, endothelial cells, skeletal muscle cells, epithelial cells, and peripheral blood mononuclear cells (e.g., human aortic endothelial cells, human skeletal muscle cells, human microvascular endothelial cells, human renal tubular epithelial cells, human peripherial blood CD3+ cells, and human peripheral blood mononuclear cells); 33) have a greater affinity for human CD47 at an acidic pH compared to physiological pH; 34) do not have a greater affinity for human CD47 at an acidic pH compared to physiological pH; and 35) cause an increase in annexin A1 release by human tumor cells. The anti-CD47 mAbs of the disclosure are useful in various therapeutic methods for treating diseases and conditions associated with CD47 in humans and animals, including the prevention and treatment of solid and hematological cancers, autoimmune diseases, inflammatory diseases, IRI, and cardiovascular diseases. The antibodies of the disclosure are also useful as diagnostics to determine the level of CD47 expression in tissue samples. Embodiments of the disclosure include isolated antibodies and immunologically active binding fragments thereof; pharmaceutical compositions comprising one or more of the anti-CD47 mAbs, preferably chimeric or humanized forms of said anti-CD47 mAbs; methods of therapeutic use of such anti-CD47 monoclonal antibodies; and cell lines that produce these anti-CD47 mAbs.

The embodiments of the disclosure include the mAbs, or antigen-binding fragments thereof, which are defined herein by reference to specific structural characteristics, i.e., specified amino acid sequences of either the CDRs or entire heavy chain or light chain variable domains. All antibodies of the disclosure bind to CD47.

The monoclonal antibodies, or antigen binding fragments thereof, may comprise at least one, usually at least three, CDR sequences as provided herein, usually in combination with framework sequences from a human variable region or as an isolated CDR peptide. In some embodiments, an antibody comprises at least one light chain comprising the three light chain CDR sequences provided herein situated in a variable region framework, which may be, without limitation, a murine or human variable region framework, and at least one heavy chain comprising the three heavy chain CDR sequences provided herein situated in a variable region framework, which may be, without limitation, a human or murine variable region framework.

Some embodiments of the disclosure are anti-CD47 mAbs, or antigen binding fragments thereof, comprising a heavy chain variable domain comprising a variable heavy chain CDR1, variable heavy chain CDR2, and a variable heavy chain CDR3, wherein said variable heavy chain CDR1 comprises an amino acid sequence selected from the group consisting of: SEQ ID NO:1, SEQ ID NO:2, and SEQ ID NO:3; said variable heavy chain CDR2 comprises an amino acid sequence selected from the group consisting of: SEQ ID NO:4, SEQ ID NO:5, and SEQ ID NO:6; and said variable heavy chain CDR3 comprises an amino acid sequence selected from the group consisting of: SEQ ID NO:7, SEQ ID NO:8, SEQ ID NO:9, and SEQ ID NO:10.

The heavy chain variable ($V_H$) domain may comprise any one of the listed variable heavy chain CDR1 sequences (HCDR1) in combination with any one of the variable heavy chain CDR2 sequences (HCDR2) and any one of the variable heavy chain CDR3 sequences (HCDR3). However, certain embodiments of HCDR1 and HCDR2 and HCDR3 are are provided that derive from a single common $V_H$ domain, examples of which are described herein.

The antibody or antigen binding fragment thereof may additionally comprise a light chain variable ($V_L$) domain, which is paired with the $V_H$ domain to form an antigen binding domain. In some embodiments, light chain variable domains are those comprising a variable light chain CDR1, variable light chain CDR2, and a variable light chain CDR3, wherein said variable light chain CDR1 comprises an amino acid sequence selected from the group consisting of: SEQ ID NO:11, SEQ ID NO:12, SEQ ID NO:13, and SEQ ID NO:14; said variable light chain CDR2 optionally comprises an amino acid sequence selected from the group consisting of: SEQ ID NO:15, SEQ ID NO:16, and SEQ ID NO:17; and said variable light chain CDR3 optionally comprises an amino acid sequence selected from the group consisting of: SEQ ID NO:18, SEQ ID NO:19, and SEQ ID NO:20.

The light chain variable domain may comprise any one of the listed variable light chain CDR1 sequences (LCDR1) in combination with any one of the variable light chain CDR2 sequences (LCDR2) and any one of the variable light chain CDR3 sequences (LCDR3). However, certain embodiments of LCDR1 and LCDR2 and LCDR3 are provided that derive from a single common $V_L$ domain, examples of which are described herein.

Any given CD47 antibody or antigen binding fragment thereof comprising a $V_H$ domain paired with a $V_L$ domain will comprise a combination of 6 CDRs: variable heavy chain CDR1 (HCDR1), variable heavy chain CDR2 (HCDR2), variable heavy chain CDR3 (HCDR3), variable light chain CDR1 (LCDR1), variable light chain CDR2 (LCDR2), and variable light chain CDR3 (LCDR3). Although all combinations of 6 CDRs selected from the CDR sequence groups listed above are permissible, and within the scope of the disclosure, certain combinations of 6 CDRs are provided.

In some embodiments, combinations of 6 CDRs include, but are not limited to, the combinations of variable heavy chain CDR1 (HCDR1), variable heavy chain CDR2 (HCDR2), variable heavy chain CDR3 (HCDR3), variable light chain CDR1 (LCDR1), variable light chain CDR2 (LCDR2), and variable light chain CDR3 (LCDR3) selected from the group consisting of:

(i) HCDR1 comprising SEQ ID NO:1, HCDR2 comprising SEQ ID NO:4, HCDR3 comprising SEQ ID NO:7, LCDR1 comprising SEQ ID NO:11, LCDR2 comprising SEQ ID NO:15, LCDR3 comprising SEQ ID NO:18;

(ii) HCDR1 comprising SEQ ID NO:1, HCDR2 comprising SEQ ID NO:4, HCDR3 comprising SEQ ID NO:8, LCDR1 comprising SEQ ID NO:11, LCDR2 comprising SEQ ID NO:15, LCDR3 comprising SEQ ID NO:18;

(iii) HCDR1 comprising SEQ ID NO:2, HCDR2 comprising SEQ ID NO:5, HCDR3 comprising SEQ ID NO:9, LCDR1 comprising SEQ ID NO:12, LCDR2 comprising SEQ ID NO:16, LCDR3 comprising SEQ ID NO:19;

(iv) HCDR1 comprising SEQ ID NO:2, HCDR2 comprising SEQ ID NO:5, HCDR3 comprising SEQ ID NO:9, LCDR1 comprising SEQ ID NO:13, LCDR2 comprising SEQ ID NO:16, LCDR3 comprising SEQ ID NO:19; and (v) HCDR1 comprising SEQ ID NO:3, HCDR2 comprising SEQ ID NO:6, HCDR3 comprising SEQ ID NO:10, LCDR1 comprising SEQ ID NO:14, LCDR2 comprising SEQ ID NO:17, LCDR3 comprising SEQ ID NO:20.

In some embodiments, anti-CD47 mAbs include antibodies or antigen binding fragments thereof, comprising a heavy chain variable domain having an amino acid sequence selected from the group consisting of: the amino acid sequences of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, and SEQ ID NO:40, and amino acid sequences exhibiting at least 90%, 95%, 97%, 98%, or 99% sequence identity to one of the recited sequences. Alternatively, or in addition, anti-CD47 mAbs including antibodies or antigen binding fragments thereof, may comprise a light chain variable domain having an amino acid sequence selected from the group consisting of: the amino acid sequences of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, and SEQ ID NO:52, and amino acid sequences exhibiting at least 90%, 95%, 97%, 98%, or 99% sequence identity to one of the recited sequences.

Although all possible pairing of $V_H$ domains and $V_L$ domains selected from the $V_H$ and $V_L$ domain sequence groups listed above are permissible, and within the scope of the disclosure, some embodiments provide certain combinations of $V_H$ and $V_L$ domains. Accordingly, in some embodiments, anti-CD47 mAbs, or antigen binding fragments thereof, are those comprising a combination of a heavy chain variable domain ($V_H$) and a light chain variable domain ($V_L$), wherein the combination is selected from the group consisting of:

(i) a heavy chain variable domain comprising the amino acid sequence of SEQ ID NO:21 and a light chain variable domain comprising the amino acid sequence SEQ ID NO:41;
(ii) a heavy chain variable domain comprising the amino acid sequence of SEQ ID NO:23 and a light chain variable domain comprising the amino acid sequence SEQ ID NO:43;
(iii) a heavy chain variable domain comprising the amino acid sequence of SEQ ID NO:34 and a light chain variable domain comprising the amino acid sequence SEQ ID NO:49;
(iv) a heavy chain variable domain comprising the amino acid sequence of SEQ ID NO:36 and a light chain variable domain comprising the amino acid sequence SEQ ID NO:52;
(v) a heavy chain variable domain comprising the amino acid sequence of SEQ ID NO:38 and a light chain variable domain comprising the amino acid sequence SEQ ID NO:52;
(vi) a heavy chain variable domain comprising the amino acid sequence of SEQ ID NO:39 and a light chain variable domain comprising the amino acid sequence SEQ ID NO:52;
(vii) a heavy chain variable domain comprising the amino acid sequence of SEQ ID NO:24 and a light chain variable domain comprising the amino acid sequence SEQ ID NO:43;
(viii) a heavy chain variable domain comprising the amino acid sequence of SEQ ID NO:37 and a light chain variable domain comprising the amino acid sequence SEQ ID NO:52;
(ix) a heavy chain variable domain comprising the amino acid sequence of SEQ ID NO:33 and a light chain variable domain comprising the amino acid sequence SEQ ID NO:48;
(x) a heavy chain variable domain comprising the amino acid sequence of SEQ ID NO:26 and a light chain variable domain comprising the amino acid sequence SEQ ID NO:44;
(xi) a heavy chain variable domain comprising the amino acid sequence of SEQ ID NO:27 and a light chain variable domain comprising the amino acid sequence SEQ ID NO:44; and
(xii) a heavy chain variable domain comprising the amino acid sequence of SEQ ID NO:38 and a light chain variable domain comprising the amino acid sequence SEQ ID NO:51;
(xiii) a heavy chain variable domain comprising the amino acid sequence of SEQ ID NO:39 and a light chain variable domain comprising the amino acid sequence SEQ ID NO:51;
(xiv) a heavy chain variable domain comprising the amino acid sequence of SEQ ID NO:40 and a light chain variable domain comprising the amino acid sequence SEQ ID NO:52;
(xv) a heavy chain variable domain comprising the amino acid sequence of SEQ ID NO:36 and a light chain variable domain comprising the amino acid sequence SEQ ID NO:51;
(xvi) a heavy chain variable domain comprising the amino acid sequence of SEQ ID NO:29 and a light chain variable domain comprising the amino acid sequence SEQ ID NO:47;
(xvii) a heavy chain variable domain comprising the amino acid sequence of SEQ ID NO:30 and a light chain variable domain comprising the amino acid sequence SEQ ID NO:47;
(xviii) a heavy chain variable domain comprising the amino acid sequence of SEQ ID NO:31 and a light chain variable domain comprising the amino acid sequence SEQ ID NO:47;
(xix) a heavy chain variable domain comprising the amino acid sequence of SEQ ID NO:32 and a light chain variable domain comprising the amino acid sequence SEQ ID NO:47;
(xx) a heavy chain variable domain comprising the amino acid sequence of SEQ ID NO:33 and a light chain variable domain comprising the amino acid sequence SEQ ID NO:47;
(xxi) a heavy chain variable domain comprising the amino acid sequence of SEQ ID NO:29 and a light chain variable domain comprising the amino acid sequence SEQ ID NO:48;
(xxii) a heavy chain variable domain comprising the amino acid sequence of SEQ ID NO:30 and a light chain variable domain comprising the amino acid sequence SEQ ID NO:48;
(xxiii) a heavy chain variable domain comprising the amino acid sequence of SEQ ID NO:31 and a light chain variable domain comprising the amino acid sequence SEQ ID NO:48;
(xxiv) a heavy chain variable domain comprising the amino acid sequence of SEQ ID NO:32 and a light chain variable domain comprising the amino acid sequence SEQ ID NO:48;
(xxv) a heavy chain variable domain comprising the amino acid sequence of SEQ ID NO:26 and a light chain variable domain comprising the amino acid sequence SEQ ID NO:43;
(xxvi) a heavy chain variable domain comprising the amino acid sequence of SEQ ID NO:27 and a light chain variable domain comprising the amino acid sequence SEQ ID NO:43;
(xxvii) a heavy chain variable domain comprising the amino acid sequence of SEQ ID NO:28 and a light chain variable domain comprising the amino acid sequence SEQ ID NO:46;
(xxviii) a heavy chain variable domain comprising the amino acid sequence of SEQ ID NO:35 and a light chain variable domain comprising the amino acid sequence SEQ ID NO:50;
(xxix) a heavy chain variable domain comprising the amino acid sequence of SEQ ID NO:29 and a light chain variable domain comprising the amino acid sequence SEQ ID NO:48;
(xxx) a heavy chain variable domain comprising the amino acid sequence of SEQ ID NO:30 and a light chain variable domain comprising the amino acid sequence SEQ ID NO:48;
(xxxi) a heavy chain variable domain comprising the amino acid sequence of SEQ ID NO:31 and a light chain variable domain comprising the amino acid sequence SEQ ID NO:48;
(xxxii) a heavy chain variable domain comprising the amino acid sequence of SEQ ID NO:32 and a light chain variable domain comprising the amino acid sequence SEQ ID NO:48;
(xxxiii) a heavy chain variable domain comprising the amino acid sequence of SEQ ID NO:37 and a light chain variable domain comprising the amino acid sequence SEQ ID NO:51; and (xxxiv) a heavy chain variable domain comprising the amino acid sequence of SEQ ID NO:40 and a light chain variable domain comprising the amino acid sequence SEQ ID NO:51.

In some embodiments, anti-CD47 antibodies or antigen binding fragments thereof may also comprise a combination of a heavy chain variable domain and a light chain variable domain wherein the heavy chain variable domain comprises a $V_H$ sequence with at least 85% sequence identity, or at least 90% sequence identity, or at least 95% sequence identity, or at least 97%, 98% or 99% sequence identity, to the heavy chain amino acid sequences shown above in (i) to (xxxiv) and/or the light chain variable domain comprises a $V_L$ sequence with at least 85% sequence identity, or at least 90% sequence identity, or at least 95% sequence identity, or at least 97%, 98% or 99% sequence identity, to the light chain amino acid sequences shown above in (i) to (xxxiv). The specific $V_H$ and $V_L$ pairings or combinations in parts (i) through (xxxiv) may be preserved for anti-CD47 antibodies having $V_H$ and $V_L$ domain sequences with a particular percentage sequence identity to these reference sequences.

For all embodiments wherein the heavy chain and/or light chain variable domains of the antibodies or antigen binding fragments are defined by a particular percentage sequence identity to a reference sequence, the $V_H$ and/or $V_L$ domains may retain identical CDR sequences to those present in the reference sequence such that the variation is present only within the framework regions.

In another embodiment, CD47 antibodies, or antigen binding fragments thereof, may comprise a combination of a heavy chain (HC) and a light chain (LC), wherein the combination is selected from the group consisting of:

(i) a heavy chain comprising the amino acid sequence of SEQ ID NO:78 and a light chain comprising the amino acid sequence SEQ ID NO:67;

(ii) a heavy chain comprising the amino acid sequence of SEQ ID NO:79 and a light chain comprising the amino acid sequence SEQ ID NO:69;

(iii) a heavy chain comprising the amino acid sequence of SEQ ID NO:80 and a light chain comprising the amino acid sequence SEQ ID NO:70;

(iv) a heavy chain comprising the amino acid sequence of SEQ ID NO:81 and a light chain comprising the amino acid sequence SEQ ID NO:71;

(v) a heavy chain comprising the amino acid sequence of SEQ ID NO:82 and a light chain comprising the amino acid sequence SEQ ID NO:71;

(vi) a heavy chain comprising the amino acid sequence of SEQ ID NO:83 and a light chain comprising the amino acid sequence SEQ ID NO:71;

(vii) a heavy chain comprising the amino acid sequence of SEQ ID NO:84 and a light chain comprising the amino acid sequence SEQ ID NO:69;

(viii) a heavy chain comprising the amino acid sequence of SEQ ID NO:85 and a light chain comprising the amino acid sequence SEQ ID NO:71;

(ix) a heavy chain comprising the amino acid sequence of SEQ ID NO:86 and a light chain comprising the amino acid sequence SEQ ID NO:72;

(x) a heavy chain comprising the amino acid sequence of SEQ ID NO:87 and a light chain comprising the amino acid sequence SEQ ID NO:73;

(xi) a heavy chain comprising the amino acid sequence of SEQ ID NO:88 and a light chain comprising the amino acid sequence SEQ ID NO:73;

(xii) a heavy chain comprising the amino acid sequence of SEQ ID NO:82 and a light chain comprising the amino acid sequence SEQ ID NO:74;

(xiii) a heavy chain comprising the amino acid sequence of SEQ ID NO:83 and a light chain comprising the amino acid sequence SEQ ID NO:74;

(xiv) a heavy chain comprising the amino acid sequence of SEQ ID NO:89 and a light chain comprising the amino acid sequence SEQ ID NO:71;

(xv) a heavy chain comprising the amino acid sequence of SEQ ID NO:81 and a light chain comprising the amino acid sequence SEQ ID NO:74;

(xvi) a heavy chain comprising the amino acid sequence of SEQ ID NO:90 and a light chain comprising the amino acid sequence SEQ ID NO:75;

(xvii) a heavy chain comprising the amino acid sequence of SEQ ID NO:91 and a light chain comprising the amino acid sequence SEQ ID NO:75;

(xviii) a heavy chain comprising the amino acid sequence of SEQ ID NO:92 and a light chain comprising the amino acid sequence SEQ ID NO:75;

(xix) a heavy chain comprising the amino acid sequence of SEQ ID NO:93 and a light chain comprising the amino acid sequence SEQ ID NO:75;

(xx) a heavy chain comprising the amino acid sequence of SEQ ID NO:86 and a light chain comprising the amino acid sequence SEQ ID NO:75;

(xxi) a heavy chain comprising the amino acid sequence of SEQ ID NO:94 and a light chain comprising the amino acid sequence SEQ ID NO:72;

(xxii) a heavy chain comprising the amino acid sequence of SEQ ID NO:91 and a light chain comprising the amino acid sequence SEQ ID NO:72;

(xxiii) a heavy chain comprising the amino acid sequence of SEQ ID NO:92 and a light chain comprising the amino acid sequence SEQ ID NO:72;

(xxiv) a heavy chain comprising the amino acid sequence of SEQ ID NO:93 and a light chain comprising the amino acid sequence SEQ ID NO:72;

(xxv) a heavy chain comprising the amino acid sequence of SEQ ID NO:87 and a light chain comprising the amino acid sequence SEQ ID NO:69;

(xxvi) a heavy chain comprising the amino acid sequence of SEQ ID NO:88 and a light chain comprising the amino acid sequence SEQ ID NO:69;

(xxvii) a heavy chain comprising the amino acid sequence of SEQ ID NO:95 and a light chain comprising the amino acid sequence SEQ ID NO:76;

(xxviii) a heavy chain comprising the amino acid sequence of SEQ ID NO:96 and a light chain comprising the amino acid sequence SEQ ID NO:77;

(xxix) a heavy chain comprising the amino acid sequence of SEQ ID NO:97 and a light chain comprising the amino acid sequence SEQ ID NO:72;

(xxx) a heavy chain comprising the amino acid sequence of SEQ ID NO:98 and a light chain comprising the amino acid sequence SEQ ID NO:72;

(xxxi) a heavy chain comprising the amino acid sequence of SEQ ID NO:99 and a light chain comprising the amino acid sequence SEQ ID NO:72;

(xxxii) a heavy chain comprising the amino acid sequence of SEQ ID NO:100 and a light chain comprising the amino acid sequence SEQ ID NO:72;

(xxxiii) a heavy chain comprising the amino acid sequence of SEQ ID NO:85 and a light chain comprising the amino acid sequence SEQ ID NO:74;

(xxxiv) a heavy chain comprising the amino acid sequence of SEQ ID NO:89 and a light chain comprising the amino acid sequence SEQ ID NO:74;
wherein the VH amino acid sequence is at least 90%, 95%, 97%, 98% or 99% identical thereto and the a VL amino acid sequence is at least 90%, 95%, 97%, 98% or 99% identical thereto.

In some embodiments, anti-CD47 antibodies as described herein may also be characterized by combinations of properties which are not exhibited by prior art anti-CD47 antibodies proposed for human therapeutic use. Accordingly, in some embodiments, anti-CD47 antibodies described herein are characterized by:
 a. binds to human CD47;
 b. blocks SIRPα binding to human CD47;
 c. increases phagocytosis of human tumor cells; and
 d. induces death of susceptible human tumor cells.

In another embodiment described herein, the anti-CD47 antibodies are characterized by:
 a. binds to human CD47;
 b. blocks SIRPα binding to human CD47;
 c. increases phagocytosis of human tumor cells;
 d. induces death of susceptible human tumor cells; and
 e. causes no detectable agglutination of human red blood cells (hRBCs).

In yet another embodiment described herein, the anti-CD47 antibodies are characterized by:
 a. binds to human CD47;
 b. blocks SIRPα binding to human CD47;
 c. increases phagocytosis of human tumor cells;
 d. induces death of susceptible human tumor cells; and
 e. causes reduced agglutination of human red blood cells (hRBCs).

In another embodiment described herein, the anti-CD47 antibodies are characterized by:
 a. binds to human CD47;
 b. blocks SIRPα binding to human CD47;
 c. increases phagocytosis of human tumor cells;
 d. induces death of susceptible human tumor cells; and
 e. has reduced hRBC binding.

In another embodiment described herein, the anti-CD47 antibodies are characterized by:
 a. binds to human CD47,
 b. blocks SIRPα binding to human CD47,
 c. increases phagocytosis of human tumor cells,
 d. causes no detectable agglutination of human red blood cells (hRBCs); and
 e. has minimal binding to hRBCs.

In another embodiment described herein, the anti-CD47 antibodies are characterized by:
 a. binds to human CD47;
 b. blocks SIRPα binding to human CD47;
 c. increases phagocytosis of human tumor cells;
 d. causes no detectable agglutination of human red blood cells (hRBCs); and
 e. has reduced hRBC binding.

Additional embodiments of the anti-CD47 antibodies described herein, are also characterized by combinations of properties which are not exhibited by prior art anti-CD47 antibodies proposed for human therapeutic use. Accordingly, anti-CD47 antibodies as described herein may be further characterized by one or more among the following characteristics:
 a. causes an increase in cell surface calreticulin expression on human tumor cells;
 b. causes an increase in adenosine triphosphate (ATP) release by human tumor cells;
 c. causes an increase in high mobility group box 1 (HMGB1) release by human tumor cells;
 d. causes an increase in annexin A1 release by human tumor cells;
 e. causes an increase in Type I Interferon release by human tumor cells;
 f. causes an increase in C-X-C Motif Chemokine Ligand 10 (CXCL10) release by human tumor cells;
 g. causes an increase in cell surface protein disulfide-isomerase A3 (PDIA3) expression on human tumor cells;
 h. causes an increase in cell surface heat shock protein 70 (HSP70) expression on human tumor cells; and
 i. causes an increase in cell surface heat shock protein 90 (HSP90) expression on human tumor cells.

In another embodiment described herein, the monoclonal antibody, or antigen binding fragment thereof binds to human, non-human primate, mouse, rabbit, and rat CD47.

In yet another embodiment described herein, the monoclonal antibody, or antigen binding fragment thereof specifically also binds to non-human primate CD47, wherein non-human primate may include, but is not limited to, cynomolgus monkey, green monkey, rhesus monkey, and squirrel monkey.

In yet another embodiment described herein, the monoclonal antibody, or antigen binding fragment thereof, has reduced binding to normal human cells, which includes, but is not limited to, endothelial cells, skeletal muscle cells, epithelial cells, and peripheral blood mononuclear cells (e.g., human aortic endothelial cells, human skeletal muscle cells, human microvascular endothelial cells, human renal tubular epithelial cells, human peripheral blood CD3+ cells, and human peripheral blood mononuclear cells).

In yet another embodiment described herein, the monoclonal antibody, or antigen binding fragment thereof, has a greater have a greater affinity for human CD47 at an acidic pH compared to physiological pH.

In some embodiments, the monoclonal antibody, or antigen binding fragment thereof, may additionally possess one or more of the following characteristics: 1) exhibit cross-reactivity with one or more species homologs of CD47; 2) block the interaction between CD47 and its ligand SIRPα; 3) increase phagocytosis of human tumor cells; 4) induce death of susceptible human tumor cells; 5) do not induce cell death of human tumor cells; 6) do not have reduced or minimal binding to human red blood cells (hRBCs); 7) have reduced binding to hRBCs; 8) have minimal binding to hRBCs; 9) cause reduced agglutination of hRBCs; 10) cause no detectable agglutination of hRBCs; 11) reverse TSP1 inhibition of the nitric oxide (NO) pathway; 12) do not reverse TSP1 inhibition of the NO pathway; 13) cause loss of mitochondrial membrane potential; 14) do not cause cause loss of mitochondrial membrane potential; 15) cause an increase in cell surface calreticulin expression on human tumor cells; 16) do not cause an increase in cell surface calreticulin expression on human tumor cells; 17) cause an increase in adenosine triphosphate (ATP) release by human tumor cells; 18) do not cause an increase in adenosine triphosphate (ATP) release by human tumor cells; 19) cause an increase in high mobility group box 1 (HMGB1) release by human tumor cells; 20) do not cause an increase in high mobility group box 1 (HMGB1) release by human tumor cells; 21) cause an increase in type I interferon release by human tumor cells; 22) do not cause an increase in type I interferon release by human tumor cells; 23) cause an increase in C-X-C Motif Chemokine Ligand 10 (CXCL10) release by human tumor cells; 24) do not cause an increase in C-X-C Motif Chemokine Ligand 10 (CXCL10) release by human tumor cells; 25) cause an increase in cell surface protein disulfide-isomerase A3 (PDIA3) expression on human tumor cells; 26) do not cause an increase in cell surface protein disulfide-isomerase A3 (PDIA3) expression on human tumor cells; 27) cause an increase in cell surface heat shock protein 70 (HSP70) expression on human tumor cells; 28) do not cause an increase in cell surface heat shock protein 70 (HSP70) expression on human tumor cells; 29) cause an increase in cell surface heat shock protein 90 (HSP90) expression on human tumor cells; 30) do not cause an increase in cell surface heat shock protein 90 (HSP90) expression on human tumor cells; 31) have reduced binding to normal human cells, which includes, but is not limited to, endothelial cells, skeletal muscle cells, epithelial cells, and peripheral blood mononuclear cells (e.g., human aortic endothelial cells, human skeletal muscle cells, human microvascular endothelial cells, human renal tubular epithelial cells, human peripherial blood CD3+ cells, and human peripherial blood mononuclear cells); 32) do not have reduced binding to normal human cells, which includes, but is not limited to, endothelial cells, skeletal muscle cells, epithelial cells, and peripheral blood mononuclear cells (e.g., human aortic endothelial cells, human skeletal muscle cells, human microvascular endothelial cells, human renal tubular epithelial cells, human peripherial blood CD3+ cells, and human peripherial blood mononuclear cells); 33) have a greater affinity for human CD47 at an acidic pH compared to physiological pH; 34) do not have a greater affinity for human CD47 at an acidic pH compared to physiological pH; and 35) cause an increase in annexin A1 release by human tumor cells.

Various forms of the anti-CD47 mAbs disclosed are contemplated herein. For example, the anti-CD47 mAbs can be full-length humanized antibodies with human frameworks and constant regions of the isotypes, IgA, IgD, IgE, IgG, and IgM, more particularly, IgG1, IgG2, IgG3, IgG4, and in some cases with various mutations to alter Fc receptor function or prevent Fab arm exchange or an antibody fragment, e.g., a F(ab')2 fragment, a F(ab) fragment, a single chain Fv fragment (scFv), etc., as disclosed herein.

In some embodiments, pharmaceutical or veterinary compositions are provided that comprise one or more of the anti-CD47 mAbs or fragments disclosed herein, optionally chimeric or humanized forms, and a pharmaceutically acceptable carrier, diluent, or excipient.

Prior to the present disclosure, there was a need to identify anti-CD47 mAbs that possess the functional profiles as described herein. The anti-CD47 mAbs of the present disclosure exhibit distinct combinations of properties, particularly combinations of properties that render the mAbs particularly advantageous or suitable for use in human therapy, particularly in the prevention and/or treatment of solid and hematological cancers, ischemia-reperfusion injury, autoimmune and/or inflammatory diseases.

In some embodiments, the disclosure provides a monoclonal antibody, or an antigen binding fragment thereof, which: binds to human CD47; blocks SIRPα binding to human CD47; increases phagocytosis of human tumor cells; and induces death of human tumor cells; wherein said monoclonal antibody, or an antigen binding fragment thereof, exhibits pH-dependent binding to CD47 present on a cell. In other embodiments, the disclosure provides a monoclonal antibody, or an antigen binding fragment thereof, which: binds to human CD47; blocks SIRPα binding to human CD47; increases phagocytosis of human tumor cells; wherein said monoclonal antibody, or an antigen binding fragment thereof, exhibits pH-dependent binding to CD47 present on a cell. In other embodiments, the disclosure provides a monoclonal antibody, or an antigen binding fragment thereof, which: binds to human CD47; blocks SIRPα binding to human CD47; increases phagocytosis of human tumor cells; and induces death of human tumor cells; wherein said monoclonal antibody, or an antigen binding fragment thereof, exhibits reduced binding to normal cells. In one embodiment, these cells may be an endothelial cell, a skeletal muscle cell, an epithelial cell, a PBMC or a RBC (e.g., human aortic endothelial cells, human skeletal muscle cells, human microvascular endothelial cells, human renal tubular epithelial cells, human peripherial blood CD3+ cells, human peripherial blood mononuclear cells or human RBC). In other embodiments, the disclosure provides a monoclonal antibody, or an antigen binding fragment thereof, which: binds to human CD47; blocks SIRPα binding to human CD47; increases phagocytosis of human tumor cells; wherein said monoclonal antibody, or an antigen binding fragment thereof, exhibits reduced binding to normal cells. In one embodiment, these cells may be an endothelial cell, a skeletal muscle cell, an epithelial cell, a PBMC or a RBC (e.g., human aortic endothelial cells, human skeletal muscle cells, human microvascular endothelial cells, human renal tubular epithelial cells, human peripherial blood CD3+ cells, human peripherial blood mononuclear cells or human RBC). In another embodiment, the monoclonal antibody, or an antigen binding fragment thereof, exhibits both pH dependent binding and reduced binding to a cell.

Further scope of the applicability of the present disclosure will become apparent from the detailed description provided below. However, it should be understood that the detailed description and specific examples, while indicating some embodiments of the disclosure, are given by way of illustration only since various changes and modifications within the spirit and scope of the disclosure will become apparent to those skilled in the art from this detailed description.

BRIEF DESCRIPTION OF THE DRAWINGS

The above and other aspects, features, and advantages of the present disclosure will be better understood from the following detailed descriptions taken in conjunction with the accompanying drawing(s), all of which are given by way of illustration only, and are not limitative of the present disclosure.

FIG. 4A. Binding of VLX8 Humanized mAbs to Human RBCs. Binding of VLX8 IgG4PE xi or humanized mAbs (VLX8hum_01 IgG4PE, VLX8hum_03 IgG4PE, VLX8hum_07 IgG4PE, and VLX8hum_10 IgG4PE) to human CD47 was determined using freshly isolated human RBCs. RBCs were incubated for 1 hr at 37° C. with various concentrations of VLX8 mAbs, washed and incubated for 1 hr with FITC-labelled donkey anti-human antibody. Cells were washed and antibody binding measured using flow cytometry.

FIG. 4B. Binding of VLX8 Humanized mAbs to Human RBCs. Binding of VLX8 IgG4PE xi or humanized mAbs (VLX8hum_06 IgG2, VLX8hum_07 IgG2, VLX8hum_08 IgG2 and VLX8hum_09 IgG2) to human CD47 was determined using freshly isolated human RBCs. RBCs were incubated for 1 hr at 37° C. with various concentrations of VLX8 mAbs, washed and incubated for 1 hr with FITC-labelled donkey anti-human antibody. Cells were washed and antibody binding measured using flow cytometry.

FIG. 8E. Binding of VLX Humanized mAbs to Human Peripheral Blood $CD3^+$ Cells. Binding of VLX humanized mAbs (VLX4hum_07 IgG4PE, VLX8hum_10 IgG4PE, VLX8hum_11 IgG4PE, VLX4hum_01 IgG4PE, VLX9hum_06 IgG2, VLX9hum_08 IgG2, VLX9hum_09 IgG2, VLX9hum_03 IgG2 and VLX9hum_04 IgG2) to $CD3^+$ cells was determined by flow cytometry. PBMC were plated into 96 well plates. Various concentrations of mAbs were added to the cells for 1 hr. Cells were washed and then incubated with FITC-labelled secondary antibody and (APC)-labelled anti-CD3 antibody for 1 hr followed by measurement of FITC-labelled APC-positive cells by flow cytometry.

FIG. 8F. Binding of VLX Humanized mAbs to Human Peripheral Blood Mononuclear Cells (PBMC). Binding of VLX humanized mAbs (VLX4hum_07 IgG4PE, VLX8hum_10 IgG4PE, VLX8hum_11 IgG4PE, VLX4hum_01 IgG4PE, VLX9hum_06 IgG2, VLX9hum_08 IgG2, VLX9hum_09 IgG2, VLX9hum_03 IgG2 and VLX9hum_04 IgG2) to PBMC was determined by flow cytometry. PBMCs were plated into 96 well plates. Various concentrations of mAbs were added to the cells for 1 hr. Cells were washed and then incubated with FITC-labelled secondary antibody for 1 hr followed by measurement of FITC label by flow cytometry.

FIG. 9A. pH Dependent and pH Independent Binding of Humanized mAb to His-CD47. Binding of VLX9hum_09 IgG2 to human CD47 was determined using a solid-phase CD47 ELISA assay. His-CD47 was adsorbed to microtiter wells, washed and various concentrations of humanized mAbs were added to the wells for 1 hr at pH 6 or 8. The wells were washed and then incubated with HRP-labelled secondary antibody for 1 hour followed by addition of peroxidase substrate.

FIG. 9C. pH Dependent and pH Independent Binding of Humanized mAb to His-CD47. Binding of VLX4hum_07 IgG4PE to human CD47 was determined using a solid-phase CD47 ELISA assay. His-CD47 was adsorbed to microtiter wells, washed and various concentrations of humanized mAbs were added to the wells for 1 hr at pH 6 or 8. The wells were washed and then incubated with HRP-labelled secondary antibody for 1 hour followed by addition of peroxidase substrate.

FIG. 10. VLX4, VLX8, and VLX9 Humanized mAbs Block SIRPα binding to CD47 on Human Jurkat Cells. $1.5 \times 10^6$ Jurkat cells were incubated with 5 μg/ml of VLX4, VLX8 and VLX9 CD47 humanized mAbs (VLX4hum_01 IgG4PE, VLX4hum_07 IgG4PE, VLX8hum_10 IgG4PE, VLX4hum_11 IgG4PE, VLX9hum_03 IgG2, VLX9hum_06 IgG2, and VLX9hum_08 IgG2) or a control antibody or no antibody in RPMI containing 10% FBS for 30 min at 37° C. An equal volume of media containing fluorescently labelled SIRPα-Fc fusion protein was added and incubated for an additional 30 min at 37° C. Cells were washed and binding was assessed using flow cytometry.

FIG. 13A. VLX8 CD47 Chimeric mAbs Increase Phagocytosis of Human Jurkat Cells by Human Macrophages. Human macrophages were plated at a concentration of $1\times10^4$ cells per well in a 96 well plate and allowed to adhere for 24 hrs. $5\times10^4$ CFSE-labelled human Jurkat cells and 1 μg/ml of the VLX8 chimeric mAbs (VLX8 IgG1 N297Q xi and VLX8 Ig4PE xi) were added to the macrophage cultures and incubated at 37° C. for 2 hrs. Non-phagocytosed Jurkat cells were removed and macrophage cultures were washed extensively. Macrophages were trypsinized and stained for CD14. Flow cytometry was used to determine the percentage of $CD14^+/CFSE^+$ cells in the total $CD14^+$ population.

FIG. 13B. VLX8 Humanized mAbs Increase Phagocytosis of Human Jurkat Cells by Human Macrophages. Human macrophages were plated at a concentration of $1\times10^4$ cells per well in a 96 well plate and allowed to adhere for 24 hrs. $5\times10^4$ CFSE-labelled human Jurkat cells and 1 μg/ml of antibody (VLX8 IgG4PE xi, VLX8hum_01 IgG4PE, VLX8hum_03 IgG4PE, VLX8hum_07 IgG4PE, VLX8hum_08 IgG4PE and VLX8hum_09 IgG4PE) were added to the macrophage cultures and incubated at 37° C. for 2 hrs. Non-phagocytosed Jurkat cells were removed and macrophage cultures were washed extensively. Macrophages were trypsinized and stained for CD14. Flow cytometry was used to determine the percentage of $CD14^+/CFSE^+$ cells in the total $CD14^+$ population.

FIG. 16A. Induction of Cell Death in Human Jurkat Cells by Soluble VLX8 CD47 Chimeric mAbs. Jurkat cells ($1\times10^4$) were incubated with 1 μg/ml VLX8 chimeric mAbs (VLX8 IgG1 N297Q xi and VLX8 IgG4PE xi) in RPMI media for 24 hrs at 37° C. Cells were then stained with annexin V and analyzed by flow cytometry. The data are presented as % of cells that are annexin V positive (annexin $V^+$).

FIG. 16B. Induction of Cell Death in Human Jurkat Cells by Soluble VLX8 Chimeric mAbs. Jurkat cells ($1\times10^4$) were incubated with 1 μg/ml VLX8 chimeric mAbs (VLX8 IgG1 N297Q xi and VLX8 IgG4PE xi) in RPMI media for 24 hrs at 37° C. Cells were then stained with annexin V and 7-AAD and analyzed by flow cytometry. The data are presented as the % of cells that are annexin V positive/7-AAD negative (annexin $V^+/7\text{-}AAD^-$).

FIG. 16C. Induction of Cell Death in Human Jurkat Cells by Soluble VLX8 Chimeric mAbs. Jurkat cells ($1\times10^4$) were incubated with 1 μg/ml VLX8 chimeric mAbs (VLX8 IgG1 N297Q xi and VLX8 IgG4PE (xi)) in RPMI media for 24 hrs at 37° C. Cells were then stained with annexin V and 7-AAD and analyzed by flow cytometry. The data are presented as the % of cells that are annexin V positive/7-AAD positive (annexin V+/7-AAD+).

FIG. 16D. Induction of Cell Death in Human Jurkat Cells by Soluble VLX8 Humanized mAbs. Jurkat cells ($1\times10^4$) were incubated with 1 μg/ml VLX8 humanized mAbs (VLX8hum_02 IgG4PE, VLX8hum_04 IgG4PE, VLX8hum_07 IgG4PE and VLX8hum_08 IgG4PE) and chimeric mAb VLX8 IgG4PE in RPMI media for 24 hrs at 37° C. Cells were then stained with annexin V and analyzed by flow cytometry. The data are presented as the % of cells that are annexin V positive (annexin V+).

FIG. 16E. Induction of Cell Death in Human Jurkat Cells by Soluble VLX8 Humanized mAbs. Jurkat cells ($1\times10^4$) were incubated with 1 μg/ml VLX8 humanized mAbs (VLX8hum_02 IgG4PE, VLX8hum_04 IgG4PE, VLX8hum_07 IgG4PE and VLX8hum_08 IgG4PE) and chimeric mAb VLX8 IgG4PE in RPMI media for 24 hrs at 37° C. Cells were then stained with annexin V and 7-AAD and analyzed by flow cytometry. The data are shown as the % of cells that are annexin V positive/7-AAD negative (annexin V+/7-AAD−).

FIG. 16F. Induction of Cell Death in Human Jurkat Cells by Soluble VLX8 Humanized mAbs. Jurkat cells ($1\times10^4$) were incubated with 1 μg/ml VLX8 humanized mAbs (VLX8hum_02 IgG4PE, VLX8hum_04 IgG4PE, VLX8hum_07 IgG4PE and VLX8hum_08 IgG4PE) and chimeric mAb VLX8 IgG4PE in RPMI media for 24 hrs at 37° C. Cells were then stained with annexin V and 7-AAD and analyzed by flow cytometry. The data are shown as the % of cells that are annexin V positive/7-AAD positive (annexin V+/7-AAD+).

FIG. 17A. Induction of Cell Death of Human Jurkat Cells by Soluble VLX9 Chimeric mAbs. $1\times10^4$ Jurkat cells were incubated with 1 μg/ml of the VLX9 CD47 chimeric mAbs (VLX9 IgG1 N297Q xi, VLX9 IgG2 xi and VLX9 IgG4PE xi) in RPMI media for 24 hours 37° C. Cells were then stained with annexin V and the signal analyzed by flow cytometry. The data are shown as % of cells that are annexin V positive (annexin V+).

FIG. 17B. Induction of Cell Death of Human Jurkat Cells by Soluble VLX9 Chimeric mAbs. $1\times10^4$ Jurkat cells were incubated with 1 μg/ml of the VLX9 CD47 chimeric mAbs (VLX9 IgG1 N297Q xi, VLX9 IgG2 xi and VLX9 IgG4PE xi) in RPMI media for 24 hours 37° C. Cells were then stained with annexin V and 7-AAD and analyzed by flow cytometry. The data are shown as % of cells that are annexin V positive/7-AAD negative (annexin V+/7-AAD−).

FIG. 17C. Induction of Cell Death of Human Jurkat Cells by Soluble VLX9 Chimeric mAbs. $1\times10^4$ Jurkat cells were incubated with 1 μg/ml of the VLX9 CD47 chimeric mAbs (VLX9 IgG1 N297Q xi, VLX9 IgG2 xi and VLX9 IgG4PE xi) in RPMI media for 24 hours 37° C. Cells were then stained with annexin V and 7-AAD and analyzed by flow cytometry. The data are shown as % of cells that are annexin V positive/7-AAD positive (annexin V+/7-AAD+).

FIG. 17D. Induction of Cell Death in Human Jurkat Cells by Soluble VLX9 Humanized mAbs. Jurkat cells ($1\times10^4$) were incubated with 1 μg/ml VLX9 humanized mAbs (VLX9hum_01 to 10 IgG2) and chimeric mAb VLX9 IgG2 xi in RPMI media for 24 hours at 37° C. Cells were then stained with annexin V and the signal was detected by flow cytometry. VLX9 IgG2 (xi) is a murine/human chimera. The data are shown as % of cells that are annexin V positive (annexin V+).

FIG. 17E. Induction of Cell Death in Human Jurkat Cells by Soluble VLX9 Humanized mAbs. Jurkat cells ($1\times10^4$) were incubated with 1 μg/ml VLX9 humanized mAbs (VLX9hum_01 to 10 IgG2) and chimeric mAb VLX9 IgG2 xi in RPMI media for 24 hours at 37° C. Cells were then stained with annexin V and 7-AAD and analyzed by flow cytometry. VLX9 IgG2 (xi) is a murine/human chimera. The data are shown as % of cells that are annexin V positive/7-AAD negative (annexin V+/7-AAD−).

FIG. 17F. Induction of Cell Death in Human Jurkat Cells by Soluble VLX9 Humanized mAbs. Jurkat cells ($1\times10^4$) were incubated with 1 μg/ml VLX9 humanized mAbs (VLX9hum_01 to 10 IgG2) and chimeric mAb VLX9 IgG2 xi in RPMI media for 24 hours at 37° C. Cells were then stained with annexin V and 7-AAD and analyzed by flow cytometry. VLX9 IgG2 (xi) is a murine/human chimera. The data are shown as the % of cells that are annexin V positive/7-AAD positive (annexin V+/7-AAD+).

FIG. 32. Soluble VLX4, VLX8 and VLX9 Humanized mAbs Increase HMGB1 Release by Human Jurkat Cells. $1 \times 10^4$ Jurkat cells were incubated with 10 µg/ml of VLX4, VLX8 and VLX9 CD47 humanized mAbs (VLX4hum_01 IgG4PE, VLX4hum_07 IgG4PE, VLX8hum_11 IgG4PE, VLX9hum_03 IgG2, VLX9hum_06 IgG2 and VLX9hum_08 IgG2), a negative IgG control antibody or 1 µM of mitoxantrone as a positive control in RPMI media at 37° C. for 24 hours. Cell-free supernatant was collected and analyzed using an HMGB1 immunoassay. The data are expressed as ng/ml of HMGB1 in the supernatant.

DETAILED DESCRIPTION OF THE DISCLOSURE

Definitions

Figure 1A:
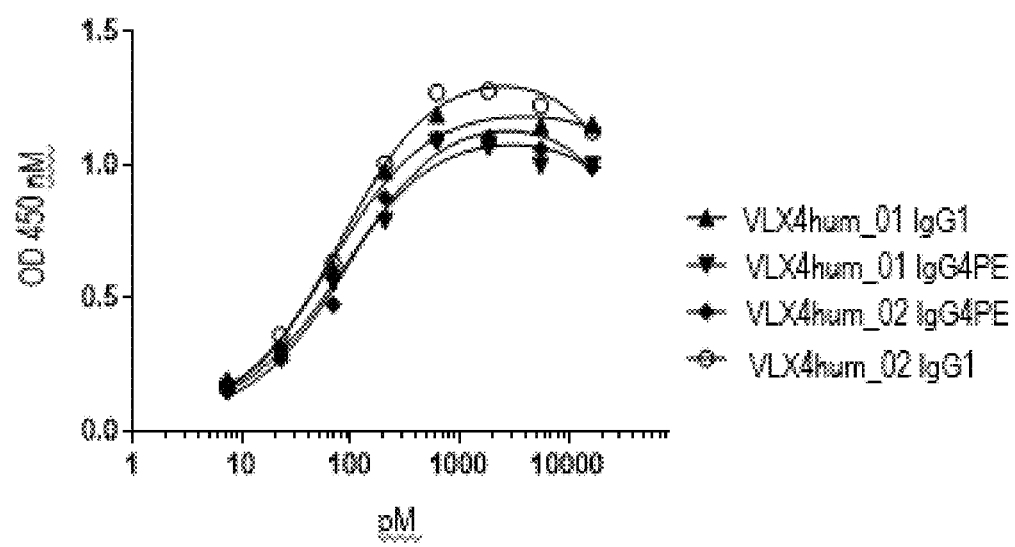
FIG. 1A. Binding of VLX4 Humanized mAbs to Human OV10 Cells Expressing Human CD47. Binding of VLX4 humanized mAbs (VLX4hum_01 IgG1, VLX4hum_02 IgG1, VLX4hum_01 IgG4PE, and VLX4hum_02 IgG4PE) to human CD47 was determined using a OV10 cell line expressing human CD47 (OV10 hCD47) cell-based ELISA. OV10 hCD47 cells were plated into 96 well plates and were confluent at the time of assay. Various concentrations of mAbs were added to the cells for 1 hr. Cells were washed and then incubated with HRP-labelled secondary antibody for 1 hr followed by addition of peroxidase substrate.

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo or polynucleotide chemistry and hybridization described herein are those well-known and commonly used in the art.

As used herein, the term "CD47," "integrin-associated protein (IAP)," "ovarian cancer antigen OA3," "Rh-related antigen," and "MERG" are synonymous and may be used interchangeably.

The term "anti-CD47 antibody" refer to an antibody of the disclosure which is intended for use as a therapeutic or diagnostic agent, and therefore will typically possess the binding affinity required to be useful as a therapeutic and/or diagnostic agent.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" or "directed against" is meant that the antibody reacts with one or more antigenic determinants of the desired antigen and does not react with other polypeptides or binds at a much lower affinity ($Kd > 10^{-6}$). Antibodies include but are not limited to, polyclonal, monoclonal, chimeric, Fab fragments, Fab' fragments, F(ab')2 fragments, single chain Fv fragments, and one-armed antibodies.

As used herein, the term "monoclonal antibody" (mAb) as applied to the present antibody compounds refers to an antibody that is derived from a single copy or clone including, for example, any eukaryotic, prokaryotic, or phage clone, and not the method by which it is produced. mAbs of the present disclosure preferably exist in a homogeneous or substantially homogeneous population. Complete mAbs contain 2 heavy chains and 2 light chains.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g., scFv); and multispecific antibodies formed from antibody fragments.

As disclosed herein, "antibody compounds" refers to mAbs and antigen-binding fragments thereof. Additional antibody compounds exhibiting similar functional properties according to the present disclosure can be generated by conventional methods. For example, mice can be immunized with human CD47 or fragments thereof, the resulting antibodies can be recovered and purified, and determination of whether they possess binding and functional properties similar to or the same as the antibody compounds disclosed herein can be assessed by the methods described in Examples 3-17 below. Antigen-binding fragments can also be prepared by conventional methods. Methods for producing and purifying antibodies and antigen-binding fragments are well known in the art and can be found, for example, in Harlow and Lane (1988) Antibodies, A Laboratory Manual, Cold Spring Harbor Laboratory Press, Cold Spring Harbor, N.Y., chapters 5-8 and 15.

The monoclonal antibodies encompass antibodies in which a portion of the heavy and/or light chain is identical with, or homologous to, corresponding sequences in murine antibodies, in particular the murine CDRs, while the remainder of the chain(s) is (are) identical with, or homologous to, corresponding sequences in human antibodies. Other embodiments of the disclosure include antigen-binding fragments of these monoclonal antibodies that exhibit binding and biological properties similar or identical to the monoclonal antibodies. The antibodies of the present disclosure can comprise kappa or lambda light chain constant regions, and heavy chain IgA, IgD, IgE, IgG, or IgM constant regions, including those of IgG subclasses IgG1, IgG2, IgG3, and IgG4 and in some cases with various mutations to alter Fc receptor function.

The monoclonal antibodies containing the presently disclosed murine CDRs can be prepared by any of the various methods known to those skilled in the art, including recombinant DNA methods.

Reviews of current methods for antibody engineering and improvement can be found, for example, in P. Chames, Ed., (2012) Antibody Engineering: Methods and Protocols, Second Edition (Methods in Molecular Biology, Book 907), Humana Press, ISBN-10: 1617799734; C. R. Wood, Ed., (2011) Antibody Drug Discovery (Molecular Medicine and Medicinal Chemistry, Book 4), Imperial College Press; R. Kontermann and S. Dubel, Eds., (2010) Antibody Engineering Volumes 1 and 2 (Springer Protocols), Second Edition; and W. Strohl and L. Strohl (2012) Therapeutic antibody engineering: Current and future advances driving the strongest growth area in the pharmaceutical industry, Woodhead Publishing.

Methods for producing and purifying antibodies and antigen-binding fragments are well known in the art and can be found, for example, in Harlow and Lane (1988) Antibodies, A Laboratory Manual, Cold Spring Harbor Laboratory Press, Cold Spring Harbor, N.Y., chapters 5-8 and 15.

A full-length antibody as it exists naturally is a "Y" shaped immunoglobulin (Ig) molecule comprising four polypeptide chains: two identical heavy (H) chains and two identical light (L) chains, interconnected by disulfide bonds. The amino terminal portion of each chain, termed the fragment antigen binding region (FAB), includes a variable region of about 100-110 or more amino acids primarily responsible for antigen recognition via the complementarity determining regions (CDRs) contained therein. The carboxy-terminal portion of each chain defines a constant region (the "Fc" region) primarily responsible for effector function.

The CDRs are interspersed with regions that are more conserved, termed frameworks ("FRs"). Amino acid sequences of many FRs are well known in the art. Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions are in accordance with the well-known Kabat numbering convention Kabat et al. (1991) Sequences of Proteins of Immunological Interest, Fifth Edition. NIH Publication No. 91-3242.

As described herein, the "antigen-binding site" can also be defined as the "hypervariable regions," "HVRs," or "HVs," and refer to the structurally hypervariable regions of antibody variable domains as defined by Chothia and Lesk (Chothia and Lesk, *Mol. Biol.* 196:901-917, 1987). There are six HVRs, three in VH (H1, H2, H3) and three in VL (L1, L2, L3). The CDRs used herein are as defined by Kabat except in H-CDR1, which is extended to include H1.

There are five types of mammalian immunoglobulin (Ig) heavy chains, denoted by the Greek letters α (alpha), δ (delta), ε (epsilon), γ (gamma), and μ (mu), which define the class or isotype of an antibody as IgA, IgD, IgE, IgG, or IgM, respectively. IgG antibodies can be further divided into subclasses, for example, IgG1, IgG2, IgG3, and IgG4.

Each heavy chain type is characterized by a particular constant region with a sequence well known in the art. The constant region is identical in all antibodies of the same isotype, but differs in antibodies of different isotypes. Heavy chains γ, α, and δ have a constant region composed of three tandem immunoglobulin (Ig) domains, and a hinge region for added flexibility. Heavy chains μ and ε have a constant region composed of four Ig domains.

The hinge region is a flexible amino acid stretch that links the Fc and Fab portions of an antibody. This regions contains cysteine residues that can form disulfide bonds, connecting two heavy chains together.

The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, light chains are classified as kappa (κ) or lambda (λ), and are characterized by a particular constant region as known in the art. A light chain has two successive domains: one variable domain at the amino-terminal end, and one constant domain at the carboxy-terminal end. Each antibody contains two light chains that are always identical; only one type of light chain, κ or λ, is present per antibody in mammals.

The Fc region, composed of two heavy chains that contribute three or four constant domains depending on the class of the antibody, plays a role in modulating immune cell activity. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects, including opsonization, cell lysis, and degranulation of mast cells, basophils and eosinophils.

As used herein, the term "epitope" refers to a specific arrangement of amino acids located on a peptide or protein to which an antibody or antibody fragment binds. Epitopes often consist of a chemically active surface grouping of molecules such as amino acids or sugar side chains, and have specific three dimensional structural characteristics as well as specific charge characteristics. Epitopes can be linear, i.e., involving binding to a single sequence of amino acids, or conformational, i.e., involving binding to two or more sequences of amino acids in various regions of the antigen that may not necessarily be contiguous in the linear sequence.

As used herein, the terms "specifically binds," "bind specifically," "specific binding," and the like as applied to the present antibody compounds refer to the ability of a specific binding agent (such as an antibody) to bind to a target molecular species in preference to binding to other molecular species with which the specific binding agent and target molecular species are admixed. A specific binding agent is said specifically to recognize a target molecular species when it can bind specifically to that target.

As used herein, the term "binding affinity" refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules as measured in a 1:1 interaction. Affinities as used herein to describe interactions between molecules of the described methods which can be used to compare the relative strength with which one molecule (e.g., an antibody or other specific binding partner) will bind two other molecules (e.g., two versions or variants of a peptide) in a univalent interaction. The concepts of binding affinity, association constant, and dissociation constant are well known.

As used herein, the term "apparent binding affinity" refers to the apparent strength of binding of one molecule to another at a site on the molecule. If a particular molecule will bind to or specifically associate with another particular molecule, these two molecules are said to exhibit binding affinity for each other. Apparent binding affinity is related to the association constant and dissociation constant for a pair of molecules, and relates to a non 1:1 or multivalent association between the pair of molecules. Apparent affinities as used herein to describe interactions between molecules of the described methods are observed in empirical studies, which can be used to compare the relative strength with which one molecule (e.g., an antibody or other specific binding partner) will bind two other molecules (e.g., two versions or variants of a peptide). The concept of binding affinity may be described as apparent Kd, apparent binding constant, $EC_{50}$ or other measurements of binding.

As used herein, the term "sequence identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs.

Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, Altschul, S. F. et al., *J. Mol. Biol.* 215: 403-410 (1990) and Altschul et al. *Nucl. Acids Res.* 25: 3389-3402 (1997).

One example of an algorithm that is suitable for determining percent sequence identity and sequence similarity is the BLAST algorithm, which is described in (Altschul, S. et al., NCBI NLM NIH Bethesda, Md. 20894; and Altschul, S. et al., *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold.

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always; 0) and N (penalty score for mismatching residues; always; 0). For amino acid sequences, a scoring matrix is used to calculate the cumulative score. Extension of the word hits in each direction are halted when: the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in still another embodiment less than about 0.001.

As used herein, the terms "humanized," "humanization," and the like, refer to grafting of the murine monoclonal antibody CDRs disclosed herein to human FRs and constant regions. Also encompassed by these terms are possible further modifications to the murine CDRs, and human FRs, by the methods disclosed in, for example, Kashmiri et al. (2005) Methods 36(1):25-34 and Hou et al. (2008) *J. Biochem.* 144(1):115-120, respectively, to improve various antibody properties, as discussed below.

As used herein, the term "humanized antibodies" refers to mAbs and antigen binding fragments thereof, including antibody compounds, that have binding and functional properties similar to those disclosed herein, and that have FRs and constant regions that are substantially human or fully human surrounding CDRs derived from a non-human antibody.

As used herein, the term "FR" or "framework sequence" refers to any one of FRs 1 to 4. Humanized antibodies and antigen binding fragments encompassed by the present disclosure include molecules wherein any one or more of FRs 1 to 4 is substantially or fully human, i.e., wherein any of the possible combinations of individual substantially or fully human FRs 1 to 4, is present. For example, this includes molecules in which FR1 and FR2, FR1 and FR3, FR1, FR2, and FR3, etc., are substantially or fully human. Substantially human frameworks are those that have at least 80% sequence identity to a known human germline framework sequence. Preferably, the substantially human frameworks have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, to a framework sequence disclosed herein, or to a known human germline framework sequence.

Fully human frameworks are those that are identical to a known human germline framework sequence. Human FR germline sequences can be obtained from the international ImMunoGeneTics (IMGT) database and from The Immunoglobulin FactsBook by Marie-Paule Lefranc and Gerard Lefranc, Academic Press, 2001, the contents of which are herein incorporated by reference in their entirety.

The Immunoglobulin Facts Book is a compendium of the human germline immunoglobulin genes that are used to create the human antibody repertoire, and includes entries for 203 genes and 459 alleles, with a total of 837 displayed sequences. The individual entries comprise all the human immunoglobulin constant genes, and germline variable, diversity, and joining genes that have at least one functional or open reading frame allele, and which are localized in the three major loci. For example, germline light chain FRs can be selected from the group consisting of: IGKV3D-20, IGKV2-30, IGKV2-29, IGKV2-28, IGKV1-27, IGKV3-20, IGKV1-17, IGKV1-16, 1-6, IGKV1-5, IGKV1-12, IGKV1D-16, IGKV2D-28, IGKV2D-29, IGKV3-11, IGKV1-9, IGKV1-39, IGKV1D-39, IGKV1D-33, and IGKJ1-5; and germline heavy chain FRs can be selected from the group consisting of: IGHV1-2, IGHV1-18, IGHV1-46, IGHV1-69, IGHV2-5, IGHV2-26, IGHV2-70, IGHV1-3, IGHV1-8, IGHV3-9, IGHV3-11, IGHV3-15, IGHV3-20, IGHV3-66, IGHV3-72, IGHV3-74, IGHV4-31, IGHV3-21, IGHV3-23, IGHV3-30, IGHV3-48, IGHV4-39, IGHV4-59, IGHV5-51, and IGHJ1-6.

Substantially human FRs are those that have at least 80% sequence identity to a known human germline FR sequence. Preferably, the substantially human frameworks have at least 85%, at least 90%, at least 95%, at least 96%, at least 97%, at least 98%, or at least 99% sequence identity, to a framework sequences disclosed herein, or to a known human germline framework sequence.

CDRs encompassed by the present disclosure include not only those specifically disclosed herein, but also CDR sequences having sequence identities of at least 80%, at least 85%, at least 90%, at least 95%, at least 96%, at least 97%, at least 98%, or at least 99% sequence identity to a CDR sequence disclosed herein. Alternatively, CDRs encompassed by the present disclosure include not only those specifically disclosed herein, but also CDR sequences having 1, 2, 3, 4, or 5 amino acid changes at corresponding positions compared to CDR sequences disclosed herein. Such sequence identical, or amino acid modified, CDRs preferably bind to the antigen recognized by the intact antibody.

Humanized antibodies in addition to those disclosed herein exhibiting similar functional properties according to the present disclosure can be generated using several different methods, including those disclosed by Almagro et al. (Frontiers in Biosciences. Humanization of antibodies. 2008, Jan. 1; 13:1619-33).

In one approach, the parent antibody compound CDRs are grafted into a human framework that has a high sequence identity with the parent antibody compound framework. The sequence identity of the new framework will generally be at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identical to the sequence of the corresponding framework in the parent antibody compound. In the case of frameworks having fewer than 100 amino acid residues, one, two, three, four, five, six, seven, eight, nine, or ten amino acid residues can be changed. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci. USA* 88:2869. Additional references describing methods useful to generate humanized variants based on homology and back mutations include as described in Olimpieri et al. (*Bioinformatics* 2015 Feb. 1; 31(3):434-435) and U.S. Pat. Nos. 4,816,397, 5,225,539, and 5,693,761; and the method of Winter and co-workers (Jones et al. (1986) *Nature* 321:522-525; Riechmann et al. (1988) *Nature* 332:323-327; and Verhoeyen et al. (1988) *Science* 239:1534-1536).

Humanization began with chimerization, a method developed during the first half of the 1980's (Morrison, S. L., M. J. Johnson, L. A. Herzenberg & V. T. Oi: Chimeric human antibody molecules: mouse antigen-binding domains with human constant region domains. *Proc. Natl. Acad. Sci. USA* 81, 6851-5 (1984)), consisting of combining the variable (V) domains of murine antibodies with human constant (C) domains to generate molecules with ~70% of human content.

Several different methods can be used to generate humanized antibodies, which are described herein. In one approach, the parent antibody compound CDRs are grafted into a human FR that has a high sequence identity with the parent antibody compound framework. The sequence identity of the new FR will generally be at least 60%, at least 65%, at least 70%, at least 75%, at least 80%, at least 85%, at least 90%, at least 95%, at least 96%, at least 97%, at least 98%, or at least 99% identical to the sequence of the corresponding FR in the parent antibody compound. In the case of FRs having fewer than 100 amino acid residues, one, two, three, four, five, or more amino acid residues can be changed. This grafting may result in a reduction in binding affinity compared to that of the parent antibody. If this is the case, the FR can be back-mutated to the parent framework at certain positions based on specific criteria disclosed by Queen et al. (1991) *Proc. Natl. Acad. Sci. USA* 88:2869. Additional references describing methods useful to generate humanized variants based on homology and back mutations include as described in Olimpieri et al. (Bioinformatics. 2015 Feb. 1; 31(3):434-435) and U.S. Pat. Nos. 4,816,397, 5,225,539, and 5,693,761; and the method of Winter and co-workers (Jones et al. (1986) *Nature* 321:522-525; Riechmann et al. (1988) *Nature* 332:323-327; and Verhoeyen et al. (1988) *Science* 239:1534-1536).

The identification of residues to consider for back-mutation can be carried out as described below. When an amino acid falls under the following category, the framework amino acid of the human germ-line sequence that is being used (the "acceptor FR") is replaced by a framework amino acid from a framework of the parent antibody compound (the "donor FR"):

(a) the amino acid in the human FR of the acceptor framework is unusual for human frameworks at that position, whereas the corresponding amino acid in the donor immunoglobulin is typical for human frameworks at that position;

(b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model.

When each of the amino acids in the human FR of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody compound.

Another approach to generating humanized antibodies exhibiting similar functional properties to the antibody compounds disclosed herein involves randomly mutating amino acids within the grafted CDRs without changing the framework, and screening the resultant molecules for binding affinity and other functional properties that are as good as, or better than, those of the parent antibody compounds. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific FRs in addition to introducing amino acid changes in the CDRs. This methodology is described in Wu et al. (1999, *J. Mol. Biol.* 294: 151-162).

Applying the teachings of the present disclosure, a person skilled in the art can use common techniques, e.g., site-directed mutagenesis, to substitute amino acids within the presently disclosed CDR and FR sequences and thereby generate further variable region amino acid sequences derived from the present sequences. Up to all naturally occurring amino acids can be introduced at a specific substitution site. The methods disclosed herein can then be used to screen these additional variable region amino acid sequences to identify sequences having the indicated in vivo functions. In this way, further sequences suitable for preparing humanized antibodies and antigen-binding portions thereof in accordance with the present disclosure can be identified. Preferably, amino acid substitution within the frameworks is restricted to one, two, three, four, or five positions within any one or more of the four light chain and/or heavy chain FRs disclosed herein. Preferably, amino acid substitution within the CDRs is restricted to one, two, three, four, or five positions within any one or more of the three light chain and/or heavy chain CDRs. Combinations of the various changes within these FRs and CDRs described above are also possible.

That the functional properties of the antibody compounds generated by introducing the amino acid modifications discussed above conform to those exhibited by the specific molecules disclosed herein can be confirmed by the methods in Examples disclosed herein.

As described above, to circumvent the problem of eliciting human anti-murine antibody (HAMA) response in patients, murine antibodies have been genetically manipulated to progressively replace their murine content with the amino acid residues present in their human counterparts by grafting their complementarity determining regions (CDRs) onto the variable light (VL) and variable heavy (VH) frameworks of human immunoglobulin molecules, while retaining those murine framework residues deemed essential for the integrity of the antigen-combining site. However, the xenogeneic CDRs of the humanized antibodies may evoke anti-idiotypic (anti-Id) response in patients.

To minimize the anti-Id response, a procedure to humanize xenogeneic antibodies by grafting onto the human frameworks only the CDR residues most crucial in the antibody-ligand interaction, called "SDR grafting", has been developed, wherein only the crucial specificity determining residues (SDRs) of CDRS are grafted onto the human frameworks. This procedure, described in Kashmiri et al. (2005, Methods 36(1):25-34), involves identification of SDRs through the help of a database of the three-dimensional structures of the antigen-antibody complexes of known structures, or by mutational analysis of the antibody-combining site. An alternative approach to humanization involving retention of more CDR residues is based on grafting of the 'abbreviated' CDRs, the stretches of CDR residues that include all the SDRs. Kashmiri et al. also discloses a procedure to assess the reactivity of humanized antibodies to sera from patients who had been administered the murine antibody.

Another strategy for constructing human antibody variants with improved immunogenic properties is disclosed in Hou et al. (2008, *J. Biochem.* 144(1):115-120). These authors developed a humanized antibody from 4C8, a murine anti-human CD34 monoclonal antibody, by CDR grafting using a molecular model of 4C8 built by computer-assisted homology modelling. Using this molecular model, the authors identified FR residues of potential importance in antigen binding. A humanized version of 4C8 was generated by transferring these key murine FR residues onto a human antibody framework that was selected based on homology to the murine antibody FR, together with the murine CDR residues. The resulting humanized antibody was shown to possess antigen-binding affinity and specificity similar to that of the original murine antibody, suggesting that it might be an alternative to murine anti-CD34 antibodies routinely used clinically.

Embodiments of the present disclosure encompass antibodies created to avoid recognition by the human immune system containing CDRs disclosed herein in any combinatorial form such that contemplated mAbs can contain the set of CDRs from a single murine mAb disclosed herein, or light and heavy chains containing sets of CDRs comprising individual CDRs derived from two or three of the disclosed murine mAbs. Such mAbs can be created by standard techniques of molecular biology and screened for desired activities using assays described herein. In this way, the disclosure provides a "mix and match" approach to create novel mAbs comprising a mixture of CDRs from the disclosed murine mAbs to achieve new, or improved, therapeutic activities.

Monoclonal antibodies or antigen-binding fragments thereof encompassed by the present disclosure that "compete" with the molecules disclosed herein are those that bind human CD47 at site(s) that are identical to, or overlapping with, the site(s) at which the present molecules bind. Competing monoclonal antibodies or antigen-binding fragments thereof can be identified, for example, via an antibody competition assay. For example, a sample of purified or partially purified human CD47 extracellular domain can be bound to a solid support. Then, an antibody compound, or antigen binding fragment thereof, of the present disclosure and a monoclonal antibody or antigen-binding fragment thereof suspected of being able to compete with such disclosure antibody compound are added. One of the two molecules is labelled. If the labelled compound and the unlabelled compound bind to separate and discrete sites on CD47, the labelled compound will bind to the same level whether or not the suspected competing compound is present. However, if the sites of interaction are identical or overlapping, the unlabelled compound will compete, and the amount of labelled compound bound to the antigen will be lowered. If the unlabelled compound is present in excess, very little, if any, labelled compound will bind. For purposes of the present disclosure, competing monoclonal antibodies or antigen-binding fragments thereof are those that decrease the binding of the present antibody compounds to CD47 by about 50%, about 60%, about 70%, about 80%, about 85%, about 86%, about 87%, about 88%, about 89%, about 90%, about 91%, about 92%, about 93%, about 94%, about 95%, about 96%, about 97%, about 98%, or about 99%. Details of procedures for carrying out such competition assays are well known in the art and can be found, for example, in Harlow and Lane (1988) Antibodies, A Laboratory Manual, Cold Spring Harbor Laboratory Press, Cold Spring Harbor, N.Y. Such assays can be made quantitative by using purified antibodies. A standard curve is established by titrating one antibody against itself, i.e., the same antibody is used for both the label and the competitor. The capacity of an unlabelled competing monoclonal antibody or antigen-binding fragment thereof to inhibit the binding of the labelled molecule to the plate is titrated. The results are plotted, and the concentrations necessary to achieve the desired degree of binding inhibition are compared.

Whether mAbs or antigen-binding fragments thereof that compete with antibody compounds of the present disclosure in such competition assays possess the same or similar functional properties of the present antibody compounds can be determined via these methods in conjunction with the methods described in Examples below. In various embodiments, competing antibodies for use in the therapeutic methods encompassed herein possess biological activities as described herein in the range of from about 50% to about 100% or about 125%, or more, compared to that of the antibody compounds disclosed herein. In some embodiments, competing antibodies possess about 50%, about 60%, about 70%, about 80%, about 85%, about 90%, about 91%, about 92%, about 93%, about 94%, about 95%, about 96%, about 97%, about 98%, about 99%, or identical biological activity compared to that of the antibody compounds disclosed herein as determined by the methods disclosed in the Examples presented below.

The mAbs or antigen-binding fragments thereof, or competing antibodies useful in the compositions and methods can be any of the isotypes described herein. Furthermore, any of these isotypes can comprise further amino acid modifications as follows.

The monoclonal antibody or antigen-binding fragment thereof, or competing antibody described herein can be of the human IgG1 isotype.

The human IgG1 constant region of the monoclonal antibody, antigen-binding fragment thereof, or competing antibody described herein can be modified to alter antibody half-life. Antibody half-life is regulated in large part by Fc-dependent interactions with the neonatal Fc receptor (Roopenian and Alikesh, 2007). The human IgG1 constant region of the monoclonal antibody, antigen-binding fragment thereof, or competing antibody can be modified to increase half-life include, but are not limited to amino acid modifications N434A, T307A/E380A/N434A (Petkova et al., 2006, Yeung et al., 2009); M252Y/S254T/T256E (Dall'Acqua et al., 2006); T250Q/M428L (Hinton et al., 2006); and M428L/N434S (Zalevsky et al., 2010).

As opposed to increasing half-life, there are some circumstances where decreased half-life would be desired, such as to reduce the possibility of adverse events associated with high Antibody-Dependent Cellular Cytotoxicity (ADCC) and Complement-Dependent Cytotoxicity (CDC) antibodies (Presta 2008). The human IgG1 constant region of the monoclonal antibody, antigen-binding fragment thereof, or competing antibody described herein can be modified to decrease half-life and/or decrease endogenous IgG include, but are not limited to amino acid modifications I253A (Petkova et al., 2006); P257I/N434H, D376V/N434H (Datta-Mannan et al., 2007); and M252Y/S254T/T256E/ H433K/N434F (Vaccaro et al., 2005).

The human IgG1 constant region of the monoclonal antibody, antigen-binding fragment thereof, or competing antibody described herein can be modified to increase or decrease antibody effector functions. These antibody effector functions include, but are not limited to, Antibody-Dependent Cellular Cytotoxicity (ADCC), Complement-Dependent Cytotoxicity (CDC), Antibody-Dependent Cellular Phagocytosis (ADCP), C1q binding, and altered binding to Fc receptors.

The human IgG1 constant region of the monoclonal antibody, antigen-binding fragment thereof, or competing antibody described herein can be modified to increase antibody effector function include, but are not limited to amino acid modifications S298A/E333A/K334 (Shields et al., 2001); S239D/I332E and S239D/A330L/I332E (Lazar et al., 2006); F234L/R292P/Y300L, F234L/R292P/Y300L/ P393L, and F243L/R292P/Y300L/V305I/P396L (Stevenhagen et al., 2007); G236A, G236A/S239D/I332E, and G236A/S239D/A330L/I332E (Richards et al., 2008); K326A/E333A, K326A/E333S and K326W/E333S (Idusogie et al., 2001); S267E and S267E/L328F (Smith et al., 2012); H268F/S324T, S267E/H268F, S267E/S234T, and S267E/H268F/S324T (Moore et al., 2010); S298G/T299A (Sazinsky et al., 2008); E382V/M428I (Jung et al., 2010).

The human IgG1 constant region of the monoclonal antibody, antigen-binding fragment thereof, or competing antibody described herein can be modified to decrease antibody effector function include, but are not limited to amino acid modifications N297A and N297Q (Bolt et al., 1993, Walker et al., 1989); L234A/L235A (Xu et al., 2000); K214T/E233P/L234V/L235A/G236-deleted/A327G/ P331A/D356E/L358M (Ghevaert et al., 2008); C226S/ C229S/E233P/L234V/L235A (McEarchern et al., 2007); S267E/L328F (Chu et al., 2008).

The human IgG1 constant region of the monoclonal antibody, antigen-binding fragment thereof, or competing antibody described herein can be modified to decrease antibody effector function include, but are not limited to amino acid modifications V234A/G237A (Cole et al., 1999); E233D, G237D, P238D, H268Q, H268D, P271G, V309L, A330S, A330R, P331S, H268Q/A330S/V309L/P331S, H268D/A330S/V309L/P331S, H268Q/A330R/V309L/P331S, H268D/A330R/V309L/P331S, E233D/A330R, E233D/A330S, E233D/P271G/A330R, E233D/P271G/A330S, G237D/H268D/P271G, G237D/H268Q/P271G, G237D/P271G/A330R, G237D/P271G/A330S, E233D/H268D/P271G/A330R, E233D/H268Q/P271G/A330R, E233D/H268D/P271G/A330S, E233D/H268Q/P271G/A330S, G237D/H268D/P271G/A330R, G237D/H268Q/P271G/A330R, G237D/H268D/P271G/A330S, G237D/H268Q/P271G/A330S, E233D/G237D/H268D/P271G/A330R, E233D/G237D/H268Q/P271G/A330R, E233D/G237D/H268D/P271G/A330S, E233D/G237D/H268Q/P271G/A330S, P238D/E233D/A330R, P238D/E233D/A330S, P238D/E233D/P271G/A330R, P238D/E233D/P271G/A330S, P238D/G237D/H268D/P271G, P238D/G237D/H268Q/P271G, P238D/G237D/P271G/A330R, P238D/G237D/P271G/A330S, P238D/E233D/H268D/P271G/A330R, P238D/E233D/H268Q/P271G/A330R, P238D/E233D/H268D/P271G/A330S, P238D/E233D/H268Q/P271G/A330S, P238D/G237D/H268D/P271G/A330R, P238D/G237D/H268Q/P271G/A330R, P238D/G237D/H268D/P271G/A330S, P238D/G237D/H268Q/P271G/A330S, P238D/E233D/G237D/H268D/P271G/A330R, P238D/E233D/G237D/H268Q/P271G/A330R, P238D/E233D/G237D/H268D/P271G/A330S, P238D/E233D/G237D/H268Q/P271G/A330S (An et al., 2009, Mimoto, 2013).

The monoclonal antibody or antigen-binding fragment thereof, or competing antibody described herein can be of the human IgG2 isotype.

The human IgG2 constant region of the monoclonal antibody, antigen-binding fragment thereof, or competing antibody described herein can be modified to increase or decrease antibody effector functions. These antibody effector functions include, but are not limited to, Antibody-Dependent Cellular Cytotoxicity (ADCC), Complement-Dependent Cytotoxicity (CDC), Antibody-Dependent Cellular Phagocytosis (ADCP), and C1q binding, and altered binding to Fc receptors.

The human IgG2 constant region of the monoclonal antibody, antigen-binding fragment thereof, or competing antibody described herein can be modified to increase antibody effector function include, but are not limited to the amino acid modification K326A/E333S (Idusogie et al., 2001).

The human IgG2 constant region of the monoclonal antibody, antigen-binding fragment thereof, or competing antibody described herein can be modified to decrease antibody effector function include, but are not limited to amino acid modifications V234A/G237A (Cole et al., 1999); V234A, G237A, P238S, H268A, E233D, G237D, P238D, H268Q, H268D, P271G, V309L, A330S, A330R, P331S, P238S/H268A, V234A/G237A/P238S/H268A/V309L/A330S/P331S, H268Q/A330S/V309L/P331S, H268D/A330S/V309L/P331S, H268Q/A330R/V309L/P331S, H268D/A330R/V309L/P331S, E233D/A330R, E233D/A330S, E233D/P271G/A330R, E233D/P271G/A330S, G237D/H268D/P271G, G237D/H268Q/P271G, G237D/P271G/A330R, G237D/P271G/A330S, E233D/H268D/P271G/A330R, E233D/H268Q/P271G/A330R, E233D/H268D/P271G/A330S, E233D/H268Q/P271G/A330S, G237D/H268D/P271G/A330R, G237D/H268Q/P271G/A330R, G237D/H268D/P271G/A330S, G237D/H268Q/P271G/A330S, E233D/G237D/H268D/P271G/A330R, E233D/G237D/H268Q/P271G/A330R, E233D/G237D/H268D/P271G/A330S, E233D/G237D/H268Q/P271G/A330S, P238D/E233D/A330R, P238D/E233D/A330S, P238D/E233D/P271G/A330R, P238D/E233D/P271G/A330S, P238D/G237D/H268D/P271G, P238D/G237D/H268Q/P271G, P238D/G237D/P271G/A330R, P238D/G237D/P271G/A330S, P238D/E233D/H268D/P271G/A330R, P238D/E233D/H268Q/P271G/A330R, P238D/E233D/H268D/P271G/A330S, P238D/E233D/H268Q/P271G/A330S, P238D/G237D/H268D/P271G/A330R, P238D/G237D/H268Q/P271G/A330R, P238D/G237D/H268D/P271G/A330S, P238D/G237D/H268Q/P271G/A330S, P238D/E233D/G237D/H268D/P271G/A330R, P238D/E233D/G237D/H268Q/P271G/A330R, P238D/E233D/G237D/H268D/P271G/A330S, P238D/E233D/G237D/H268Q/P271G/A330S (An et al., 2009, Mimoto, 2013).

The Fc region of a human IgG2 of the monoclonal antibody, antigen-binding fragment thereof, or competing antibody described herein can be modified to alter isoform and/or agonistic activity, include, but are not limited to amino acid modifications C127S (CH1 domain), C232S, C233S, C232S/C233S, C236S, and C239S (White et al., 2015, Lightle et al., 2010).

The monoclonal antibody or antigen-binding fragment thereof, or competing antibody described herein can be of the human IgG3 isotype.

The human IgG3 constant region of the monoclonal antibody, or antigen binding fragment thereof, wherein said human IgG3 constant region of the monoclonal antibody, or antigen-binding fragment thereof can be modified at one or more amino acid(s) to increase antibody half-life, Antibody-Dependent Cellular Cytotoxicity (ADCC), Complement-Dependent Cytotoxicity (CDC), or apoptosis activity.

The human IgG3 constant region of the monoclonal antibody, or antigen-binding fragment thereof, wherein said human IgG3 constant region of the monoclonal antibody, or antigen-binding fragment thereof can be modified at amino acid R435H to increase antibody half-life.

The monoclonal antibody or antigen-binding fragment thereof, or competing antibody described herein can be of the human IgG4 isotype.

The human IgG4 constant region of the monoclonal antibody, antigen-binding fragment thereof, or competing antibody described herein can be modified to decrease antibody effector functions. These antibody effector functions include, but are not limited to, Antibody-Dependent Cellular Cytotoxicity (ADCC) and Antibody-Dependent Cellular Phagocytosis (ADCP).

The human IgG4 constant region of the monoclonal antibody, antigen-binding fragment thereof, or competing antibody described herein can be modified to prevent Fab arm exchange and/or decrease antibody effector function include, but are not limited to amino acid modifications F234A/L235A (Alegre et al., 1994); S228P, L235E and S228P/L235E (Reddy et al., 2000).

As used herein, the term "tumor" refers to all neoplastic cell growth and proliferation, whether malignant or benign, and all pre-cancerous and cancerous cells and tissues.

The terms "cancer," "cancerous," and "tumor" are not mutually exclusive as used herein.

The terms "cancer" and "cancerous" refer to or describe the physiological condition in mammals that is typically characterized by aberrant cell growth/proliferation. Examples of cancers include, but are not limited to, carcinoma, lymphoma (i.e., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "susceptible cancer" as used herein refers to a cancer, cells of which express CD47, and are responsive to treatment with an anti-CD47 antibody or antigen binding fragment thereof, or competing antibody or antigen binding fragment thereof, of the present disclosure.

"Nitric oxide (NO) donor, precursor, or nitric oxide generating topical agent" refers to a compound or agent that either delivers NO, or that can be converted to NO through enzymatic or non-enzymatic processes. Examples include, but are not limited to, NO gas, isosorbide dinitrite, nitrite, nitroprusside, nitroglycerin, 3-Morpholinosydnonimine (SIN-1), S-nitroso-N-acetyl-penicillamine (SNAP), Diethylenetriamine/NO (DETA/NO), S-nitrosothiols, Bidil®, and arginine.

"Soluble guanylyl cyclase (sGC)" is the receptor for nitric oxide in vascular smooth muscle. In the cardiovascular system, nitric oxide is endogenously generated by endothelial nitric oxide synthase from L-arginine, and activates soluble guanylyl cyclase in adjacent vascular smooth muscle cells to increase cGMP levels, inducing vascular relaxation. Nitric oxide binds to the normally reduced heme moiety of soluble guanylyl cyclase, and increases the formation of cGMP from GTP, leading to a decrease in intracellular calcium, vasodilation, and anti-inflammatory effects. Oxidation of the heme iron on sGC decreases responsiveness of the enzyme to nitric oxide, and promotes vasoconstriction. The nitric oxide-sGC-cGMP pathway therefore plays an important role in cardiovascular diseases. Nitrogen-containing compounds such as sodium azide, sodium nitrite, hydroxylamine, nitroglycerin, and sodium nitroprusside have been shown to stimulate sGC, causing an increase in cGMP, and vascular relaxation. In contrast to stimulators of sGC, which bind to reduced sGC, activators of sGC activate the oxidized or heme-deficient sGC enzyme that is not responsive to nitric oxide, i.e., they stimulate sGC independent of redox state. While stimulators of of sGC can enhance the sensitivity of reduced sGC to nitric oxide, activators of sGC can increase sGC enzyme activity even when the enzyme is oxidized and is therefore less, or unresponsive, to nitric oxide. Thus, sGC activators are non-nitric oxide based. Note the reviews of Nossaman et al. (2012) *Critical Care Research and Practice*, Volume 2012, article 290805, and Derbyshire and Marletta (2012) *Ann. Rev. Biochem.* 81:533-559.

"An agent that activates soluble guanylyl cyclase" refers, for example, to organic nitrates (Artz et al. (2002) *J. Biol. Chem.* 277:18253-18256); protoporphyrin IX (Ignarro et al. (1982) *Proc. Natl. Acad. Sci. USA* 79:2870-2873); YC-1 (Ko et al. (1994) *Blood* 84:4226-4233); BAY 41-2272 and BAY 41-8543 (Stasch et al. (2001 *Nature* 410 (6825): 212-5), CMF-1571, and A-350619 (reviewed in Evgenov et al. (2006) *Nat. Rev. Drug. Discov.* 5:755-768); BAY 58-2667 (Cinaciguat; Frey et al. (2008) *Journal of Clinical Pharmacology* 48 (12): 1400-10); BAY 63-2521 (Riociguat; Mittendorf et al. (2009) *Chemmedchem* 4 (5): 853-65). Additional soluble guanylyl cyclase activators are disclosed in Stasch et al. (2011) *Circulation* 123:2263-2273; Derbyshire and Marletta (2012) *Ann. Rev. Biochem.* 81:533-559, and Nossaman et al. (2012) *Critical Care Research and Practice*, Volume 2012, Article ID 290805, pages 1-12.

cGMP can also be increased by inhibiting degradation using phosphodiesterase inhibitors. Examples of "an agent that inhibits cyclic nucleotide phosphodiesterases" include, tadalafil, vardenafil, udenafil, and sildenafil avanafil.

As used herein, term "treating" or "treat" or "treatment" means slowing, interrupting, arresting, controlling, stopping, reducing, or reversing the progression or severity of a sign, symptom, disorder, condition, or disease, but does not necessarily involve a total elimination of all disease-related signs, symptoms, conditions, or disorders. The term "treating" and the like refer to a therapeutic intervention that ameliorates a sign or symptom of a disease or pathological condition after it has begun to develop.

As used herein, term "effective amount" refers to the amount or dose of an antibody compound of the present disclosure which, upon single or multiple dose administration to a patient or organ, provides the desired treatment or prevention.

The precise effective amount for any particular subject will depend upon their size and health, the nature and extent of their condition, and the therapeutics or combination of therapeutics selected for administration. The effective amount for a given patient is determined by routine experimentation and is within the judgment of a clinician. Therapeutically effective amounts of the present antibody compounds can also comprise an amount in the range of from about 0.1 mg/kg to about 150 mg/kg, from about 0.1 mg/kg to about 100 mg/kg, from about 0.1 mg/kg to about 50 mg/kg, or from about 0.05 mg/kg to about 10 mg/kg per single dose administered to a harvested organ or to a patient. Known antibody-based pharmaceuticals provide guidance in this respect. For example, Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m2; for example.

A therapeutically effective amount for any individual patient can be determined by the health care provider by monitoring the effect of the antibody compounds on tumor regression, circulating tumor cells, tumor stem cells or anti-tumor responses. Analysis of the data obtained by these methods permits modification of the treatment regimen during therapy so that optimal amounts of antibody compounds of the present disclosure, whether employed alone or in combination with one another, or in combination with another therapeutic agent, or both, are administered, and so that the duration of treatment can be determined as well. In this way, the dosing/treatment regimen can be modified over the course of therapy so that the lowest amounts of antibody compounds used alone or in combination that exhibit satisfactory efficacy are administered, and so that administration of such compounds is continued only so long as is necessary to successfully treat the patient. Known antibody-based pharmaceuticals provide guidance relating to frequency of administration e.g., whether a pharmaceutical should be delivered daily, weekly, monthly, etc. Frequency and dosage may also depend on the severity of symptoms.

In some embodiments antibody compounds of the present disclosure can be used as medicaments in human and veterinary medicine, administered by a variety of routes including, but not limited to, oral, intravenous, intramuscular, intra-arterial, intramedullary, intraperitoneal, intrathecal, intraventricular, transdermal, transcutaneous, topical, subcutaneous, intratumoral, intranasal, enteral, sublingual, intravaginal, intravesicular or rectal routes. The compositions can also be administered directly into a lesion such as a tumor. Dosage treatment may be a single dose schedule or a multiple dose schedule. Hypo sprays may also be used to administer the pharmaceutical compositions. Typically, the therapeutic compositions can be prepared as injectables, either as liquid solutions or suspensions. Solid forms suitable for solution in, or suspension in, liquid vehicles prior to injection can also be prepared. Veterinary applications include the treatment of companion/pet animals, such as cats and dogs; working animals, such as guide or service dogs, and horses; sport animals, such as horses and dogs; zoo animals, such as primates, cats such as lions and tigers, bears, etc.; and other valuable animals kept in captivity.

Such pharmaceutical compositions can be prepared by methods well known in the art. See, e.g., Remington: The Science and Practice of Pharmacy, 21st Edition (2005), Lippincott Williams & Wilkins, Philadelphia, Pa., and comprise one or more antibody compounds disclosed herein, and a pharmaceutically or veterinarily acceptable, for example, physiologically acceptable, carrier, diluent, or excipient.

The present disclosure describes anti-CD47 mAbs with distinct functional profiles. These antibodies possess distinct combinations of properties selected from the following: These antibodies possess distinct combinations of properties selected from the following: 1) exhibit cross-reactivity with one or more species homologs of CD47; 2) block the interaction between CD47 and its ligand SIRPα; 3) increase phagocytosis of human tumor cells; 4) induce death of susceptible human tumor cells; 5) do not induce cell death of human tumor cells; 6) do not have reduced or minimal binding to human red blood cells (hRBCs); 7) have reduced binding to hRBCs; 8) have minimal binding to hRBCs; 9) cause reduced agglutination of hRBCs; 10) cause no detectable agglutination of hRBCs; 11) reverse TSP1 inhibition of the nitric oxide (NO) pathway; 12) do not reverse TSP1 inhibition of the NO pathway; 13) cause loss of mitochondrial membrane potential; 14) do not cause cause loss of mitochondrial membrane potential; 15) cause an increase in cell surface calreticulin expression on human tumor cells; 16) do not cause an increase in cell surface calreticulin expression on human tumor cells; 17) cause an increase in adenosine triphosphate (ATP) release by human tumor cells; 18) do not cause an increase in adenosine triphosphate (ATP) release by human tumor cells; 19) cause an increase in high mobility group box 1 (HMGB1) release by human tumor cells; 20) do not cause an increase in high mobility group box 1 (HMGB1) release by human tumor cells; 21) cause an increase in type I interferon release by human tumor cells; 22) do not cause an increase in type I interferon release by human tumor cells; 23) cause an increase in C-X-C Motif Chemokine Ligand 10 (CXCL10) release by human tumor cells; 24) do not cause an increase in C-X-C Motif Chemokine Ligand 10 (CXCL10) release by human tumor cells; 25) cause an increase in cell surface protein disulfide-isomerase A3 (PDIA3) expression on human tumor cells; 26) do not cause an increase in cell surface protein disulfide-isomerase A3 (PDIA3) expression on human tumor cells; 27) cause an increase in cell surface heat shock protein 70 (HSP70) expression on human tumor cells; 28) do not cause an increase in cell surface heat shock protein 70 (HSP70) expression on human tumor cells; 29) cause an increase in cell surface heat shock protein 90 (HSP90) expression on human tumor cells; 30) do not cause an increase in cell surface heat shock protein 90 (HSP90) expression on human tumor cells; 31) have reduced binding to normal human cells, which includes, but is not limited to, endothelial cells, skeletal muscle cells, epithelial cells, and peripheral blood mononuclear cells (e.g., human aortic endothelial cells, human skeletal muscle cells, human microvascular endothelial cells, human renal tubular epithelial cells, human peripherial blood CD3+ cells, and human peripheral blood mononuclear cells); 32) do not have reduced binding to normal human cells, which includes, but is not limited to, endothelial cells, skeletal muscle cells, epithelial cells, and peripheral blood mononuclear cells (e.g., human aortic endothelial cells, human skeletal muscle cells, human microvascular endothelial cells, human renal tubular epithelial cells, human peripherial blood CD3+ cells, and human peripheral blood mononuclear cells); 33) have a greater affinity for human CD47 at an acidic pH compared to physiological pH; 34) do not have a greater affinity for human CD47 at an acidic pH compared to physiological pH; and 35) cause an increase in annexin A1 release by human tumor cells.

The anti-CD47 antibodies and antigen binding fragments thereof of the present disclosure possess combinations of properties that are distinct from the anti-CD47 antibodies of the prior art. These properties and characteristics will now be described in further detail.

As used herein, the term "binds to human CD47" refers to binding with an apparent Kd greater than 50 nM, for example, in a solid phase ELISA assay or cell based assay.

As used herein, the terms "apparent binding affinity and apparent Kd" are determined by non-linear fit (Prism GraphPad software) of the binding data at the various antibody concentrations.

Binding to CD47 of Different Species

The anti-CD47 antibodies, and antigen binding fragments thereof, of the present disclosure bind human CD47. In certain embodiments, the anti-CD47 antibodies exhibit cross-reactivity with one or more species homologs of CD47, for example CD47 homologs of non-human primate origin. In certain embodiments, the anti-CD47 antibodies and antigen binding fragments thereof of the present disclosure bind to human CD47 and to CD47 of non-human primate, mouse, rat, and/or rabbit origin. The cross-reactivity with other species homologs can be particularly advantageous in the development and testing of therapeutic antibodies. For example, pre-clinical toxicology testing of therapeutic antibodies is frequently carried out in non-human primate species including, but not limited to, cynomolgus monkey, green monkey, rhesus monkey and squirrel monkey. Cross-reactivity with these species homologs can therefore be particularly advantageous for the development of antibodies as clinical candidates.

As used herein, the term "cross-reacts with one or more species homologs of CD47" refers to binding with an apparent Kd greater than 50 nM.

Blocking the Interaction Between CD47 and SIRPα and Promoting Phagocytosis

CD47, also known as integrin associated protein (IAP), is a 50 kDa cell surface receptor that is comprised of an extracellular N-terminal IgV domain, a five membrane-spanning transmembrane domain, and a short C-terminal intracellular tail that is alternatively spliced.

Two ligands bind to CD47: Signal Regulatory Protein alpha (SIRPα) and Thrombospondin-1 (TSP1). TSP1 is present in plasma and synthesized by many cells, including platelets. SIRPα is expressed on hematopoietic cells, which include macrophages and dendritic cells.

When SIRPα on a phagocyte engages CD47 on a target cell, this interaction prevents phagocytosis of the target cell. The interaction of CD47 and SIRPα effectively sends a "don't eat me" signal to the phagocyte (Oldenborg et al. *Science* 288: 2051-2054, 2000). Blocking the interaction of SIRPα and CD47 with an anti-CD47 mAb in a therapeutic context can provide an effective anti-cancer treatment by promoting the uptake and clearance of cancer cells by the host's immune system. Thus, an important functional characteristic of some anti-CD47 mAbs is the ability to block the interaction of CD47 and SIRPα, resulting in phagocytosis of CD47 expressing tumor cells by phagocytes including macrophages. Several anti-CD47 mAbs have been shown to block the interaction of CD47 and SIRPα, including B6H12 (Seiffert et al. *Blood* 94:3633-3643, 1999; Latour et al. *J. Immunol.* 167: 2547-2554, 2001; Subramanian et al. *Blood* 107: 2548-2556, 2006; Liu et al. *J Biol. Chem.* 277: 10028-10036, 2002; Rebres et al. *J. Cellular Physiol.* 205: 182-193, 2005), BRIC126 (Vernon-Wilson et al. *Eur J Immunol.* 30: 2130-2137, 2000; Subramanian et al. *Blood* 107: 2548-2556, 2006), CC2C6 (Seiffert et al. *Blood* 94:3633-3643, 1999), 1F7 (Rebres et al. *J. Cellular Physiol.* 205: 182-193, 2005), 5F9 (Liu et al. *PLoS One.* 2015 Sep. 21; 10(9): e0137345) and CC-90002 (Narla et al. *Proc Am Assoc Cancer Res* 58: 1200, 2017; abst 469)4. B6H12 and BRIC126 have also been shown to cause phagocytosis of human tumor cells by human and mouse macrophages (Willingham et al. *Proc Natl Acad Sci USA* 109(17):6662-6667, 2012; Chao et al. *Cell* 142:699-713, 2012; EP 2 242 512 B1). Other existing anti-CD47 mAbs, such as 2D3, does not block the interaction of CD47 and SIRPα (Seiffert et al. Blood 94:3633-3643, 1999; Latour et al. *J. Immunol.* 167: 2547-2554, 2001; Rebres et al. *J. Cellular Physiol.* 205: 182-193, 2005), and does not cause phagocytosis of tumor cells (Willingham et al. *Proc Natl Acad Sci USA* 109(17):6662-6667, 2012; Chao et al. *Cell* 142:699-713, 2012; EP 2 242 512 B1).

As used herein, the term "blocks SIRPα binding to human CD47" refers to a greater than 50% reduction of SIRPα-Fc binding to CD47 on cells by an anti-CD47 mAb compared to either untreated cells or cells treated with a negative antibody.

The anti-CD47 mAbs of the disclosure described herein, block the interaction of CD47 and SIRPα and increase phagocytosis of human tumor cells.

"Phagocytosis" of cancer cells refers to the engulfment and digestion of such cells by phagocytes including, but not limited to, macrophages and dendritic cells, and the eventual digestion or degradation of these cancer cells and the release of digested or degraded cellular components extracellularly, or intracellularly to undergo further processing. Anti-CD47 monoclonal antibodies that block SIRPα binding to CD47 increase phagocytosis of cancer cells. SIRPα binding to CD47 on cancer cells would otherwise allow these cells to escape phagocytosis. The cancer cell may be viable or living cancer cells.

As used herein, the term "increases phagocytosis of human tumor cells" refers to a greater than 2-fold increase in phagocytosis of human tumor cells by human macrophages in the presence of an anti-CD47 mAb compared to either untreated cells or cells treated with a negative control antibody.

Inducing Death of Tumor Cells

Some soluble anti-CD47 mAbs initiate a cell death program on binding to CD47 on tumor cells, resulting in collapse of mitochondrial membrane potential, loss of ATP generating capacity, increased cell surface expression of phosphatidylserine (detected by increased staining for annexin V) and cell death without the participation of caspases or fragmentation of DNA. Such soluble anti-CD47 mAbs have the potential to treat a variety of solid and hematological cancers. Several soluble anti-CD47 mAbs which have been shown to induce tumor cell death, including MABL-1, MABL-2 and fragments thereof (U.S. Pat. No. 8,101,719; Uno et al. *Oncol Rep.* 17: 1189-94, 2007; Kikuchi et al. *Biochem Biophys Res. Commun.* 315: 912-8, 2004), Ad22 (Pettersen et al. *J. Immuno.* 166: 4931-4942, 2001; Lamy et al. *J. Biol. Chem.* 278: 23915-23921, 2003), and 1F7 (Manna et al. *J. Immunol.* 170: 3544-3553, 2003; Manna et al. *Cancer Research,* 64: 1026-1036, 2004). Some of the anti-CD47 mAbs of the disclosure described herein induce cell death of human tumor cells.

Induction of cell death refers to the ability of certain of the soluble anti-CD47 antibodies, murine antibodies, chimeric antibodies, humanized antibodies, or antigen-binding fragments thereof (and competing antibodies and antigen-binding fragments thereof) disclosed herein to kill cancer cells via a cell autonomous mechanism without participation of complement or other cells including, but not limited to, T cells, neutrophils, natural killer cells, macrophages, or dendritic cells.

The terms "inducing cell death" or "kills" and the like, are used interchangeably herein.

As used herein, the term "induces death of human tumor cells" refers to increased binding of annexin V (in the presence of calcium) and increased 7-aminoactinomycin D (7-AAD) or propidium iodide uptake in response to treatment with an anti-CD47 mAb. These features may be quantitated in three cell populations: annexin V positive (annexin $V^+$), annexin V positive/7-AAD negative (annexin $V^+/7\text{-}AAD^-$) and annexin V positive/7-AAD positive (annexin $V^+/7\text{-}AAD^+$) by flow cytometry. Induction of cell death may be defined by a greater than 2-fold increase in each of the above cell populations in human tumor cells caused by soluble anti-CD47 mAb compared to the background obtained with the negative control antibody, (humanized, isotype-matched antibody) or untreated cells.

Another indicator of cell death is loss of mitochondrial function and membrane potential by the tumor cells as assayed by one of several available measures (potentiometric fluorescent dyes such as DiO-C6 or JC1 or formazan-based assays such as MTT or WST-1).

As used herein, the term "causes loss of mitochondrial membrane potential" refers to a statistically significant ($p<0.05$) decrease in mitochondrial membrane potential by a soluble anti-CD47 mAb compared to the background obtained with a negative control, humanized isotype-matched antibody or no treatment.

Among the present humanized or chimeric mAbs, those that induce cell death of human tumor cells cause increased annexin V binding similar to the findings reported for anti-CD47 mAbs Ad22 (Pettersen et al. *J. Immunol.* 166: 4931-4942, 2001; Lamy et al. *J. Biol. Chem.* 278: 23915-23921, 2003); 1F7 (Manna and Frazier *J. Immunol.* 170: 3544-3553, 2003; Manna and Frazier *Cancer Res.* 64:1026-1036, 2004); and MABL-1 and 2 (U.S. Pat. No. 7,531,643 B2; U.S. Pat. No. 7,696,325 B2; U.S. Pat. No. 8,101,719 B2).

Cell viability assays are described in NCI/NIH guidance manual that describes numerous types of cell based assays that can be used to assess induction of cell death caused by CD47 antibodies: "Cell Viability Assays", Terry L Riss, PhD, Richard A Moravec, B S, Andrew L Niles, M S, Helene A Benink, PhD, Tracy J Worzella, M S, and Lisa Minor, PhD. Contributor Information, published May 1, 2013.

Binding to hRBCs

CD47 is expressed on human erythrocytes (hRBCs) (Brown. *J Cell Biol.* 111: 2785-2794, 1990; Avent. *Biochem J.*, (1988) 251: 499-505; Knapp. *Blood*, (1989) Vol. 74, No. 4, 1448-1450; Oliveira et al. *Biochimica et Biophysica Acta* 1818: 481-490, 2012; Petrova P. et al. *Cancer Res* 2015; 75(15 Suppl): Abstract no. 4271). It has been shown that anti-CD47 mAbs bind to RBCs, including B6H12 (Brown et al. J. Cell Biol., 1990, Oliveira et al. *Biochimica et Biophysica Acta* 1818: 481-490, 2012, Petrova P. et al. *Cancer Res* 2015; 75(15 Suppl): Abstract no. 4271), BRIC125 (Avent. *Biochem J.*, (1988) 251: 499-505), BRIC126 (Avent. *Biochem J.*, (1988) 251: 499-505; Petrova P. et al. *Cancer Res* 2015; 75(15 Suppl): Abstract no. 4271), 5F9 (Uger R. et al. *Cancer Res* 2014; 74(19 Suppl): Abstract no. 5011, Liu et al. *PLoS One.* 2015 Sep. 21; 10(9): e0137345; Sikic B. et al. *J Clin Oncol* 2016; 34 (suppl; abstract 3019)), anti-CD47 antibodies disclosed in US Patent Publication 2014/0161799, WO Publication 2014/093678, US Patent Publication 2014/0363442, and CC2C6 (Petrova P. et al. *Cancer Res* 2015; 75(15 Suppl): Abstract no. 4271, Uger R. et al. *Cancer Res* 2014; 74(19 Suppl): Abstract no. 5011). It has also been shown that a SIRPα-Fc fusion protein, which binds to human CD47, has reduced binding to human RBCs compared to other human cells (Uger R. et al. *Cancer Res* 2014; 74(19 Suppl: Abstract no. 5011; Petrova et al. *Clin Cancer Res* 23: 1068-1079, 2017). Binding to RBCs can be reduced by generation of bi-specific antibodies with only one CD47 binding arm (Masternak et al. *Cancer Res* 2015; 75(15 Suppl): Abstract no. 2482). Because some anti-CD47 mAbs have been shown to result in reduction of RBCs when administered to cynomolgus monkeys (Mounho-Zamora B. et al. The Toxicologist, Supplement to Toxicological Sciences, 2015; 144 (1): Abstract 596: 127, Liu et al. *PLoS One.* 2015 Sep. 21; 10(9): e0137345; Pietsch et al. *Cancer Res* 2015; 75(15 Suppl): Abstract nr 2470), it is highly desirable to identify anti-CD47 mAbs that have reduced or minimal binding to CD47-expressing RBCs.

As used herein, the terms "red blood cell(s)" and "erythrocyte(s)" are synonymous and used interchangeably herein.

As used herein, the term "reduced binding to hRBCs" refers to an apparent Kd of an anti-CD47 mAb binding to a hRBC which is 8-fold or greater than the apparent Kd on a human tumor cell, wherein the tumor cell is an OV10 hCD47 cell (human OV10 ovarian cancer cell line expressing human CD47).

As used herein, the term "minimal binding" or "MB" refers to no measurable binding to hRBCs at an anti-CD47 mAb concentration up to 5,000 pM.

Prior to the disclosure described herein, no monospecific anti-CD47 mAbs have been reported that have minimal binding to human RBCs expressing CD47.

Some of the anti-CD47 mAbs, disclosed herein, have reduced or minimal binding to human RBCs.

Binding to Human Endothelial Cells and Other Normal Human Cells

In addition to expression/overexpression on most hematological malignancies and solid tumors (Willingham et al., *Proc Natl Acad Sci* 2012), CD47 is also expressed, by many but not all, normal cell types, including, but not limited to RBCs (see previous section), lymphocytes and mononuclear cells, endothelial cells, and brain, liver, muscle cells and/or tissues (Brown et al., *J Cell Biol* 1990; Reinhold et al., *J Cell Sci.* 1995; Matozaki et al., *Cell* 2009; Stefanidakis et al., *Blood* 2008; Xiao et al., *Cancer Letters* 2015). Because of this expression, it is expected that some anti-CD47 mAbs would bind to these normal cell types/tissues in addition to the cancer cells which are the therapeutic target. It is therefore desirable to identify anti-CD47 mAbs that either have reduced or minimal binding to some of these normal cells to both reduce potential non-desired effects on these normal cells and also allow more available antibody for binding to the tumor cells. Anti-CD47 mAbs with such reduced or minimal binding to normal cells have not been described.

As used herein, the terms "reduced binding to normal human cells which includes, but is not limited to, endothelial cells, skeletal muscle cells, epithelial cells, and peripheral blood mononuclear cells (e.g., human aortic endothelial cells, human skeletal muscle cells, human microvascular endothelial cells, human renal tubular epithelial cells, human peripherial blood CD3+ cells, and human peripheral blood mononuclear cells) refers to the apparent Kd of an anti-CD47 mAb binding to these cells which is 8-fold or greater than the apparent Kd of the anti-CD47 mAb binding to a human tumor cell, wherein the tumor cell is OV10 hCD47.

As used herein, the term "minimal binding" or "MB" refers to no measurable binding of an antibody or other molecule as described herein to normal human cells which includes, but is not limited to, endothelial cells, skeletal muscle cells, epithelial cells, and peripheral blood mononuclear cells (e.g., human aortic endothelial cells, human skeletal muscle cells, human microvascular endothelial cells, human renal tubular epithelial cells, human peripherial blood CD3+ cells, and human peripheral blood mononuclear cells) at an anti-CD47 mAb concentration up to 5,000 pM.

Agglutination of RBCs

Red blood cell (RBC) agglutination or hemagglutination is a homotypic interaction that occurs when RBCs aggregate or clump together following incubation with various agents, including antibodies to RBC antigens and cell surface proteins such as CD47. Many anti-CD47 antibodies have been reported to cause hemagglutination of washed human RBCs in vitro, in a concentration dependent manner, including B6H12, BRIC126, MABL-1, MABL-2, CC2C6, and 5F9 (Uger R. et al. *Cancer Res* 2014; 74(19 Suppl): Abstract no. 5011, U.S. Pat. No. 9,045,541, Uno et al. *Oncol Rep.* 17: 1189-94, 2007; Kikuchi et al. *Biochem Biophys Res. Commun.* 315: 912-8, 2004; Sikic B. et al. *J Clin Oncol* 2016; 34 (suppl; abstract 3019)). This functional effect requires binding to RBCs by an intact, bivalent antibody and can be reduced or eliminated by generating antibody fragments, either a F(ab') or svFv (Uno et al. *Oncol Rep.* 17: 1189-94, 2007; Kikuchi et al. *Biochem Biophys Res. Commun.* 315: 912-8, 2004) or bi-specific antibodies with only one CD47 binding arm (Masternak et al. *Cancer Res* 2015; 75(15 Suppl): Abstract no. 2482). Other functional properties of these fragments, including cell killing, were shown to be either reduced or retained in these fragments (Uno et al. *Oncol Rep.* 17: 1189-94, 2007; Kikuchi et al. *Biochem Biophys Res. Commun.* 315: 912-8, 2004). The mouse antibody 2D3 is an example of an anti-CD47 antibody that binds to CD47 on red blood cells but does not cause hemagglutination (U.S. Pat. No. 9,045,541, Petrova et al. *Cancer Res* 2015; 75(15 Suppl): Abstract no. 4271).

Hemagglutination has been shown to be reduced/eliminated by reducing the binding selectively to human RBCs, but not other cells, using a SIRPα-Fc fusion protein (Uger R. et al. *Blood* 2013; 122(21): 3935). In addition, mouse anti-CD47 mAb 2A1 and humanized versions of 2A1 have been reported to block CD47/SIRPα but do not exhibit hemagglutination activity in a washed RBC assay (U.S. Pat. No. 9,045,541; Narla et al. *Proc Am Assoc Cancer Res* 58: 1200, 2017; abst 4694). A small number of a panel of mouse anti-human CD47 antibodies (8 of 23) were reported to not cause hemagglutination of human RBCs (Pietsch E et al. *Blood Cancer Journal* (2017) 7, e536; doi:10.1038/bcj.2017.7). Therefore, prior to the disclosure described herein, there was a need to identify CD47 mAbs that block SIRPα/CD47 binding, have reduced or minimal binding to RBCs and/or cause no detectable hemagglutination. The term "agglutination" refers to cellular clumping, while the term "hemagglutination" refers to clumping of a specific subset of cells, i.e., RBCs. Thus, hemagglutination is a type of agglutination.

As used herein, the term "reduced hemagglutination" refers to detectable agglutination activity of hRBCs at anti-CD47 mAb concentrations greater than or equal to 1.85 μg/ml, and no measurable activity at concentrations less than 1.85 μg/ml in a washed RBC assay, as visualized by discrete punctate dot compared to a diffuse pattern that represents hemagglutination.

As used herein, the term "no detectable hemagglutination" refers to no visible or detectable agglutination activity of hRBCs at anti-CD47 mAb concentrations greater or equal to 0.3 pg/ml to a concentration less than or equal to 10 μg/ml in a washed RBC assay, as visualized by discrete punctate dot compared to a diffuse pattern that represents hemagglutination.

Some of the anti-CD47 antibodies described herein, cause reduced or no detectable hemagglutination of human RBCs.

Modulation of the NO Pathway

As noted above, TSP1 is also a ligand for CD47. The TSP1/CD47 pathway opposes the beneficial effects of the NO pathway in many cell types, including, but not limited to, vascular cells. The NO pathway consists of any of three enzymes (nitric oxide synthases, NOS I, NOS II and NOS III) that generate bioactive gas NO using arginine as a substrate. NO can act within the cell in which it is produced, or in neighboring cells, to activate the enzyme soluble guanylyl cyclase that produces the messenger molecule cyclic GMP (cGMP). The proper functioning of the NO/cGMP pathway is essential for protecting the cardiovascular system against stresses including, but not limited to, those resulting from wounding, inflammation, hypertension, metabolic syndrome, ischemia, and IRI. In the context of these cellular stresses the inhibition of the NO/cGMP pathway by the TSP1/CD47 system exacerbates the effects of stress. This is a particular problem in the cardiovascular system where both cGMP and cAMP play important protective roles. There are many cases in which ischemia and reperfusion injury cause or contribute to disease, trauma, and poor outcomes of surgical procedures.

As disclosed herein, one of more of the chimeric or humanized anti-CD47 antibodies will reverse TSP1 inhibition of cGMP production. Reversal will be complete (>80%) or intermediate (20%-80%). This reversal of TSP1 inhibition of cGMP production will demonstrate that the anti-CD47 mAbs have the ability to increase NO signaling and suggest utility in protecting the cardiovascular system against stresses including, but not limited to, those resulting from wounding, inflammation, hypertension, metabolic syndrome, ischemia, and ischemia-reperfusion injury (IRI). Additional assay systems, for example smooth muscle cell contraction, will also be expected to show that some of the chimeric or humanized antibodies reverse the inhibitory actions of TSP1 on downstream effects resulting from the activation of NO signaling.

As disclosed herein, "complete reversal of NO pathway inhibition" refers to greater than 80% reversal of TSP1 inhibition of NO signaling by an anti-CD47 mAb compared to a negative control, humanized isotype-matched antibody or no treatment.

As disclosed herein, "intermediate reversal of NO pathway inhibition" refers to 20-80% reversal of TSP1 inhibition of NO signaling by an anti-CD47 mAb compared to a negative control, humanized isotype-matched antibody or no treatment.

As disclosed herein, "no reversal of NO pathway inhibition" refers to less than 20% reversal of TSP1 inhibition of NO signaling by an anti-CD47 mAb compared to a negative control, humanized isotype-matched antibody or no treatment.

Immunogenic Cell Death

The concept of immunogenic cell death (ICD) has emerged in recent years. This form of cell death, unlike non-immunogenic cell death, stimulates an immune response against antigens from cancer cells. ICD is induced by specific chemotherapy drugs, including anthracyclines (doxorubicin, daurorubicin and mitoxantrone) and oxaliplatin, but not by cisplatin and other chemotherapy drugs. ICD is also induced by bortezomib, cardiac glycosides, photodynamic therapy and radiation Galluzi et al. *Nat Rev Immunol* 17: 97-111, 2016). The distinctive characteristics of ICD of tumor cells are the release from or exposure on tumor cell surfaces of specific ligands: 1) the pre-apoptotic cell surface exposure of calreticulin, 2) the secretion of adenosine triphosphate (ATP), 3) release of high mobility group box 1 (HMGB1), 4) annexin A1 release, 5) type I interferon release and 6) C-X-C motif chemokine ligand 10 (CXCL10) release. These ligands are endogenous damage-associated molecular patterns (DAMPs), which include the cell death-associated molecules (CDAMs) (Kroemer et al. *Annu Rev Immunol* 31: 51-72, 2013). Importantly, each of these ligands induced during ICD binds to specific receptors, referred to as pattern recognition receptors (PRRs), that contribute to an anti-tumor immune response. ATP binds the purinergic receptors PY2, G-protein coupled, 2 (P2RY2) and PX2, ligand-gated ion channel, 7 (P2RX7) on dendritic cells causing dendritic cell recruitment and activation, respectively. Annexin A1 binds to formyl peptide receptor 1 (FPR1) on dendritic cells causing dendritic cell homing. Calreticulin expressed on the surface of tumor cells binds to LRP1 (CD91) on dendritic cells promoting antigen uptake by dendritic cells. HMGB1 binds to toll-like receptor 4 (TLR4) on dendritic cells to cause dendritic cell maturation. As a component of ICD, tumor cells release type I interferon leading to signaling via the type I interferon receptor and the release of the CXCL10 which favors the recruitment of effector CXCR3+ T cells Together, the actions of these ligands on their receptors facilitate recruitment of DCs into the tumor, the engulfment of tumor antigens by DCs and optimal antigen presentation to T cells. Kroemer et al. have proposed that a precise combination of the CDAMs mentioned above elicited by ICD can overcome the mechanisms that normally prevent the activation of anti-tumor immune responses (Kroemer et al. *Annu Rev Immunol* 31: 51-72, 2013; Galluzi et al. *Nat Rev Immunol* 17: 97-111, 2016). When mouse tumor cells treated in vitro with ICD-inducing modalities are administered in vivo to syngeneic mice, they provide effective vaccination that leads to an anti-tumor adaptive immune response, including memory. This vaccination effect cannot be tested in xenograft tumor models because the mice used in these studies lack a complete immune system. The available data indicate that ICD effects induced by chemotherapy or radiation will promote an adaptive anti-tumor immune response in cancer patients. The components of ICD are described in more detail below.

In 2005, it was reported that tumor cells which were dying in response to anthracycline chemotherapy in vitro caused an effective anti-tumor immune response when administered in vivo in the absence of adjuvant (Casares et al. *J Exp Med* 202: 16911701, 2005). This immune response protected mice from subsequent re-challenge with viable cells of the same tumor and caused regression of established tumors. Anthracyclines (doxorubicin, daunorubicin and idarubicin) and mitomycin C induced tumor cell apoptosis with caspase activation, but only apoptosis induced by anthracyclines resulted in immunogenic cell death. Caspase inhibition did not inhibit cell death induced by doxorubicin but did suppress the immunogenicity of tumor cells dying in response to doxorubicin. The central roles of dendritic cells and CD8+ T cells in the immune response elicited by doxorubicin-treated apoptotic tumor cells were established by the demonstration that depletion of these cells abolished the immune response in vivo.

Calreticulin is one of the most abundant proteins in the endoplasmic reticulum (ER). Calreticulin was shown to rapidly translocate preapoptotically from the ER lumen to the surface of cancer cells in response to multiple ICD inducers, including anthracyclines (Obeid et al. Nat Med 13: 54-61, 2007; Kroemer et al. Annu Rev Immunol 31: 51-72, 2013). Blockade or knockdown of calretiulin suppressed the phagocytosis of anthracycline-treated tumor cells by dendritic cells and abolished their immunogenicity in mice. The exposure of calreticulin caused by anthracyclines or oxaliplatin is activated by an ER stress response that involves the phosphorylation of the eukaryotic translation initiation factor eIF2α by the PKR-like ER kinase. Calretiulin, which has a prominent function as an "eat-me" signal (Gardai et al. *Cell* 123: 321-334, 2005) binds to LRP1 (CD91) on dendritic cells and macrophages resulting in phagocytosis of the calreticulin expressing cell, unless the calreticulin-expressing cell expresses a don't eat me signal, such as CD47. Calreticulin also signals through CD91 on antigen presenting cells to cause the release of proinflammatory cytokines and to program Th17 cell responses. In summary, calreticulin expressed as part of immunogenic cell death stimulates antigen presenting cells to engulf dying cells, process their antigens and prime an immune response.

In addition to calreticulin, protein disulfide-isomerase A3 (PDIA3), also called Erp57, was shown to translocate from the ER to the surface of tumor cells following treatment with mitoxantrone, oxaliplatin and irradiation with UVC light (Panaretakis et al. *Cell Death Differ* 15: 1499-1509, 2008; Panaretakis et al. *EMBL J* 28: 578-590, 2009). A human ovarian cancer cell line, primary ovarian cancer cells and a human prostate cancer cell line expressed cell-surface calreticulin, HSP70 and HSP90 following treatment with the anthracyclines doxorubicin and idarubicin (Fucikova et al. *Cancer Res* 71: 4821-4833, 2011). HSP70 and HSP90 bind to the PRR LRP1 on antigen presenting cells; the PRR to which PDIA3 binds has not been identified (Galluzi et al. *Nat Rev Immunol* 17: 97-111, 2016).

TLR4 was shown to be required for cross-presentation of dying tumor cells and to control tumor antigen processing and presentation. Among proteins that were known to bind to and stimulate TLR4, HMGB1 was uniquely released by mouse tumor cells in which ICD was induced by irradiation or doxorubicin (Apetoh et al. *Nat Med* 13: 1050-1059, 2007). The highly efficient induction of an in vivo anti-tumor immune by doxorubicin treatment of mouse tumor cells required the presence of HMGB1 and TLR4, as demonstrated by abrogation of the immune response by inhibition of HMGB1 and knock-out TLR4. These preclinical findings are clinically relevant. Patients with breast cancer who carry a TLR4 loss-of-function allele relapse more quickly after radiotherapy and chemotherapy than those carrying the normal TLR4 allele.

Ghiringhelli et al. showed that mouse tumor cells treated with oxaliplatin, doxorubicin and mitoxanthrone in vitro released ATP and that the ATP binds to the purinergic receptors PY2, G-protein coupled, 2 (P2RY2) and PX2, ligand-gated ion channel, 7 (P2RX7) on dendritic cells (Ghiringhelli et al. Nat Med 15: 1170-1178, 2009). Binding of ATP to P2RX7 on DCs triggers the NOD-like receptor family, pyrin domain containing-3 protein (NLRP3)-dependent caspase-1 activation complex (inflammasome), allowing for the secretion of interleukin-1β (IL-1β), which is essential for the priming of interferon-gamma-producing CD8+ T cells by dying tumor cells. Therefore, the ATP-elicited production of IL-β by DCs appears to be one of the critical factors for the immune system to perceive cell death induced by certain chemotherapy drugs as immunogenic. This paper also reports that HMGB1, a TLR4 agonist, also contributes to the stimulation of the NLRP3 inflammasome in DCs and the secretion of IL-1β. These preclinical results have been shown to have clinical relevance; in a breast cancer cohort, the presence of the P2RX7 loss-of-function allele had a significant negative prognostic impact of metastatic disease-free survival. ATP binding to P2RY2 causes the recruitment of myeloid cells into the tumor microenvironment (Vacchelli et al. *Oncoimmunology* 5: e1118600, 2016)

Michaud et al. demonstrated that autophagy is required for the immunogenicity of chemotherapy-induced cell death (Michaud et al. *Science* 334: 1573-1577, 2011). Release of ATP from dying tumor cells required autophagy and autophagy-competent, but not autophagy-deficient, mouse tumors attracted dendritic cells and T lymphocytes into the tumor microenvironment in response to chemotherapy that induces ICD.

Ma et al. addressed the question of how chemotherapy-induced cell death leads to efficient antigen presentation to T cells (Ma et al. *Immunity* 38: 729-741, 2013). They found that at specific kind of tumor infiltrating lymphocyte, $CD11c^+CD11b^+Ly6C^{hi}$ cells, are particularly important for the induction of anticancer immune responses by anthracyclines. ATP released by dying cancer cells recruited myeloid cells into tumors and stimulated the local differentiation of $CD11c^+CD11b^+Ly6C^{hi}$ cells. These cells were shown to be particularly efficient in capturing and presenting tumor cell antigens and, after adoptive transfer into naïve mice, conferring protection to challenge with living tumor cells of the same cell line.

It has been shown that anthracyclines stimulate the rapid production of type I interferons by tumor cells after activation of TLR3 (Sistugu et al. *Nat Med* 20: 1301-1309, 2014). Type I interferons (IFN) bind to IFN-α and IFN-β receptors on cancer cells and trigger autocrine and paracrine signaling pathways that result in release of CXCL10. Tumors lacking Tlr3 or Ifnar failed to respond to chemotherapy unless type I IFN or CXCL10, respectively, was supplied. These preclinical findings have clinical relevance. A type I IFN-related gene expression signature predicted clinical responses to anthracycline-based chemotherapy in independent cohorts of breast cancer patients.

Another receptor on dendritic cells that is involved in chemotherapy-induced anti-cancer immune response was recently identified: formyl peptide receptor-1, which binds annexin A1 (Vacchelli et al. *Science* 350: 972-978, 2015). Vacchelli et al. designed a screen to identify candidate genetic defects that negatively affect responses to chemotherapy. They identified a loss-of-function allele of the gene encoding formyl peptide receptor 1 (FPR1) that was associated with poor metastatis-free survival and overall survival in breast and colorectal cancer patients receiving adjuvant chemotherapy. The therapeutic effects of anthracyclines were abrogated in tumor-bearing Fpr1−/− mice due to impaired antitumor immunity. FPR1-deficient DCs did not approach dying tumor cells and, therefore, could not elicit antitumor T cell immunity. Two anthracyclines, doxorubicin and mitoxantrone, stimulated the secretion of annexin A1, one of four known ligands of FPR1. FPR1 and annexin A1 promoted stable interactions between dying cancer cells and human or mouse leukocytes.

In addition to anthracyclines and oxaliplatin, other drugs have been shown to induce immunogenic cell death. Cardiac glycosides, including clinically used digoxin and digitoxin, were also shown to be efficient inducers of immunogenic cell death of tumor cells (Menger et al. *Sci Transl Med* 4: 143ra99, 2012). Other chemotherapy agents and cancer drugs that have been reported to induce DAMP expression or release are bleomycin, bortezomib, cyclophosphamide, paclitaxel, vorinistat and cisplatin (Garg et al. *Front Immunol* 588: 1-24, 2015; Menger et al. Sci Transl Med 4: 143ra99, 2012; Martins et al. *Oncogene* 30: 1147-1158, 2011). Importantly, these results have clinical relevance. Administration of digoxin during chemotherapy had a significant positive impact on the overall survival of patients with breast, colorectal, head and neck, and hepatocellular cancers, but failed to improve overall survival of lung and prostate cancer patients.

The anti-CD20 monoclonal antibody rituximab has improved outcomes in multiple B-cell malignancies. The success of rituximab, referred to as a type I anti-CD20 mAb, led to the development of type II anti-CD20 mAbs, including obinutuzumab and tositumomab. Cheadle et al., investigated the induction of immunogenic cell death by anti-CD20 mAbs (Cheadle et al. *Brit J Haematol* 162: 842-862, 2013). They found that the cell death induced by obinutuzumab and tositumomab is a form of immunogenic cell death characterized by the release of HMGB1, HSP90 and ATP. A type I anti-CD20 mAb did not cause release of HMGB1, HSP90 and ATP. Incubation of supernatants from a human tumor cell line treated with obinutuzumab caused maturation of human dendritic cells, consistent with the previously described effects of HMGB1 and ATP on dendritic cells. In contrast to the results reported by Cheadle et al., Zhao et al. reported that both type I and II anti-CD20 mAbs increased HMGB1 release from human diffuse large B cell lymphoma cell lines, but did not cause ATP release or cell surface expression of calreticulin (Zhao et al. *Oncotarget* 6: 27817-27831, 2015).

The release from or exposure on tumor cell surfaces of the DAMPs calreticulin, ATP, HMGB1, annexin A1, type I interferon release, CXCL10, PDIA3, HSP70 and/or HSP90 in response to anti-CD47 mAbs has not been reported. As disclosed herein, anti-CD47 mAbs cause release from or exposure on tumor cell surfaces of one or more of the DAMPs listed above (characteristics of ICD), an unexpected result. These DAMPS are expected to promote a therapeutically beneficial adaptive anti-tumor immune response.

As disclosed herein, "causes an increase in cell surface calreticulin expression on human tumor cells" refers to a statistically significant increase ($p<0.05$) in calreticulin expression by a soluble anti-CD47 mAb compared to the background obtained with a negative control, humanized isotype-matched antibody or no treatment.

As disclosed herein, the term "the release of" is synonymous with secretion and is defined as the extracellular appearance of ATP, HMGB1, annexin A1, type I interferon and CXCL10.

As disclosed herein, "cause an increase in the release of adenosine triphosphate by human tumor cells" refers to a statistically significant increase ($p<0.05$) in ATP in the supernatant caused by a soluble anti-CD47 mAb compared to the background obtained with a negative control, humanized isotype-matched antibody or no treatment.

As disclosed herein, "cause an increase in the release of high mobility group box 1 by human tumor cells" refers to a statistically significant increase ($p<0.05$) in HMGB1 in the supernatant caused by a soluble anti-CD47 mAb compared to the background obtained with a negative control, humanized isotype-matched antibody or no treatment.

As disclosed herein, "causes an increase in the release of type I interferon by human tumor cells" refers to a statistically significant increase ($p<0.05$) in type I interferon in the supernatant or type I interferon mRNA caused by a soluble anti-CD47 mAb compared to the background obtained with a negative control, humanized isotype-matched antibody or no treatment.

As disclosed herein, "causes an increase in the release of C-X-C Motif Chemokine Ligand 10 (CXCL10) by human tumor cells" refers to a statistically significant increase ($p<0.05$) in CXCL10 in the supernatant or CXCL10 mRNA caused by a soluble anti-CD47 mAb compared to the background obtained with a negative control, humanized isotype-matched antibody or no treatment.

As disclosed herein, "causes an increase in cell surface PDIA3 expression on human tumor cells" refers to a statistically significant increase ($p<0.05$) in PDIA3 expression by a soluble anti-CD47 mAb compared to the background obtained with a negative control, humanized isotype-matched antibody or no treatment.

As disclosed herein, "causes an increase in cell surface HSP70 expression on human tumor cells" refers to a statistically significant increase ($p<0.05$) in HSP70 expression by a soluble anti-CD47 mAb compared to the background obtained with a negative control, humanized isotype-matched antibody or no treatment.

As disclosed herein, "causes an increase in cell surface HSP90 expression on human tumor cells" refers to statistically significant increase ($p<0.05$) in HSP90 expression by a soluble anti-CD47 mAb compared to the background obtained with a negative control, humanized isotype-matched antibody or no treatment.

pH Dependence of Anti-CD47 mAb Binding

Most antibody binding, particularly in the blood compartment and to normal cells occurs at physiological pH (approximately 7.4). Therefore, the binding affinity of therapeutic mAbs is normally assessed in vitro at physiological pH. However, the tumor microenvironment (TME) is more acidic in nature, with pH values below 7.4. This appears to be due to a number of differences including hypoxia, anaerobic glycolysis leading to the production of lactic acid and hydrolysis of ATP (Tannock and Rotin, *Cancer Res* 1989; Song et al., *Cancer Drug Discovery and Development* 2006; Chen and Pagel, *Advan Radiol* 2015). The acidic pH may provide an advantage to the tumor by promoting invasiveness, metastatic behavior, chronic autophagy, resistance to chemotherapies and reduced efficacy of immune cells in the tumor microenvironment (Estrella et al. *Cancer Res* 2013; Wojtkowiak et al., *Cancer Res* 2012; Song et al., *Cancer*

*Drug Discovery and Development* 2006; Barar, *BioImpacts*, 2012). The identification of anti-CD47 antibodies with the property of increased binding affinity at acidic pH would confer a therapeutic advantage with higher binding to CD47 on tumor cells within the acidic TME compared to cells at physiological pH. Antibodies with pH-dependent properties have been generated with the goal of recycling antibodies. However, in contrast to exhibiting the properties of enhanced binding at acidic pH, these bind with high affinity to their target antigen at physiological pH, but release their target at acidic pH (Bonvin et al., *mAbs* 2015; Igawa and Hattori, *Biochem Biophys Acta* 2014).

As disclosed herein, "has a greater affinity for CD47 at an acidic pH compared to physiological pH" refers to an apparent Kd that is increased 5-fold or more at acidic pH (<7.4) compared to physiological pH (7.4).

Combinations of Functional Properties

In some embodiments, the anti-CD47 antibodies described herein, are also characterized by combinations of properties which are not exhibited by prior art anti-CD47 antibodies proposed for human therapeutic use. Accordingly, in some embodiments, anti-CD47 antibodies described herein may be characterized by:
 a. binds to human CD47;
 b. blocks SIRPα binding to human CD47;
 c. increases phagocytosis of human tumor cells; and
 d. induces death of susceptible human tumor cells.

In another embodiment described herein, the anti-CD47 antibodies are characterized by:
 a. binds to human CD47;
 b. blocks SIRPα binding to human CD47;
 c. increases phagocytosis of human tumor cells;
 d. induces death of susceptible human tumor cells; and
 e. causes no detectable agglutination of human red blood cells (hRBCs).

In yet another embodiment described herein, the anti-CD47 antibodies are characterized by:
 a. binds to human CD47;
 b. blocks SIRPα binding to human CD47;
 c. increases phagocytosis of human tumor cells;
 d. induces death of susceptible human tumor cells; and
 e. causes reduced agglutination of human red blood cells (hRBCs).

In another embodiment described herein, the anti-CD47 antibodies are characterized by:
 a. binds to human CD47;
 b. blocks SIRPα binding to human CD47;
 c. increases phagocytosis of human tumor cells;
 d. induces death of susceptible human tumor cells; and
 e. has reduced hRBC binding.

In another embodiment described herein, the anti-CD47 antibodies are characterized by:
 a. binds to human CD47;
 b. blocks SIRPα binding to human CD47;
 c. increases phagocytosis of human tumor cells;
 d. causes no detectable agglutination of human red blood cells (hRBCs); and
 e. has minimal binding to hRBCs.

In another embodiment described herein, the anti-CD47 antibodies are characterized by:
 a. binds to human CD47;
 b. blocks SIRPα binding to human CD47;
 c. increases phagocytosis of human tumor cells;
 d. causes no detectable agglutination of human red blood cells (hRBCs); and
 e. has reduced hRBC binding.

In another embodiment described herein, the monoclonal antibody, or antigen binding fragment thereof binds to human, non-human primate, mouse, rabbit, and rat CD47.

In yet another embodiment described herein, the monoclonal antibody, or antigen binding fragment thereof specifically also binds to non-human primate CD47, wherein non-human primate may include, but is not limited to, cynomolgus monkey, green monkey, rhesus monkey and squirrel monkey.

In another embodiment, the anti-CD47 monoclonal antibody, or antigen binding fragment thereof, may additionally possess one or more of the following characteristics: 1) exhibit cross-reactivity with one or more species homologs of CD47; 2) block the interaction between CD47 and its ligand SIRPα; 3) increase phagocytosis of human tumor cells; 4) induce death of susceptible human tumor cells; 5) do not induce cell death of human tumor cells; 6) do not have reduced or minimal binding to human red blood cells (hRBCs); 7) have reduced binding to hRBCs; 8) have minimal binding to hRBCs; 9) cause reduced agglutination of hRBCs; 10) cause no detectable agglutination of hRBCs; 11) reverse TSP1 inhibition of the nitric oxide (NO) pathway; 12) do not reverse TSP1 inhibition of the NO pathway; 13) cause loss of mitochondrial membrane potential; 14) do not cause cause loss of mitochondrial membrane potential; 15) cause an increase in cell surface calreticulin expression on human tumor cells; 16) do not cause an increase in cell surface calreticulin expression on human tumor cells; 17) cause an increase in adenosine triphosphate (ATP) release by human tumor cells; 18) do not cause an increase in adenosine triphosphate (ATP) release by human tumor cells; 19) cause an increase in high mobility group box 1 (HMGB1) release by human tumor cells; 20) do not cause an increase in high mobility group box 1 (HMGB1) release by human tumor cells; 21) cause an increase in type I interferon release by human tumor cells; 22) do not cause an increase in type I interferon release by human tumor cells; 23) cause an increase in C-X-C Motif Chemokine Ligand 10 (CXCL10) release by human tumor cells; 24) do not cause an increase in C-X-C Motif Chemokine Ligand 10 (CXCL10) release by human tumor cells; 25) cause an increase in cell surface protein disulfide-isomerase A3 (PDIA3) expression on human tumor cells; 26) do not cause an increase in cell surface protein disulfide-isomerase A3 (PDIA3) expression on human tumor cells; 27) cause an increase in cell surface heat shock protein 70 (HSP70) expression on human tumor cells; 28) do not cause an increase in cell surface heat shock protein 70 (HSP70) expression on human tumor cells; 29) cause an increase in cell surface heat shock protein 90 (HSP90) expression on human tumor cells; 30) do not cause an increase in cell surface heat shock protein 90 (HSP90) expression on human tumor cells; 31) have reduced binding to normal human cells, which includes, but is not limited to, endothelial cells, skeletal muscle cells, epithelial cells, and peripheral blood mononuclear cells (e.g., human aortic endothelial cells, human skeletal muscle cells, human microvascular endothelial cells, human renal tubular epithelial cells, human peripherial blood CD3+ cells, and human peripheral blood mononuclear cells); 32) do not have reduced binding to normal human cells, which includes, but is not limited to, endothelial cells, skeletal muscle cells, epithelial cells, and peripheral blood mononuclear cells (e.g., human aortic endothelial cells, human skeletal muscle cells, human microvascular endothelial cells, human renal tubular epithelial cells, human peripherial blood CD3+ cells, and human peripheral blood mononuclear cells); 33) have a greater affinity for human CD47 at an acidic pH compared to physiological pH; 34) do not have a greater affinity for human CD47 at an acidic pH compared to physiological pH; and 35) cause an increase in annexin A1 release by human tumor cells.

In some embodiments, a monoclonal antibody, or an antigen binding fragment thereof, is provided, which: binds to human CD47; blocks SIRPα binding to human CD47; increases phagocytosis of human tumor cells; and induces death of human tumor cells; wherein said monoclonal antibody, or an antigen binding fragment thereof, exhibits pH-dependent binding to CD47 present on a cell. In other embodiments, the disclosure provides a monoclonal antibody, or an antigen binding fragment thereof, which: binds to human CD47; blocks SIRPα binding to human CD47; increases phagocytosis of human tumor cells; and induces death of human tumor cells; wherein said monoclonal antibody, or an antigen binding fragment thereof, exhibits reduced binding to normal cells. In some embodiments, a cell to which such an antibody may bind may be of any cell type as described herein. In other embodiments, a monoclonal antibody as described herein, or an antigen binding fragment thereof, may exhibit any combination of characteristics provided in the present disclosure. For example, a monoclonal antibody may beneficially exhibit both pH dependent binding and reduced binding to a cell. These cells may be an endothelial cell, a skeletal muscle cell, an epithelial cell, a PBMC or a RBC (e.g., human aortic endothelial cells, human skeletal muscle cells, human microvascular endothelial cells, human renal tubular epithelial cells, human peripherial blood CD3+ cells, human peripheral blood mononuclear cells or human RBC). Such characteristics may be exhibited individually or in any combination as described herein. As used herein, pH dependent binding of an antibody of the disclosure may refer to altered binding of the antibody at a particular pH, for example an antibody that exhibits increased binding affinity at acidic pH.

CD47 Antibodies

Many human cancers up-regulate cell surface expression of CD47 and those expressing the highest levels of CD47 appear to be the most aggressive and the most lethal for patients. Increased CD47 expression is thought to protect cancer cells from phagocytic clearance by sending a "don't eat me" signal to macrophages via SIRPα, an inhibitory receptor that prevents phagocytosis of CD47-bearing cells (Oldenborg et al. *Science* 288: 2051-2054, 2000; Jaiswal et al. (2009) *Cell* 138(2):271-851; Chao et al. (2010) *Science Translational Medicine* 2(63):63ra94). Thus, the increase of CD47 expression by many cancers provides them with a cloak of "selfness" that slows their phagocytic clearance by macrophages and dendritic cells.

Antibodies that block CD47 and prevent its binding to SIRPα have shown efficacy in human tumor in murine (xenograft) tumor models. Such blocking anti-CD47 mAbs exhibiting this property increase the phagocytosis of cancer cells by macrophages, which can reduce tumor burden (Majeti et al. (2009) *Cell* 138 (2): 286-99; U.S. Pat. No. 9,045,541; Willingham et al. (2012) *Proc Natl Acad. Sci. USA* 109(17):6662-6667; Xiao et al. (2015) *Cancer Letters* 360:302-309; Chao et al. (2012) *Cell* 142:699-713; Kim et al. (2012) *Leukemia* 26:2538-2545).

Anti-CD47 mAbs have also been shown to promote an adaptive immune response to tumors in vivo (Tseng et al. (2013) *PNAS* 110 (27):11103-11108; Soto-Pantoja et al. (2014) *Cancer Res.* 74 (23): 6771-6783; Liu et al. (2015) *Nat. Med.* 21 (10): 1209-1215; Xu et al. (2017) *Immunity* 47: 363-373).

However, there are mechanisms by which anti-CD47 mAbs can attack transformed cells that have not yet been exploited in the treatment of cancer. Multiple groups have shown that particular anti-human CD47 mAbs induce cell death of human tumor cells. Anti-CD47 mAb Ad22 induces cell death of multiple human tumor cells lines (Pettersen et al. *J. Immunol.* 166: 4931-4942, 2001; Lamy et al. *J. Biol. Chem.* 278: 23915-23921, 2003). AD22 was shown to indice rapid mitochondrial dysfunction and rapid cell death with early phosphatidylserine exposure and a drop in mitochondrial membrane potential (Lamy et al. *J. Biol. Chem.* 278: 23915-23921, 2003). Anti-CD47 mAb MABL-2 and fragments thereof induce cell death of human leukemia cell lines, but not normal cells in vitro and had an anti-tumor effect in in vivo xenograft models. (Uno et al. (2007) *Oncol. Rep.* 17 (5): 1189-94). Anti-human CD47 mAb 1F7 induces cell death of human T cell leukemias (Manna and Frazier (2003) *J. Immunol.* 170: 3544-53) and several breast cancers (Manna and Frazier (2004) *Cancer Research* 64 (3):1026-36). 1F7 kills CD47-bearing tumor cells without the action of complement or cell mediated killing by NK cells, T cells, or macrophages. Instead, anti-CD47 mAb 1F7 acts via a non-apoptotic mechanism that involves a direct CD47-dependent attack on mitochondria, discharging their membrane potential and destroying the ATP-generating capacity of the cell leading to rapid cell death. It is noteworthy that anti-CD47 mAb 1F7 does not kill resting leukocytes, which also express CD47, but only those cells that are "activated" by transformation. Thus, normal circulating cells, many of which express CD47, are spared while cancer cells are selectively killed by the tumor-toxic CD47 mAb (Manna and Frazier (2003) *J. Immunol.* 170: 3544-53). This mechanism can be thought of as a proactive, selective and direct attack on tumor cells in contrast to the passive mechanism of causing phagocytosis by simply blocking CD47/SIRPα binding. Importantly, mAb 1F7 also blocks binding of SIRPα to CD47 (Rebres et al., *J. Cellular Physiol.* 205: 182-193, 2005) and thus it can act via two mechanisms: (1) direct tumor toxicity, and (2) causing phagocytosis of cancer cells. A single mAb that can accomplish both functions may be superior to one that only blocks CD47/SIRPα binding.

An additional mechanism by which anti-CD47 mAbs can be exploited in the treatment of cancer is through the promotion of an anti-tumor immune response. The discovery that anti-CD47 mAbs cause tumor cells to release DAMPs that cause maturation, activation and homing of DCs and attraction of T cells connects anti-CD47 mAb treatment to the development of the therapeutically desirable anti-tumor immune response. Anti-CD47 mAbs have not been previously shown to cause tumor cell release of ATP, HMGB1, annexin A1, type I interferons and CXCL10 and tumor cell expression of calreticulin, PDIA3, HSP70 and HSP90.

Following periods of tissue ischemia, the initiation of blood flow causes damage referred to as "ischemia-reperfusion injury" or IRI. IRI contributes to poor outcomes in many surgical procedures where IRI occurs due to the necessity to stop blood flow for a period of time, in many forms/causes of trauma in which blood flow is interrupted and later restored by therapeutic intervention and in procedures required for organ transplantation, cardio/pulmonary bypass procedures, reattachment of severed body parts, reconstructive and cosmetic surgeries and other situations involving stopping and restarting blood flow. Ischemia itself causes many physiological changes that, by themselves would eventually lead to cell and tissue necrosis and death. Reperfusion poses its own set of damaging events including generation of reactive oxygen species, thrombosis, inflammation and cytokine mediated damage. The pathways that are limited by the TSP1-CD47 system are precisely those that would be of most benefit in combating the damage of IRI, including the NO pathway. Thus, blocking the TSP1-CD47 pathway, as with the antibodies disclosed herein, will provide more robust functioning of these endogenous protective pathways. Anti-CD47 mAbs have been shown to reduce organ damage in rodent models of renal warm ishchemia (Rogers et al. *J Am Soc Nephrol.* 23: 1538-1550, 2012), liver ischemia-reperfusion injury (Isenberg et al. *Surgery.* 144: 752-761, 2008), renal transplantation (Lin et al. *Transplantation.* 98: 394-401, 2014; Rogers et al. *Kidney International.* 90: 334-347, 2016)) and liver transplantation, including steatotic livers (Xiao et al. *Liver Transpl.* 21: 468-477, 2015; Xiao et al. *Transplantation.* 100: 1480-1489, 2016). In addition, anti-CD47 mAb caused significant reductions of right ventricular systolic pressure and right ventricular hypertrophy in the monocrotaline model of pulmonary arterial hypertension (Bauer et al. *Cardiovasc Res.* 93: 682-693, 2012). Studies in skin flap models have shown that modulation of CD47, including with anti-CD47 mAbs, inhibits TSP1-mediated CD47 signaling. This results in increased activity of the NO pathway, resulting in reduced IRI (Maxhimer et al. *Plast Reconstr Surg.* 124: 1880-1889, 2009; Isenberg et al. *Arterioscler Throm Vasc Biol.* 27: 2582-2588, 2007; Isenberg et al. *Curr Drug Targets.* 9: 833-841, 2008; Isenberg et al. *Ann Surg.* 247: 180-190, 2008)

Anti-CD47 mAbs have also been shown to be efficacious in models of other cardiovascular diseases. In the mouse transverse aortic constriction model of pressure overload left ventricular heart failure, anti-CD47 mAb mitigated cardiac myocyte hypertrophy, decreased left ventricular fibrosis, prevented an increase in left ventricular weight, decreased ventricular stiffness, and normalized changes in the pressure volume loop profile (Sharifi-Sanjani et al. *J Am Heart Assoc.,* 2014). An anti-CD47 mAb ameliorated atherosclerosis in multiple mouse models (Kojima et al. *Nature.,* 2016).

Cancer Indications

Presently disclosed are anti-CD47 mAbs and antigen binding fragments thereof effective as cancer therapeutics which can be administered to patients, preferably parenterally, with susceptible hematologic cancers and solid tumors including, but not limited to, leukemias, including systemic mastocytosis, acute lymphocytic (lymphoblastic) leukemia (ALL), T cell-ALL, acute myeloid leukemia (AML), myelogenous leukemia, chronic lymphocytic leukemia (CLL), chronic myeloid leukemia (CML), myeloproliferative disorder/neoplasm, monocytic cell leukemia, and plasma cell leukemia; multiple myeloma (MM); Waldenstrom's Macroglobulinemia; lymphomas, including histiocytic lymphoma and T cell lymphoma, B cell lymphomas, including Hodgkin's lymphoma and non-Hodgkin's lymphoma, such as low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL; solid tumors, including ovarian cancer, breast cancer, endometrial cancer, colon cancer (colorectal cancer), rectal cancer, bladder cancer, urothelial cancer, lung cancer (non-small cell lung cancer, adenocarcinoma of the lung, squamous cell carcinoma of the lung), bronchial cancer, bone cancer, prostate cancer, pancreatic cancer, gastric cancer, hepatocellular carcinoma (liver cancer, hepatoma), gall bladder cancer, bile duct cancer, esophageal cancer, renal cell carcinoma, thyroid cancer, squamous cell carcinoma of the head and neck (head and neck cancer), testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, meduloblastoma, astrocytoma, glioma, meningioma, gastrinoma, neuroblastoma, myelodysplastic syndrome, and sarcomas including, but not limited to, osteosarcoma, Ewing's sarcoma, leiomyosarcoma, synovial sarcoma, alveolar soft part sarcoma, angiosarcoma, liposarcoma, fibrosarcoma, rhabdomyosarcoma, chrondrosarcoma, and melanoma.

Treatment of Cancer

As is well known to those of ordinary skill in the art, combination therapies are often employed in cancer treatment as single-agent therapies or procedures may not be sufficient to treat or cure the disease or condition. Conventional cancer treatments often involve surgery, radiation treatment, the administration of a combination of cytotoxic drugs to achieve additive or synergistic effects, and combinations of any or all of these approaches. Especially useful chemotherapeutic and biologic therapy combinations employ drugs that work via different mechanisms of action, increasing cancer cell control or killing, increasing the ability of the immune system to control cancer cell growth, reducing the likelihood of drug resistance during therapy, and minimizing possible overlapping toxicities by permitting the use of reduced doses of individual drugs.

Classes of conventional anti-tumor/anti-neoplastic agents useful in the combination therapies encompassed by the present methods are disclosed, for example, in Goodman & Gilman's The Pharmacological Basis of Therapeutics, Twelfth Edition (2010) L. L. Brunton, B. A. Chabner, and B. C. Knollmann Eds., Section VIII, "Chemotherapy of Neoplastic Diseases", Chapters 60-63, pp. 1665-1770, McGraw-Hill, NY, and include, for example, alkylating agents, antimetabolites, natural products, a variety of miscellaneous agents, hormones and antagonists, targeted drugs, monoclonal antibodies and other protein therapeutics.

In addition to the foregoing, the methods of the present disclosure are related to treatment of cancer indications and further comprises treating the patient via surgery, radiation, and/or administering to a patient in need thereof an effective amount of a chemical small molecule or biologic drug including, but not limited to, a peptide, polypeptide, protein, nucleic acid therapeutic, conventionally used or currently being developed, to treat tumorous conditions. This includes antibodies and antigen-binding fragments, other than those disclosed herein, cytokines, antisense oligonucleotides, siRNAs, and miRNAs.

The therapeutic methods disclosed and claimed herein include the use of the antibodies disclosed herein alone, and/or in combinations with one another, and/or with antigen-binding fragments thereof of the present disclosure that bind to CD47, and/or with competing antibodies exhibiting appropriate biological/therapeutic activity, as well, for example, all possible combinations of these antibody compounds to achieve the greatest treatment efficacy.

In addition, the present therapeutic methods also encompass the use of these antibodies, antigen-binding fragments thereof, competing antibodies and combinations thereof further in combination with: (1) any one or more anti-tumor therapeutic treatments selected from surgery, radiation, antitumor, anti-neoplastic agents, and combinations of any of these, or (2) any one or more of anti-tumor biological agents, or (3) equivalents of any of the foregoing of (1) or (2) as would be apparent to one of ordinary skill in the art, in appropriate combination(s) to achieve the desired therapeutic treatment effect for the particular indication.

Antibody and small molecule drugs that increase the immune response to cancer by modulating co-stimulatory or inhibitory interactions that influence the T cell response to tumor antigens, including inhibitors of immune checkpoints and modulators of co-stimulatory molecules, are also of particular interest in the context of the combination therapeutic methods encompassed herein and include, but are not limited to, other anti-CD47 antibodies. Administration of therapeutic agents that bind to the CD47 protein, for example, antibodies or small molecules that bind to CD47 and prevent interaction between CD47 and SIRPα, are administered to a patient, causing the clearance of cancer cells via phagocytosis. The therapeutic agent that binds to the CD47 protein is combined with a therapeutic agent such as an antibody, a chemical small molecule or biologic drug disclosed herein, directed against one or more additional cellular targets of CD70 (Cluster of Differentiation 70), CD200 (OX-2 membrane glycoprotein, Cluster of Differentiation 200), CD154 (Cluster of Differentiation 154, CD40L, CD40 ligand, Cluster of Differentiation 40 ligand), CD223 (Lymphocyte-activation gene 3, LAG3, Cluster of Differentiation 223), KIR (Killer-cell immunoglobulin-like receptors), GITR (TNFRSF18, glucocorticoid-induced TNFR-related protein, activation-inducible TNFR family receptor, AITR, Tumor necrosis factor receptor superfamily member 18), CD28 (Cluster of Differentiation 28), CD40 (Cluster of Differentiation 40, Bp50, CDW40, TNFRSF5, Tumor necrosis factor receptor superfamily member 5, p50), CD86 (B7-2, Cluster of Differentiation 86), CD160 (Cluster of Differentiation 160, BY55, NK1, NK28), CD258 (LIGHT, Cluster of Differentiation 258, Tumor necrosis factor ligand superfamily member 14, TNFSF14, HVEML, HVEM ligand, herpesvirus entry mediator ligand, LTg), CD270 (HVEM, Tumor necrosis factor receptor superfamily member 14, herpesvirus entry mediator, Cluster of Differentiation 270, LIGHTR, HVEA), CD275 (ICOSL, ICOS ligand, Inducible T-cell co-stimulator ligand, Cluster of Differentiation 275), CD276 (B7-H3, B7 homolog 3, Cluster of Differentiation 276), OX40L (OX40 Ligand), B7-H4 (B7 homolog 4, VTCN1, V-set domain-containing T-cell activation inhibitor 1), GITRL (Glucocorticoid-induced tumor necrosis factor receptor-ligand, glucocorticoid-induced TNFR-ligand), 4-1BBL (4-1BB ligand), CD3 (Cluster of Differentiation 3, T3D), CD25 (IL2Rα, Cluster of Differentiation 25, Interleukin-2 Receptor α chain, IL-2 Receptor α chain), CD48 (Cluster of Differentiation 48, B-lymphocyte activation marker, BLAST-1, signaling lymphocytic activation molecule 2, SLAMF2), CD66a (Ceacam-1, Carcinoembryonic antigen-related cell adhesion molecule 1, biliary glycoprotein, BGP, BGP1, BGPI, Cluster of Differentiation 66a), CD80 (B7-1, Cluster of Differentiation 80), CD94 (Cluster of Differentiation 94), NKG2A (Natural killer group 2A, killer cell lectin-like receptor subfamily D member 1, KLRD1), CD96 (Cluster of Differentiation 96, TActILE, T cell activation increased late expression), CD112 (PVRL2, nectin, Poliovirus receptor-related 2, herpesvirus entry mediator B, HVEB, nectin-2, Cluster of Differentiation 112), CD115 (CSF1R, Colony stimulating factor 1 receptor, macrophage colony-stimulating factor receptor, M-CSFR, Cluster of Differentiation 115), CD205 (DEC-205, LY75, Lymphocyte antigen 75, Cluster of Differentiation 205), CD226 (DNAM1, Cluster of Differentiation 226, DNAX Accessory Molecule-1, PTA1, platelet and T cell activation antigen 1), CD244 (Cluster of Differentiation 244, Natural killer cell receptor 2B4), CD262 (DR5, TrailR2, TRAIL-R2, Tumor necrosis factor receptor superfamily member 10b, TNFRSF10B, Cluster of Differentiation 262, KILLER, TRICK2, TRICKB, ZTNFR9, TRICK2A, TRICK2B), CD284 (Toll-like Receptor-4, TLR4, Cluster of Differentiation 284), CD288 (Toll-like Receptor-8, TLR8, Cluster of Differentiation 288), TNFSF15 (Tumor necrosis factor superfamily member 15, Vascular endothelial growth inhibitor, VEGI, TL1A), TDO2 (Tryptophan 2,3-dioxygenase, TPH2, TRPO), IGF-1R (Type I Insulin-like Growth Factor), GD2 (Disialoganglioside 2), TMIGD2 (Transmembrane and immunoglobulin domain-containing protein 2), RGMB (RGM domain family, member B), VISTA (V-domain immunoglobulin-containing suppressor of T-cell activation, B7-H5, B7 homolog 5), BTNL2 (Butyrophilin-like protein 2), Btn (Butyrophilin family), TIGIT (T cell Immunoreceptor with Ig and ITIM domains, Vstm3, WUCAM), Siglecs (Sialic acid binding Ig-like lectins), Neurophilin, VEGFR (Vascular endothelial growth factor receptor), ILT family (LIRs, immunoglobulin-like transcript family, leukocyte immunoglobulin-like receptors), NKG families (Natural killer group families, C-type lectin transmembrane receptors), MICA (MHC class I polypeptide-related sequence A), TGFβ (Transforming growth factor β), STING pathway (Stimulator of interferon gene pathway), Arginase (Arginine amidinase, canavanase, L-arginase, arginine transamidinase), EGFRvIII (Epidermal growth factor receptor variant III), and HHLA2 (B7-H7, B7y, HERV-H LTR-associating protein 2, B7 homolog 7), inhibitors of PD-1 (Programmed cell death protein 1, PD-1, CD279, Cluster of Differentiation 279), PD-L1 (B7-H1, B7 homolog 1, Programmed death-ligand 1, CD274, cluster of Differentiation 274), PD-L2 (B7-DC, Programmed cell death 1 ligand 2, PDCD1LG2, CD273, Cluster of Differentiation 273), CTLA-4 (Cytotoxic T-lymphocyte-associated protein 4, CD152, Cluster of Differentiation 152), BTLA (B- and T-lymphocyte attenuator, CD272, Cluster of Differentiation 272), Indoleamine 2,3-dioxygenase (IDO, IDO1), TIM3 (HAVCR2, Hepatitis A virus cellular receptor 2, T cell immunoglobulin mucin-3, KIM-3, Kidney injury molecule 3, TIMD-3, T cell immunoglobulin mucin-domain 3), A2A adenosine receptor (ADO receptor), CD39 (ectonucleoside triphosphate diphosphohydrolase-1, Cluster of Differentiation 39, ENTPD1), and CD73 (Ecto-5'-nucleotidase, 5'-nucleotidase, 5'-NT, Cluster of Differentiation 73), CD27 (Cluster of Differentiation 27), ICOS (CD278, Cluster of Differentiation 278, Inducible T-cell Co-stimulator), CD137 (4-1BB, Cluster of Differentiation 137, tumor necrosis factor receptor superfamily member 9, TNFRSF9), OX40 (CD134, Cluster of Differentiation 134), and TNFSF25 (Tumor necrosis factor receptor superfamily member 25), including antibodies, small molecules, and agonists, are also specifically contemplated herein. Additional agents include IL-10 (Interleukin-10, human cytokine synthesis inhibitory factor, CSIF) and Galectins.

YERVOY® (ipilimumab; Bristol-Meyers Squibb) is an example of an approved anti-CTLA-4 antibody.

KEYTRUDA® (pembrolizumab; Merck) and OPDIVO® (nivolumab; Bristol-Meyers Squibb Company) are examples of approved anti-PD-1 antibodies.

TECENTRIQ® (atezolizumab; Roche) is an example of an approved anti-PD-L1 antibody.

Ischemia-Reperfusion Injury (IRI)-Related, Autoimmune, Autoinflammatory, Inflammatory, Cardiovascular Conditions and Diseases Administration of a CD47 mAb or antigen binding fragment thereof disclosed herein can be used to treat a number of diseases and conditions in which IRI is a contributing feature, and to treat various autoimmune, autoinflammatory, inflammatory and cardiovascular diseases. These include: organ transplantation in which a mAb or antigen binding fragment thereof of the present disclosure is administered to the donor prior to organ harvest, to the harvested donor organ in the organ preservation solution, to the recipient patient, or to any combination thereof; skin grafting; surgical resections or tissue reconstruction in which such mAb or fragment is administered either locally by injection to the affected tissue or parenterally to the patient; reattachment of body parts; treatment of traumatic injury; pulmonary hypertension; pulmonary arterial hypertension; sickle cell disease (crisis); myocardial infarction; cerebrovascular disease; stroke; surgically-induced ischemia; acute kidney disease/kidney failure; any other condition in which IRI occurs and contributes to the pathogenesis of disease; autoimmune and inflammatory diseases, including arthritis, rheumatoid arthritis, multiple sclerosis, psoriasis, psoriatic arthritis, Crohn's disease, inflammatory bowel disease, ulcerative colitis, lupus, systemic lupus erythematous, juvenile rheumatoid arthritis, juvenile idiopathic arthritis, Grave's disease, Hashimoto's thyroiditis, Addison's disease, celiac disease, dermatomyositis, multiple sclerosis, myasthenia gravis, pernicious anemia, Sjögren syndrome, type I diabetes, vasculitis, uveitis, and ankylosing spondylitis; autoinflammatory diseases, including familial Mediterranean fever, neonatal onset multisystem inflammatory disease, tumor necrosis factor (TNF) receptor-associated periodic syndrome, deficiency of the interleukin-1 receptor antagonist, Behçet's disease; cardiovascular diseases, including coronary heart disease, coronary artery disease, atherosclerosis, myocardial infarction, heart failure, and left ventricular heart failure.

Anti-CD47 mAbs and antigen binding fragments thereof of the present disclosure can also be used to increase tissue perfusion in a subject in need of such treatment. Such subjects can be identified by diagnostic procedures indicating a need for increased tissue perfusion. In addition, the need for increased tissue perfusion may arise because the subject has had, is having, or will have, a surgery selected from integument surgery, soft tissue surgery, composite tissue surgery, skin graft surgery, resection of a solid organ, organ transplant surgery, or reattachment or an appendage or other body part.

Treatment of Ischemia-Reperfusion Injury (IRI)-Related Indications

The methods of the present disclosure, for example those related to treatment of IRI-related indications, can further comprise administering to a patient in need thereof an effective amount of therapeutic agent that binds to the CD47 protein and a nitric oxide donor, precursor, or both; a nitric oxide generating topical agent; an agent that activates soluble guanylyl cyclase; an agent that inhibits cyclic nucleotide phosphodiesterases; or any combination of any of the foregoing.

In these methods, the nitric oxide donor or precursor can be selected from NO gas, isosorbide dinitrate, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, Bidil®, and arginine.

The agent that activates soluble guanylyl cyclase can be a non-NO (nitric oxide)-based chemical activator of soluble guanylyl cyclase that increases cGMP levels in vascular cells. Such agents bind soluble guanylyl cyclase in a region other than the NO binding motif, and activate the enzyme regardless of local NO or reactive oxygen stress (ROS). Non-limiting examples of chemical activators of soluble guanylyl cyclase include organic nitrates (Artz et al. (2002) *J. Biol. Chem.* 277:18253-18256); protoporphyrin IX (Ignarro et al. (1982) *Proc. Natl. Acad. Sci. USA* 79:2870-2873); YC-1 (Ko et al. (1994) *Blood* 84:4226-4233); BAY 41-2272 and BAY 41-8543 (Stasch et al. (2001 *Nature* 410 (6825): 212-5), CMF-1571, and A-350619 (reviewed in Evgenov et al. (2006) *Nat. Rev. Drug. Discov.* 5:755-768); BAY 58-2667 (Cinaciguat; Frey et al. (2008) *Journal of Clinical Pharmacology* 48 (12): 1400-10); BAY 63-2521 (Riociguat; Mittendorf et al. (2009) *Chemmedchem* 4 (5): 853-65). Additional soluble guanylyl cyclase activators are disclosed in Stasch et al. (2011) *Circulation* 123:2263-2273; Derbyshire and Marletta (2012) *Ann. Rev. Biochem.* 81:533-559, and Nossaman et al. (2012) *Critical Care Research and Practice*, Volume 2012, Article ID 290805, pages 1-12.

The agent that inhibits cyclic nucleotide phosphodiesterases can be selected from, tadalafil, vardenafil, udenafil, sildenafil and avanafil.

Treatment of Autoimmune, Autoinflammatory, Inflammatory, and Cardiovascular Diseases A therapeutic agent that binds to the CD47 protein for the treatment of an autoimmune, autoinflammatory, inflammatory disease and/or cardiovascular disease can be combined with one or more therapeutic agent(s) such as an antibody, a chemical small molecule, or biologic or a medical or surgical procedure which include, but are not limited to the following. For the treatment of autoimmune, autoinflammatory and inflammatory diseases, the combined therapeutic agents are: hydroxychloroquine, leflunomide, methotrexate, minocycline, sulfasalazine, abatacept, rituximab, tocilizumab, anti-TNF inhibitors or blockers (adalimumab, etanercept, infliximab, certolizumab pegol, golimumab), non-steroidal anti-inflammatory drugs, glucocorticoids, corticosteroids, intravenous immunoglobulin, anakinra, canakinumab, rilonacept, cyclophosphamide, mycophenolate mofetil, azathioprine, 6-mercaptopurine, belimumab, beta interferons, glatiramer acetate, dimethyl fumarate, fingolimod, teriflunomide, natalizumab, 5-aminosalicylic acid, mesalamine, cyclosporine, tacrolimus, pimecrolimus, vedolizumab, ustekinumab, secukinumab, ixekizumab, apremilast, budesonide and tofacitinib. For the treatment of atherosclerosis, the combined therapeutic agents or procedures are: medical procedures and/or surgery, including percutaneous coronary intervention (coronary angioplasty and stenting), coronary artery bypass grafting, and carotid endarterectomy; therapeutic agents, including angiotensin-converting enzyme (ACE) inhibitors (including ramipril, quinapril, captopril, and enalapril), calcium channel blockers (including amiodipine, nifedipine, verapamil, felodipine and diltiazem), angiotensin-receptor blockers (including eposartan, olmesarten, azilsartan, valsartan, telmisartan, losartan, candesartan, and irbesartan), the combination of ezetimibe and simvastatin, PCSK9 inhibitors (including alirocumab and evolocumab), anacetrapib, and HMG-CoA inhibitors (including atorvastatin, pravastatin, simvastatin, rosuvastatin, pitavastatin, lovastatin and fluvastatin). For the treatment of heart failure, the combined therapeutic agents are: ACE inhibitors, angiotensin receptor blockers, angiotensin receptor neprilsyn inhibitors (including the combination of sacubitril and valsartan), diuretics, digoxin, inotropes, beta blockers and aldosterone antagonists. For the treatment of pumonary hypertension the combined therapeutic agents are: sildenafil, tadalafil, ambrisentan, bosentan, macitentan, riociguat, treprostinil, epoprostenol, iloprost, and selexipag.

As disclosed herein, the anti-CD47 mAb is administered before, at the same time or after the combined therapeutic agents or medical or surgical procedures.

Another useful class of compounds for the combination therapies contemplated herein includes modulators of SIRPα/CD47 binding such as antibodies to SIRPα, as well as soluble protein fragments of this ligand, or CD47 itself, inhibiting binding of, or interfering with binding of, SIRPα to CD47. It should be noted that the therapeutic methods encompassed herein include the use of the antibodies disclosed herein alone, in combination with one another, and/or with antigen-binding fragments thereof as well, for example, all possible combinations of these antibody compounds.

The examples illustrate various embodiments of the present disclosure, but should not be considered as limiting the disclosure to only these particularly disclosed embodiments.

Diagnostics for CD47 Expression

Diagnostics (including complementary and companion) have been an area of focus in the field of oncology. A number of diagnostic assays have been developed for targeted therapeutics such as Herceptin (Genentech), Tarceva (OSI Pharmaceuticals/Genentech), Iressa (Astra Zeneca), and Erbitux (Imclone/Bristol Myers Squibb). The anti-CD47 mAbs antibodies of the disclosure are particularly well-suited to use in diagnostic applications. Accordingly, the disclosure provides a method to measure CD47 expression in tumor and/or immune cells, using an anti-CD47 mAb of the disclosure.

The anti-CD47 mAbs of the disclosure may be used in a diagnostic assay and/or in vitro method to measure CD47 expression in tumor and/or immune cells present in a patient's tumor sample. In particular, the anti-CD47 mAbs of the disclosure may bind CD47 on approximately 1% or more of tumor and/or immune cells present in a patient's sample as compared to a reference level. In another embodiment, the anti-CD47 mAbs may bind CD47 on approximately 5% or more of tumor and/or immune cells in a patient's sample as compared to a reference level, for example, or binding at least 10%, or at least 20%, or at least 30%, or at least about 40%, or at least about 50%, or at least about 60%, or at least about 70%, or at least about 80%, or at least about 90%, or between 10-100% as compared to a reference level. In yet another embodiment, the anti-CD47 mAbs may bind CD47 on tumor and/or immune cells in a patient's sample to at least about a 2-fold increase as compared to a reference level, or at least about 3-fold, or at least about a 4-fold, or at least about a 5-fold or at least about a 8-fold increase, or between 2-fold and 8-fold, or about 10-fold or greater as compared to a reference level. As described herein, the measurement of CD47 expression in a patient's sample provides biological and/or clinical information that enables decision making about the development and use of a potential drug therapy, notably the use of anti-CD47 antibodies for treating solid and hematological cancers, autoimmune disease, inflammatory disease, atherosclerosis, heart failure, in which the CD47 receptor plays a role.

In one embodiment, the in vitro method comprises, obtaining a patient sample, contacting the patient sample with a monoclonal antibody, or antigen-binding fragment thereof, which specifically binds to an epitope within the sequence of SEQ ID NO:66, and assaying for binding of the antibody to the patient sample, wherein binding of the antibody to the patient sample is diagnostic of CD47 expression in a patient sample.

Accordingly, a diagnostic assay in accordance with the disclosure may comprise contacting tumor and/or immune cells in a patient's sample with an anti-CD47 mAb, or an antigen binding fragment thereof, and assaying for binding of the anti-CD47 mAb to a patient's tumor sample, wherein binding of the anti-CD47 mAb to the patient sample is diagnostic of CD47 expression. Preferably, the patient's sample is a sample containing tumor cells. In this case, binding of the anti-CD47 mAb of the disclosure, or antigen binding fragment thereof, to the tumor cells may be assessed for CD47 expression. The levels of CD47 expression by tumor cells and/or immune cells of a patient's tumor sample may be predictive of clinical outcome in a patient.

Increased binding of anti-CD47 mAbs binding to cells in a patient's sample is associated with increased CD47 expression. In one embodiment, the anti-CD47 mAbs of the disclosure may bind to approximately 5% or more of tumor cells in a patient's sample and this may indicate that the patient would benefit from rapid intervention to a solid and hematological cancer. A diagnostic assay of this sort may be used to determine suitable therapeutic regimes for solid and hematological cancers with relatively high binding of anti-CD47 mAbs of the disclosure, i.e., increased CD47 expression.

It will be appreciated that the diagnostic assay disclosed herein has a number of advantages. The most important of these advantages is that the diagnostic assay of the disclosure may allow the user a greater deal of confidence in the CD47 expression in tumor and/or immune cells. The increased sensitivity of the diagnostic assay of the disclosure allows detection of CD47 in a patient's sample at lower levels than has previously been the case.

The anti-CD47 mAbs of the disclosure may be used as a diagnostic assay in relation to many forms of cancer. Particular forms of cancer that may advantageously be investigated for CD47 expression include susceptible hematologic cancers and solid tumors including, but not limited to, leukemias, lymphomas, and solid tumors.

The diagnostic assays of the disclosure may utilize any suitable means for detecting binding of an anti-CD47 mAb to measure CD47 expression. Suitable methods may be selected with reference to the nature of any reporter moiety used to label the anti-CD47 mAbs of the disclosure. Suitable techniques include, but are by no means limited to, flow cytometry, and enzyme linked immunosorbent assays (ELISA) and assays utilizing nanoparticles.

EXAMPLES

Example 1

Amino Acid Sequences

| Light Chain CDRs | | |
|---|---|---|
| LCDR1 | LCDR2 | LCDR3 |
| Vx4-LCDR1<br>RSRQSIVHTNGNTYLG<br>(SEQ ID NO: 11) | Vx4-LCDR2<br>KVSNRFS<br>(SEQ ID NO: 15) | Vx4-LCDR3<br>FQGSHVPYT<br>(SEQ ID NO: 18) |
| Vx8-LCDR1<br>RASQDISNYLN<br>(SEQ ID NO: 12) | Vx8-LCDR2<br>YTSRLYS<br>(SEQ ID NO: 16) | Vx8-LCDR3<br>QQGNTLPWT<br>(SEQ ID NO: 19) |
| Vx8-LCDR1<br>RASQSISNYLN<br>(SEQ ID NO: 13) | | |
| Vx9-LCDR1<br>RSSQNIVQSNGNTYLE<br>(SEQ ID NO: 14) | Vx9-LCDR2<br>KVFHRFS<br>(SEQ ID NO: 17) | Vx9-LCDR3<br>FQGSHVPWT<br>(SEQ ID NO: 20) |
| Heavy Chain CDRs | | |
| HCDR1 | HCDR2 | HCDR3 |
| Vx4-HCDR1<br>GYTFTNYVIH<br>(SEQ ID NO: 1) | Vx4-HCDR2<br>YIYPYNDGILYNEKFKG<br>(SEQ ID NO: 4) | Vx4-HCDR3<br>GGYYVPDY<br>(SEQ ID NO: 7) |
| | | Vx4-HCDR3<br>GGYYVYDY<br>(SEQ ID NO: 8) |
| Vx8-HCDR1<br>GYSFTNYYIH<br>(SEQ ID NO: 2) | Vx8-HCDR2<br>YIDPLNGDTTYNQKFKG<br>(SEQ ID NO: 5) | Vx8-HCDR3<br>GGKRAMDY<br>(SEQ ID NO: 9) |
| Vx9-HCDR1<br>GYTFTNYWIH<br>(SEQ ID NO: 3) | Vx9-HCDR2<br>YTDPRTDYTEYNQKFKD<br>(SEQ ID NO: 6) | Vx9-HCDR3<br>GGRVGLGY<br>(SEQ ID NO: 10) |

Murine Light Chain Variable Domains

>Vx4murL01
DVLMTQTPLSLPVNLGDQASISCRSRQSIVHTNGNTYLGWFLQKPGQSPKLLIYKVSNRF
SGVPDRFSGSGSGTDFTLTISRVEAEDLGVYYCFQGSHVPYTFGGGTKLEIK (SEQ ID
NO: 41).

>Vx4murL02
DVLMTQTPLSLPVNLGDQASISCRSRQSIVHTNGNTYLGWFLQKPGQSPKLLIYKVSNRF
SGVPDRFSGSGSGTDFTLTISRVEAEDLGVYYCFQGSHVPYTFGQGTKVEIK (SEQ ID
NO: 42).

>Vx8murL03
DIQMTQTTSSLSASLGDRVTISCRASQDISNYLNWYQQKPDGTVKLLIYYTSRLYSGVPS
RFSGSGSGTDYSLTISNLEQEDIATYFCQQGNTLPWTFGGGTKLEIK (SEQ ID NO: 46).

>Vx9murL04
DVFMTQTPLSLPVSLGDQASISCRSSQNIVQSNGNTYLEWYLQKPGQSPKLLIYKVFHRF
SGVPDRFSGSGSGTDFTLKISRVEAEDLGVYYCFQGSHVPWTFGGGTKVEIK(SEQ ID
NO: 50)

Murine Heavy Chain Variable Domains

>Vx4murH01
EVQLQQSGPELVKPGASVKMSCKASGYTFTNYVIHWVKRRPGQGLEWIGYIYPYNDGIL
YNEKFKGKATVTSDKSSSTAYMDLSSLTSEDSAVYYCTRGGYYVPDYWGQGTTLTVSS
(SEQ ID NO: 21).

-continued

>Vx4mur-H02
EVQLQQSGPELVKPGASVKMSCKASGYTFTNYVIHWVKRRPGQGLEWIGYIYPYNDGIL
YNEKFKGKATVTSDKSSSTAYMDLSSLTSEDSAVYYCTRGGYYVPDYWGQGTLVTVSS
(SEQ ID NO: 22).

>Vx8murH03
EVQLQQSGPELMKPGASVKISCKASGYSFTNYYIHWVNQSHGKSLEWIGYIDPLNGDTT
YNQKFKGKATLTVDKSSSTAYMRLSSLTSADSAVYYCARGGKRAMDYWGQGTSVTVS
S (SEQ ID NO: 28).

>Vx9murH04
QVQLQQFGAELAKPGASVQMSCKASGYTFTNYWIHWVKQRPGQGLEWIGYTDPRTDY
TEYNQKFKDKATLAADRSSSTAYMRLSSLTSEDSAVYYCAGGGRVGLGYWGHGSSVT
VSS (SEQ ID NO: 35)

Human Light Chain Variable Domains

>Vx4humL01
DIVMTQSPLSLPVTPGEPASISCRSRQSIVHTNGNTYLGWYLQKPGQSPRLLIYKVSNRFS
GVPDRFSGSGSGTDFTLKISRVEADDVGIYYCFQGSHVPYTFGQGTKLEIK (SEQ ID
NO: 43)

>Vx4humL02
DVVMTQSPLSLPVTLGQPASISCRSRQSIVHTNGNTYLGWFQQRPGQSPRRLIYKVSNRF
SGVPDRFSGSGSGTDFTLKISRVEAEDVGVYYCFQGSHVPYTFGQGTKLEIK (SEQ ID
NO: 44)

>Vx4humL03
DIVMTQSPDSLAVSLGERATINCRSRQSIVHTNGNTYLGWYQQKPGQPPKLLIYKVSNRF
SGVPDRFSGSGSGTDFTLTISSLQAEDVAVYYCFQGSHVPYTFGQGTKLEIK (SEQ ID
NO: 45)

>Vx8humL04
DIQMTQSPSSLSASVGDRVTITCRASQDISNYLNWYQQKPGKAPKLLIYYTSRLYSGVPS
RFSGSGSGTDFTFTISSLQPEDIATYYCQQGNTLPWTFGQGTKVEIK (SEQ ID NO: 47).

>Vx8humL05
DIQMTQSPSSLSASVGDRVTITCRASQSISNYLNWYQQKPGKAPKLLIYYTSRLYSGVPS
RFSGSGSGTDFTLTISSLQPEDFATYYCQQGNTLPWTFGQGTKVEIK (SEQ ID NO: 48).

>Vx8humL06
DIVMTQSPLSLPVTPGEPASISCRASQDISNYLNWYLQKPGQSPRLLIYYTSRLYSGVPDR
FSGSGSGTDFTLKISRVEADDVGIYYCQQGNTLPWTFGQGTKLEIK (SEQ ID NO: 49)

>Vx9humL07
DVVMTQSPLSLPVTLGQPASISCRSSQNIVQSNGNTYLEWFQQRPGQSPRRLIYKVFHRF
SGVPDRFSGSGSGTDFTLKISRVEAEDVGVYYCFQGSHVPYTFGQGTKLEIK (SEQ ID
NO: 51).

>Vx9humL08
DIVMTQSPDSLAVSLGERATINCRSSQNIVQSNGNTYLEWYQQKPGQPPKLLIYKVFHRF
SGVPDRFSGSGSGTDFTLTISSLQAEDVAVYYCFQGSHVPYTFGQGTKLEIK (SEQ ID
NO: 52).

Human Heavy Chain Variable Domains

>Vx4humH01
QVQLVQSGAEVKKPGASVQVSCKASGYTFTNYVIHWLRQAPGQGLEWMGYIYPYNDG
ILYNEKFKGRVTMTSDTSISTAYMELSSLRSDDTAVYYCARGGYYVPDYWGQATLVTV
SS (SEQ ID NO: 23).

>Vx4humH02
QVQLVQSGAEVKKPGASVQVSCKASGYTFTNYVIHWLRQAPGQGLEWMGYIYPYNDG
ILYNEKFKGRVTMTSDTSISTAYMELSSLRSDDTAVYYCARGGYYVYDYWGQATLVTV
SS (SEQ ID NO: 24).

>Vx4humH03
EVQLVQSGAEVKKPGATVKISCKVSGYTFTNYVIHWVQQAPGKGLEWMGYIYPYNDGI
LYNEKFKGRVTITADTSTDTAYMELSSLRSEDTAVYYCATGGYYVPDYWGQGTTVTVS
S (SEQ ID NO: 25)

>Vx4humH04
EVQLVQSGAEVKKPGESLKISCKGSGYTFTNYVIHWVRQMPGKGLEWMGYIYPYNDGI
LYNEKFKGQVTISADKSISTAYLQWSSLKASDTAMYYCARGGYYVPDYWGQGTTVTVS
S (SEQ ID NO: 26)

>Vx4humH05
QVQLVQSGAEVKKPGASVKVSCKASGYTFTNYVIHWVRQAPGQGLEWMGYIYPYNDG
ILYNEKFKGRVTMTTDTSTSTAYMELRSLRSDDTAVYYCARGGYYVPDYWGQGTTVT
VSS (SEQ ID NO: 27)

>Vx8humH06
QVQLVQSGAEVKKPGASVKVSCKASGYSFTNYYIHWVRQAPGQGLEWMGYIDPLNGD
TTYNQKFKGRVTMTRDTSTSTVYMELSSLRSEDTAVYYCARGGKRAMDYWGQGTLVT
VSS (SEQ ID NO: 29).

>Vx8humH07
QVQLVQSGAEVKKPGSSVKVSCKASGYSFTNYYIHWVRQAPGQGLEWMGYIDPLNGD
TTYNQKFKGRVTITADESTSTAYMELSSLRSEDTAVYYCARGGKRAMDYWGQGTLVT
VSS (SEQ ID NO: 30).

>Vx8humH08
EVQLVQSGAEVKKPGESLKISCKGSGYSFTNYYIHWVRQMPGKGLEWMGYIDPLNGDT
TYNQKFKGQVTISADKSISTAYLQWSSLKASDTAMYYCARGGKRAMDYWGQGTLVTV
SS (SEQ ID NO: 31).

>Vx8humH09
QVQLVQSGAEVKKPGSSVKVSCKASGYSFTNYYIHWVRQAPGQGLEWMGYIDPLNGD
TTYAQKFQGRVTITADESTSTAYMELSSLRSEDTAVYYCARGGKRAMDYWGQGTLVT
VSS (SEQ ID NO: 32).

>Vx8humH10
EVQLVQSGAEVKKPGESLKISCKGSGYSFTNYYIHWVRQMPGKGLEWMGYIDPLNGDT
TYSPSFQGQVTISADKSISTAYLQWSSLKASDTAMYYCARGGKRAMDYWGRGTLVTVS
S (SEQ ID NO: 33).

>Vx8humH11
QVQLVQSGAEVKKPGASVQVSCKASGYSFTNYYIHWLRQAPGQGLEWMGYIDPLNGD
TTYNQKFKGRVTMTSDTSISTAYMELSSLRSDDTAVYYCARGGKRAMDYWGQATLVT
VSS (SEQ ID NO: 34)

>Vx9humH12
QVQLVQSGAEVKKPGASVKVSCKASGYTFTNYWIHWVRQAPGQGLEWMGYTDPRTD
YTEYNQKFKDRVTMTRDTSTSTVYMELSSLRSEDTAVYYCARGGRVGLGYWGQGTLV
TVSS (SEQ ID NO: 36).

>Vx9humH13
QVQLVQSGAEVKKPGSSVKVSCKASGYTFTNYWIHWVRQAPGQGLEWMGYTDPRTD
YTEYNQKFKDRVTITADESTSTAYMELSSLRSEDTAVYYCARGGRVGLGYWGQGTLVT
VSS (SEQ ID NO: 37).

>Vx9humH14
[1]EVQLVQS GAEVKKPGESLKISCKGSGYTFTNYWIHWVRQMPGKGLEWMGYTDP
RTDYTEYNQKFKDQVTISADKSISTAYLQWSSLKASDTAMYYCARGGRVGLGYWGQG
TLVTVSS (SEQ ID NO: 38).

>Vx9humH15
QVQLVQSGAEVKKPGSSVKVSCKASGYTFTNYWIHWVRQAPGQGLEWMGYTDPRTD
YTEYAQKFQGRVTITADESTSTAYMELSSLRSEDTAVYYCARGGRVGLGYWGQGTLVT
VSS (SEQ ID NO: 39).

>Vx9humH16
EVQLVQSGAEVKKPGESLKISCKGSGYTFTNYWIHWVRQMPGKGLEWMGYTDPRTDY
TEYSPSFQGQVTISADKSISTAYLQWSSLKASDTAMYYCARGGRVGLGYWGQGTLVTV
SS (SEQ ID NO: 40).

---

Human IgG-Fc

>Human Fc IgG1
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 53).

>Human Fc IgG1-N297Q
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQY
QSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 54).

```
>Human Fc-IgG2
ASTKGPSVFPLAPCSRSTSESTAALGCLVKDYFPEPVTVSWNSGALTSGVHTFPAVLQSS
GLYSLSSVVTVPSSNFGTQTYTCNVDHKPSNTKVDKTVERKCCVECPPCPAPPVAGPSV
FLFPPKPKDTLMISRTPEVTCVVVDVSHEDPEVQFNWYVDGVEVHNAKTKPREEQFNST
FRVVSVLTVVHQDWLNGKEYKCKVSNKGLPAPIEKTISKTKGQPREPQVYTLPPSREEM
TKNQVSLTCLVKGFYPSDIAVEWESNGQPENNYKTTPPMLDSDGSFFLYSKLTVDKSRW
QQGNVFSCSVMHEALHNHYTQKSLSLSPGK (SEQ ID NO: 56).

>Human Fc-IgG3
ASTKGPSVFPLAPCSRSTSGGTAALGCLVKDYFPEPVTVSWNSGALTSGVHTFPAVLQSS
GLYSLSSVVTVPSSSLGTQTYTCNVNHKPSNTKVDKRVELKTPLGDTTHTCPRCPEPKSC
DTPPPCPRCPEPKSCDTPPPCPRCPEPKSCDTPPPCPRCPAPELLGGPSVFLFPPKPKDTLMI
SRTPEVTCVVVDVSHEDPEVQFKWYVDGVEVHNAKTKPREEQYNSTFRVVSVLTVLHQ
DWLNGKEYKCKVSNKALPAPIEKTISKTKGQPREPQVYTLPPSREEMTKNQVSLTCLVK
GFYPSDIAVEWESSGQPENNYNTTPPMLDSDGSFFLYSKLTVDKSRWQQGNIFSCSVMH
EALHNRFTQKSLSLSPGK (SEQ ID NO: 57)

>Human Fc-IgG4
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPSCPAPEFLGGPSV
FLFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRW
QEGNVFSCSVMHEALHNHYTQKSLSLSLG (SEQ ID NO: 58).

>Human Fc-IgG4 S228P
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFLGGPSV
FLFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRW
QEGNVFSCSVMHEALHNHYTQKSLSLSLG (SEQ ID NO: 59).

>Human Fc-IgG4PE
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFEGGPSV
FLFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRW
QEGNVFSCSVMHEALHNHYTQKSLSLSLGK (SEQ ID NO: 60)

>Human Fc-IgG4PE'
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFEGGPSV
FLFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRW
QEGNVFSCSVMHEALHNHYTQKSLSLSLG (SEQ ID NO: 101)

>Human kappa LC
RTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC (SEQ ID NO: 61).

>Rat Fc-IgG2c
ARTTAPSVYPLVPGCSGTSGSLVTLGCLVKGYFPEPVTVKWNSGALSSGVHTFPAVLQS
GLYTLSSSVTVPSSTWSSQTVTCSVAHPATKSNLIKRIEPRRPKPRPPTDICSCDDNLGRPS
VFIFPPKPKDILMITLTPKVTCVVVDVSEEEPDVQFSWFVDNVRVFTAQTQPHEEQLNGT
FRVVSTLHIQHQDWMSGKEFKCKVNNKDLPSPIEKTISKPRGKARTPQVYTIPPPREQMS
KNKVSLTCMVTSFYPASISVEWERNGELEQDYKNTLPVLDSDESYFLYSKLSVDTDSW
MRGDIYTCSVVHEALHNHHTQKNLSRSPGK (SEQ ID NO: 62).

>Rat kappa LC
RADAAPTVSIFPPSMEQLTSGGATVVCFVNNFYPRDISVKWKIDGSEQRDGVLDSVTDQ
DSKDSTYSMSSTLSLTKVEYERHNLYTCEVVHKTSSSPVVKSFNRNEC (SEQ ID NO: 63).
```

Rabbit IgG-Fc

```
>Rabbit IgG
GQPKAPSVFPLAPCCGDTPSSTVTLGCLVKGYLPEPVTVTWNSGTLTNGVRTFPSVRQSS
GLYSLSSVVSVTSSSQPVTCNVAHPATNTKVDKTVAPSTCSKPTCPPPELLGGPSVFIFPP
KPKDTLMISRTPEVTCVVVDVSQDDPEVQFTWYINTNEQVRTARPPLREQQFNSTIRVVST
LPIAHQDWLRGKEFKCKVHNKALPAPIEKTISKARGQPLEPKVYTMGPPREELSSRSVSL
TCMINTGFYPSDISVEWEKNGKAEDNYKTTPAVLDSDGSYFLYSKLSVPTSEWQRGDVFT
CSVMHEALHNHYTQKSISRSPGK (SEQ ID NO: 64).

>Rabbit kappa LC
RDPVAPTVLIFPPAADQVATGTVTIVCVANKYFPDVTVTWEVDGTTQTTGIENSKTPQN
SADCTYNLSSTLTLTSTQYNSHKEYTCKVTQGTTSVVQSFNRGDC (SEQ ID NO: 65).
```

```
>CD47
MWPLVAALLLGSACCGSAQLLFNKTKSVEFTFCNDTVVIPCFVTNMEAQNTTEVYVKW
KFKGRDIYTFDGALNKSTVPTDFSSAKIEVSQLLKGDASLKMDKSDAVSHTGNYTCEVT
ELTREGETIIELKYRVVSWFSPNENILIVIFPIFAILLFWGQFGIKTLKYRSGGMDEKTIALL
VAGLVITVIVIVGAILFVPGEYSLKNATGLGLIVTSTGILILLHYYVFSTAIGLTSFVIAILVI
QVIAYILAVVGLSLCIAACIPMHGPLLISGLSILALAQLLGLVYMKFVE (SEQ ID NO: 66).
```

Chimera and Human Light Chains

```
>Vx4murL01 Full length
DVLMTQTPLSLPVNLGDQASISCRSRQSIVHTNGNTYLGWFLQKPGQSPKLLIYKVSNRF
SGVPDRFSGSGSGTDFTLTISRVEAEDLGVYYCFQGSHVPYTFGGGTKLEIKRTVAAPSV
FIFPPSDEQLKSGTASVVCLLNNFYPREAKVQWKVDNALQSGNSQESVTEQDSKDSTYS
LSST LTLSKADYEKHKVYACEVTHQGLSSPVTKSFNRGEC (SEQ ID NO: 67).

>Vx4murL01 Full length
DVLMTQTPLSLPVNLGDQASISCRSRQSIVHTNGNTYLGWFLQKPGQSPKLLIYKVSNRF
SGVPDRFSGSGSGTDFTLTISRVEAEDLGVYCFQGSHVPYTFGQGTKVEIKRTVAAPSV
FIFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC (SEQ ID NO: 68).

>Vx4humL01 Full length LC
DIVMTQSPLSLPVTPGEPASISCRSRQSIVHTNGNTYLGWYLQKPGQSPRLLIYKVSNRFS
GVPDRFSGSGSGTDFTLKISRVEADDVGIYYCFQGSHVPYTFGQGTKLEIKRTVAAPSVFI
FPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 69).

>Vx8humL03 Full length LC
DIVMTQSPLSLPVTPGEPASISCRASQDISNYLNWYLQKPGQSPRLLIYYTSRLYSGVPDR
FSGSGSGTDFTLKISRVEADDVGIYYCQQGNTLPWTFGQGTKLEIKRTVAAPSVFIFPPSD
EQLKSGTASVVCLLNNFYPREAKVQWKVDNALQSGNSQESVTEQDSKDSTYSLSST
LTLSKADYEKHKVYACEVTHQGLSSPVTKSFNRGEC (SEQ ID NO: 70).

>Vx9humL02 Full length LC
DIVMTQSPDSLAVSLGERATINCRSSQNIVQSNGNTYLEWYQQKPGQPPKLLIYKVFHRF
SGVPDRFSGSGSGTDFTLTISSLQAEDVAVYYCFQGSHVPYTFGQGTKLEIKRTVAAPSV
FIFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC (SEQ ID NO: 71).

>Vx8humL02 Full length LC
DIQMTQSPSSLSASVGDRVTITCRASQSISNYLNWYQQKPGKAPKLLIYYTSRLYSGVPS
RFSGSGSGTDFTLTISSLQPEDFATYYCQQGNTLPWTFGQGTKVEIKRTVAAPSVFIFPPS
DEQLKSGTASVVCLLNNFYPREAKVQWKVDNALQSGNSQESVTEQDSKDSTYSLSST
LTLSKADYEKHKVYACEVTHQGLSSPVTKSFNRGEC (SEQ ID NO: 72).

>Vx4humL02 Full length LC
DVVMTQSPLSLPVTLGQPASISCRSRQSIVHTNGNTYLGWFQQRPGQSPRRLIYKVSNRF
SGVPDRFSGSGSGTDFTLKISRVEAEDVGVYYCFQGSHVPYTFGQGTKLEIKRTVAAPSV
FIFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC (SEQ ID NO: 73).

>Vx9humL07 Full length LC
DVVMTQSPLSLPVTLGQPASISCRSSQNIVQSNGNTYLEWFQQRPGQSPRRLIYKVFHRF
SGVPDRFSGSGSGTDFTLKISRVEAEDVGVYYCFQGSHVPYTFGQGTKLEIKRTVAAPSV
FIFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC (SEQ ID NO: 74).

>Vx8humL01 Full length LC
DIQMTQSPSSLSASVGDRVTITCRASQDISNYLNWYQQKPGKAPKLLIYYTSRLYSGVPS
RFSGSGSGTDFTFTISSLQPEDIATYYCQQGNTLPWTFGQGTKVEIKRTVAAPSVFIFPPSD
EQLKSGTASVVCLLNNFYPREAKVQWKVDNALQSGNSQESVTEQDSKDSTYSLSST
LTLSKADYEKHKVYACEVTHQGLSSPVTKSFNRGEC (SEQ ID NO: 75).

>Vx8murL03 Full length LC
DIQMTQTTSSLSASLGDRVTISCRASQDISNYLNWYQQKPDGTVKLLIYYTSRLYSGVPS
RFSGSGSGTDYSLTISNLEQEDIATYFCQQGNTLPWTFGGGTKLEIKRTVAAPSVFIFPPS
DEQLKSGTASVVCLLNNFYPREAKVQWKVDNALQSGNSQESVTEQDSKDSTYSLSST
LTLSKADYEKHKVYACEVTHQGLSSPVTKSFNRGEC (SEQ ID NO: 76).

>Vx9mur_L04 Full length LC
DVFMTQTPLSLPVSLGDQASISCRSSQNIVQSNGNTYLEWYLQKPGQSPKLLIYKVFHRF
SGVPDRFSGSGSGTDFTLKISRVEAEDLGVYYCFQGSHVPWTFGGGTKVEIKRTVAAPS
VFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 77).
```

Chimera and Human Heavy Chains

>Vx4murH01 Full length HC
EVQLQQSGPELVKPGASVKMSCKASGYTFTNYVIHWVKRRPGQGLEWIGYIYPYNDGIL
YNEKFKGKATVTSDKSSSTAYMDLSSLTSEDSAVYYCTRGGYYVPDYWGQGTTLTVSS
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFEGGPSV
FLFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRW
QEGNVFSCSVMHEALHNHYTQKSLSLSLGK (SEQ ID NO: 78).

>Vx4humH01 Full length HC
QVQLVQSGAEVKKPGASVQVSCKASGYTFTNYVIHWLRQAPGQGLEWMGYIYPYNDG
ILYNEKFKGRVTMTSDTSISTAYMELSSLRSDDTAVYYCARGGYYVPDYWGQATLVTV
SSASTKGPSVFPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPPCPAPEFEGGP
SVFLFPPKPKDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKS
RWQEGNVFSCSVMHEALHNHYTQKSLSLSLGK (SEQ ID NO: 79).

>Vx8humH11 Full length HC
QVQLVQSGAEVKKPGASVQVSCKASGYSFTNYYIHWLRQAPGQGLEWMGYIDPLNGD
TTYNQKFKGRVTMTSDTSISTAYMELSSLRSDDTAVYYCARGGKRAMDYWGQATLVT
VSSASTKGPSVFPLAPCSRSTSESTAALGCLVKDYFPEPVTVSWNSGALTSGVHTFPAVL
QSSGLYSLSSVVTVPSSSLGTKTYTCNVDHKPSNTKVDKRVESKYGPPCPPCPAPEFEGG
PSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQ
EEMTKNQVSLTCLVKGFYPSDIAVEWESNGQPENNYKTTPPVLDSDGSFFLYSRLTVDK
SRWQEGNVFSCSVMHEALHNHYTQKSLSLSLGK (SEQ ID NO: 80).

>Vx9humH12 Full length HC
QVQLVQSGAEVKKPGASVKVSCKASGYTFTNYWIHWVRQAPGQGLEWMGYTDPRTD
YTEYNQKFKDRVTMTRDTSTSTVYMELSSLRSEDTAVYYCARGGRVGLGYWGQTLV
TVSSASTKGPSVFPLAPCSRSTSESTAALGCLVKDYFPEPVTVSWNSGALTSGVHTFPAV
LQSSGLYSLSSVVTVPSSNFGTQTYTCNVDHKPSNTKVDKTVERKCCVECPPCPAPPVA
GPSVFLFPPKPKDTLMISRTPEVTCVVVDVSHEDPEVQFNWYVDGVEVHNAKTKPREEQ
FNSTFRVVSVLTVVHQDWLNGKEYKCKVSNKGLPAPIEKTISKTKGQPREPQVYTLPPS
REEMTKNQVSLTCLVKGFYPSDIAVEWESNGQPENNYKTTPPMLDSDGSFFLYSKLTVD
KSRWQQGNVFSCSVMHEALHNHYTQKSLSLSPGK (SEQ ID NO: 81).

>Vx9humH14 Full length HC
EVQLVQSGAEVKKPGESLKISCKGSGYTFTNYWIHWVRQMPGKGLEWMGYTDPRTDY
TEYNQKFKDQVTISADKSISTAYLQWSSLKASDTAMYYCARGGRVGLGYWGQGTLVT
VSSASTKGPSVFPLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPPSR
EEMTKNQVSLTCLVKGFYPSDIAVEWESNGQPENNYKTTPPMLDSDGSFFLYSKLTVDK
SRWQQGNVFSCSVMHEALHNHYTQKSLSLSPGK (SEQ ID NO: 82).

>Vx9humH15 Full length HC
QVQLVQSGAEVKKPGSSVKVSCKASGYTFTNYWIHWVRQAPGQGLEWMGYTDPRTD
YTEYAQKFQGRVTITADESTSTAYMELSSLRSEDTAVYYCARGGRVGLGYWGQGTLVT
VSSASTKGPSVFPLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPPSR
EEMTKNQVSLTCLVKGFYPSDIAVEWESNGQPENNYKTTPPMLDSDGSFFLYSKLTVDK
SRWQQGNVFSCSVMHEALHNHYTQKSLSLSPGK (SEQ ID NO: 83).

>Vx4humH02 Full length HC
QVQLVQSGAEVKKPGASVQVSCKASGYTFTNYVIHWLRQAPGQGLEWMGYIYPYNDG
ILYNEKFKGRVTMTSDTSISTAYMELSSLRSDDTAVYYCARGGYYVYDYWGQATLVTV
SSASTKGPSVFPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPPCPAPEFEGGP
SVFLFPPKPKDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKS
RWQEGNVFSCSVMHEALHNHYTQKSLSLSLGK (SEQ ID NO: 84).

>Vx9humH13 Full length HC
QVQLVQSGAEVKKPGSSVKVSCKASGYTFTNYWIHWVRQAPGQGLEWMGYTDPRTD
YTEYNQKFKDRVTITADESTSTAYMELSSLRSEDTAVYYCARGGRVGLGYWGQGTLVT
VSSASTKGPSVFPLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNAKTKPREEQF NSTFRVVSVLTVVHQDWLNGKEYKCKVSNKGLPAPIEKTISKTKGQPREPQVYTLPPSR
EEMTKNQVSLTCLVKGFYPSDIAVEWESNGQPENNYKTTPPMLDSDGSFFLYSKLTVDK
SRWQQGNVFSCSVMHEALHNHYTQKSLSLSPGK (SEQ ID NO: 85).

>Vx8humH10 Full length HC
EVQLVQSGAEVKKPGESLKISCKGSGYSFTNYYTHWVRQMPGKGLEWMGYIDPLNGDT
TYSPSFQGQVTISADKSISTAYLQWSSLKASDTAMYYCARGGKRAMDYWGRGTLVTVS
SASTKGPSVFPLAPCSRSTSESTAALGCLVKDYFPEPVTVSWNSGALTSGVHTFPAVLQS
SGLYSLSSVVTVPSSSLGTKTYTCNVDHKPSNTKVDKRVESKYGPPCPPCPAPEFEGGPS
VFLFPPKPKDTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLYSRLTVDKSR
WQEGNVFSCSVMHEALHNHYTQKSLSLSLGK (SEQ ID NO: 86).

>Vx4humH04 Full length HC
EVQLVQSGAEVKKPGESLKISCKGSGYTFTNYVIHWVRQMPGKGLEWMGYIYPYNDGI
LYNEKFKGQVTISADKSISTAYLQWSSLKASDTAMYYCARGGYYVPDYWGQGTTVTVS
SASTKGPSVFPLAPCSRSTSESTAALGCLVKDYFPEPVTVSWNSGALTSGVHTFPAVLQS
SGLYSLSSVVTVPSSSLGTKTYTCNVDHKPSNTKVDKRVESKYGPPCPPCPAPEFEGGPS
VFLFPPKPKDTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLYSRLTVDKSR
WQEGNVFSCSVMHEALHNHYTQKSLSLSLGK (SEQ ID NO: 87).

>Vx4humH05 Full length HC
QVQLVQSGAEVKKPGASVKVSCKASGYTFTNYVIHWVRQAPGQGLEWMGYIYPYNDG
ILYNEKFKGRVTMTTDTSTSTAYMELRSLRSDDTAVYYCARGGYYVPDYWGQGTTVT
VSSASTKGPSVFPLAPCSRSTSESTAALGCLVKDYFPEPVTVSWNSGALTSGVHTFPAVL
QSSGLYSLSSVVTVPSSSLGTKTYTCNVDHKPSNTKVDKRVESKYGPPCPPCPAPEFEGG
PSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQ
EEMTKNQVSLTCLVKGFYPSDIAVEWESNGQPENNYKTTPPVLDSDGSFFLYSRLTVDK
SRWQEGNVFSCSVMHEALHNHYTQKSLSLSLGK (SEQ ID NO: 88).

>Vx9humH16 Full length HC
EVQLVQSGAEVKKPGESLKISCKGSGYTFTNYWIHWVRQMPGKGLEWMGYTDPRTDY
TEYSPSFQGQVTISADKSISTAYLQWSSLKASDTAMYYCARGGRVGLGYWGQGTLVTV
SSASTKGPSVFPLAPCSRSTSESTAALGCLVKDYFPEPVTVSWNSGALTSGVHTFPAVLQ
SSGLYSLSSVVTVPSSNFGTQTYTCNVDHKPSNTKVDKTVERKCCVECPPCPAPPVAGPS
VFLFPPKPKDTLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQVYTLPPSREE
MTKNQVSLTCLVKGFYPSDIAVEWESNGQPENNYKTTPPMLDSDGSFFLYSKLTVDKSR
WQQGNVFSCSVMHEALHNHYTQKSLSLSPGK (SEQ ID NO: 89).

>Vx8humH06 Full length HC
[2]QVQLVQSGAEVKKPGASVKVSCKASGYSFTNYYIHWVRQAPGQGLEWMGYIDP
LNGDTTYNQKFKGRVTMTRDTSTSTVYMELSSLRSEDTAVYYCARGGKRAMDYWGQ
GTLVTVSSASTKGPSVFPLAPCSRSTSESTAALGCLVKDYFPEPVTVSWNSGALTSGVHT
FPAVLQSSGLYSLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRL
TVDKSRWQEGNVFSCSVMHEALHNHYTQKSLSLSLGK (SEQ ID NO: 90).

>Vx8humH07 Full length HC
QVQLVQSGAEVKKPGSSVKVSCKASGYSFTNYYIHWVRQAPGQGLEWMGYIDPLNGD
TTYNQKFKGRVTITADESTSTAYMELSSLRSEDTAVYYCARGGKRAMDYWGQGTLVT
VSSASTKGPSVFPLAPCSRSTSESTAALGCLVKDYFPEPVTVSWNSGALTSGVHTFPAVL
QSSGLYSLSSVVTVPSSSLGTKTYTCNVDHKPSNTKVDKRVESKYGPPCPPCPAPEFEGG
PSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQ
EEMTKNQVSLTCLVKGFYPSDIAVEWESNGQPENNYKTTPPVLDSDGSFFLYSRLTVDK
SRWQEGNVFSCSVMHEALHNHYTQKSLSLSLGK (SEQ ID NO: 91).

>Vx8humH08 Full length HC
EVQLVQSGAEVKKPGESLKISCKGSGYSFTNYYIHWVRQMPGKGLEWMGYIDPLNGDT
TYNQKFKGQVTISADKSISTAYLQWSSLKASDTAMYYCARGGKRAMDYWGQGTLVTV
SSASTKGPSVFPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPPCPAPEFEGGP
SVFLFPPKPKDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKS
RWQEGNVFSCSVMHEALHNHYTQKSLSLSLGK (SEQ ID NO: 92).

>Vx8humH09 Full length HC
QVQLVQSGAEVKKPGSSVKVSCKASGYSFTNYYIHWVRQAPGQGLEWMGYIDPLNGD
TTYAQKFQGRVTITADESTSTAYMELSSLRSEDTAVYYCARGGKRAMDYWGQGTLVT
VSSASTKGPSVFPLAPCSRSTSESTAALGCLVKDYFPEPVTVSWNSGALTSGVHTFPAVL
QSSGLYSLSSVVTVPSSSLGTKTYTCNVDHKPSNTKVDKRVESKYGPPCPPCPAPEFEGG

```
PSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQ
EEMTKNQVSLTCLVKGFYPSDIAVEWESNGQPENNYKTTPPVLDSDGSFFLYSRLTVDK
SRWQEGNVFSCSVMHEALHNHYTQKSLSLSLGK (SEQ ID NO: 93).

>Vx8humH06 Full length HC
QVQLVQSGAEVKKPGASVKVSCKASGYSFTNYYIHWVRQAPGQGLEWMGYIDPLNGD
TTYNQKFKGRVTMTRDTSTSTVYMELSSLRSEDTAVYYCARGGKRAMDYWGQGTLVT
VSSASTKGPSVFPLAPCSRSTSESTAALGCLVKDYFPEPVTVSWNSGALTSGVHTFPAVL
QSSGLYSLSSVVTVPSSSLGTKTYTCNVDHKPSNTKVDKRVESKYGPPCPPCPAPEFEGG
PSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQ
EEMTKNQVSLTCLVKGFYPSDIAVEWESNGQPENNYKTTPPVLDSDGSFFLYSRLTVDK
SRWQEGNVFSCSVMHEALHNHYTQKSLSLSLGK (SEQ ID NO: 94).

>Vx8mur-H03 Full length HC
EVQLQQSGPELMKPGASVKISCKASGYSFTNYYIHWVNQSHGKSLEWIGYIDPLNGDTT
YNQKFKGKATLTVDKSSSTAYMRLSSLTSADSAVYYCARGGKRAMDYWGQGTSVTVS
SASTKGPSVFPLAPCSRSTSESTAALGCLVKDYFPEPVTVSWNSGALTSGVHTFPAVLQS
SGLYSLSSVVTVPSSSLGTKTYTCNVDHKPSNTKVDKRVESKYGPPCPPCPAPEFEGGPS
VFLFPPKPKDTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLYSRLTVDKSR
WQEGNVFSCSVMHEALHNHYTQKSLSLSLGK (SEQ ID NO: 95).

>Vx9mur-H04 Full length HC
QVQLQQFGAELAKPGASVQMSCKASGYTFTNYWIHWVKQRPGQGLEWIGYTDPRTDY
TEYNQKFKDKATLAADRSSSTAYMRLSSLTSEDSAVYYCAGGGRVGLGYWHGHSSVT
VSSASTKGPSVFPLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPPSR
EEMTKNQVSLTCLVKGFYPSDIAVEWESNGQPENNYKTTPPMLDSDGSFFLYSKLTVDK
SRWQQGNVFSCSVMHEALHNHYTQKSLSLSPGK (SEQ ID NO: 96).

>Vx8humH06 Full length HC
QVQLVQSGAEVKKPGASVKVSCKASGYSFTNYYIHWVRQAPGQGLEWMGYIDPLNGD
TTYNQKFKGRVTMTRDTSTSTVYMELSSLRSEDTAVYYCARGGKRAMDYWGQGTLVT
VSSASTKGPSVFPLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPPSR
EEMTKNQVSLTCLVKGFYPSDIAVEWESNGQPENNYKTTPPMLDSDGSFFLYSKLTVDK
SRWQQGNVFSCSVMHEALHNHYTQKSLSLSPGK (SEQ ID NO: 97).

>Vx8humH07 Full length HC
QVQLVQSGAEVKKPGSSVKVSCKASGYSFTNYYIHWVRQAPGQGLEWMGYIDPLNGD
TTYNQKFKGRVTITADESTSTAYMELSSLRSEDTAVYYCARGGKRAMDYWGQGTLVT
VSSASTKGPSVFPLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPPSR
EEMTKNQVSLTCLVKGFYPSDIAVEWESNGQPENNYKTTPPMLDSDGSFFLYSKLTVDK
SRWQQGNVFSCSVMHEALHNHYTQKSLSLSPGK (SEQ ID NO: 98).

>Vx8humH08 Full length HC
EVQLVQSGAEVKKPGESLKISCKGSGYSFTNYYIHWVRQMPGKGLEWMGYIDPLNGDT
TYNQKFKGQVTISADKSISTAYLQWSSLKASDTAMYYCARGGKRAMDYWGQGTLVTV
SSASTKGPSVFPLAPCSRSTSESTAALGCLVKDYFPEPVTVSWNSGALTSGVHTFPAVLQ
SSGLYSLSSVVTVPSSNFGTQTYTCNVDHKPSNTKVDKTVERKCCVECPPCPAPPVAGPS
VFLFPPKPKDTLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQVYTLPPSREE
MTKNQVSLTCLVKGFYPSDIAVEWESNGQPENNYKTTPPMLDSDGSFFLYSKLTVDKSR
WQQGNVFSCSVMHEALHNHYTQKSLSLSPGK (SEQ ID NO: 99).

>Vx8humH09 Full length HC
QVQLVQSGAEVKKPGSSVKVSCKASGYSFTNYYIHWVRQAPGQGLEWMGYIDPLNGD
TTYAQKFQGRVTITADESTSTAYMELSSLRSEDTAVYYCARGGKRAMDYWGQGTLVT
VSSASTKGPSVFPLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPPSR
EEMTKNQVSLTCLVKGFYPSDIAVEWESNGQPENNYKTTPPMLDSDGSFFLYSKLTVDK
SRWQQGNVFSCSVMHEALHNHYTQKSLSLSPGK (SEQ ID NO: 100).
```

Example 2

Production of CD47 Antibodies

Chimeric antibodies disclosed herein comprise a mouse heavy chain variable domain and a light chain variable domain combined with a human kappa or human Fc IgG1, IgG1-N297Q, IgG2, IgG4, IgG4 S228P, and IgG4 PE constant domains, respectively. These were designed to incorporate a secretion signal and cloned into a mammalian expression system, and transfected into CHO cells to generate chimeric (murine-human) antibodies. The chimeric variants were expressed as full length IgG molecules, secreted into the medium, and purified using protein A.

Multiple methods for humanizing antibodies are well-known to those of ordinary skill in the art. One such method, as used herein, has previously been described (Making and Using Antibodies a Practical Handbook, Second Edition, Ed. Matthew R. Kase, Chapter 15: Humanization of Antibodies, Juan Carlos Almagro et al., CRC Press 2013). As such, the humanized antibodies disclosed herein comprise frameworks derived from the human genome. The collection covers the diversity found in the human germ line sequences, yielding functionally expressed antibodies in vivo. The complementarity determining regions (CDRs) in the light and heavy chain variable regions of the murine and chimeric (murine-human) are described herein and were determined by following commonly accepted rules disclosed in "Protein Sequence and Structure Analysis of Antibody Variable Domains," In: Antibody Engineering Lab Manual, eds. S. Duebel and R. Kontermann, Springer-Verlag, Heidelberg (2001)). The human light chain variable domains were then designed. The humanized variable domains were then combined with a secretion signal and human kappa and human Fc IgG1, IgG1-N297Q, IgG2, IgG3, IgG4 S228P and IgG4 PE constant domains, cloned into a mammalian expression system, and transfected into CHO cells to generate humanized mAbs. The humanized variants were expressed as full length IgG molecules, secreted into the medium and purified using protein A.

A non-glycosylated version (IgG1-N297Q) was created by site directed mutagenesis of heavy chain position 297 to change the asparagine to glutamine (Human Fc IgG1-N297Q, SEQ ID NO:54). An IgG4 variant was created by site-directed mutagenesis at position 228 to change the serine to proline thereby preventing in vivo Fab arm exchange. An IgG4 double mutant was created by site-directed mutagenesis at positions 228 (serine to proline) and 235 (leucine to glutamate) to prevent Fab arm exchange and to further reduce Fc effector function. IgG2, IgG3, IgG4 S228P, and IgG4PE isotypes were constructed by cloning the heavy chain variable domain in frame with the human IgG2, IgG3, IgG4 S228P, and IgG4PE constant domains (Human Fc-IgG2, SEQ ID NO:56 Human Fc-IgG3, SEQ ID NO:57; Human Fc-IgG4 S228P, SEQ ID NO:59; and Human Fc-IgG4PE, SEQ ID NO:60).

Example 3

Binding of CD47 Monoclonal Antibodies (mAbs)

The binding of chimeric (murine-human) and humanized antibodies of the present disclosure was determined by ELISA using OV10 cells transfected with human CD47 (OV10 hCD47) or using freshly isolated human red blood cells (hRBCs), which display CD47 on their surface (Kamel et al. (2010) *Blood. Transfus.* 8(4):260-266).

Binding activities of VLX4, VLX8, and VLX9 chimeric (xi) and humanized mAbs were determined using a cell-based ELISA assay with human OV10 hCD47cells expressing cell surface human CD47. OV10 hCD47 cells were grown in IMDM medium containing 10% heat inactivated fetal bovine serum (BioWest; S01520). One day before assay, $3\times10^4$ cells were plated in 96 well cell bind plates (Corning #3300, VWR #66025-626) and were 95-100% confluent at the time of assay. Cells were washed, various concentrations of purified antibodies added in IMDM and incubated at 37° C. for 1 hr in 95% $O_2$/5% $CO_2$. Cells were then washed with media and incubated for an additional hour at 37° C. with HRP labelled secondary anti-human antibody (Promega) diluted 1/2500 in media. Cells were washed three times with PBS, and the peroxidase substrate 3,3', 5,5'-tetramethylbenzidine was added (Sigma; Catalog #T4444). Reactions were terminated by the addition of HCl to 0.7N, and absorbance at 450 nM determined using a Tecan model Infinite M200 plate reader. The apparent binding affinities of these clones to human OV10 hCD47 cells was determined by non-linear fit (Prism GraphPad software).

Binding activities of chimeric and humanized VLX4, VLX8, and VLX9 mAbs to human CD47 on hRBCs were also determined using flow cytometry. Blood was obtained from normal volunteers and RBCs were washed 3 times with phosphate buffered saline, pH 7.2 containing 2.5 mM EDTA (PBS+E). hRBCs were incubated for 60 min at 37° C. with various concentrations of the chimeric or humanized antibodies in a PBS+E. Cells were then washed with cold PBS+E and incubated for an additional hour on ice with FITC labelled donkey anti-human antibody (Jackson Immuno Research Labs, West Grove, Pa.; Catalogue #709-096-149) in PBS+E. Cells were washed with PBS+E, antibody binding was analyzed using a C6 Accuri Flow Cytometer (Becton Dickinson) and apparent binding affinities determined by non-linear fit (Prism GraphPad software) of the median fluorescence intensities at the various antibody concentrations.

All of the VLX4 chimeric (murine-human) mAbs bound to human OV10 hCD47 tumor cells with apparent affinities in the picomolar (pM) range (Table 1).

Figure 1B:
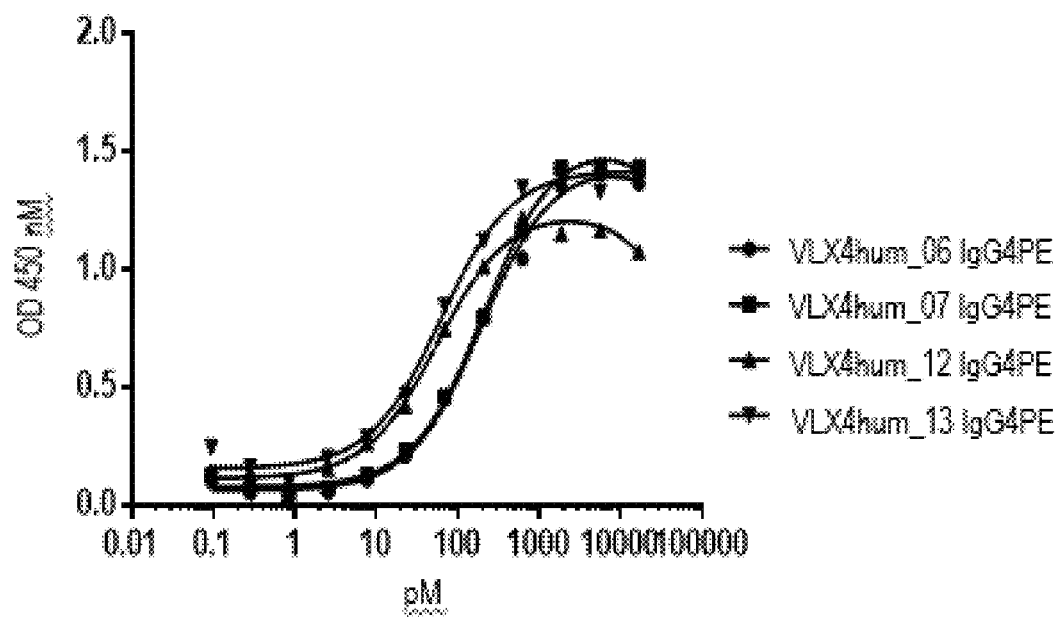
FIG. 1B. Binding of VLX4 Humanized mAbs to Human OV10 Cells Expressing Human CD47. Binding of VLX4 humanized mAbs (VLX4hum_06 IgG4PE, VLX4hum_07 IgG4PE, VLX4hum_12 IgG4PE, and VLX4hum_13 IgG4PE) to human CD47 was determined using an OV10 CD47 cell-based ELISA. OV10 hCD47 cells were plated into 96 well plates and were confluent at the time of assay. Various concentrations of VLX4 representative mAbs were added to the cells for 1 hr. Cells were washed and then incubated with HRP-labelled secondary antibody for 1 hr followed by addition of peroxidase substrate.

Similarly, the humanized VLX4 mAbs bound to human OV10 hCD47 tumor cells in a concentration-dependent manner (FIG. 1A and FIG. 1B) with apparent binding affinities ranging from the picomolar to low nanomolar range (Table 2).

All of the chimeric VLX4 mAbs bound to human RBCs with apparent Kd values in the picomolar range and these were similar to the Kd values obtained for OV10 hCD47 tumor cells by ELISA (Table 1).

Figure 2A:
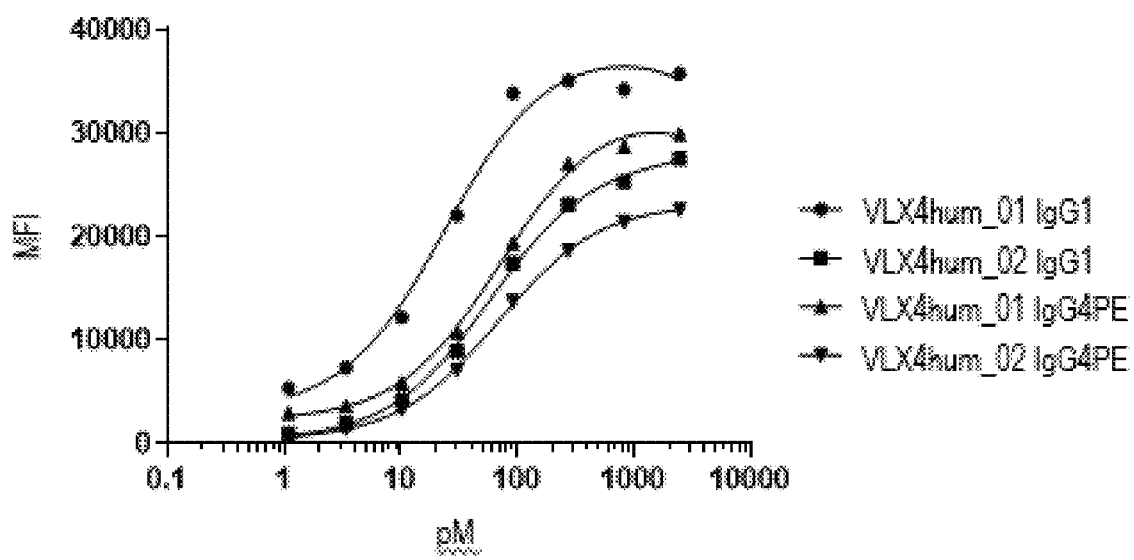
FIG. 2A. Binding of VLX4 Humanized mAbs to Human RBCs (hRBCs). Binding of VLX4 humanized mAbs (VLX4hum_01 IgG1, VLX4hum_02 IgG1, VLX4hum_01 IgG4PE, and VLX4hum_02 IgG4PE) to human CD47 was determined using freshly isolated hRBCs. hRBCs were incubated for 60 minutes at 37° C. with various concentrations of VLX4 mAbs, washed and incubated for 1 hr with FITC-labelled donkey anti-human antibody. Cells were washed and antibody binding measured using flow cytometry.
Figure 2B:
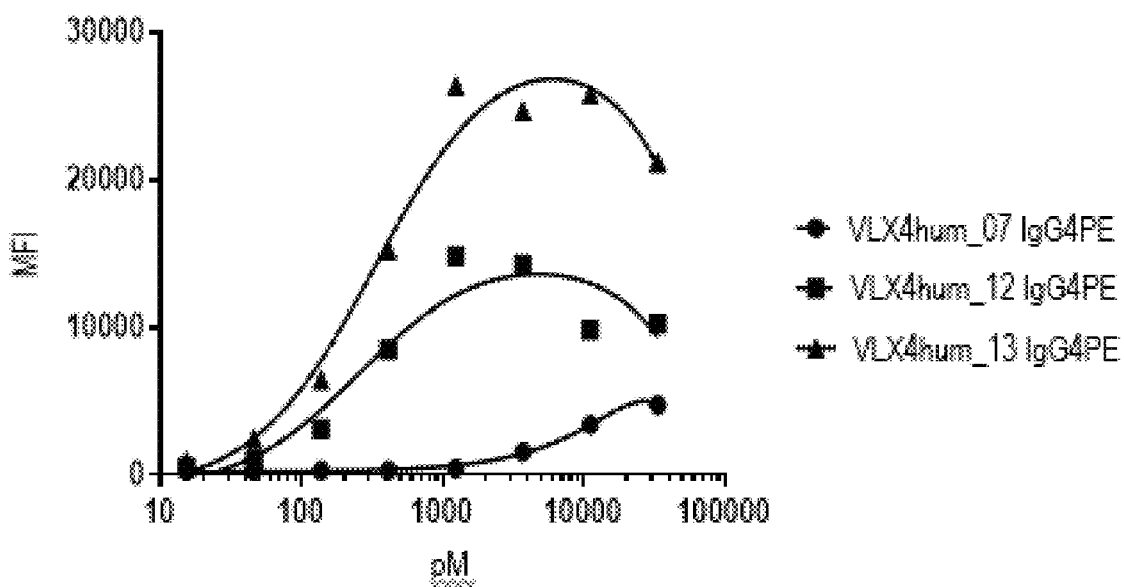
FIG. 2B. Binding of VLX4 Humanized mAbs to Human RBCs. Binding of VLX4 humanized mAbs (VLX4hum_07 IgG4PE, VLX4hum_12 IgG4PE, and VLX4hum_13 IgG4PE) to human CD47 was determined using freshly isolated hRBCs. hRBCs were incubated for 60 minutes at 37° C. with various concentrations of VLX4 mAbs, washed and incubated for 1 hr with FITC-labelled donkey anti-human antibody. Cells were washed and antibody binding measured using flow cytometry.

The humanized VLX4 mAbs VLX4hum_01 IgG1 N297Q, VLX4hum_02 IgG1 N297Q, VLX4hum_01 IgG4PE, VLX4hum_02 IgG4PE, VLX4hum_12 IgG4PE, and VLX4hum_13 IgG4PE bound to human RBCs with Kd values similar to those obtained for OV10 hCD47 tumor cells whereas VLX4hum_06 IgG4PE and VLX4hum_07 IgG4 PE exhibited reduced binding to hRBCs (FIG. 2A, FIG. 2B, and Table 2). This differential binding of the humanized mAbs to tumor cells and RBCs was unexpected as the VLX4 IgG4PE chimeric mAb bound with similar apparent Kd values to both tumor and RBC CD47 (Table 1).

As shown in Table 1, all the VLX8 chimeric mAbs bound to human OV10 hCD47 tumor cells in a concentration-dependent manner with apparent affinities in the picomolar (pM) range.

Figure 3A:
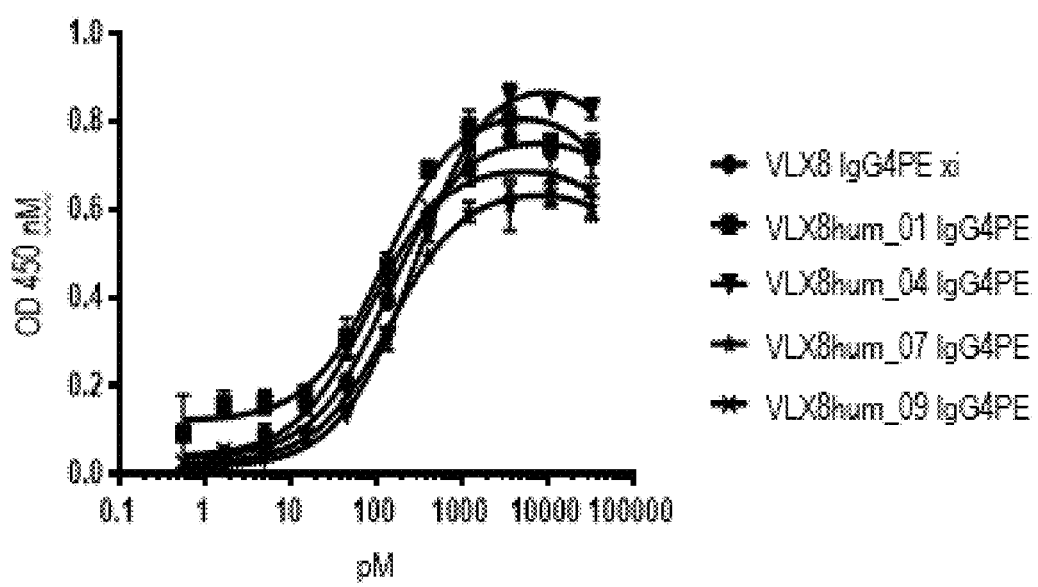
FIG. 3A. Binding of VLX8 Humanized mAbs to Human OV10 hCD47 Cells. Binding of VLX8 IgG4PE chimera (xi) or humanized mAbs (VLX8hum_01 IgG4PE, VLX8hum_04 IgG4PE, VLX8hum_07 IgG4PE, and VLX8hum_09 IgG4PE) to human CD47 was determined using an OV10 hCD47 cell-based ELISA. OV10 hCD47 cells were plated into 96 well plates and were confluent at the time of assay. Various concentrations of VLX8 representative mAbs were added to the cells for 1 hr. Cells were washed and then incubated with HRP-labelled secondary antibody for 1 hr followed by addition of peroxidase substrate.
Figure 3B:
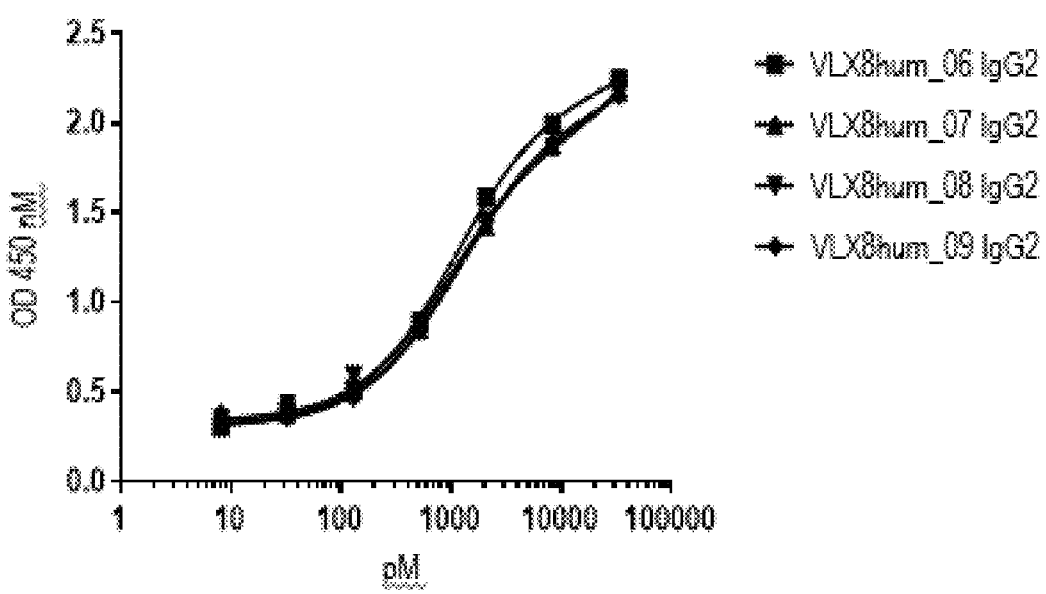
FIG. 3B. Binding of VLX8 Humanized mAbs to Human OV10 hCD47 Cells. Binding of VLX8 chimera or humanized mAbs (VLX8hum_06 IgG2, VLX8hum_07 IgG2, VLX8hum_08 IgG2, and VLX8hum_09 IgG2) to human CD47 was determined using an OV10 hCD47 cell-based ELISA. OV10 hCD47 cells were plated into 96 well plates and were confluent at the time of assay. Various concentrations of VLX8 representative mAbs were added to the cells for 1 hr. Cells were washed and then incubated with HRP-labelled secondary antibody for 1 hr followed by addition of peroxidase substrate.

Similarly, the humanized VLX8 mAbs bound to human OV10 hCD47 tumor cells in a concentration-dependent manner (FIG. 3A and FIG. 3B) with apparent affinities in the picomolar range (Table 2).

All the VLX8 chimeric mAbs bound to hRBCs with apparent Kd values in the picomolar range and these were similar to the apparent Kd values obtained for OV10 hCD47 tumor cells by ELISA (Table 1).

The VLX8 humanized mAbs VLX8hum_01 IgG4PE, VLX8hum_02 IgG4PE, VLX8hum_03 IgG4PE, VLX8hum_04 IgG4PE, VLX8hum_05 IgG4 PE, and VLX8hum_06 IgG4PE, VLX8hum_07 IgG4PE, VLX8hum_08 IgG4 PE, VLX8hum_09 IgG4 PE, VLX8hum_11 IgG4 PE, VLX8hum_06 IgG2, VLX8hum_07 IgG2, VLX8hum_08 and VLX8hum_09 IgG2 IgG2 bound to human RBCs with Kd values similar to the values obtained for OV10 hCD47 tumor cells whereas VLX8hum_10 IgG4PE exhibited reduced to hRBCs (FIG. 4A, FIG. 4B, and Table 2). This differential binding of the humanized mAbs to tumor cells and RBCs was unexpected as the VLX8 IgG4PE chimeric mAb bound with similar apparent Kd values to both tumor and RBC CD47 (Table 1).

Figure 5A:
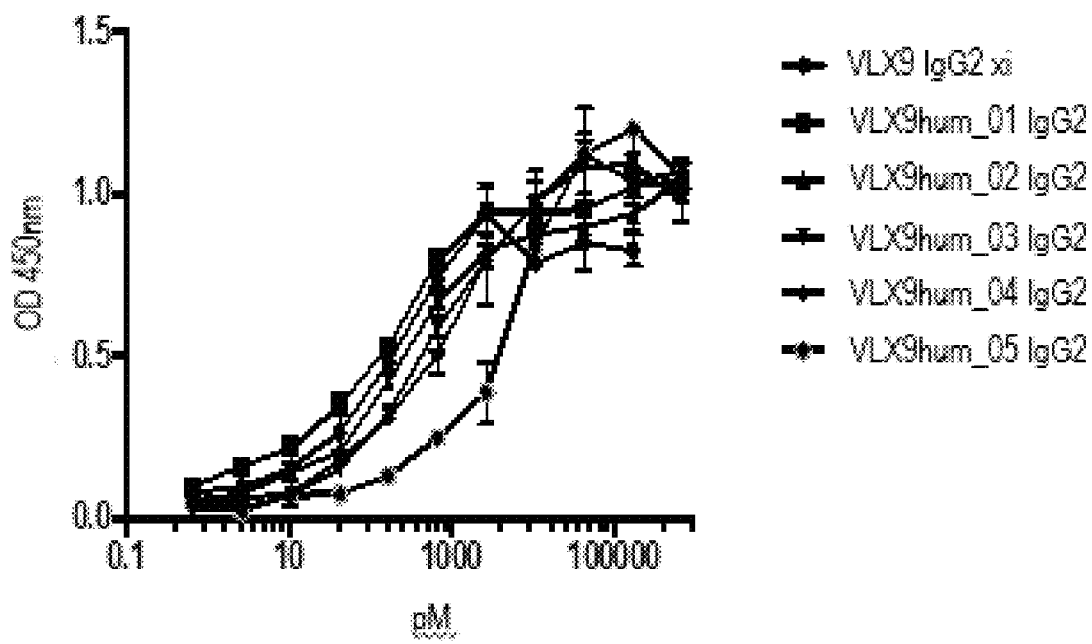
FIG. 5A. Binding of VLX9 Humanized mAbs to Human OV10 hCD47 Cells. Binding of VLX9 IgG2 xi or humanized mAbs (VLX9hum_01 IgG2, VLX9hum_02 IgG2, VLX9hum_03 IgG2, VLX9hum_04 IgG2 and VLX9hum_05 IgG2) to human CD47 was determined using an OV10 human CD47 cell-based ELISA. OV10 hCD47 cells were plated into 96 well plates and were confluent at the time of assay. Various concentrations of mAbs were added to the cells for 1 hr. Cells were washed and then incubated with HRP-labelled secondary antibody for 1 hr followed by addition of peroxidase substrate.
Figure 5B:
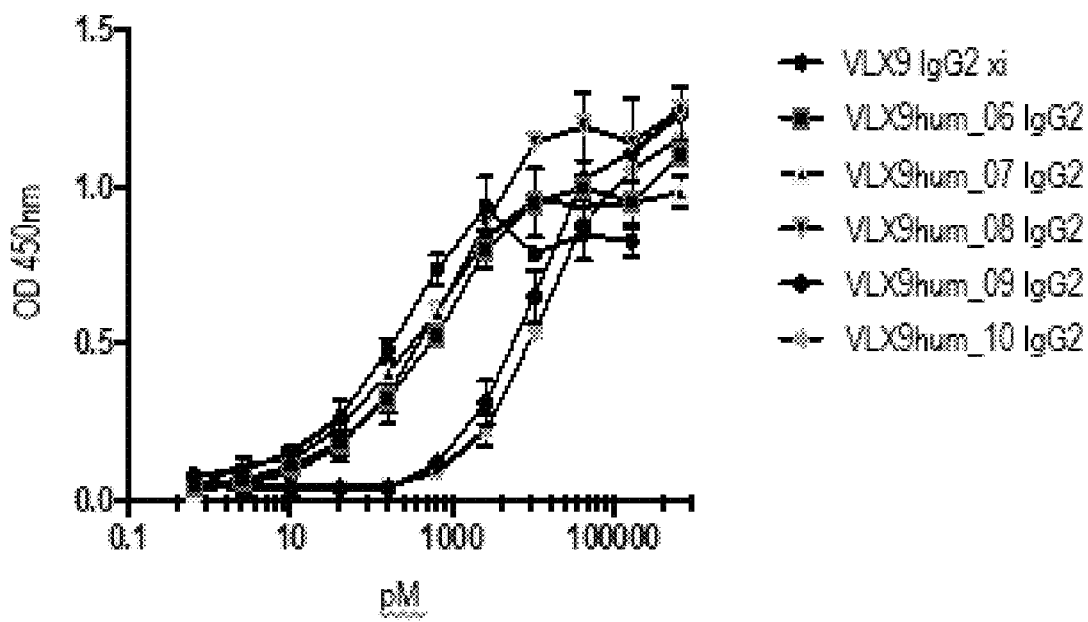
FIG. 5B. Binding of VLX9 Humanized mAbs to Human OV10 hCD47 Cells. Binding of VLX9 IgG2 xi or humanized mAbs (VLX9hum_06 IgG2, VLX9hum_07 IgG2, VLX9hum_08 IgG2, VLX9hum_09 IgG2 and VLX9hum_10 IgG2) to human CD47 was determined using a OV10 hCD47 cell-based ELISA. OV10 hCD47 cells were plated into 96 well plates and were confluent at the time of assay. Various concentrations of mAbs were added to the cells for 1 hr. Cells were washed and then incubated with HRP-labelled secondary antibody for 1 hr followed by addition of peroxidase substrate.

Table 1 shows the apparent binding affinities of VLX9 chimeric mAbs to human OV10 hCD47 cells and to human RBCs. All of the chimeric mAbs bound to OV10 hCD47 tumor cells with apparent binding constants in the picomolar range. Similarly, the humanized VLX9 mAbs bound to human OV10 hCD47 tumor cells in a concentration-dependent manner (FIG. 5A and FIG. 5B) with apparent affinities in the picomolar to nanomolar range (Table 2).

Figure 7:
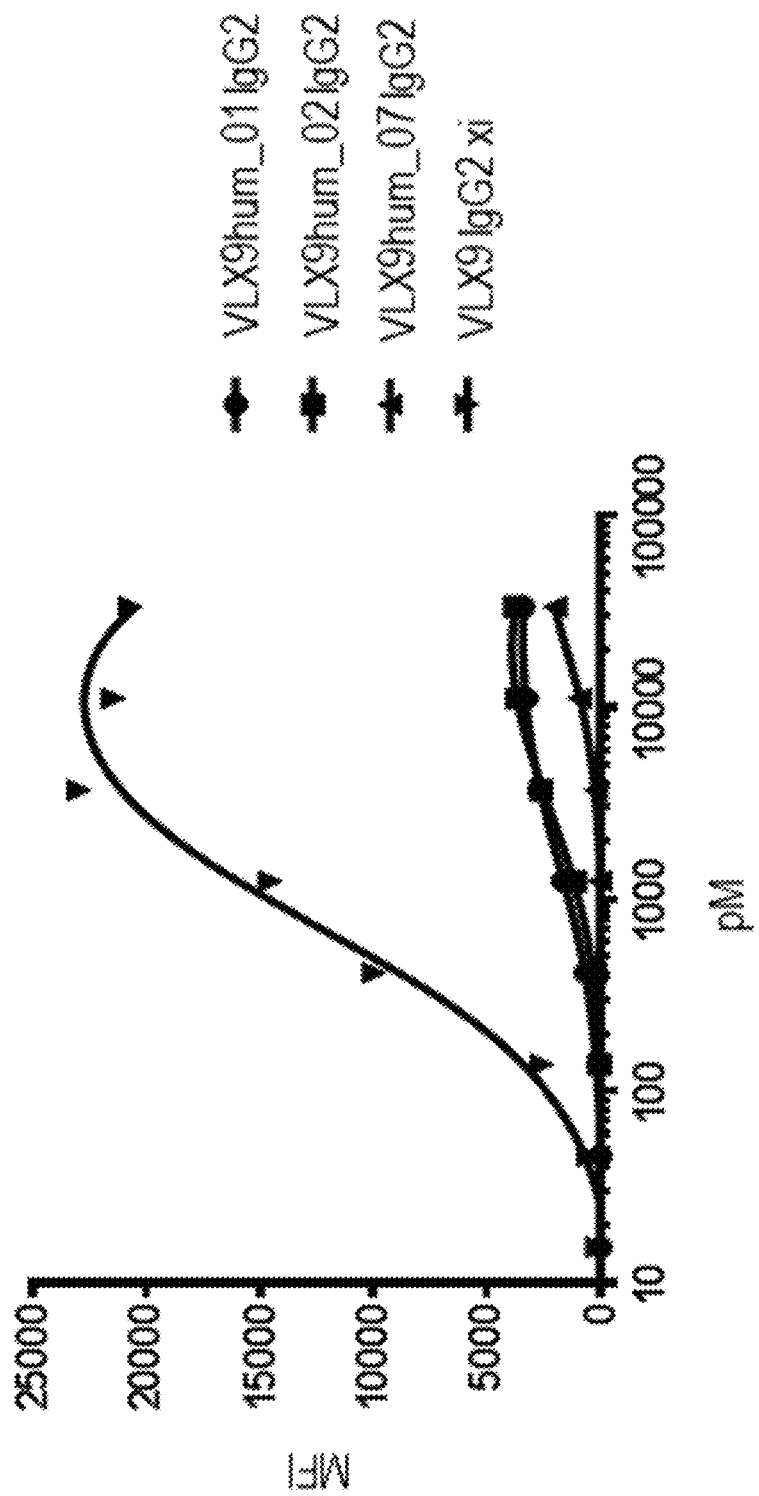
FIG. 7. Binding of VLX9 Humanized mAbs to Human RBCs. Binding of VLX9 IgG2 xi or humanized VLX9 mAbs to human CD47 (VLX9hum_01 IgG2, VLX9hum_02 IgG2 and VLX9hum_07 IgG2) was determined using freshly isolated human hRBCs. RBCs were incubated for 60 minutes at 37° C. with various concentrations of VLX9 mAbs, washed and incubated for 1 hr with FITC-labelled donkey anti-human antibody. Cells were washed and antibody binding measured using flow cytometry.

All the VLX9 chimeric mAbs bound to hRBCs with apparent Kd values in the picomolar range and these were similar to the apparent Kd values obtained for OV10 hCD47 tumor cells by ELISA (Table 1). In contrast to the chimeric mAbs, the VLX9 humanized mAbs VLX9hum_01 IgG2, VLX9hum_02 IgG2 and VLX9hum_07 IgG2 exhibited reduced binding to human RBCs (FIG. 7, Table 2). By contrast, the humanized mAbs VLX9hum_03 IgG2, VLX9hum_04 IgG2, VLX9hum_05 IgG2, VLX9hum_06 IgG2, VLX9hum_08 IgG2, VLX9hum_09 IgG2 and VLX9hum_10 IgG2 exhibited no measureable binding to RBCs up to 5,000 pM (Table 2). This differential binding of the humanized mAbs to tumor cells and RBCs was unexpected as the VLX9 IgG2 chimeric mAbs all bound with similar apparent Kd values to both tumor and RBC CD47 (Table 1).

Specific binding of CD47 humanized mAbs was demonstrated using Jurkat wildtype and Jurkat CD47 knockout (KO) cells. Jurkat wildtype and Jurkat CD47 KO cells were grown in RPMI medium containing 10% heat inactivated fetal bovine serum (BioWest; S01520). The cells were washed and $1 \times 10^4$ cells were resuspended media and incubated with various antibody concentrations for one hour at 37° in 5% $CO_2$ Cells were then washed twice with 1×PBS and then resuspended 1:1000 in secondary antibody (goat anti-human IgG (H+L) FITC-labelled, Jackson Labs, 109-095-003) for one hour at 37° in 5% $CO_2$. Cells were then washed twice with 1×PBS and resuspended in 1×PBS. Median fluorescence intensity was determined by flow cytometry and the apparent binding affinities determined by non-linear fit (Prism GraphPad software).

Figure 6B:
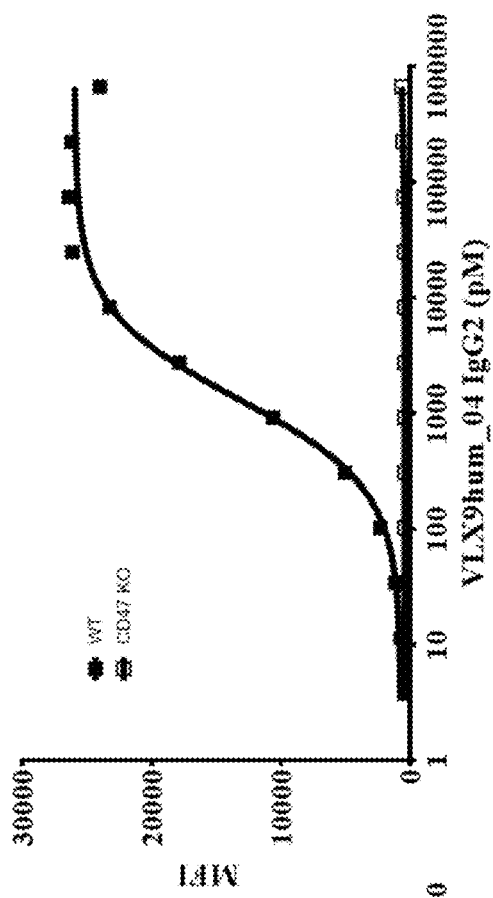
FIG. 6B. Specific Binding of VLX Humanized mAbs to CD47. Binding of VLX humanized mAb VLX9hum_04 IgG2 to wildtype and CD47 knockout Jurkat cells was determined by flow cytometry. Various concentrations of mAbs were added to $1 \times 10^4$ cells for 1 hr. The cells were washed and then incubated with FITC-labelled secondary antibody for 1 hr. Cells were washed and antibody binding measured using flow cytometry.
Figure 6A:
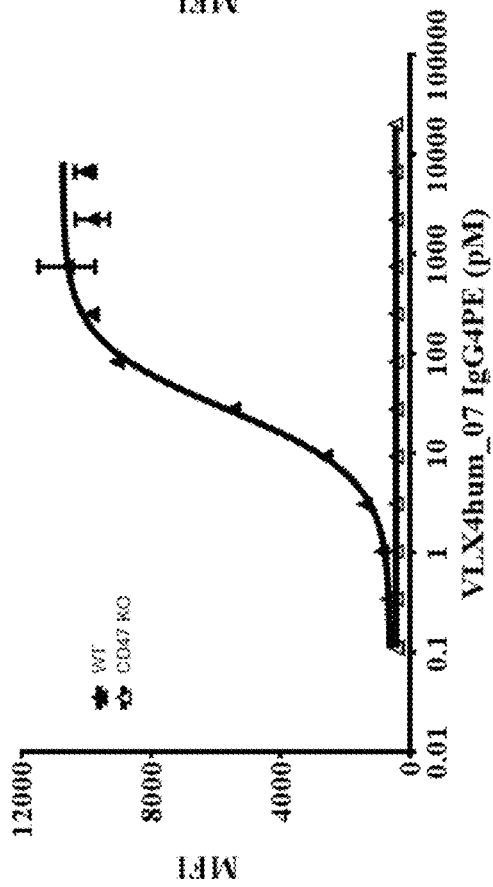
FIG. 6A. Specific Binding of VLX Humanized mAbs to CD47. Binding of VLX humanized mAb VLX4hum_07 IgG4PE to wildtype and CD47 knockout Jurkat cells was determined by flow cytometry. Various concentrations of mAbs were added to $1 \times 10^4$ cells for 1 hr. The cells were washed and then incubated with FITC-labelled secondary antibody for 1 hr. Cells were washed and antibody binding measured using flow cytometry.

As shown in FIG. 6, VLX4hum_07 IgG4PE (FIG. 6A) and VLX9hum_09 IgG2 (FIG. 6B) bound to Jurkat cells expressing CD47, whereas no binding is observed to Jurkat CD47KO cells.

TABLE 1

Binding of VLX4, VLX8, and VLX9 Chimeric (xi) mAbs to OV10 hCD47 Cells and Human Red Blood Cells (hRBCs).

| | Kd (pM) OV10 hCD47 Cell-based ELISA | Kd (pM) hRBC | HA hRBC |
|---|---|---|---|
| VLX4 IgG1 (xi) | 315 | 104 | Yes |
| VLX4 IgG1 N297Q (xi) | 258 | 92 | Yes |
| VLX4 IgG2 (xi) | 431 | 184 | Yes |
| VLX4 IgG4 S228P (xi) | 214 | 99 | No |
| VLX4 IgG4 PE (xi) | 225 | 303 | No |
| VLX8 IgG1 N297Q (xi) | 42 | 91 | Yes |
| VLX8 IgG4 PE (xi) | 56 | 77 | Yes |
| VLX9 IgG1 (xi) | 280 | 381 | Yes |
| VLX9 IgG1 N297Q (xi) | 275 | 190 | Yes |
| VLX9 IgG2 (xi) | 880 | 742 | Yes |
| VLX9 IgG4 PE (xi) | 293 | 126 | Yes |

TABLE 2

Binding of VLX4, VLX8, and VLX9 Humanized mAbs to Human OV10 hCD47 and Human Red Blood Cells (hRBCs).

| | Kd (pM) OV10 hCD47 Cell-based ELISA | Kd (pM) hRBC | HA hRBC |
|---|---|---|---|
| VLX4hum_01 IgG1 | 73 | 23 | Yes |
| VLX4hum_02 IgG1 | 80 | 70 | Yes |
| VLX4hum_01 IgG4 PE | 82 | 80 | No |
| VLX4hum_02 IgG4 PE | 95 | 75 | R*** |
| VLX4hum_06 IgG4 PE | 196 | >33,000** | Yes |
| VLX4hum_07 IgG4 PE | 209 | >33,000** | Yes |
| VLX4hum_12 IgG4 PE | 56 | 263 | Yes |
| VLX4hum_13 IgG4 PE | 62 | 340 | Yes |
| VLX8hum_01 IgG4 PE | 54 | 209 | No |
| VLX8hum_02 IgG4 PE | 50 | 221 | No |
| VLX8hum_03 IgG4 PE | 67 | 183 | No |
| VLX8hum_04 IgG4 PE | 49 | 119 | No |
| VLX8hum_05 IgG4 PE | 68 | 264 | No |
| VLX8hum_06 IgG4 PE | 61 | 274 | Yes |
| VLX8hum_07 IgG4 PE | 24 | 241 | Yes |
| VLX8hum_08 IgG4 PE | 97 | 217 | Yes |
| VLX8hum_09 IgG4 PE | 82 | 336 | Yes |
| VLX8hum_10 IgG4 PE | 183 | >33,000** | Yes |
| VLX8hum_11 IgG4 PE | 90 | 87 | No |
| VLX8hum_06 IgG2 | 403 | 246 | Yes |
| VLX8hum_07 IgG2 | 460 | 671 | Yes |
| VLX8hum_08 IgG2 | 464 | 820 | Yes |
| VLX8hum_09 IgG2 | 680 | 1739 | Yes |
| VLX9hum_01 IgG2 | 162 | 1653** | No |
| VLX9hum_02 IgG2 | 227 | 4103** | No |
| VLX9hum_03 IgG2 | 606 | *MB | No |
| VLX9hum_04 IgG2 | 823 | *MB | No |
| VLX9hum_05 IgG2 | 6372 | *MB | No |
| VLX9hum_06 IgG2 | 547 | *MB | No |
| VLX9hum_07 IgG2 | 341 | >66,000** | ***R |
| VLX9hum_08 IgG2 | 688 | *MB | No |
| VLX9hum_09 IgG2 | 8340 | *MB | No |
| VLX9hum_10 IgG2 | 12232 | *MB | No |

*MB—Minimal binidimg; no measureable binding detected at mAb concentration up to 5,000 pM.
**—Reduced RBC binding.
***R—Reduced hemagglutination.

Cross-species binding of humanized VLX4, VLX8, and VLX9 mAbs was determined using flow cytometry. Mouse, rat, rabbit or cynomolgus monkey RBCs were incubated for 60 min on at 37° C. with various concentrations of the humanized antibodies in a solution of phosphate buffered saline, pH 7.2, 2.5 mM EDTA (PBS+E). Cells were then washed with cold PBS+E, and incubated for an additional hr on ice with FITC labelled donkey anti-human antibody (Jackson Immuno Research Labs, West Grove, Pa.; Catalogue #709-096-149) in PBS+E. Cells were washed with PBS+E, and antibody binding analyzed using a C6 Accuri Flow Cytometer (Becton Dickinson).

Table 3 shows the apparent binding affinities of the humanized VLX4 and VLX8 mAbs to RBCs from mouse, rat, and cynomolgus monkey determined by non-linear fit (Prism GraphPad software) of the median fluorescence intensities at various antibody concentrations. This data demonstrates that humanized VLX4 and VLX8 mAbs bind to mouse, rat, rabbit (data not shown) and cynomolgus monkey RBCs with apparent Kd values in the picomolar to nanomolar range.

TABLE 3

Binding of VLX4 and VLX8 Humanized mAbs to Mouse, Rat and Cynomolgus Monkey RBCs.

| | Kd (pM) Mouse RBC | Kd (pM) Rat RBC | Kd (pM) Cynomolgus Monkey RBC |
|---|---|---|---|
| VLX4hum_01 IgG4 PE | 13001 | 30781 | 56 |
| VLX4hum_07 IgG4 PE | 15192 | 14274 | 13522 |
| VLX8hum_11 IgG4 PE | 9123 | 8174 | 55 |

Example 4

Binding of Humanized Anti-CD47 mAbs Determined by Surface Plasmon Resonance

Binding of soluble anti-CD47 mAbs to recombinant human His-CD47 was measured in vitro by surface plasmon resonance on a Biacore 2000. An Anti-Human IgG (GE Lifesciences) was amine coupled to a CM5 chip on flow cells 1 and 2. The humanized mAbs VLX4hum_07 IgG4PE, VLX8hum_11 IgG4PE, VLX9hum_08 IgG2 or VLX9hum_03 IgG2 diluted in HBS-EP$^+$ running buffer (pH 7.2) were captured onto flow cell 2. Multi-cycle kinetics were determined using 0 to 1000 nM His-tagged human CD47 (Acro Biosystems) diluted in HBS-EP$^+$ running buffer (pH 7.2) with contact time of 180 seconds and dissociation time of 300 seconds. A 1:1 binding model was employed for kinetic analysis of binding curves. The on-rate, off-rate and Dissociation constants for VLX4hum_07 IgG4PE, VLX8hum_11 IgG4PE, VLX9hum_08 IgG2 and VLX9hum_03 IgG2 are shown in Table 4.

TABLE 4

Binding of VLX4, VLX8 and VLX9 Humanized mAbs to Human Recombinant His-CD47 by Surface Plasmon Resonance at pH 7.2.

| | $k_a$ | $k_d$ | $K_D$ (nM) |
|---|---|---|---|
| VLX4hum_07 IgG4PE | $1.7e^5$ | $8.7e^{-4}$ | 5.1 |
| VLX8hum_11 IgG4PE | $6.8e^5$ | $7.9e^{-4}$ | 1.2 |
| VLX9_08 IgG2 | $7.6e^4$ | $6.5e^{-4}$ | 8.6 |
| VLX9_03 IgG2 | $6.5e^4$ | $7.3e^{-4}$ | 11.1 |

Example 5

Differential Binding of Anti-CD47 mAbs

Some soluble CD47 antibodies described herein have been shown to differentially bind to normal cells. This additional property of selective binding is expected to have advantages compared to mAbs that bind with equal affinity to normal and tumor cells. Anti-CD47 mAbs with such reduced binding have not been described.

Binding by soluble anti-CD47 mAbs is measured in vitro. Binding activities of VLX4, VLX8, and VLX9 humanized mAbs were determined using a flow cytometry based binding assay with human aortic endothelial cells (HAEC), skeletal muscle cells (SkMC), human lung microvascular endothelial cells (HMVEC-L), renal tubular epithelial cells (RTEC), CD3$^+$ cells or peripheral blood mononuclear cells (PBMC). HAEC, SkMC, HMVEC-L and RTEC cells were purchased from Lonza and cultured according to the manufacturer's recommendations. Adherent cells were removed from the culture flask with accutase, resuspended in the recommended media and $1 \times 10^4$ cells were incubated with various antibody concentrations for one hour at 37°, 5% $CO_2$. For non-adherent cells, $1 \times 10^4$ cells were resuspended in the recommended media and incubated with various antibody concentrations for one hour at 37°, 5% $CO_2$ Cells were then washed twice with 1×PBS and then resuspended 1:1000 in secondary antibody (goat anti-human IgG (H+L)-FITC, Jackson Labs, 109-095-003) for one hour at 37° C., 5% $CO_2$.

PBMC were isolated by ficoll gradient and were incubated with an FcR blocking reagent (Miltenyi Biotec) for 10 min at 4° C. per manufacturer's recommendation immediately preceeding the addition of various concentrations of antibodies diluted in PBS. CD3 cells were detected using an allophycocyanin (APC)-labelled anti-CD3 antibody (BD BioSciences) which was added at the same time as the FITC-labelled goat anti-human IgG (H+L) antibody. Cells were washed twice with 1×PBS and antibody binding was assessed by flow cytometry analysis.

Figure 8B:
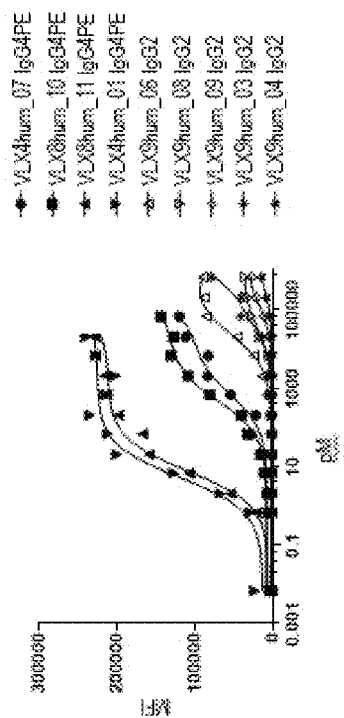
FIG. 8B. Binding of VLX Humanized mAbs to Skeletal Human Muscle Cells (SkMC). Binding of VLX humanized mAbs (VLX4hum_07 IgG4PE, VLX8hum_10 IgG4PE, VLX8hum_11 IgG4PE, VLX4hum_01 IgG4PE, VLX9hum_06 IgG2, VLX9hum_08 IgG2, VLX9hum_09 IgG2, VLX9hum_03 IgG2 and VLX9hum_04 IgG2) to SkMc was determined by flow cytometry. SkMC were removed from the flask using acutase. Various concentrations of mAbs were added to $1 \times 10^4$ cells for 1 hr. The cells were washed and then incubated with FITC-labelled secondary antibody for 1 hr followed by measurement of FITC label by flow cytometry.
Figure 8D:
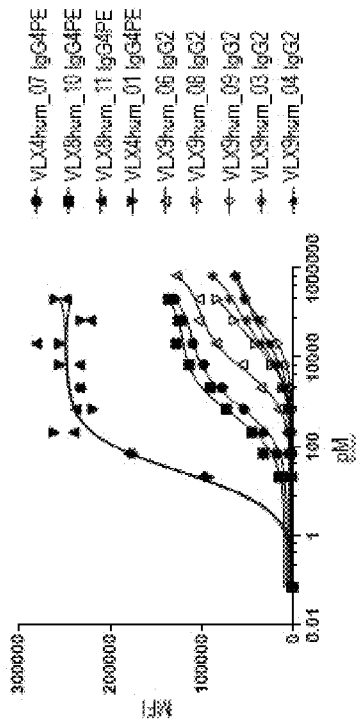
FIG. 8D. Binding of VLX Humanized mAbs to Human Renal Tubular Epithelial Cells (RTEC). Binding of VLX humanized mAbs (VLX4hum_07 IgG4PE, VLX8hum_10 IgG4PE, VLX8hum_11 IgG4PE, VLX4hum_01 IgG4PE, VLX9hum_06 IgG2, VLX9hum_08 IgG2, VLX9hum_09 IgG2, VLX9hum_03 IgG2 and VLX9hum_04 IgG2) to RTEC by flow cytometry. RTEC were removed from the flask using acutase. Various concentrations of mAbs were added to $1 \times 10^4$ cells for 1 hr. The cells were washed and then incubated with FITC-labelled secondary antibody for 1 hr followed by measurement of FITC label by flow cytometry.
Figure 8A:
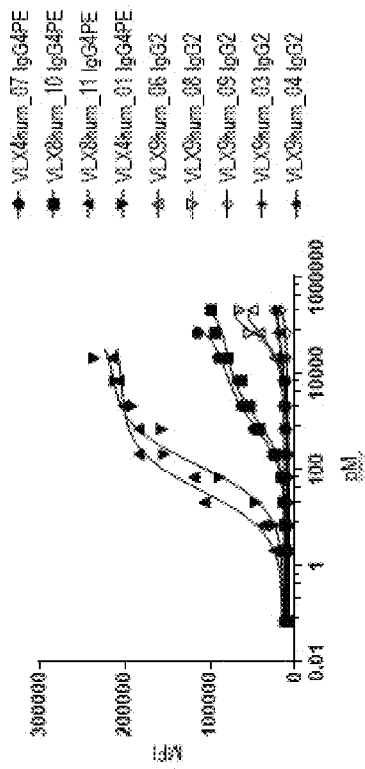
FIG. 8A. Binding of VLX Humanized mAbs to Human Aortic Endothelial Cells (HAEC). Binding of VLX humanized mAbs (VLX4hum_07 IgG4PE, VLX8hum_10 IgG4PE, VLX8hum_11 IgG4PE, VLX4hum_01 IgG4PE, VLX9hum_06 IgG2, VLX9hum_08 IgG2, VLX9hum_09 IgG2, VLX9hum_03 IgG2 and VLX9hum_04 IgG2) to HAEC was determined by flow cytometry. HAEC were removed from the flask using acutase. Various concentrations of mAbs were added to $1 \times 10^4$ cells for 1 hr. The cells were washed and then incubated with FITC-labelled secondary antibody for 1 hr followed by measurement of FITC label by flow cytometry.
Figure 8C:
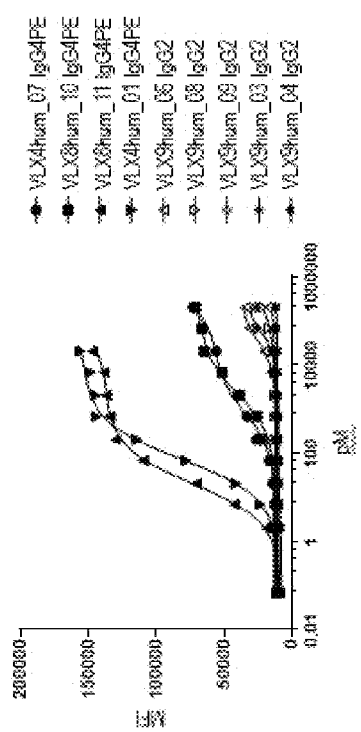
FIG. 8C. Binding of VLX Humanized mAbs to Human Lung Microvascular Endothelial Cells (HMVEC-L). Binding of VLX humanized mAbs (VLX4hum_07 IgG4PE, VLX8hum_10 IgG4PE, VLX8hum_11 IgG4PE, VLX4hum_01 IgG4PE, VLX9hum_06 IgG2, VLX9hum_08 IgG2, VLX9hum_09 IgG2, VLX9hum_03 IgG2 and VLX9hum_04 IgG2) to HMVEC-L was determined by flow cytometry. HMVEC-L were removed from the flask using acutase. Various concentrations of mAbs were added to $1 \times 10^4$ cells for 1 hr. The cells were washed and then incubated with FITC-labelled secondary antibody for 1 hr followed by measurement of FITC label by flow cytometry.

As shown in FIG. 8A, VLX4 and VLX8 humanized mAbs bound to HAEC cells whereas VLX9 humanized mAbs had reduced or minimal binding to HAEC cells as compared to tumor cells (Table 5). VLX9 humanized mAbs also showed reduced binding to SkMC cells (FIG. 8B), reduced or minimal binding to HMVEC-L cells (FIG. 8C), reduced binding to RPTEC cells (FIG. 8D) as compared to binding to tumor cells (Table 5). Reduced binding of VLX9 humanized mAbs was also observed to CD3$^+$ cells (FIG. 8E) and PBMC (FIG. 8F) as compared to tumor cells (Table 5). This selective binding imparts an additional desirable antibody property and potential therapeutic benefit in the treatment of cancer.

TABLE 5

VLX4, VLX8 and VLX9 Humanized mAbs Binding to Normal Cells.

| | Kd (pM) OV10 hCD47 Cell-based ELISA | Kd (pM) hRBC | Kd (pM) HAEC | Kd (pM) HMVEC-L | Kd (pM) SKMC | Kd (pM) RPTEC | Kd (pM) CD3$^+$ | Kd (pM) PBMC |
|---|---|---|---|---|---|---|---|---|
| VLX4hum_01 IgG4 PE | 82 | 80 | 118 | 72 | 5 | 26 | 220 | 269 |
| VLX4hum_07 IgG4 PE | 209 | >33,000** | 747 | 792 | 630 | 784 | 440 | 499 |

TABLE 5-continued

VLX4, VLX8 and VLX9 Humanized mAbs Binding to Normal Cells.

| | Kd (pM) OV10 hCD47 Cell-based ELISA | Kd (pM) hRBC | Kd (pM) HAEC | Kd (pM) HMVEC-L | Kd (pM) SKMC | Kd (pM) RPTEC | Kd (pM) CD3+ | Kd (pM) PBMC |
|---|---|---|---|---|---|---|---|---|
| VLX8hum_10 IgG4 PE | 183 | >33,000** | 1104 | 2113** | 461 | 491 | 91 | 106 |
| VLX8hum_11 IgG4 PE | 90 | 87 | 34 | 20 | 7 | 26 | 144 | 156 |
| VLX9hum_03 IgG2 | 606 | MB* | MB* | >200,000** | >200,000** | >200,000** | 10863** | 10232** |
| VLX9hum_04 IgG2 | 823 | MB* | MB* | MB* | >200,000** | >200,000** | 7426** | 7619** |
| VLX9hum_06 IgG2 | 547 | MB* | >200,000** | 71619** | 23483** | 4847** | 19354** | 17907** |
| VLX9hum_08 IgG2 | 688 | MB* | >200,000** | >200,000** | 34783** | >200,000** | 28287** | 24486** |
| VLX9hum_09 IgG2 | 8340 | MB* | MB* | MB* | MB* | >200,000** | 56146** | 48348** |

*MB—Minimal binding, no measureable binding detected at mAb concentration up to 5,000 pM.
**Reduced binding.

Example 6 pH Dependent and Independent Binding of Humanized Anti-CD47 mAbs

Some soluble anti-CD47 mAbs described herein have been shown to bind tumor cells at acidic pH with greater affinity compared to physiologic pH. This additional property is expected to have advantages compared to mAbs that bind at similar affinities to CD47 at both acidic and physiologic pH, in part due to the acidic nature of the tumor microenvironment (Tannock and Rotin, Cancer Res 1989; Song et al. Cancer Drug Discovery and Development 2006; Chen and Pagel, Advan Radiol 2015).

Binding by soluble anti-CD47 mAbs to immobilized recombinant human CD47 and to human CD47 expressed on cells was measured in vitro. For the in vitro binding to recombinant CD47, His-CD47 (AcroBiosystems) was adsorbed to high-binding microtiter plates overnight at 4° C. The wells were washed and varying concentrations of anti-CD47 mAbs were added to the wells in buffers with a of either pH 6 or pH 8 for 1 hour. The wells were washed and then incubated with HRP-labelled secondary antibody for 1 hour at pH 6 or pH 8 followed by addition of peroxidase substrate. The apparent affinities were calculated using non-linear fit model (Graphpad Prism).

For analysis of pH dependent binding by surface plasmon resonance using a Biacore 2000, an Anti-Human IgG (GE Lifesciences) was amine coupled to a CM5 chip on flow cells 1 and 2. An Fc-tagged human CD47 (Acro Biosystems) was diluted in PBS-EP+ running buffer (pH 7.5, 6.5 or 6.0) and captured onto flow cell 2. Multi-cycle kinetics were determined using 0 to 100 nM VLX8hum_11 Fab or VLX9hum_08 Fab diluted in PBS-EP+ running buffer (pH 7.5, 6.5 or 6.0) with contact time of 180 seconds and dissociation time of 300 seconds. A 1:1 binding model was employed for kinetic analysis of binding curves.

For the in vitro binding to cells expressing CD47, Jurkat cells were grown in RPMI medium containing 10% heat inactivated fetal bovine serum (BioWest; S01520). The cells were washed and 1×10$^4$ cells were resuspended in PBS supplementated with 2% FBS at either pH 7.4 or 6.5 and incubated with various antibody concentrations for 1 hour at 37° C. Cells were then washed twice and resuspended with 1:1000 of secondary antibody (goat anti-human IgG (H+L) labelled with Alexa488, JacksonImmunoresearch) for 1 hour at 37° C. at pH 6 or pH 8. Cells were then washed twice and the median fluorescence intensity was determined by flow cytometry. The apparent binding affinities were determined by non-linear fit (Prism GraphPad software).

Figure 9B:
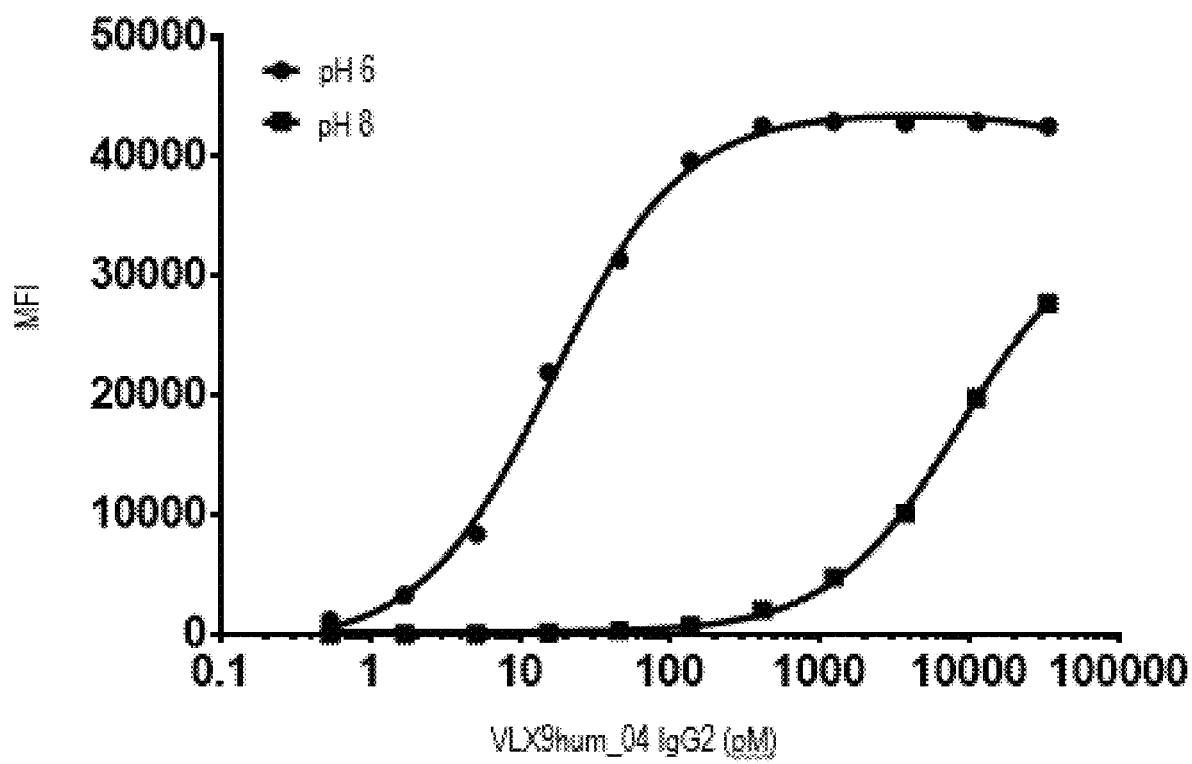
FIG. 9B. pH Dependent and pH Independent Binding of Humanized mAb to His-CD47. Binding of VLX9hum_04 IgG2 to human CD47 was determined using a solid-phase CD47 ELISA assay. His-CD47 was adsorbed to microtiter wells, washed and various concentrations of humanized mAbs were added to the wells for 1 hr at pH 6 or 8. The wells were washed and then incubated with HRP-labelled secondary antibody for 1 hour followed by addition of peroxidase substrate.
Figure 9D:
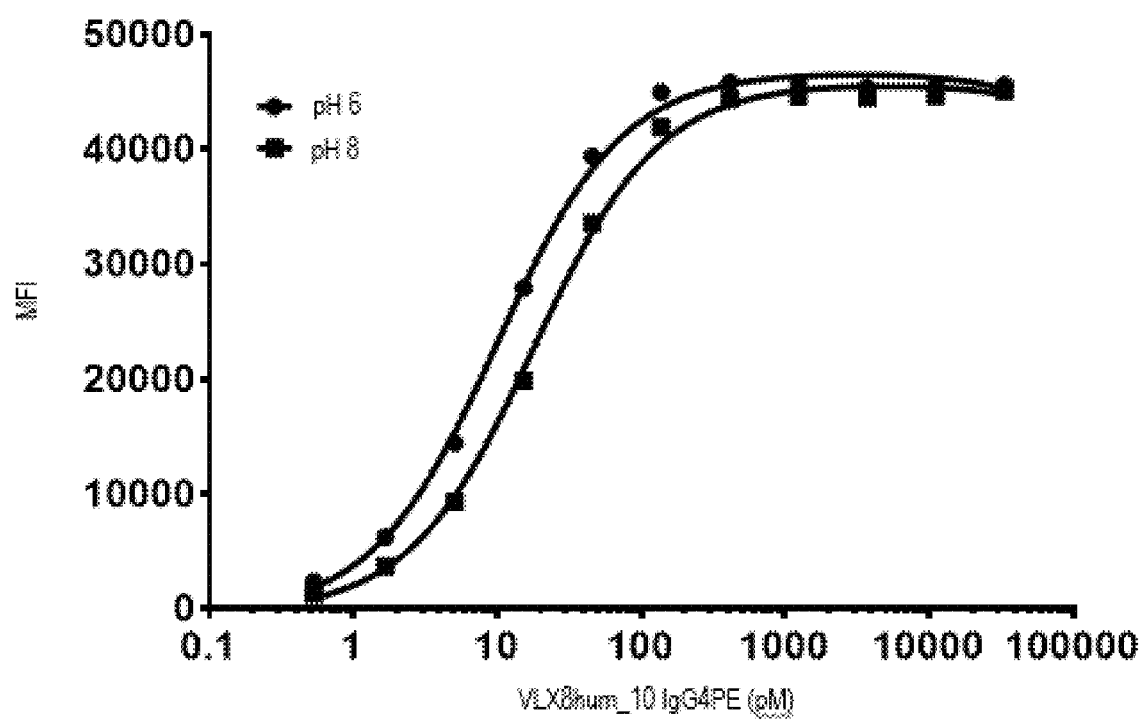
FIG. 9D. pH Dependent and pH Independent Binding of Humanized mAb to His-CD47. Binding of VLX8hum_10 IgG4PE to human CD47 was determined using a solid-phase CD47 ELISA assay. His-CD47 was adsorbed to microtiter wells, washed and various concentrations of humanized mAbs were added to the wells for 1 hr at pH 6 or 8. The wells were washed and then incubated with HRP-labelled secondary antibody for 1 hour followed by addition of peroxidase substrate.

As shown in FIG. 9A and FIG. 9B, the soluble VLX9 humanized mAbs (VLX9hum_09 IgG2 and VLX9hum_04 IgG2) bound to His-CD47 with greater affinity at the more acidic pH 6.0 than at pH 8.0. Neither VLX4hum_07 IgG4PE (FIG. 9C) nor VLX8hum_10 IgG4PE (FIG. 9D) displayed pH dependent binding. In addition, the murine VLX9 antibody and VLX9 chimeric antibodies containing human Fc from isotypes IgG1, IgG2 and IgG4PE did not display pH dependence (Table 6) whereas VLX9hum_04 as either an IgG1, IgG2 or an IgG4PE demonstrated greater binding to His-CD47 at acidic pH (Table 7). The apparent binding affinities for additional humanized mAbs to recombinant human CD47 are shown in Table 8. All humanized VLX9 mAbs exhibited pH dependent binding whereas the VLX4 and VLX8 humanized mAbs did not. To determine the effect of pH on on-rates, off-rates and dissociation constants, Biacore analysis was performed for humanized mAbs VLX8hum_11 Fab fragment and VLX9hum_08 Fab at pH 6, pH 6.5 and pH 7.5. The VLX9hum_08 Fab exhibited pH dependent binding that increased with decreasing pH whereas the VLX8hum_11 Fab did not. The on-rate, off-rate and dissociation constants for VLX8hum_11 Fab and VLX9hum_08 Fab are shown in Table 9. Table 10 illustrates the pH dependent binding exhibited by VLX9hum_04 IgG2 to CD47 expressed on Jurkat cells. No pH dependent binding was exhibited by VLX4hum_07 IgG4PE. This pH dependence of the VLX9 humanized mAbs imparts an additional desirable antibody property and therapeutic benefit in the treatment of cancer.

TABLE 6

Murine VLX9 and mouse-human chimeric VLX9 Binding to CD47 is not pH Dependent

| | KD (pM) pH 6 | KD (pM) pH 8 |
|---|---|---|
| VLX9 IgG (murine) | 91 | 76 |
| VLX9 IgG1-N297Q (xi) | 99 | 135 |
| VLX9 IgG2 (xi) | 130 | 137 |
| VLX9 IgG4PE (xi) | 133 | 160 |

TABLE 7

VLX9hum_04 Humanized mAbs Bind to CD47 in a pH Dependent Manner and Binding is not Isotype Specific

|  | KD (pM) pH 6 | KD (pM) pH 8 |
| --- | --- | --- |
| VLX9hum_04 Ig1-N297Q | 215 | >33,000 |
| VLX9hum_04 IgG2 | 470 | >33,000 |
| VLX9hum_04 IgG4PE | 256 | >33,000 |

TABLE 8 pH Dependent and Independent Binding of VLX4, VLX8 and VLX9 Humanized mAbs.

|  | KD (pM) pH 6 | KD (pM) pH 8 |
| --- | --- | --- |
| VLX9hum_03 IgG2 | 48 | >33,000 |
| VLX9hum_04 IgG2 | 43 | >33,000 |
| VLX9hum_06 IgG2 | 61 | >33,000 |
| VLX9hum_08 IgG2 | 65 | >33,000 |
| VLX9hum_09 IgG2 | 138 | >33,000 |
| VLX4hum_07 IgG4PE | 63 | 92 |
| VLX4hum_01 IgG4PE | 47 | 75 |
| VLX8hum_10 IgG4PE | 52 | 79 |
| VLX8hum_11 IgG4PE | 64 | 92 |

TABLE 9 pH Independent and Dependent Binding of VLX8hum_11 Fab and VLX9hum_08 Fab to Recombinant Human CD47

|  | $k_a$ | $k_d$ | $K_D$ (nM) |
| --- | --- | --- | --- |
| VLX8hum_11 Fab (pH 7.5) | $1.35e^6$ | $2.29e^{-3}$ | 1.7 nM |
| VLX8hum_11 Fab (pH 6.5) | $2.14e^6$ | $2.78e^{-3}$ | 1.3 nM |
| VLX8hum_11 Fab (pH 6.0) | $1.64e^6$ | $2.63e^{-3}$ | 1.6 nM |
| VLX9hum_08 Fab (pH 7.5) | $1.43e^5$ | $1.13e^{-2}$ | 79 nM |
| VLX9hum_08 Fab (pH 6.5) | $1.74e^5$ | $9.74e^{-4}$ | 5.6 nM |
| VLX9hum_08 Fab (pH 6.0) | $1.95e^5$ | $9.94e^{-4}$ | 5.1 nM |

TABLE 10 pH Dependent and Independent Binding of VLX4 and VLX9 Humanized mAbs to Jurkat Cells

|  | KD (pM) pH 6.5 | KD (pM) pH 7.4 |
| --- | --- | --- |
| VLX4hum_07 IgG4PE | 69 | 23 |
| VLX9hum_04 IgG2 | 231 | 1526 |

Example 7

CD47 Antibodies Block CD47/SIRPα Binding

To assess the effect of humanized CD47 mAbs on binding of CD47 to SIRPα in vitro the following method is employed using the binding of fluorescently-labelled SIRPα-Fc fusion protein to CD47 expressing Jurkat cells.

SIRPα-Fc fusion protein (R&D Systems, cat #4546-SA) was labelled using an Alexa Fluor® antibody labelling kit (Invitrogen Cat No. A20186) according to the manufacturers specifications. $1.5 \times 10^6$ Jurkat cells were incubated with humanized mAbs (5 µg/ml), a human control antibody in RPMI containing 10% media or media alone for 30 min at 37° C. An equal volume of fluorescently labelled SIRPα-Fc fusion protein was added and incubated for an additional 30 min at 37° C. Cells were washed once with PBS and the amount of labelled SIRPα-Fc bound to the Jurkat cells analyzed by flow cytometry.

As shown in FIG. 10, the humanized VLX4, VLX8 and VLX9 mAbs (VLX4hum_01 IgG4PE, VLX4hum_07 IgG4PE, VLX8hum_10 IgG4PE, VLX8hum_11 IgG4PE, VLX9hum_03 IgG2, VLX9hum_06 IgG2 and VLX9hum_08 IgG2) blocked the interaction of CD47 expressed on the Jurkat cells with soluble SIPRα, while the human control antibody (which does not bind to CD47) or media alone, did not block the CD47/SIRPα interaction.

Example 8

CD47 Antibodies Increase Phagocytosis

To assess the effect of chimeric (murine-human) and humanized VLX4, VLX8, and VLX9 CD47 mAbs on phagocytosis of tumor cells by macrophages in vitro the following method is employed using flow cytometry (Willingham et al. (2012) *Proc Natl Acad Sci USA* 109(17): 6662-7 and Tseng et al. (2013) *Proc Natl Acad Sci USA* 110(27):11103-8).

Human derived macrophages were derived from leukapheresis of healthy human peripheral blood and incubated in AIM-V media (Life Technologies) for 7-10 days. For the in vitro phagocytosis assay, macrophages were re-plated at a concentration of $1 \times 10^4$ cells per well in 100 ul of AIM-V media in a 96-well plate and allowed to adhere for 24 hrs. Once the effector macrophages adhered to the culture dish, the target human cancer cells (Jurkat) were labelled with 1 µM 5(6)-Carboxyfluorescein diacetate N-succinimidyl ester (CFSE; Sigma Aldrich) and added to the macrophage cultures at a concentration of $5 \times 10^4$ cells in 1 ml of AIM-V media (5:1 target to effector ratio). VLX4, VLX8, and VLX9 CD47 mAbs (1 µg/ml) were added immediately upon mixture of target and effector cells and allowed to incubate at 37° C. for 2-3 hours. After 2-3 hrs, all non-phagocytosed cells were removed and the remaining cells washed three times with phosphate buffered saline (PBS; Sigma Aldrich). Cells were then trypsinized, collected into microcentrifuge tubes, and incubated in 100 ng of allophycocyanin (APC) labelled CD14 antibodies (BD Biosciences) for 30 minutes, washed once, and analyzed by flow cytometry (Accuri C6; BD Biosciences) for the percentage of CD14+ cells that were also CFSE indicating complete phagocytosis.

Figure 11:
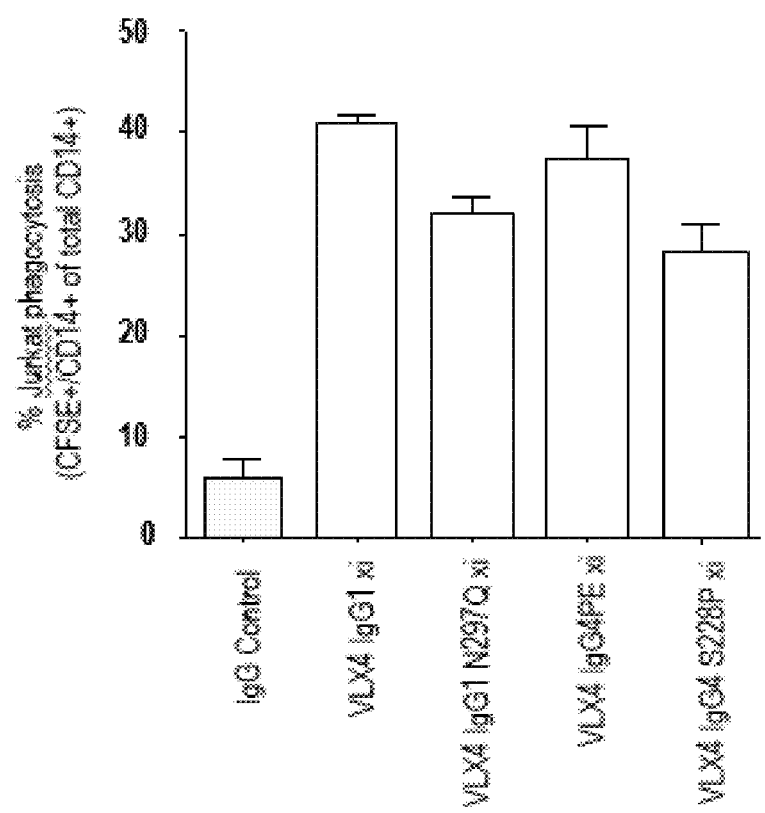
FIG. 11. VLX4 CD47 Chimeric mAbs Increase Phagocytosis of Human Jurkat Cells by Human Macrophages. Human macrophages were plated at a concentration of $1 \times 10^4$ cells per well in a 96 well plate and allowed to adhere for 24 hrs. $5 \times 10^4$ CFSE-labelled human Jurkat cells and 1 μg/ml of the VLX4 chimeric mAbs (VLX4 IgG1 xi, VLX4 IgG1 N297Q xi, VLX4 IgG4PE xi, VLX4 IgG4 S228P xi) were added to the macrophage cultures and incubated at 37° C. for 2 hrs. Non-phagocytosed Jurkat cells were removed and macrophage cultures were washed extensively. Macrophages were trypsinized and stained for CD14. Flow cytometry was used to determine the percentage of $CD14^+/CFSE^+$ cells in the total $CD14^+$ population.

As shown in FIG. 11, the VLX4 chimeric mAbs VLX4 IgG1 xi, VLX4 IgG1 N297Q xi, VLX4 IgG4PE xi, and VLX4 IgG4 S228P xi increased phagocytosis of Jurkat cells by human macrophages by blocking the CD47/SIRPα interaction. This enhanced phagocytosis is independent of Fc function.

Figure 12A:
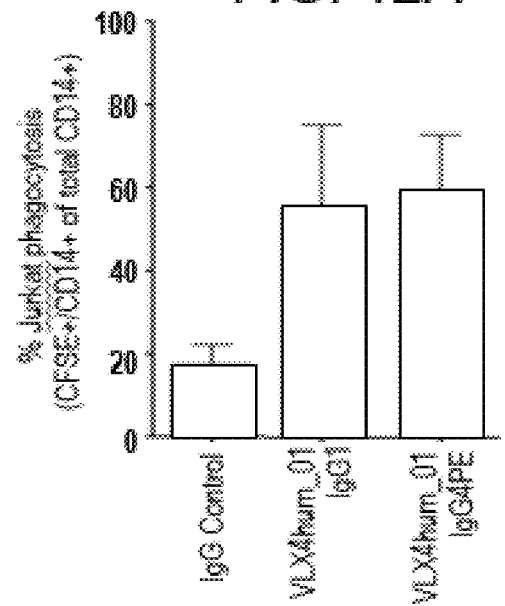
FIG. 12A. VLX4 Humanized mAbs Increase Phagocytosis of Human Jurkat Cells by Human Macrophages. Human macrophages were plated at a concentration of $1 \times 10^4$ cells per well in a 96 well plate and allowed to adhere for 24 hrs. $5 \times 10^4$ CFSE-labelled human Jurkat cells and 1 μg/ml of antibody (VLX4hum_01 IgG1 and VLX4hum_01 IgG4PE) were added to the macrophage cultures and incubated at 37° C. for 2 hrs. Non-phagocytosed Jurkat cells were removed and macrophage cultures were washed extensively. Macrophages were trypsinized and stained for CD14. Flow cytometry was used to determine the percentage of $CD14^+/CFSE^+$ cells in the total $CD14^+$ population.
Figure 12B:
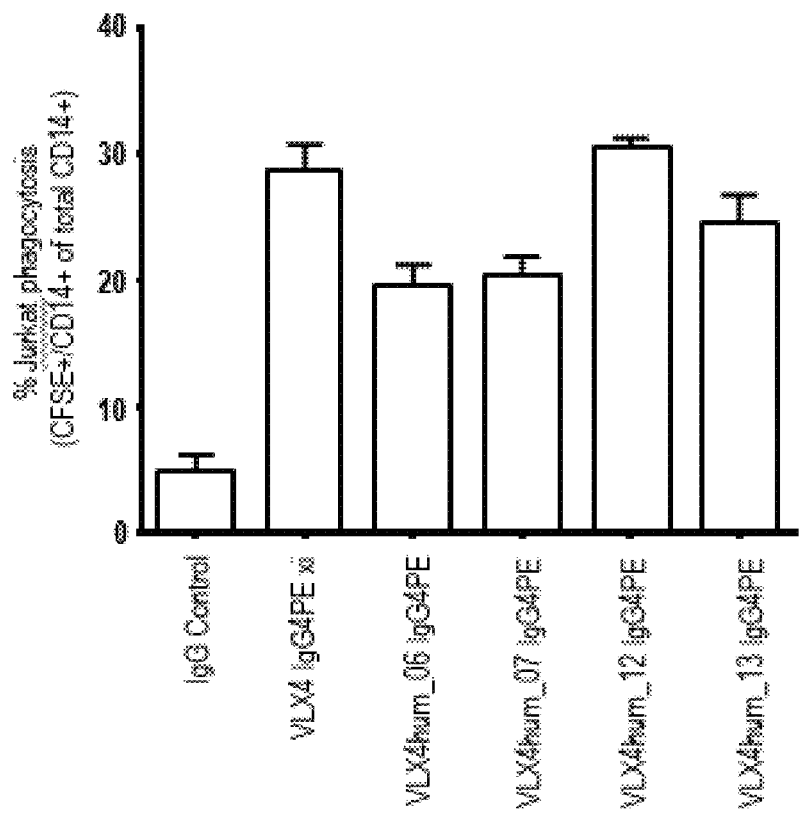
FIG. 12B. VLX4 Humanized mAbs Increase Phagocytosis of Human Jurkat Cells by Human Macrophages. Human macrophages were plated at a concentration of $1 \times 10^4$ cells per well in a 96 well plate and allowed to adhere for 24 hrs. $5 \times 10^4$ CFSE-labelled human Jurkat cells and 1 μg/ml of antibody (VLX4 IgG4PE xi, VLX4hum_06 IgG4PE, VLX4hum_07 IgG4PE, VLX4hum_012 IgG4PE and VLX4hum_13 IgG4PE) were added to the macrophage cultures and incubated at 37° C. for 2 hrs. Non-phagocytosed Jurkat cells were removed and macrophage cultures were washed extensively. Macrophages were trypsinized and stained for CD14. Flow cytometry was used to determine the percentage of $CD14^+/CFSE^+$ cells in the total $CD14^+$ population.

Similarly, as shown in FIG. 12A and FIG. 12B, humanized mAbs VLX4hum_01 IgG1, VLX4hum_01 IgG4PE, VLX4hum_06 IgG4PE, VLX4hum_07 IgG4PE, VLX4hum_12 IgG4PE, and VLX4hum_13 IgG4PE increased phagocytosis of Jurkat cells by human macrophages by blocking the CD47/SIRPα interaction. This enhanced phagocytosis is independent of Fc function.

As shown in FIG. 13A, the VLX8 chimeric mAbs VLX8 IgG1 N297Q xi and VLX8 IgG4PE xi increase phagocytosis of Jurkat cells by human macrophages by blocking the CD47/SIRPα interaction. This enhanced phagocytosis is independent of Fc function.

Similarly, as shown in FIG. 13B, humanized mAbs VLX8hum_01 IgG4PE, VLX8hum_03 IgG4PE, VLX8hum_07 IgG4PE, VLX8hum_08 IgG4PE, and VLX8hum_09 IgG4PE and chimeric mAb VLX8 IgG4PE xi increased phagocytosis of Jurkat cells by human macrophage by blocking the CD47/SIRPα interaction.

Figure 14A:
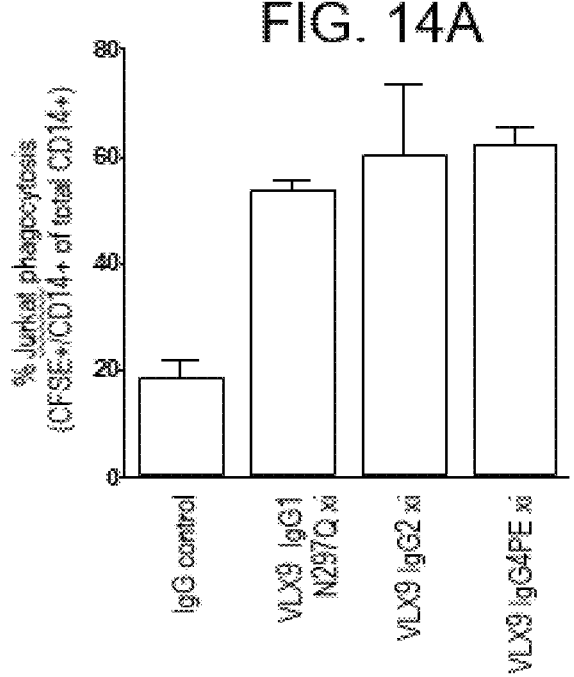
FIG. 14A. VLX9 CD47 Chimeric mAbs Increase Phagocytosis of Human Jurkat Cells by Human Macrophages. Human macrophages were plated at a concentration of $1\times10^4$ cells per well in a 96 well plate and allowed to adhere for 24 hours. $5\times10^4$ CFSE-labelled human Jurkat cells and 1 μg/ml of the VLX9 chimeric mAbs (VLX9 IgG1 N297 xi, VLX9 IgG2 xi and VLX9 IgG4PE xi) were added to the macrophage cultures and incubated at 37° C. for two hours. Non-phagocytosed Jurkat cells were removed and macrophage cultures were washed extensively. Macrophages were trypsinized and stained for CD14. Flow cytometry was used to determine the percentage of CD14+/CFSE+ cells in the total CD14+ population.
Figure 14B:
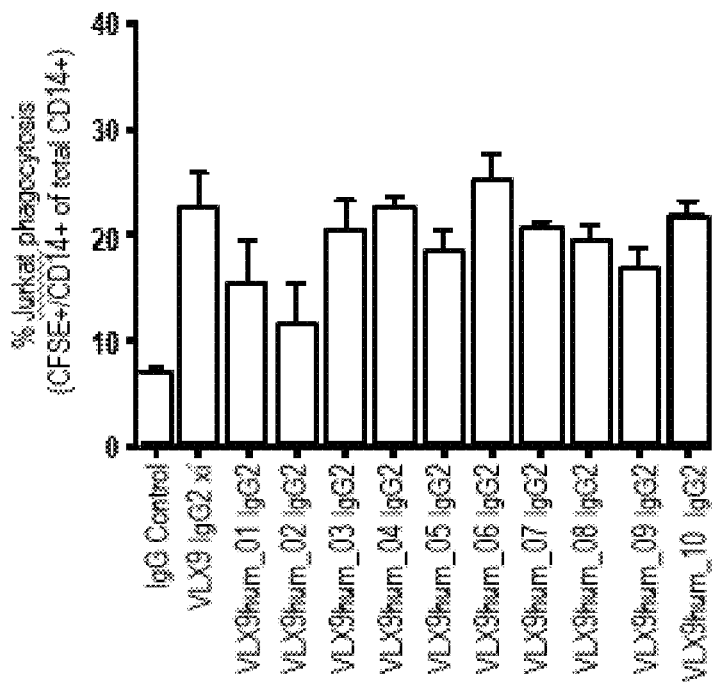
FIG. 14B. VLX9 Humanized mAbs Increase Phagocytosis of Human Jurkat Cells by Human Macrophages. Human macrophages were plated at a concentration of $1\times10^4$ cells per well in a 96 well plate and allowed to adhere for 24 hours. $5\times10^4$ CFSE-labelled human Jurkat cells and 1 μg/ml of antibody (VLX9 IgG2 xi, VLX9hum_01 IgG2, VLX9hum_02 IgG2, VLX9hum_03 IgG2, VLX9hum_04 IgG2, VLX9hum_05 IgG2, VLX9hum_06 IgG2, VLX9hum_07 IgG2, VLX9hum_08 IgG2, VLX9hum_09 IgG2 and VLX9hum_10 IgG2) were added to the macrophage cultures and incubated at 37° C. for two hours. Non-phagocytosed Jurkat cells were removed and macrophage cultures were washed extensively. Macrophages were trypsinized and stained for CD14. Flow cytometry was used to determine the percentage of CD14+/CFSE+ cells in the total CD14+ population.

As shown in FIG. 14A, the VLX9 IgG1 N297Q xi, VLX9 IgG2 xi and VLX9 IgG4PE xi chimeric mAbs all increased phagocytosis of Jurkat cells by human macrophages by blocking the CD47/SIRPα interaction. This enhanced phagocytosis is independent of Fc effector function. Similarly as shown in FIG. 14B, all of the humanized VLX9 IgG2 mAbs (VLX9hum_01 to_10 IgG2) increased phagocytosis of Jurkat cells.

Example 9

Induction of Cell Death by Soluble CD47 Antibodies

Some soluble CD47 antibodies have been shown to induce selective cell death of tumor cells. This additional property of selective toxicity to cancer cells is expected to have advantages compared to mAbs that only block SIRPα binding to CD47.

Induction of cell death by soluble anti-CD47 mAbs is measured in vitro (Manna et al. (2003) *J. Immunol.* 107 (7): 3544-53). For the in vitro cell death assay, $1 \times 10^5$ transformed human T cells (Jurkat cells) were incubated with soluble humanized VLX4, VLX8, and VLX9 CD47 mAbs (1 µg/ml) for 24 hrs at 37° C. As cell death occurs, mitochondrial membrane potential is decreased, the inner leaflet of the cell membrane is inverted, exposing phosphatidylserines (PS), and propidium iodide (PI) or 7-aminoactinomycin D (7-AAD) is able to incorporate into nuclear DNA. In order to detect these cellular changes, cells were then stained with fluorescently labelled annexin V and PI or 7-aminoactinomycin D (7-AAD) (BD Biosciences) and the signal detected using an Accuri C6 flow cytometer (BD Biosciences). The increase in PS exposure is determined by measuring the percent increase in annexin V signal and the percent of dead cells by measuring the percent increase in PI or 7-AAD signal. Annexin V positive (annexin $V^+$) or annexin V positive/7-AAD negative (annexin $V^+/7$-AAD$^-$) cells are observed in early stages of cell death and annexin V positive/7-AAD positive (annexin $V^+/7$-AAD$^+$) cells are dead cells. Importantly for therapeutic purposes, these mAbs induce cell death of tumor cells directly and do not require complement or the intervention of other cells (e.g., NK cells, T cells, or macrophages) to kill. Thus, the mechanism is independent of both other cells and of Fc effector function. Therefore, therapeutic antibodies developed from these mAbs can be engineered to reduce Fc effector functions such as ADCC and CDC and thereby limit the potential for side effects common to humanized mAbs with intact Fc effector functions.

Figure 15A:
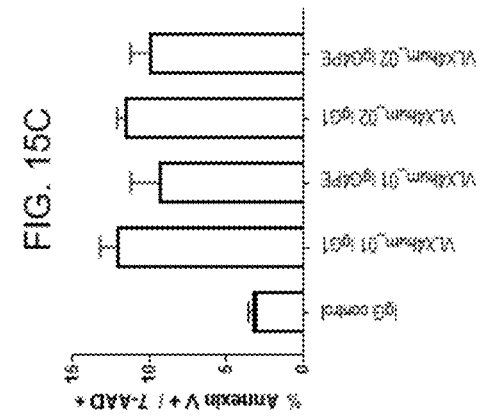
FIG. 15A. Induction of Cell Death in Human Jurkat Cells by Soluble VLX4 Humanized mAbs. Jurkat cells ($1\times10^4$) were incubated with 1 μg/ml VLX4 humanized mAbs (VLX4hum_01 IgG1, VLX4hum_01 IgG4PE, VLX4hum_02 IgG1, VLX4hum_02 IgG4PE) in RPMI media for 24 hours at 37° C. Cells were then stained with annexin V and the signal was detected by flow cytometry. The data are shown as % of cells that are annexin V positive (annexin $V^+$).
Figure 15C:
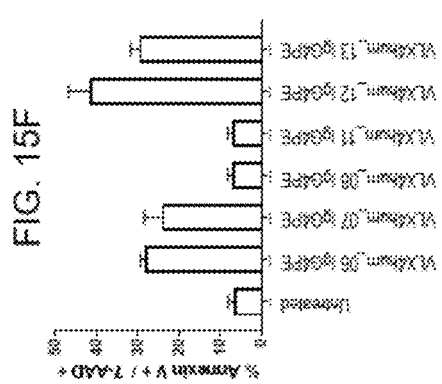
FIG. 15C. Induction of Cell Death in Human Jurkat Cells by Soluble VLX4 Humanized mAbs. Jurkat cells ($1\times10^4$) were incubated with 1 μg/ml VLX4 humanized mAbs (VLX4hum_01 IgG1, VLX4hum_01 IgG4PE, VLX4hum_02 IgG1, VLX4hum_02 IgG4PE) in RPMI media for 24 hours at 37° C. Cells were then stained with annexin V and 7-AAD and analyzed by flow cytometry. The data are shown as % of cells that are annexin V positive/7-AAD positive (annexin $V^+/7\text{-}AAD^+$).
Figure 15B:
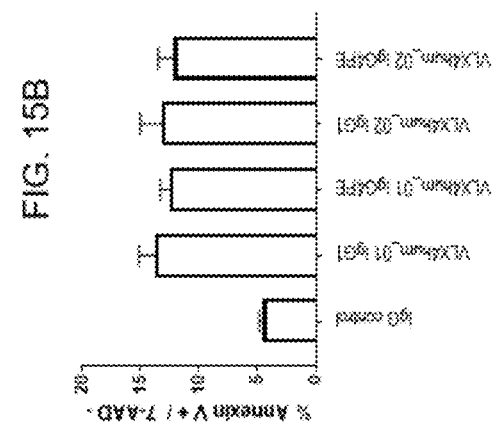
FIG. 15B. Induction of Cell Death in Human Jurkat Cells by Soluble VLX4 Humanized mAbs. Jurkat cells ($1\times10^4$) were incubated with 1 μg/ml VLX4 humanized mAbs (VLX4hum_01 IgG1, VLX4hum_01 IgG4PE, VLX4hum_02 IgG1, VLX4hum_02 IgG4PE) in RPMI media for 24 hours at 37° C. Cells were then stained with annexin V and 7-AAD and analyzed by flow cytometry. The data are shown as % of the cells that are annexin V positive/7-AAD negative (annexin $V^+/7\text{-}AAD^-$).
Figure 15E:
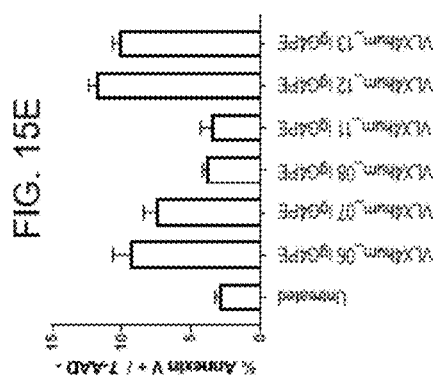
FIG. 15E. Induction of Cell Death in Human Jurkat Cells by Soluble VLX4 Humanized mAbs. Jurkat cells ($1\times10^4$) were incubated with 1 μg/ml VLX4 humanized mAbs (VLX4hum_06 IgG4PE, VLX4hum_07 IgG4PE, VLX4hum_08 IgG4PE, VLX4hum_11 IgG4PE, VLX4hum_12 IgG4PE, VLX4hum_13 IgG4PE) in RPMI media for 24 hours at 37° C. Cells were then stained with annexin V and 7-AAD by flow cytometry. The data are shown as the % of cells that are annexin V positive/7-AAD negative (annexin $V^+/7\text{-}AAD^-$).
Figure 15D:
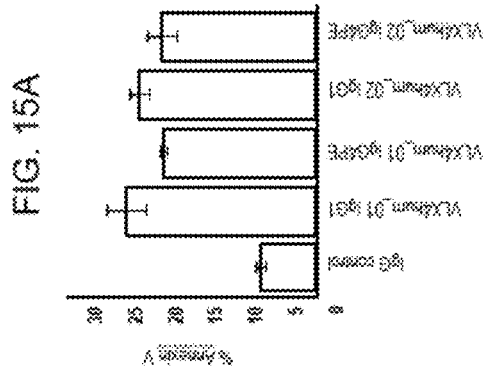
FIG. 15D. Induction of Cell Death in Human Jurkat Cells by Soluble VLX4 Humanized mAbs. Jurkat cells ($1\times10^4$) were incubated with 1 μg/ml VLX4 humanized mAbs (VLX4hum_06 IgG4PE, VLX4hum_07 IgG4PE, VLX4hum_08 IgG4PE, VLX4hum_11 IgG4PE, VLX4hum_12 IgG4PE, VLX4hum_13 IgG4PE) in RPMI media for 24 hours at 37° C. Cells were then stained with annexin V and 7-AAD and analyzed by flow cytometry. The data are shown as the % of cells that are annexin V positive (annexin $V^+$).
Figure 15F:
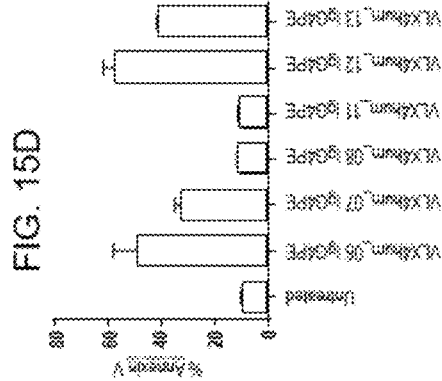
FIG. 15F. Induction of Cell Death in Human Jurkat Cells by Soluble VLX4 Humanized mAbs. Jurkat cells ($1\times10^4$) were incubated with 1 μg/ml VLX4 humanized mAbs (VLX4hum_06 IgG4PE, VLX4hum_07 IgG4PE, VLX4hum_08 IgG4PE, VLX4hum_11 IgG4PE, VLX4hum_12 IgG4PE, VLX4hum_13 IgG4PE) in RPMI media for 24 hours at 37° C. Cells were then stained with annexin V and 7-AAD and analyzed by flow cytometry. The data are shown as the % of cells that are annexin V positive/7-AAD positive (annexin$^+$/7-AAD$^+$).

As shown in FIG. 15A-F, the soluble VLX4 humanized mAbs induced increased PS exposure and cell death of Jurkat cells as measured by increased % of the cells that are annexin $V^+$ (FIG. 15A and FIG. 15D), annexin $V^+/7$-AAD$^-$ (FIG. 15B and FIG. 15E), or annexin $V^+/7$-AAD$^+$ (FIG. 15C and FIG. 15F). The humanized mAbs VLX4hum_01 IgG1, VLX4hum_01 IgG4PE, VLX4hum_02 IgG1, VLX4hum_02 IgG4PE, VLX4hum_06 IgG4 PE, VLX4hum_07 IgG4PE, VLX4hum_12 IgG4PE, and VLX4hum_13 IgG4PE caused increased PS exposure and cell death. In contrast, the humanized mAbs VLX4hum_08 IgG4PE and VLX4hum_11 IgG4PE did not cause increased PS exposure and cell death of Jurkat cells. Induction of cell death and the promotion of phagocytosis of susceptible cancer cells imparts an additional desirable antibody property and potential therapeutic benefit in the treatment of cancer.

As shown in FIGS. 16A-F, the soluble VLX8 chimeric and humanized mAbs induced increased PS exposure and cell death of Jurkat cells as measured by the % of the cells that are annexin $V^+$ (FIGS. 16A, D), annexin $V^+/7$-AAD$^-$ (FIGS. 16B, E), or annexin $V^+/7$-AAD$^+$ (FIGS. 16C, F). The chimeric mAbs, VLX8 IgG1 N297Q xi and VLX8 IgG4PE xi, and the humanized mAbs, VLX8hum_07 IgG4PE and VLX8hum_08 IgG4PE, induced increased PS exposure and cell death of Jurkat cells. In contrast, the humanized mAbs VLX8hum_02 IgG4PE and VLX8hum_04 IgG4PE did not cause increased PS exposure and cell death of Jurkat cells. Induction of cell death and the promotion of phagocytosis of susceptible cancer cells imparts an additional desirable antibody property and potential therapeutic benefit in the treatment of cancer.

As shown in FIG. 17A-FIG. 17F, the soluble VLX9 chimeric and humanized antibodies induced increased PS exposure and cell death of Jurkat cells as measured by % of the cells that are annexin $V^+$ (FIG. 17A and FIG. 17D), annexin $V^+/7$-AAD$^-$ (FIG. 17B and FIG. 17E), or annexin $V^+/7$-AAD$^+$ (FIG. 17C and FIG. 17F). The chimeric VLX9 IgG2xi mAb and the humanized mAbs VLX9hum_06 IgG2, VLX9hum_07 IgG2, VLX9hum_08 IgG2, and VLX9hum_09 IgG2 induced increased PS exposure and cell death of Jurkat cells. In contrast, the humanized mAbs VLX9hum_01 IgG2, VLX9hum_02 IgG2, VLX9hum_03 IgG2, VLX9hum_04 IgG2, VLX9hum_05 IgG2 and VLX9hum_010 IgG2 did not cause increased PS exposure and cell death of Jurkat cells. Induction of cell death and the promotion of phagocytosis of susceptible cancer cells imparts an additional desirable antibody property and potential therapeutic benefit in the treatment of cancer. Importantly, chimeric and humanized mAbs that cause cell death of tumor cells do not cause cell death of normal cells.

Example 10

Damage-Associated Molecular Pattern (DAMP) Expression and Release, Mitochondrial Depolarization and Cell Death Caused by Humanized Anti-CD47 mAb Humanized Anti-CD47 mAbs Cause Loss of Mitochondrial Membrane Potential These experiments demonstrate that humanized anti-CD47 mAbs of the present disclosure exhibit the ability to induce the loss of mitochondrial membrane potential in tumor cell as described previously (Manna and Frazier, 2014 *Journal of Immunology* 170(7):3544-3553).

Loss of mitochondrial membrane potential in the tumor cell was determined using JC-1 dye (Thermo; Catalogue #M34152). Human Raji lymphoma cells (ATCC, Manassas, Va.; Catalog #CCL-86) or other cells types that express sufficient levels of CD47 will be used. Cells were grown in RPMI-1640 medium containing 10% (v/v) heat inactivated fetal bovine serum (BioWest; Catalogue #S01520), 100 units/mL penicillin, 100 µg mL streptomycin (Sigma; Catalogue #P4222) at densities less than $1 \times 10^6$ cells/mL. For this assay, Raji cells were plated in 96 well tissue culture plates at a density of $1\times10^5$ cells/ml RPMI-1640 medium containing 10% (v/v) heat inactivated fetal bovine serum (BioWest; Catalog #S01520), 100 units/mL penicillin, 100 μg/mL streptomycin (Sigma; #P4222).

The humanized antibodies (VLX4hum_01 IgG4PE, VLX4hum_07 IgG4PE, VLX8hum_11 IgG4PE, VLX9hum_06 IgG2 VLX9hum_08 IgG2 and VLX9hum_03 IgG2) as disclosed herein, purified from transient transfections in CHO cells as described above, as well as the control chimeric antibody, were added at a final concentration of 10 μg/ml. As a positive control for loss of mitochondrial membrane potential, cells were treated with 1 μM of chemotherapeutic anthracycline mitoxantrone. The cells were incubated at 37° C. for 24 hours, after which the cells were harvested, washed twice with PBS, and incubated for 30 minutes with JC-1 dye as described above, diluted 1:2000 in PBS. After 30 minutes the cells were washed twice with PBS, resuspended in 100 μl of PBS, and analyzed for the percent of cells that shift their fluorescence emission from red to green by flow cytometry (Accuri C6, Becton Dickinson, Franklin Lakes, N.J.). Results are presented as means±SEM and analyzed for statistical significance using ANOVA in GraphPad Prism 6.

Figure 18:
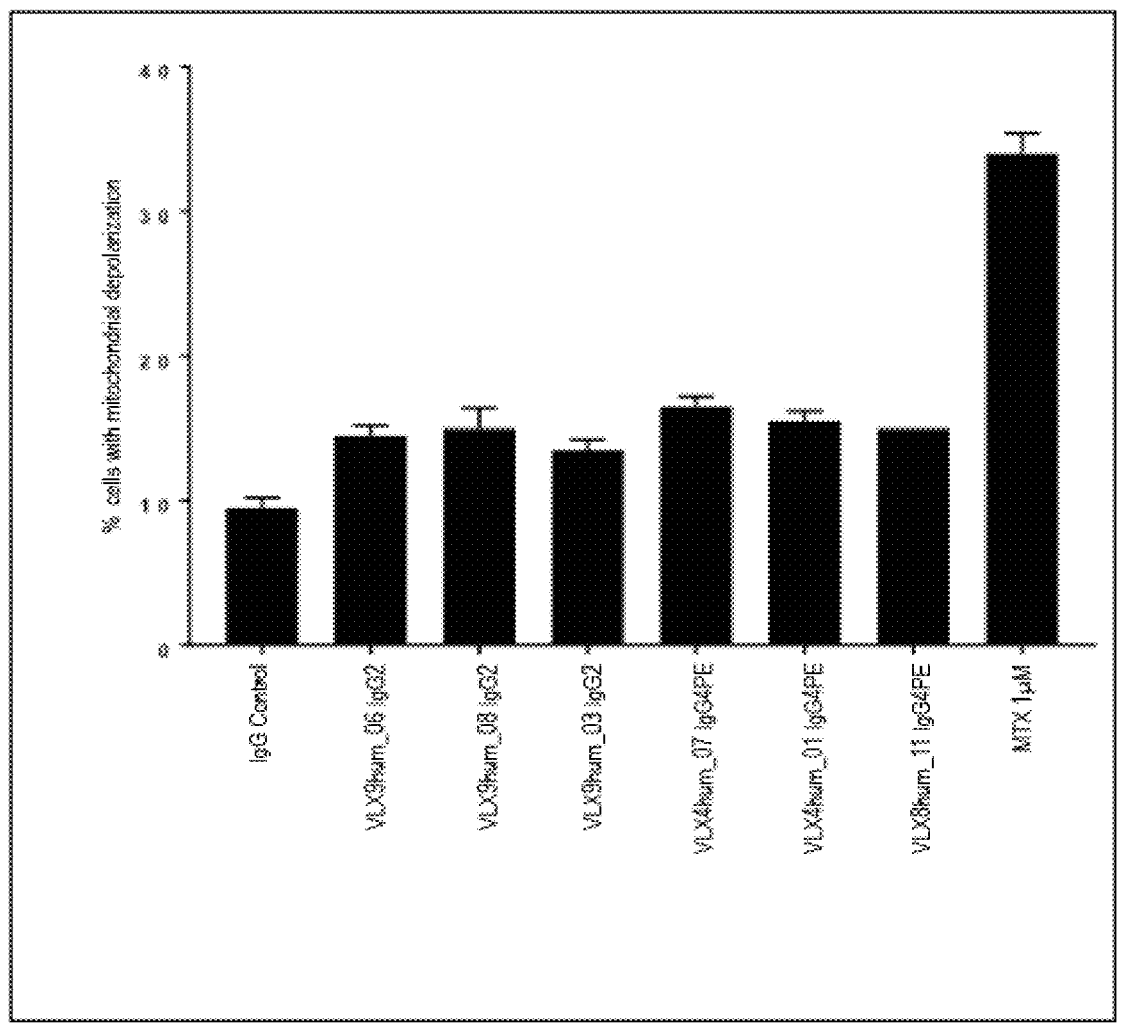
FIG. 18. Induction of Mitochondrial Depolarization in Human Raji Cells by Soluble VLX4, VLX8 and VLX9 Humanized mAbs. $1\times10^4$ Raji cells were incubated with 10 μg/ml of VLX4, VLX8 and VLX9 CD47 humanized mAbs (VLX4hum_01 IgG4PE, VLX4hum_07 IgG4PE, VLX8hum_11 IgG4PE, VLX9hum_03 IgG2, VLX9hum_06 IgG2 and VLX9hum_08 IgG2), a negative IgG control antibody or 1 μM of mitoxantrone as a positive control in RPMI media at 37° C. for 24 hours. Cells were washed and the change in JC-1 dye fluorescence was assessed using flow cytometry. The data are expressed as % of cells with mitochondrial depolarization.

Some of the chimeric or humanized antibodies induce the loss of mitochondrial membrane potential in the tumor cell. As shown in FIG. 18, the percent of cells with mitochondrial membrane depolarization in all anti-CD47 mAb treated cultures was significantly increased ($p<0.05$) compared to an isotype control. This increase in the amount of mitochondrial membrane depolarization demonstrates that anti-CD47 chimeric or humanized antibodies induce mitochondrial depolarization that leads to cell death in human tumor cells.

Humanized Anti-CD47 mAbs Cause Increase in Cell Surface Calreticulin Expression

These experiments demonstrate that humanized anti-CD47 mAbs of the present disclosure exhibit the ability to expose the endoplasmic reticulum resident chaperone calreticulin on the surface of the tumor cell as, for example, described previously using chemotherapeutic anthracyclines such as doxorubicin and mitoxantrone, as disclosed by Obeid et al. (2007) *Nat. Med.* 13(1):54-61.

Cell surface exposure of calreticulin was determined using a rabbit monoclonal antibody against calreticulin conjugated to Alexa Fluor 647 (Abcam; Catalogue #ab196159). Human Raji lymphoma cells (ATCC, Manassas, Va.; Catalog #CCL-86) or other cells types that express sufficient levels of CD47 will be used. Cells were grown in RPMI-1640 medium containing 10% (v/v) heat inactivated fetal bovine serum (BioWest; Catalogue #S01520), 100 units/mL penicillin, 100 μg mL streptomycin (Sigma; Catalogue #P4222) at densities less than $1\times10^6$ cells/mL. For this assay, cells were plated in 96 well tissue culture plates at a density of $1\times10^5$ cells/ml RPMI-1640 medium containing 10% (v/v) heat inactivated fetal bovine serum (BioWest; Catalog #S01520), 100 units/mL penicillin, 100 μg/mL streptomycin (Sigma; #P4222).

The humanized antibodies (VLX4hum_01 IgG4PE, VLX4hum_07 IgG4PE, VLX8hum_11 IgG4PE, VLX9hum_06 IgG2, VLX9hum_08 IgG2 VLX9hum_03 IgG2) as disclosed herein, purified from transient transfections in CHO cells as described above, as well as the control chimeric antibody, were added at a final concentration of 10 μg/ml. As a positive control for calreticulin exposure, cells were treated with 1 μM of chemotherapeutic anthracycline mitoxantrone. The cells were incubated at 37° C. for 24 hours, after which the cells were harvested, washed twice with PBS, and incubated for 30 minutes with anti-calreticulin antibody as described above, diluted 1:200 in PBS. After 30 minutes the cells were washed twice with PBS, resuspended in 100 μl of PBS, and analyzed for the mean fluorescence intensity of the anti-calreticulin antibody signal as well as the percent of cells that stain positive for cell surface calreticulin by flow cytometry (Accuri C6, Becton Dickinson, Franklin Lakes, N.J.). Results are presented as means±SEM and analyzed for statistical significance using ANOVA in GraphPad Prism 6.

Figure 19:
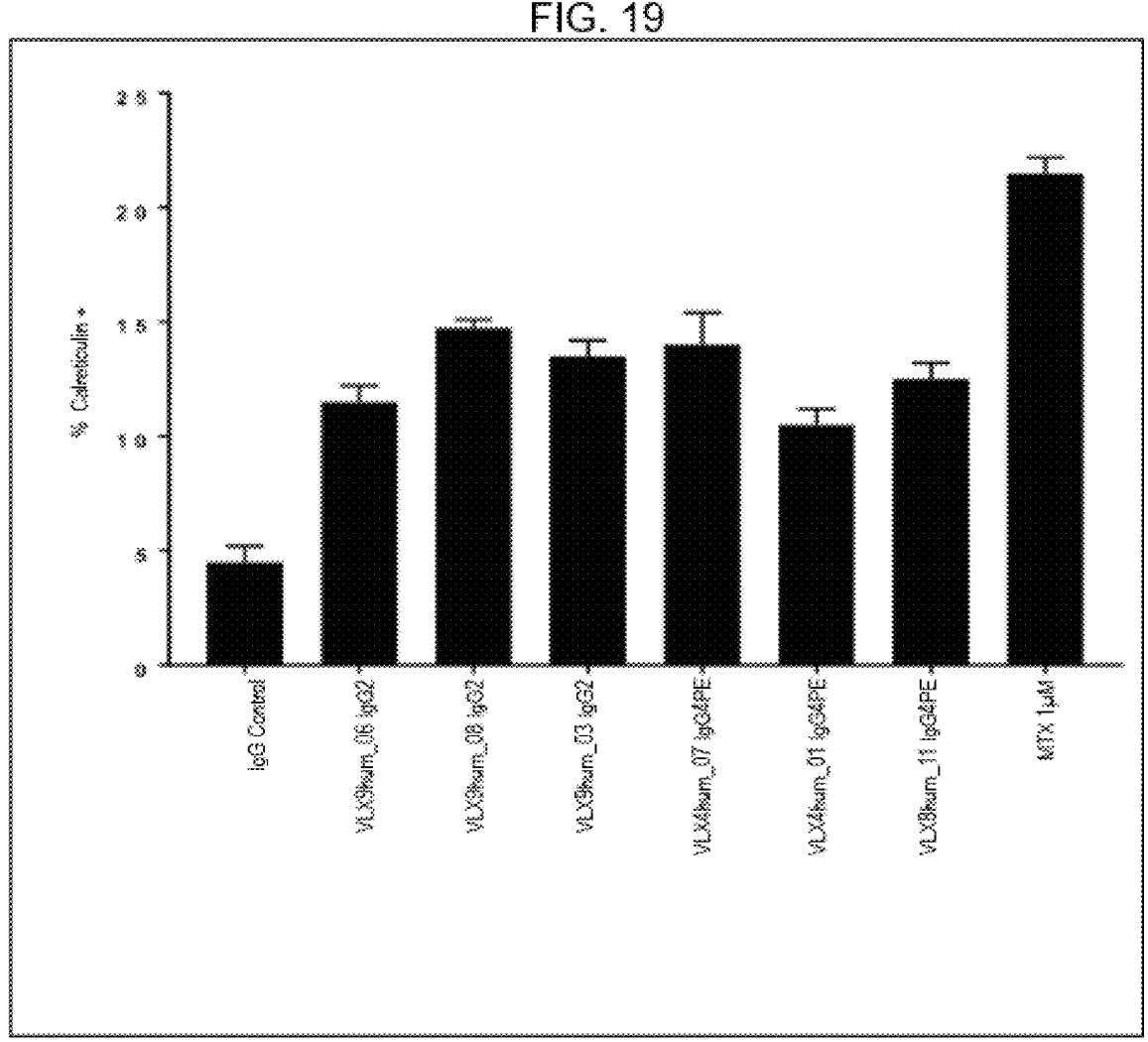
FIG. 19. Soluble VLX4, VLX8 and VLX9 Humanized mAbs Cause an Increase in Cell Surface Calreticulin Expression on Human Raji Cells. $1\times10^4$ Raji cells were incubated with 10 μg/ml of VLX4, VLX8 and VLX9 CD47 humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2), a negative IgG control antibody or 1 μM of mitoxantrone as a positive control in RPMI media at 37° C. for 24 hours. Cells were washed and calreticulin expression was assessed using flow cytometry. The data are expressed as % of cells that are calreticulin positive.

As shown in FIG. 19, the humanized antibodies induced the preapoptotic exposure of calreticulin on the tumor cell surface. The percent of calreticulin positive cells in all anti-CD47 mAb treated cultures was significantly increased ($p<0.05$) compared to an isotype control. This increase in the exposure of calreticulin on the cell surface demonstrates that some of the humanized antibodies induce DAMPs from tumor cells that can lead to phagocytosis of tumor cells and processing of tumor antigen by innate immune cells.

Humanized Anti-CD47 mAbs Cause Increased Protein Disulfide-Isomerase 3 (PDIA3) Expression These experiments demonstrate that humanized anti-CD47 mAbs of the present disclosure exhibit the ability to expose the endoplasmic reticulum resident chaperone PDIA3 on the surface of the tumor cell as, for example, described previously using chemotherapeutic anthracyclines such as doxorubicin and mitoxantrone, as disclosed by Panaretakis et al. (2008) Cell Death & Differentiation 15:1499-1509.

Cell surface exposure of PDIA3 was determined using a mouse monoclonal antibody against PDIA3 conjugated to FITC (Abcam; Catalogue #ab183396). Human Raji lymphoma cells (ATCC, Manassas, Va.; Catalog #CCL-86) or other cells types that express sufficient levels of CD47 will be used. Cells were grown in RPMI-1640 medium containing 10% (v/v) heat inactivated fetal bovine serum (BioWest; Catalogue #S01520), 100 units/mL penicillin, 100 μg mL streptomycin (Sigma; Catalogue #P4222) at densities less than $1\times10^6$ cells/mL. For this assay, cells were plated in 96 well tissue culture plates at a density of $1\times10^5$ cells/ml RPMI-1640 medium containing 10% (v/v) heat inactivated fetal bovine serum (BioWest; Catalog #S01520), 100 units/mL penicillin, 100 μg/mL streptomycin (Sigma; #P4222).

The humanized antibodies (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) as disclosed herein, purified from transient transfections in CHO cells as described above, as well as the control chimeric antibody, were added at a final concentration of 10 μg/ml. As a positive control for PDIA3 exposure, cells were treated with 1 μM of chemotherapeutic anthracycline mitoxantrone. The Raji cells were incubated at 37° C. for 24 hours, after which the cells were harvested, washed twice with PBS, and incubated for 30 minutes with anti-PDIA3 antibody as described above, diluted 1:200 in PBS. After 30 minutes the cells were washed twice with PBS, resuspended in 100 μl of PBS, and analyzed for the mean fluorescence intensity of the anti-PDIA3 antibody signal as well as the percent of cells that stain positive for cell surface calreticulin by flow cytometry (Accuri C6, Becton Dickinson, Franklin Lakes, N.J.). Results are presented as means±SEM and analyzed for statistical significance using ANOVA in GraphPad Prism 6.

Figure 20:
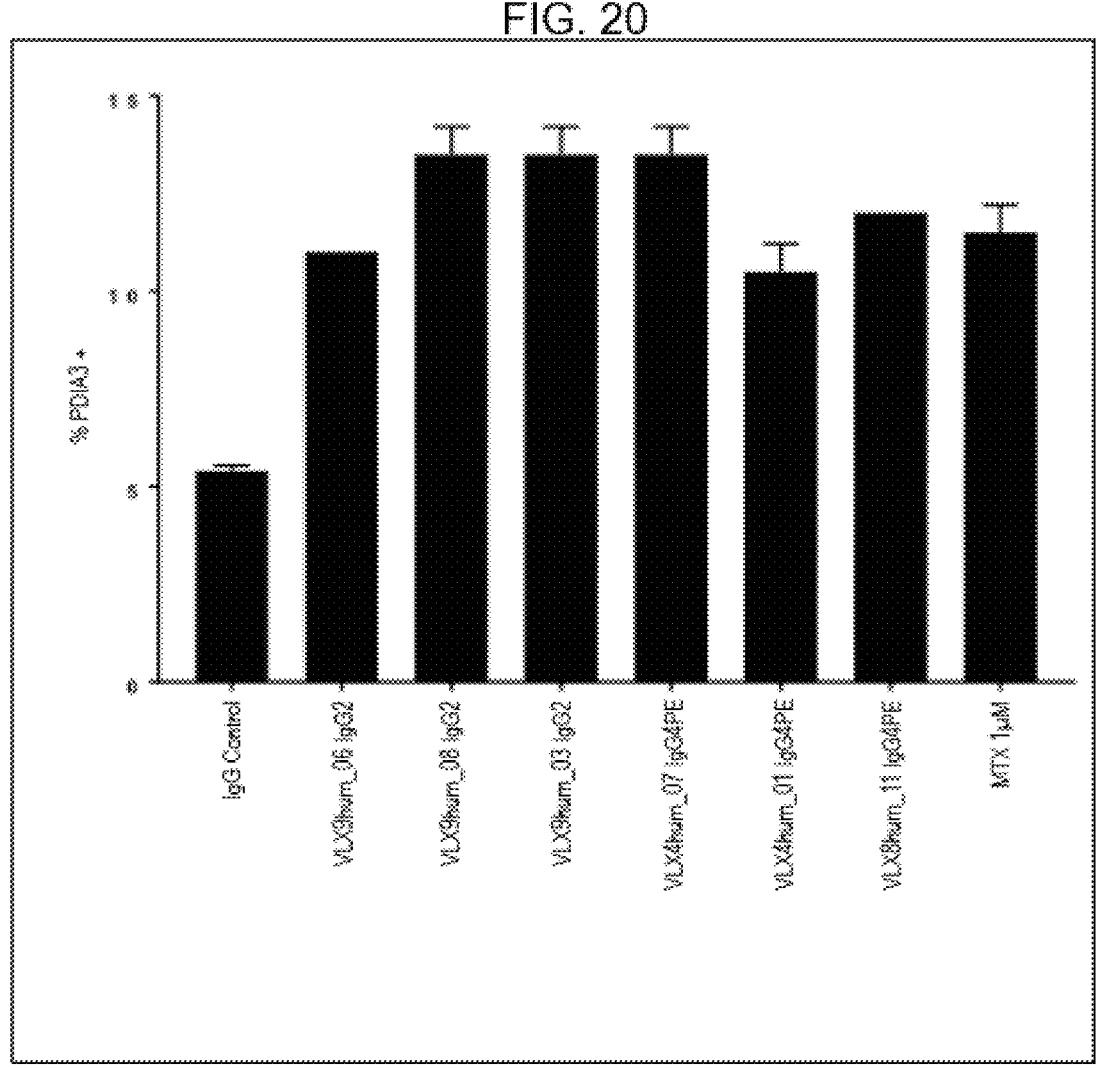
FIG. 20. Soluble VLX4, VLX8 and VLX9 Humanized mAbs Cause an Increase in Cell Surface Protein Disulfide-Isomerase A3 (PDIA3) Expression on Human Raji Cells. $1\times10^4$ Raji cells were incubated with 10 μg/ml of VLX4, VLX8 and VLX9 CD47 humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2), a negative IgG control antibody or 1 μM of mitoxantrone as a positive control in RPMI media at 37° C. for 24 hours. Cells were washed and PDIA3 expression was assessed using flow cytometry. The data are expressed as % of cells that are PDIA3 positive.

Some of the chimeric or humanized antibodies induce the preapoptotic exposure of PDIA3 on the tumor cell surface. As shown in FIG. 20, the percent of PDIA3 positive cells in all the soluble anti-CD47 mAb treated cultures was significantly increased (p<0.05) compared to the background obtained with a negative control, humanized isotype-matched antibody. This increase in the exposure of PDIA3 on the cell surface demonstrates that some of the chimeric or humanized antibodies induce DAMPs from tumor cells that can lead to phagocytosis of tumor cells and processing of tumor antigen by innate immune cells.

Humanized Anti-CD47 mAbs Cause Increased Cell Surface HSP70 Expression

These experiments demonstrate that humanized anti-CD47 mAbs of the present disclosure exhibit the ability to expose the endoplasmic reticulum resident chaperone HSP70 on the surface of the tumor cell as, for example, described previously using chemotherapeutic anthracyclines such as doxorubicin and mitoxantrone, as disclosed by Fucikova et al. (2011) Cancer Research 71(14):4821-4833.

Cell surface exposure of HSP70 was determined using a mouse monoclonal antibody against HSP70 conjugated to Phycoerythrin (Abcam; Catalogue #ab65174). Human Raji lymphoma cells (ATCC, Manassas, Va.; Catalog #CCL-86) or other cells types that express sufficient levels of CD47 were used. Cells were grown in RPMI-1640 medium containing 10% (v/v) heat inactivated fetal bovine serum (BioWest; Catalogue #S01520), 100 units/mL penicillin, 100 µg mL streptomycin (Sigma; Catalogue #P4222) at densities less than $1\times10^6$ cells/mL. For this assay, cells were plated in 96 well tissue culture plates at a density of $1\times10^5$ cells/ml RPMI-1640 medium containing 10% (v/v) heat inactivated fetal bovine serum (BioWest; Catalog #S01520), 100 units/mL penicillin, 100 µg/mL streptomycin (Sigma; #P4222).

The humanized antibodies (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) as disclosed herein, purified from transient transfections in CHO cells as described above, as well as the control chimeric antibody, were added at a final concentration of 10 µg/ml. As a positive control for HSP70 exposure, Raji cells were treated with 1 µM of chemotherapeutic anthracycline mitoxantrone. The cells were incubated at 37° C. for 24 hours, after which the cells were harvested, washed twice with PBS, and incubated for 30 minutes with anti-HSP70 antibody as described above, diluted 1:200 in PBS. After 30 minutes the cells were washed twice with PBS, resuspended in 100 µl of PBS, and analyzed for the mean fluorescence intensity of the anti-HSP70 antibody signal as well as the percent of cells that stain positive for cell surface calreticulin by flow cytometry (Accuri C6, Becton Dickinson, Franklin Lakes, N.J.). Results are presented as means±SEM and analyzed for statistical significance using ANOVA in GraphPad Prism 6.

Figure 21:
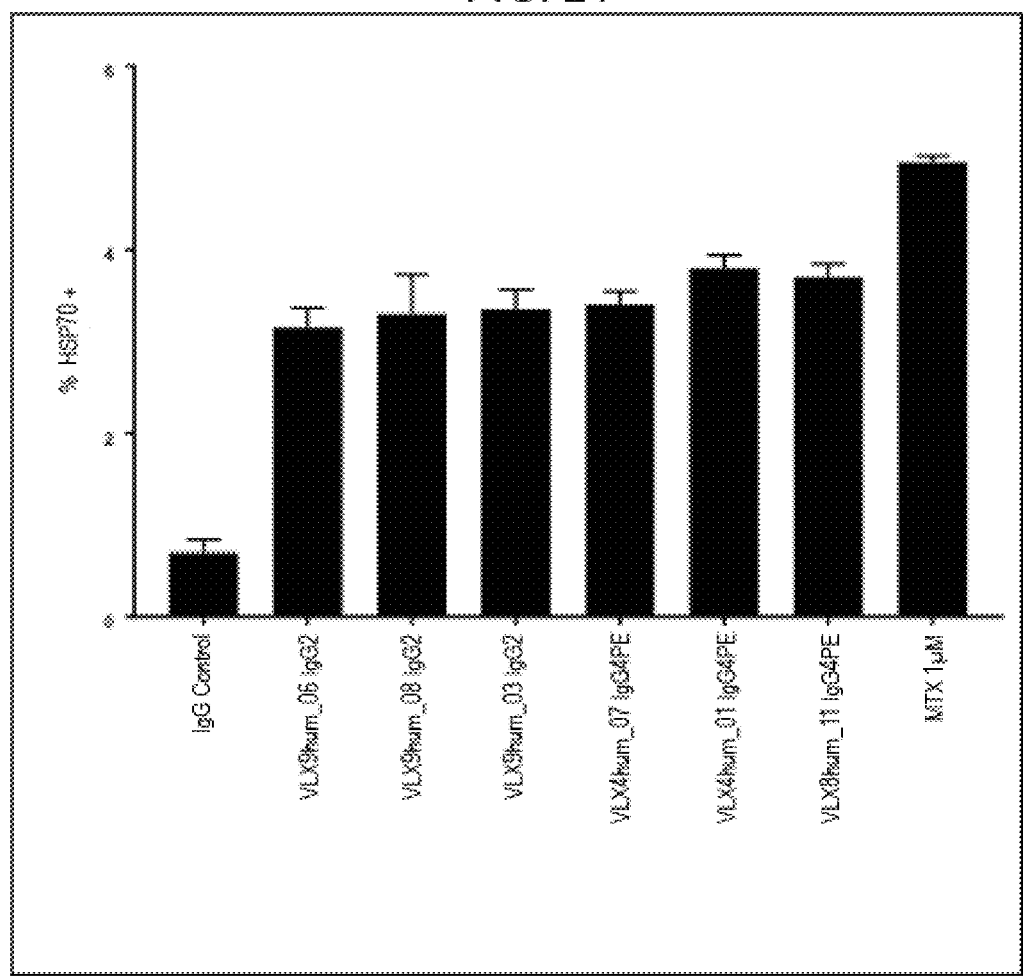
FIG. 21. Soluble VLX4, VLX8 and VLX9 Humanized mAbs Increase Cell Surface HSP70 Expression on Human Raji Cells. $1\times10^4$ Raji cells were incubated with 10 μg/ml of VLX4, VLX8 and VLX9 CD47 humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2), a negative IgG control antibody or 1 μM of mitoxantrone as a positive control in RPMI media at 37° C. for 24 hours. Cells were washed and HSP70 expression was assessed using flow cytometry. The data are expressed as % of cells that are HSP70 positive.

Some of the chimeric or humanized antibodies induce the preapoptotic exposure of HSP70 on the tumor cell surface. As shown in FIG. 21, the percent of HSP70 positive cells in all anti-CD47 mAb treated cultures was significantly increased (p<0.05) compared to those seen in isotype control treated cultures. This increase in the exposure of HSP70 on the cell surface demonstrates that some of the chimeric or humanized antibodies induce DAMPs from tumor cells and can lead to phagocytosis of tumor cells and processing of tumor antigen by innate immune cells.

Humanized Anti-CD47 mAbs Cause Increased Cell Surface HSP90 Expression

These experiments demonstrate that humanized anti-CD47 mAbs of the present disclosure expose the endoplasmic reticulum resident chaperone HSP70 on the surface of the tumor cell as, for example, described previously using chemotherapeutic anthracyclines such as doxorubicin and mitoxantrone, as disclosed by Fucikova et al. (2011) Cancer Research 71(14):4821-4833.

Cell surface exposure of HSP90 was determined using a mouse monoclonal antibody against HSP70 conjugated to Phycoerythrin (Abcam; Catalogue #ab65174). Human Raji lymphoma cells (ATCC, Manassas, Va.; Catalog #CCL-86) or other cells types that express sufficient levels of CD47 were used. Cells are grown in RPMI-1640 medium containing 10% (v/v) heat inactivated fetal bovine serum (BioWest; Catalogue #S01520), 100 units/mL penicillin, 100 µg mL streptomycin (Sigma; Catalogue #P4222) at densities less than $1\times10^6$ cells/mL. For this assay, cells were plated in 96 well tissue culture plates at a density of $1\times10^5$ cells/ml RPMI-1640 medium containing 10% (v/v) heat inactivated fetal bovine serum (BioWest; Catalog #S01520), 100 units/mL penicillin, 100 µg/mL streptomycin (Sigma; #P4222).

The humanized antibodies (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) as disclosed herein, purified from transient transfections in CHO cells as described above, as well as the control chimeric antibody, were added at a final concentration of 10 µg/ml. As a positive control for HSP90 exposure, cells were treated with 1 µM of chemotherapeutic anthracycline mitoxantrone. The Raji cells were incubated at 37° C. for 24 hours, after which the cells were harvested, washed twice with PBS, and incubated for 30 minutes with anti-HSP70 antibody as described above, diluted 1:200 in PBS. After 30 minutes the cells were washed twice with PBS, resuspended in 100 µl of PBS, and analyzed for the mean fluorescence intensity of the anti-HSP70 antibody signal as well as the percent of cells that stain positive for cell surface calreticulin by flow cytometry (Accuri C6, Becton Dickinson, Franklin Lakes, N.J.). Results are presented as means±SEM and analyzed for statistical significance using ANOVA in GraphPad Prism 6.

Figure 22:
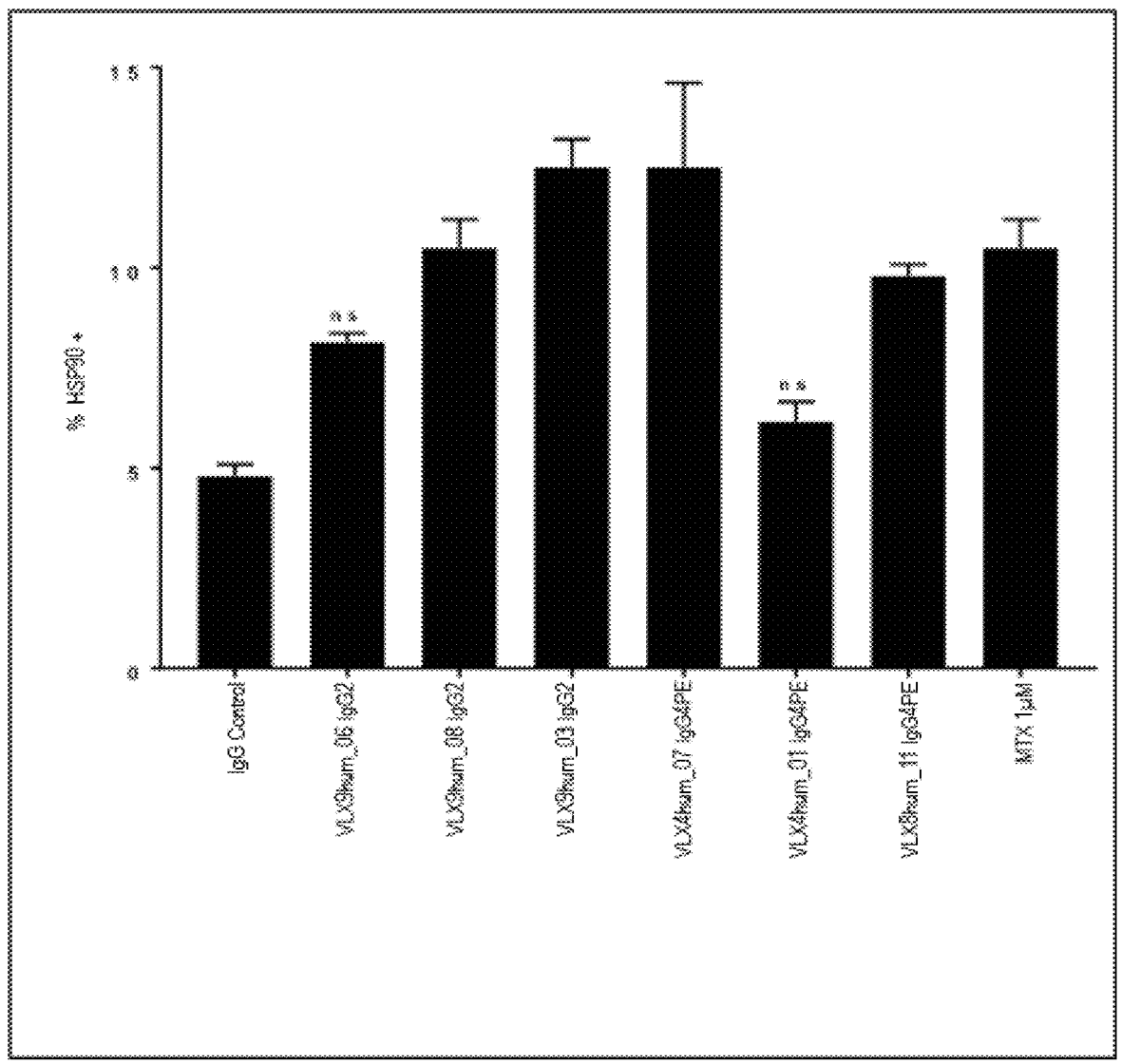
FIG. 22. Soluble VLX4, VLX8 and VLX9 Humanized mAbs Increase Cell Surface HSP90 Expression on Human Raji Cells. $1\times10^4$ Raji cells were incubated with 10 μg/ml of VLX4, VLX8 and VLX9 CD47 humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2), a negative IgG control antibody or 1 µM of mitoxantrone as a positive control in RPMI media at 37° C. for 24 hours. Cells were washed and HSP90 expression was assessed using flow cytometry. The data are expressed as % of cells that are HSP90 positive.

Some of the chimeric or humanized antibodies induce the preapoptotic exposure of HSP90 on the tumor cell surface. As shown in FIG. 22, the percent of HSP90 positive cells in soluble anti-CD47 mAb-treated cultures was significantly increased (p<0.05) compared to the background obtained with a negative control, humanized isotype-matched antibody, except for VLXhum_06 IgG2 and VLX4hum_01 IgG4PE (ns, not significant). This increase in the exposure of HSP90 on the cell surface demonstrates that some of the chimeric or humanized antibodies induce DAMPs from tumor cells and can lead to phagocytosis of tumor cells and processing of tumor antigen by innate immune cells.

Humanized Anti-CD47 mAbs Cause Increased ATP Release

These experiments demonstrate that humanized anti-CD47 mAbs of the present disclosure induce increased release of adenosine triphosphate (ATP) from the tumor cell as described previously using anthracycline chemotherapy drugs (Martins et al., 2014 Cell Death and Differentiation 21:79-91).

Release of ATP from the tumor cell is determined by quantitative bioluminescence assay as described by the manufacturer (Molecular Probes; Catalogue #A22066). Human Raji lymphoma cells (ATCC, Manassas, Va.; Catalog #CCL-86) or other cells types that express sufficient levels of CD47 were used. Cells were grown in RPMI-1640 medium containing 10% (v/v) heat inactivated fetal bovine serum (BioWest; Catalogue #S01520), 100 units/mL penicillin, 100 µg mL streptomycin (Sigma; Catalogue #P4222) at densities less than $1\times10^6$ cells/mL. For this assay, cells were plated in 96 well tissue culture plates at a density of 1×10⁵ cells/ml RPMI-1640 medium containing 10% (v/v) heat inactivated fetal bovine serum (BioWest; Catalog #S01520), 100 units/mL penicillin, 100 µg/mL streptomycin (Sigma; #P4222).

The humanized antibodies (VLX4hum_01 IgG4PE, VLX4hum_07 IgG4PE, VLX8hum_11 IgG4PE, VLX9hum_06 IgG2, VLX9hum_08 IgG2 and VLX9hum_03) as disclosed herein, purified from transient transfections in CHO cells as described above, as well as the control chimeric antibody, were added at a final concentration of 10 µg/ml. As a positive control for ATP release, cells were treated with 1 µM of chemotherapeutic anthracycline mitoxantrone. The cells were incubated at 37° C. for 24 hours, after which the cell-free supernatant was collected and stored at −80° C. After all samples have been collected, 100 of each sample was tested by the ATP determination kit as described above. Final concentrations were determined by comparing experimental values to a standard curve and displayed as the concentration of ATP (µM) released by tumor cells in response to antibody treatment. Results are presented as means±SEM and analyzed for statistical significance using ANOVA in GraphPad Prism 6.

Figure 23:
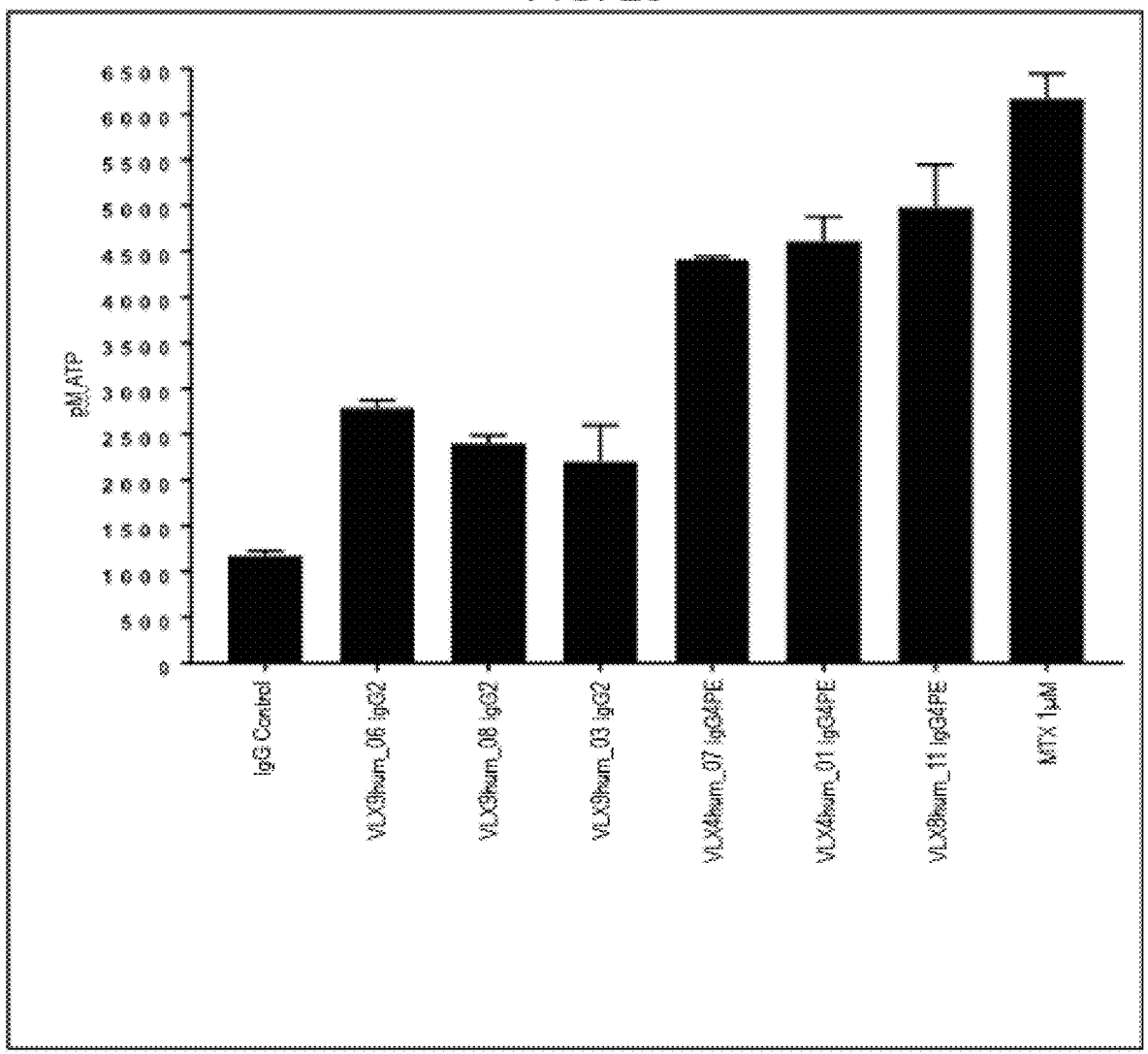
FIG. 23. Soluble VLX4, VLX8 and VLX9 Humanized mAbs Increase Release of Adenosine Triphosphate (ATP) by Human Raji Cells. $1 \times 10^4$ Raji cells were incubated with 10 µg/ml of VLX4, VLX8 and VLX9 CD47 humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2), a negative IgG control antibody or 1 µM of mitoxantrone as a positive control in RPMI media at 37° C. for 24 hours. Cell-free supernatant was collected and analyzed using an ATP determination kit. The data are expressed as pM ATP in the supernatant.

The humanized antibodies increased the release of ATP from the tumor cells. As shown in FIG. 23, the amount of released ATP in all anti-CD47 mAb treated cultures was significantly increased (p<0.05) compared to an isotype control. This increase in the release of ATP demonstrates that some of the chimeric or humanized antibodies induce the release of ATP from tumor cells and can lead to dendritic cell migration through its cognate purinergic receptors.

Humanized Anti-CD47 mAbs Cause HMGB1 Release

These experiments demonstrate that humanized anti-CD47 mAbs of the present disclosure increase the release of the non-histone chromatin protein high-mobility group box 1 (HMGB1) from the tumor cell as described previously using chemotherapy agents, such as oxaliplatin (Tesniere et al., 2010 *Oncogene*, 29:482-491) and mitoxantrone (Michaud et al., 2011 *Science* 334:1573-1577).

Release of HMGB1 protein from the tumor cell was determined by enzyme immunoassay as described by the manufacturer (IBL International; Hamburg, Germany, Catalogue #ST51011). Human Raji lymphoma cells (ATCC, Manassas, Va.; Catalog #CCL-86) or other cells types that express sufficient levels of CD47 were used. Cells will be grown in RPMI-1640 medium containing 10% (v/v) heat inactivated fetal bovine serum (BioWest; Catalogue #S01520), 100 units/mL penicillin, 100 µg mL streptomycin (Sigma; Catalogue #P4222) at densities less than 1×10⁶ cells/mL. For this assay, cells were plated in 96 well tissue culture plates at a density of 1×10⁵ cells/ml RPMI-1640 medium containing 10% (v/v) heat inactivated fetal bovine serum (BioWest; Catalog #S01520), 100 units/mL penicillin, 100 µg/mL streptomycin (Sigma; #P4222).

The humanized antibodies (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) as disclosed herein, purified from transient transfections in CHO cells as described above, as well as the control chimeric antibody, will then be added at a final concentration of 10 µg/ml. As a positive control for HMGB1 release, Raji cells were treated with 1 µM of chemotherapeutic anthracycline mitoxantrone. The cells were incubated at 37° C. for 24 hours, after which the cell-free supernatant was collected and stored at −80° C. After all samples have been collected, 100 of each sample was tested by HMGB1 ELISA as described above. Final concentrations were determined by comparing experimental values to a standard curve and reported as the concentration of HMGB1 (ng/ml) released by tumor cells in response to antibody treatment. Results are presented as means±SEM and analyzed for statistical significance using ANOVA in GraphPad Prism 6.

Figure 24:
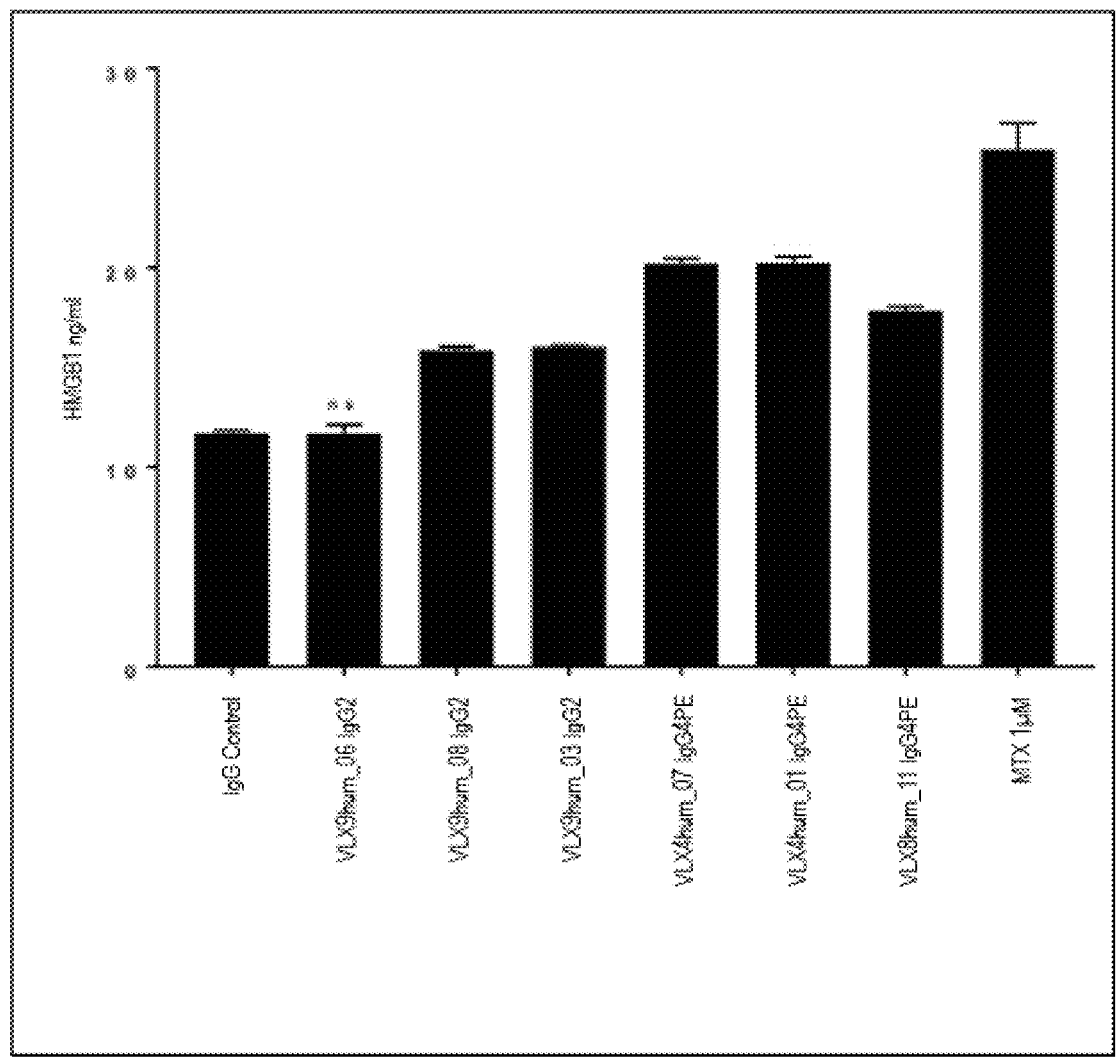
FIG. 24. Soluble VLX4, VLX8 and VLX9 Humanized mAbs Cause an Increase in Release of High Mobility Group Box 1 (HMGB1) by Human Raji Cells. $1 \times 10^4$ Raji cells were incubated with 10 µg/ml of VLX4, VLX8 and VLX9 CD47 humanized mAbs (VLX4hum_01 IgG4PE, VLX4hum_07 IgG4PE, VLX8hum_11 IgG4PE, VLX9hum_03 IgG2, VLX9hum_06 IgG2 and VLX9hum_08 IgG2), a negative IgG control antibody or 1 µM of mitoxantrone as a positive control in RPMI media at 37° C. for 24 hours. Cell-free supernatant was collected and analyzed using an HMGB1 immunoassay. The data are expressed as ng/ml of HMGB1 in the supernatant.

As shown in FIG. 24, the humanized antibodies increased the release of HMGB1 protein from the tumor cells. The amount of released HMGB1 protein in all anti-CD47 mAb treated cultures was significantly increased (p<0.05) compared to an isotype control, except for VLX9hum_06 IgG2 (ns, not significant). This increase in the release of HMGB1 demonstrates that some of the chimeric or humanized antibodies induce release of DAMPs from tumor cells and can lead to dendritic cell activation.

Humanized Anti-CD47 mAbs Cause CXCL10 Release

These experiments demonstrate that humanized anti-CD47 mAbs of the present disclosure increase the production and release of the chemokine CXCL10 from the human tumor cells as described previously using anthracycline chemotherapy drugs (Sistigu et al., 2014 *Nat. Med.* 20(11): 1301-1309).

Release of the CXCL10 from the tumor cell was determined by enzyme immunoassay as described by the manufacturer (R&D Systems; Catalogue #DIP100). Human Raji lymphoma cells (ATCC, Manassas, Va.; Catalog #CCL-86) or other cells types that express sufficient levels of CD47 will be used. Cells were grown in RPMI-1640 medium containing 5% (v/v) heat inactivated fetal bovine serum (BioWest; Catalogue #S01520), 100 units/mL penicillin, 100 µg mL streptomycin (Sigma; Catalogue #P4222) at densities less than 1×10⁶ cells/mL. For this assay, cells were plated in 96 well tissue culture plates at a density of 1×10⁵ cells/ml RPMI-1640 medium containing 5% (v/v) heat inactivated fetal bovine serum (BioWest; Catalog #S01520), 100 units/mL penicillin, 100 µg/mL streptomycin (Sigma; #P4222).

The humanized antibodies (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) as disclosed herein, purified from transient transfections in CHO cells as described above, as well as the control chimeric antibody, were added at a final concentration of 10 µg/ml. As a positive control for CXCL10 release, Raji cells were treated with 1 µM of the chemotherapeutic anthracycline mitoxantrone. The cells were incubated at 37° C. for 24 hours, after which the cell-free supernatant was collected and stored at −80° C. After all samples have been collected, 100 of each sample was tested by the CXCL10 ELISA as described above. Final concentrations were determined by comparing experimental values to a standard curve and displayed as the concentration of CXCL10 (pg/ml) released by tumor cells in response to antibody treatment.

Figure 25:
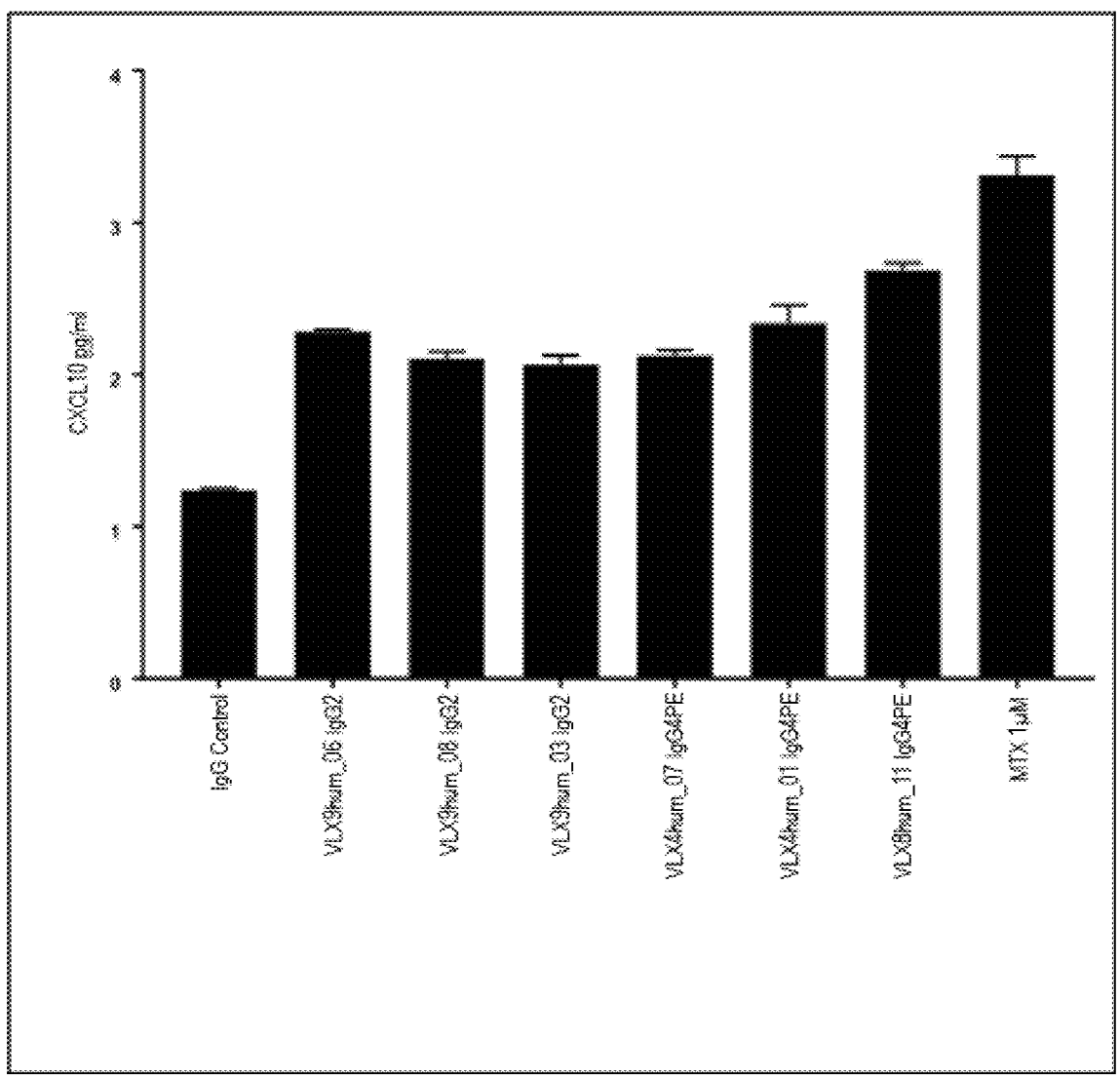
FIG. 25. Soluble VLX4, VLX8 and VLX9 Humanized mAbs Increase CXCL10 Release by Human Raji Cells. $1 \times 10^4$ Raji cells were incubated with 10 µg/ml of VLX4, VLX8 and VLX9 CD47 humanized mAbs (VLX4hum_01 IgG4PE, VLX4hum_07 IgG4PE, VLX8hum_11 IgG4PE, VLX9hum_03 IgG2, VLX9hum_06 IgG2 and VLX9hum_08 IgG2), a negative IgG control antibody or 1 µM of mitoxantrone as a positive control in RPMI media at 37° C. for 24 hours. Cell-free supernatant was collected and analyzed using an CXCL10 immunoassay. The data are expressed as pg/ml of CXCL10 in the supernatant.

Some of the chimeric or humanized antibodies induce release of CXCL10 by human tumor cells. As shown in FIG. 25, the amount of released CXCL10 in all anti-CD47 mAb treated cultures significantly increased (p<0.05) compared to an isotype control. This increase in the release of CXCL10 demonstrates that some of the chimeric or humanized antibodies induce the release of CXCL10 from tumor cells and suggest a role in the recruitment of immune cells to the tumor.

Example 11

Damage-Associated Molecular Pattern (DAMP) Expression and Release, Mitochondrial Depolarization and Cell Death Caused by Humanized Anti-CD47 mAbs These studies were conducted as described in Example 10, except that the human Jurkat ALL cell line (ATCC, Manassas, Va.; Catalog #TIB-152) was used.

Humanized Anti-CD47 mAbs Cause Loss of Mitochondrial Membrane Potential

Figure 26:
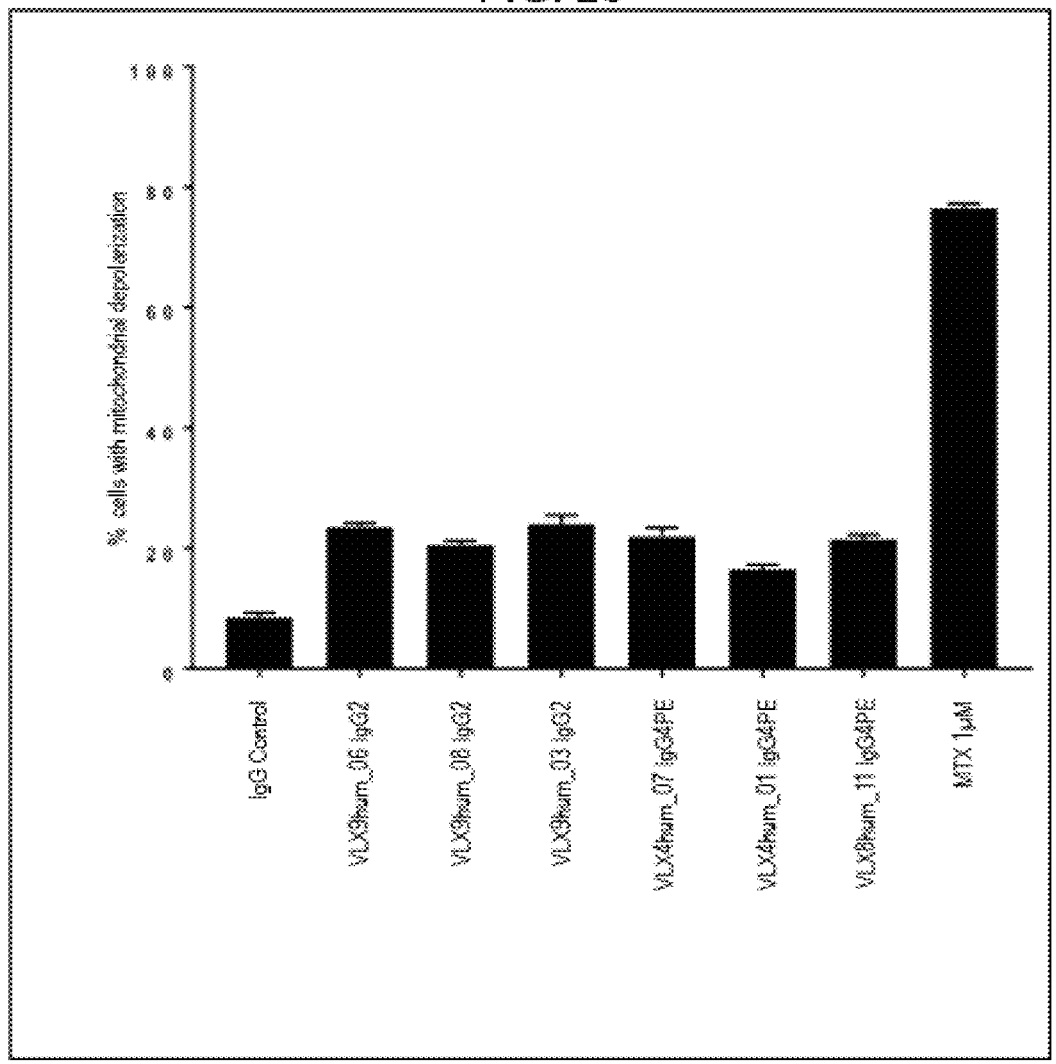
FIG. 26. Induction Mitochondrial Depolarization in Human Jurkat Cells by Soluble VLX4, VLX8 and VLX9 Humanized mAbs. $1 \times 10^4$ Jurkat cells were incubated with 10 µg/ml of VLX4, VLX8 and VLX9 CD47 humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2), a negative IgG control antibody or 1 µM of mitoxantrone as a positive control in RPMI media at 37° C. for 24 hours. Cells were washed and the change in JC-1 dye fluorescence was assessed using flow cytometry. The data are expressed as % of cells with mitochondrial depolarization.

As shown in FIG. 26, the humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) caused a significant increase in the percent of cells with mitochondrial membrane depolarization (p<0.05) compared to an isotype control. This increase in the amount of mitochondrial membrane depolarization demonstrates that some of the chimeric or humanized antibodies induce cell death in human tumor cells.

Humanized Anti-CD47 mAbs Cause Increase in Cell Surface Calreticulin Expression

Figure 27:
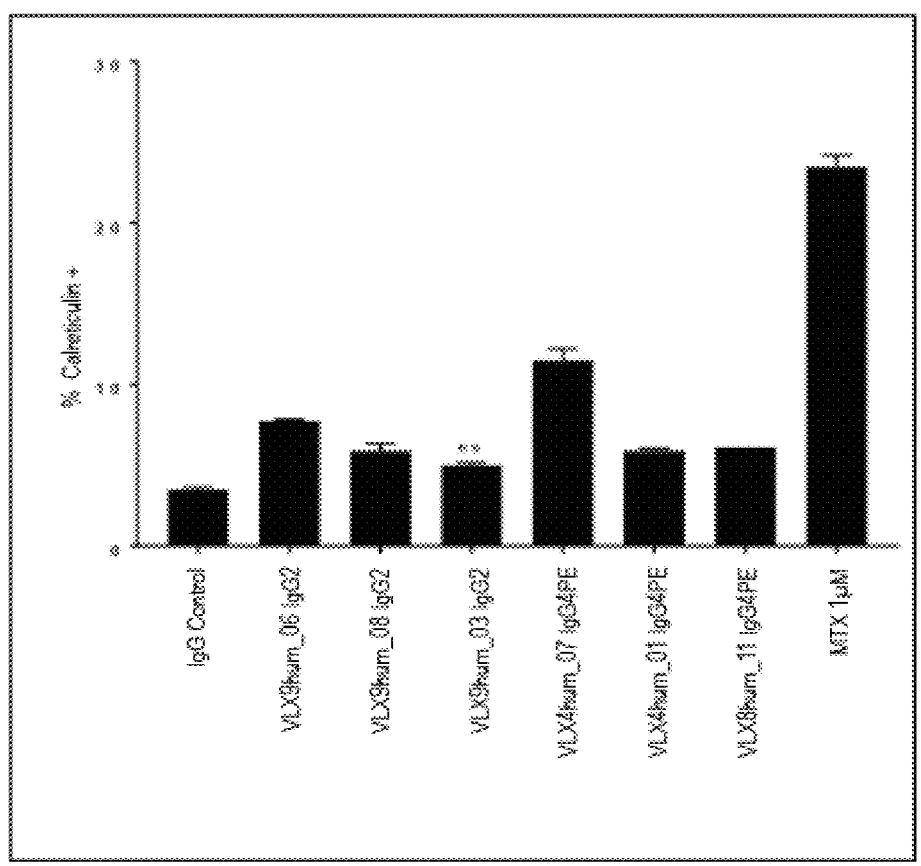
FIG. 27. Soluble VLX4, VLX8 and VLX9 Humanized mAbs Increase Cell Surface Calreticulin Expression on Human Jurkat Cells. $1 \times 10^4$ Jurkat cells were incubated with 10 µg/ml of VLX4, VLX8 and VLX9 CD47 humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2), a negative IgG control antibody or 1 µM of mitoxantrone as a positive control in RPMI media at 37° C. for 24 hours. Cells were washed and calreticulin expression was assessed using flow cytometry. The data are expressed as % of cells that are calreticulin positive.

As shown in FIG. 27, the humanized antibodies (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) induced the preapoptotic exposure of calreticulin on the tumor cell surface. The percent of calreticulin positive cells in all anti-CD47 mAb treated cultures were significantly increased (p<0.05) compared to an isotype control, except VLX9hum_03 IgG2 (ns). This increase in the exposure of calreticulin on the cell surface demonstrated that some of the humanized antibodies induce DAMPs from tumor cells and can lead to phagocytosis of tumor cells and processing of tumor antigen by innate immune cells.

Humanized Anti-CD47 mAbs Cause Increase in Cell Surface PDIA3 Expression

Figure 28:
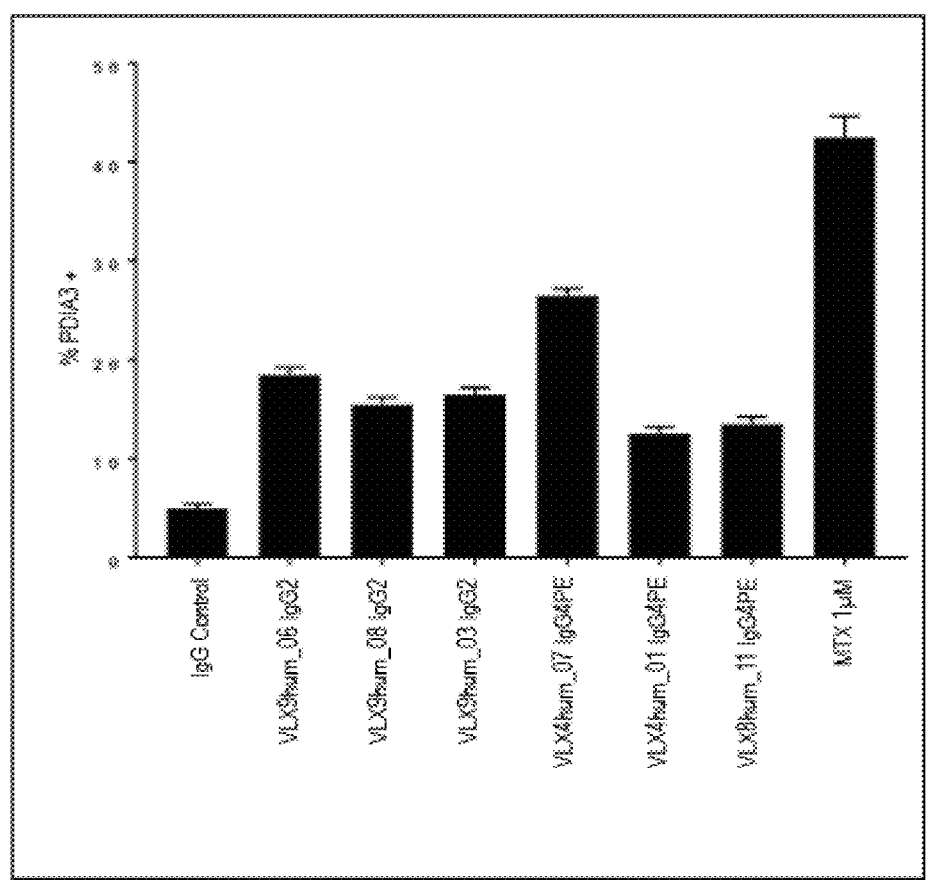
FIG. 28. Soluble VLX4, VLX8 and VLX9 Humanized mAbs Increase Cell Surface PDIA3 Expression on Human Jurkat Cells. $1 \times 10^4$ Jurkat cells were incubated with 10 µg/ml of VLX4, VLX8 and VLX9 CD47 humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2), a negative IgG control antibody or 1 µM of mitoxantrone as a positive control in RPMI media at 37° C. for 24 hours. Cells were washed and PDIA3 expression was assessed using flow cytometry. The data are expressed as % of cells that are PDIA3 positive.

As shown in FIG. 28, the percent of PDIA3 positive cells in soluble anti-CD47 mAb (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) treated cultures were significantly increased (p<0.05) compared to the background obtained with a negative control, humanized isotype-matched antibody. This increase in the exposure of PDIA3 on the cell surface demonstrates that some of the chimeric or humanized antibodies induce DAMPs from tumor cells and can lead to phagocytosis of tumor cells and processing of tumor antigen by innate immune cells.

Humanized Anti-CD47 mAbs Cause Increase in Cell Surface HSP70 Expression

Figure 29:
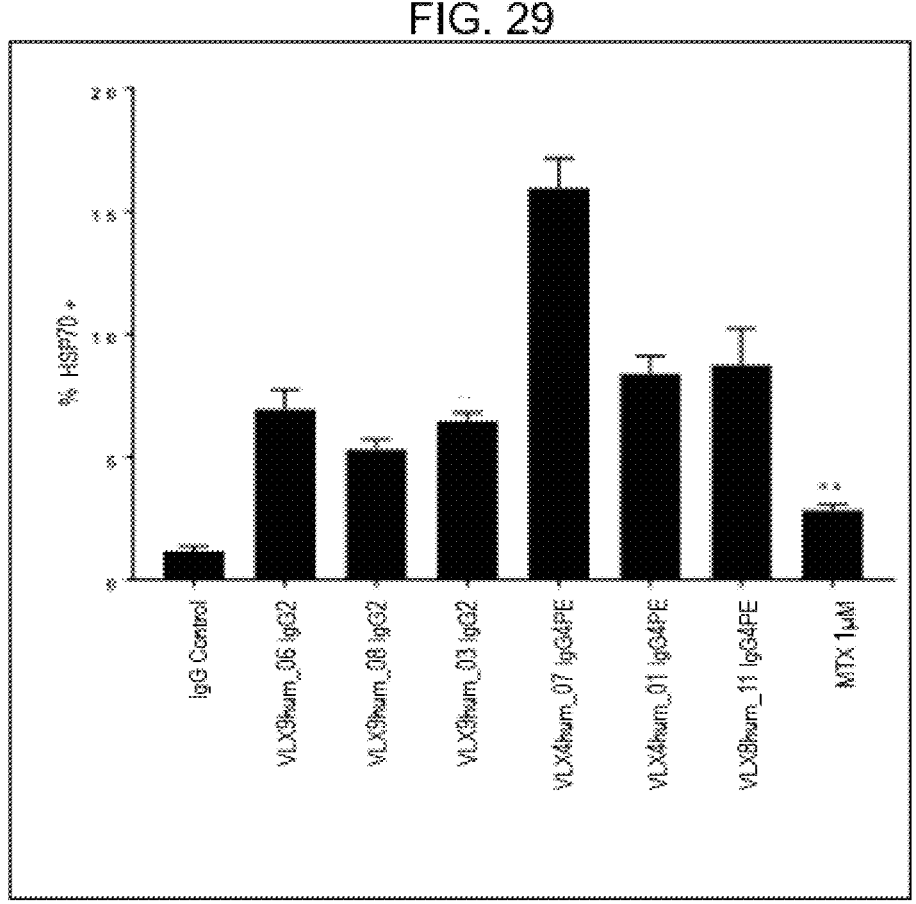
FIG. 29. Soluble VLX4, VLX8 and VLX9 Humanized mAbs Increase Cell Surface HSP70 Expression on Human Jurkat Cells. $1 \times 10^4$ Jurkat cells were incubated with 10 µg/ml of VLX4, VLX8 and VLX9 CD47 humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2), a negative IgG control antibody or 1 µM of mitoxantrone as a positive control in RPMI media at 37° C. for 24 hours. Cells were washed and HSP70 expression was assessed using flow cytometry. The data are expressed as % of cells that are HSP70 positive.

As shown in FIG. 29, the percent of HSP70 positive cells in anti-CD47 mAb (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) treated cultures were significantly increased (p<0.05) compared to those seen in isotype control treated cultures. Although each of the anti-CD47 mAbs caused a statistically significant increase in HSP70 expression, mitoxantrone did not. This increase in the exposure of HSP70 on the cell surface demonstrates that some of the chimeric or humanized antibodies induce DAMPs from tumor cells and can lead to phagocytosis of tumor cells and processing of tumor antigen by innate immune cells.

Humanized Anti-CD47 mAbs Cause Increase in Cell Surface HSP90 Expression

Figure 30:
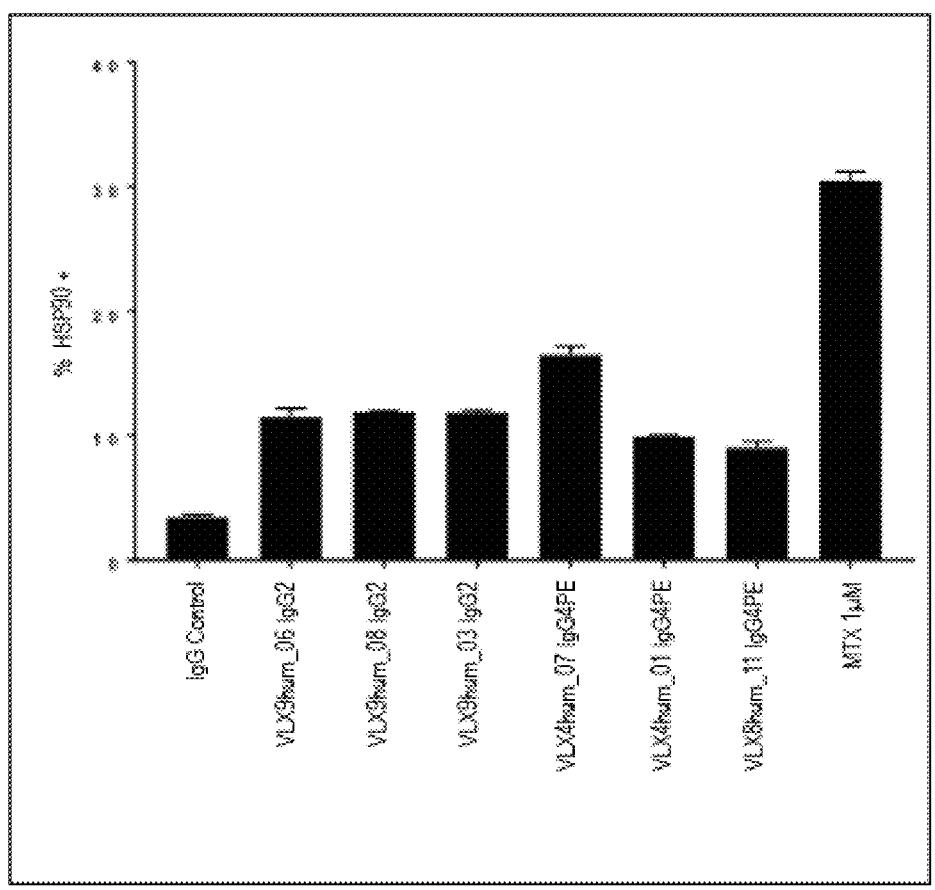
FIG. 30. Soluble VLX4, VLX8 and VLX9 Humanized mAbs Increase Cell Surface HSP90 Expression on Human Jurkat Cells. $1 \times 10^4$ Jurkat cells were incubated with 10 µg/ml of VLX4, VLX8 and VLX9 CD47 humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2), a negative IgG control antibody or 1 µM of mitoxantrone as a positive control in RPMI media at 37° C. for 24 hours. Cells were washed and HSP90 expression was assessed using flow cytometry. The data are expressed as % of cells that are HSP90 positive.

As shown in FIG. 30, the percent of HSP90 positive cells in soluble anti-CD47 mAb (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) treated cultures were significantly increased (p<0.05) compared to the background obtained with a negative control, humanized isotype-matched antibody. This increase in the exposure of HSP90 on the cell surface demonstrates that some of the chimeric or humanized antibodies induce DAMPs from tumor cells and can lead to phagocytosis of tumor cells and processing of tumor antigen by innate immune cells.

Humanized Anti-CD47 mAbs Cause Increase in ATP Release

Figure 31:
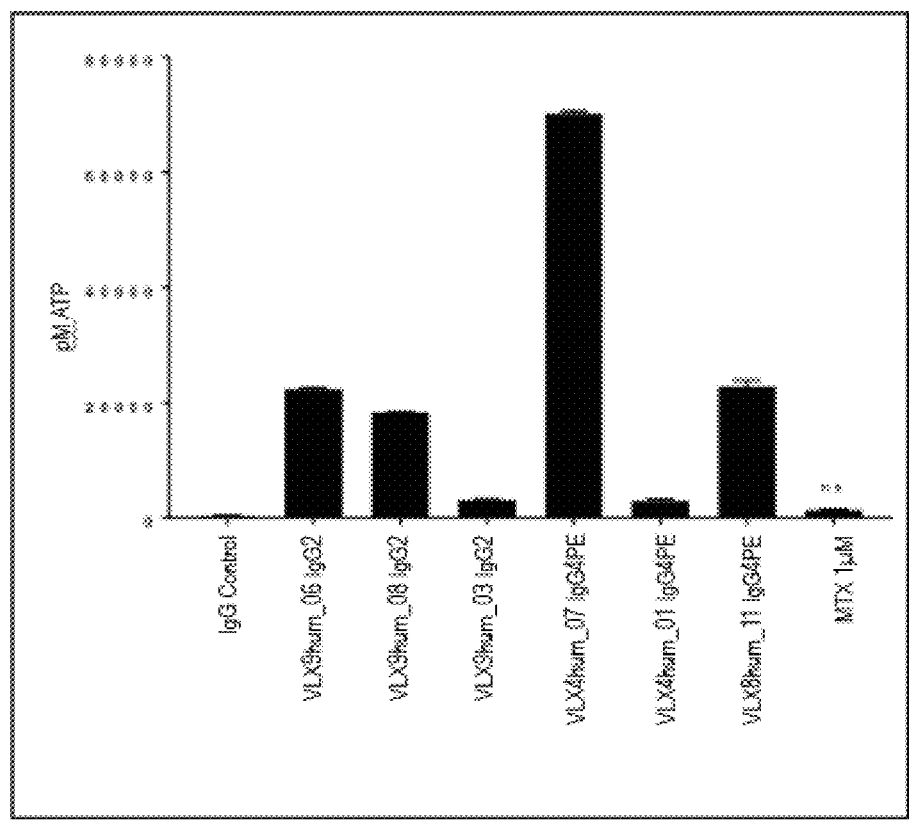
FIG. 31. Soluble VLX4, VLX8 and VLX9 Humanized mAbs Increase ATP Release by Human Jurkat Cells. $1 \times 10^4$ Jurkat cells were incubated with 10 µg/ml of VLX4, VLX8 and VLX9 CD47 humanized mAbs (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2), a negative IgG control antibody or 1 µM of mitoxantrone as a positive control in RPMI media at 37° C. for 24 hours. Cell-free supernatant was collected and analyzed using an ATP determination kit. The data are expressed as pM ATP in the supernatant.

As shown in FIG. 31, the amount of released ATP in humanized anti-CD47 mAb (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) treated cultures was significantly increased (p<0.05) compared to an isotype control. Although each of the anti-CD47 mAbs caused a statistically significant increase in HSP70 expression, mitoxantrone did not (ns). This increase in the release of ATP will demonstrates that some of the chimeric or humanized antibodies induce the release of ATP from tumor cells and can lead to dendritic cell migration through its cognate purinergic receptors.

Humanized Anti-CD47 mAbs Cause Increase in HMGB1 Release

As shown in FIG. 32, the amount of released HMGB1 protein in anti-CD47 mAb (VLX4hum_01 IgG4PE, VLX4hum_07 IgG4PE, VLX8hum_11 IgG4PE, VLX9hum_06 IgG2, VLX9hum_08 IgG2 and VLX9hum_03 IgG2) treated cultures was significantly increased (p<0.05) compared to an isotype control, except for VLX4hum_01 IgG4PE (ns). This increase in the release of HMGB1 demonstrates that some of the chimeric or humanized antibodies induce DAMPs from tumor cells and can lead to dendritic cell activation.

Example 12

Hemagglutination of Human Red Blood Cells (hRBCs)

Many CD47 antibodies, including B6H12, BRIC126, MABL1, MABL2, CC2C6, 5F9, have been shown to cause hemagglutination (HA) of washed RBCs in vitro or in vivo (Petrova P. et al. *Cancer Res* 2015; 75(15 Suppl): Abstract nr 4271; U.S. Pat. No. 9,045,541; Uno et al. *Oncol Rep.* 17: 1189-94, 2007; Kikuchi et al. *Biochem Biophys Res. Commun.* 315: 912-8, 2004; Sikic B. et al. *J Clin Oncol* 2016; 34 (suppl; abstract 3019)). Hemagglutination of hRBCs was assessed following incubation of hRBCs with various concentrations of chimeric and humanized VLX4, VLX8, and VLX9 mAbs in vitro essentially as described by Kikuchi et al. *Biochem Biophys Res. Commun* (2004) 315:912-918. Blood was obtained from healthy donors, diluted (1:50) in PBS/1 mM EDTA/BSA and washed 3 times with PBS/EDTA/BSA. hRBCs were added to U-bottomed 96 well plates with equal volumes of the antibodies (75 µl of each) and incubated for 3 hrs at 37° C. and overnight at 4° C. A tight RBC pellet is observed with antibodies that do not cause hemagglutination, and a diffuse, hazy pattern is observed with antibodies that cause hemagglutination.

Figure 33A:
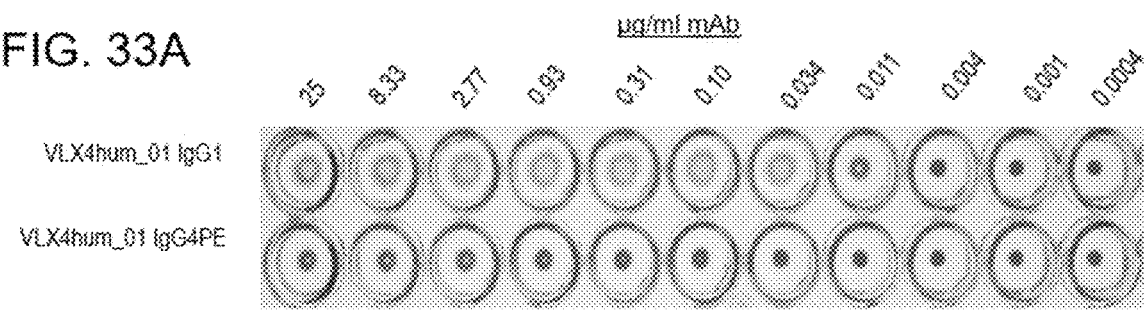
FIG. 33A. Agglutination of hRBCs by VLX4 Humanized mAbs. Hemagglutination was assessed following incubation of hRBCs with various concentrations of humanized VLX4 mAbs (VLX4hum_01 IgG1 and VLX4hum_01 IgG4PE). Blood was diluted (1:50) and washed 3 times with PBS/EDTA/BSA. hRBCs were added to U-bottomed 96 well plates with equal volumes of the antibodies (75 µl) and incubated for 3 hrs at 37° C. and overnight at 4° C.

As shown in FIG. 33A and Tables 1 and 2, The VLX4hum_01 IgG1 caused visible hemagglutination of hRBCs, whereas the humanized VLX4hum_01 IgG4PE mAb did not (mAb concentrations 50 μg/ml to 0.3 ng/ml). The lack of detectable hemagglutination by VLX4hum_01 IgG4 PE imparts an additional desirable antibody property and potential therapeutic benefit in the treatment of cancer.

Figure 33B:
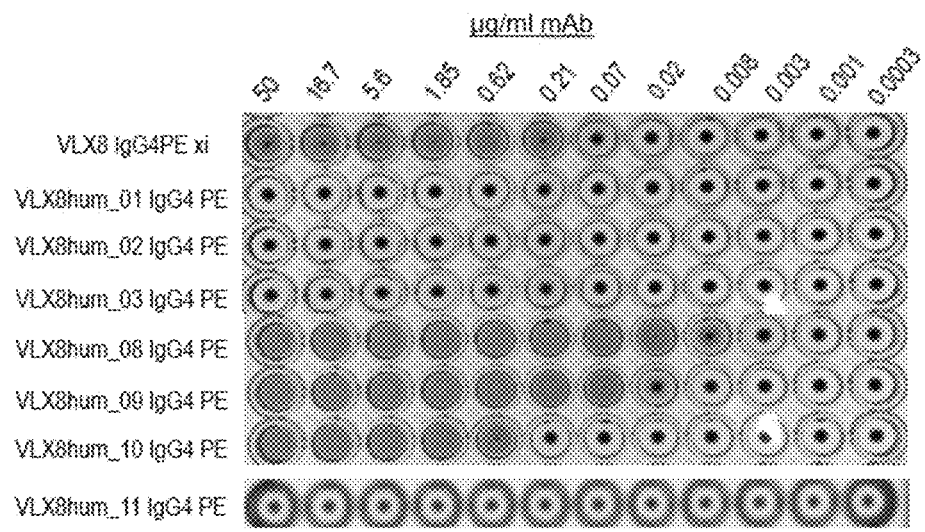
FIG. 33B. Agglutination of hRBCs by VLX8 Chimeric and Humanized mAbs. Hemagglutination was assessed following incubation of hRBCs with various concentrations of humanized VLX8 mAbs (VLX8hum_01 IgG4PE, VLX8hum_02 IgG4PE VLX8hum_03 IgG4PE, VLX8hum_08 IgG4PE, VLX8hum_09 IgG4PE, VLX8hum_10 IgG4PE and VLX8hum_11 IgG4PE) and the chimeric mAb VLX8 IgG4PE xi. Blood was diluted (1:50) and washed 3 times with PBS/EDTA/BSA. hRBCs were added to U-bottomed 96 well plates with equal volumes of the antibodies (75 µl) and incubated for 3 hrs at 37° C. and overnight at 4° C.

As shown in FIG. 33B and Tables 1 and 2, the chimeric antibody VLX8 IgG4PE (xi) and the humanized antibodies VLX8hum_08 IgG4PE, VLX8hum_09 IgG4PE, and VLX8hum_10 IgG4PE caused visible hemagglutination of hRBCs, whereas the VLX8 humanized Abs VLX8hum_01 IgG4PE, VLX8hum_02 IgG4 PE, VLX8hum_03 IgG4 PE and VLX8hum_11 IgG4PE did not (mAb concentrations 50 μg/ml to 0.3 ng/ml).

The lack of detectable hemagglutination by humanized antibodies VLX4hum_01 IgG4PE, VLX8hum_01 IgG4PE, VLX8hum_02 IgG4 PE, VLX8hum_03 IgG4 PE and VLX8hum_11 IgG4 PE imparts an additional desirable antibody property and a potential therapeutic benefit in the treatment of cancer.

Figure 34A:
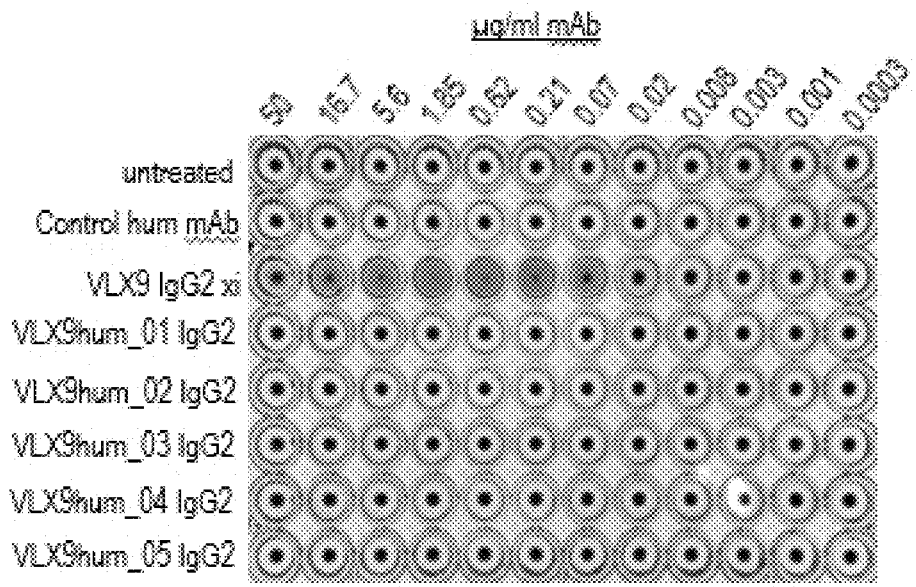
FIG. 34A. Agglutination of Human RBCs by VLX9 Humanized mAbs. Hemagglutination was assessed following incubation of human RBCs with various concentrations of VLX9 IgG2 chimera (xi) and humanized VLX9 mAbs (VLX9hum_01 to _05 IgG2). Blood was diluted (1:50) and washed 3 times with PBS/EDTA/BSA. RBCs were added to U-bottomed 96 well plates with equal volumes of the antibodies (75 µl) and incubated for 3 hrs at 37° C. and overnight at 4° C.
Figure 34B:
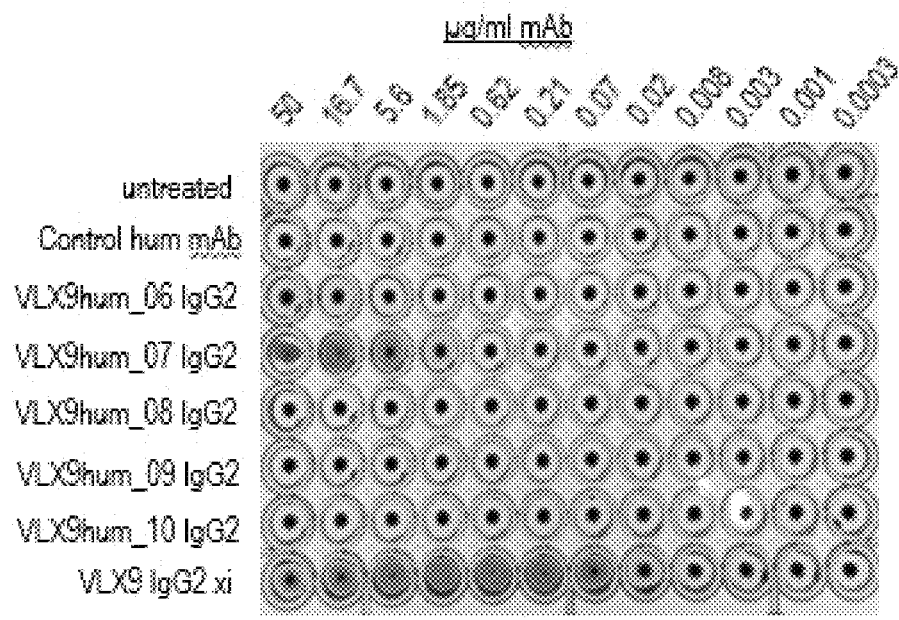
FIG. 34B. Agglutination of Human RBCs by VLX9 Humanized mAbs. Hemagglutination was assessed following incubation of human RBCs with various concentrations of VLX9 IgG2 chimera (xi) and humanized VLX9 mAbs (VLX9hum_06 to_10 IgG2). Blood was diluted (1:50) and washed 3 times with PBS/EDTA/BSA. RBCs were added to U-bottomed 96 well plates with equal volumes of the antibodies (75 µl) and incubated for 3 hrs at 37° C. and overnight at 4° C.

As shown in FIG. 34A and FIG. 34B, the chimeric antibody VLX9 IgG2 xi caused visible hemagglutination of hRBCs, whereas all of the humanized VLX9 mAbs except for VLX9hum_07 IgG2, did not cause detectable hemagglutination (at concentrations from 50 ug/ml to 0.3 pg/ml). However, the amount of detectable hemagglutination caused by VLX9hum_07 was reduced compared to the VLX9 IgG2 chimeric mAb. Again, the reduced or lack of detectable hemagglutination by the VLX9 humanized mAbs imparts an additional desirable antibody property and a potential therapeutic benefit in the treatment of cancer.

Example 13

Anti-Tumor Activity In Vivo

The purpose of this experiment was to demonstrate that VLX4, VLX8 and VLX9 humanized antibodies, exemplified by VLX4_07 IgG4PE, VLX8_10 IgG4PE and VLX9hum_08 IgG2, reduce tumor burden in vivo in a mouse xenograft model of lymphoma.

Raji human Burkitt's lymphoma cells (ATCC #CCL-86, Manassas, Va.) were maintained in RPMI-1640 (Lonza; Walkersville, Md.) supplemented with 10% Fetal Bovine Serum (FBS; Omega Scientific; Tarzana, Calif.) within a 5% $CO_2$ atmosphere. Cultures were expanded in tissue culture flasks.

Female NSG (NOD-Cg-Prkdc$^{scid}$Il2rg$^{tm1Wjl}$/SzJ) were obtained from Jackson Laboratory (Bar Harbor, Me.) at 5-6 weeks of age. Mice were acclimated prior to handling and housed in microisolator cages (Lab Products, Seaford, Del.) under specific pathogen-free conditions. Mice were fed Teklad Global Diet® 2920x irradiated laboratory animal diet (Envigo, Formerly Harlan; Indianapolis, Ind.) and provided autoclaved water ad libitum. All procedures were carried out under Institutional Animal Care and Use guidelines.

Female NSG mice were inoculated subcutaneously in the right flank with 0.1 mL of a 30% RPMI/70% Matrigel™ (BD Biosciences; Bedford, Mass.) mixture containing a suspension of $5 \times 10^6$ Raji tumor cells. Five days following inoculation, digital calipers were used to measure width and length diameters of the tumor. Tumor volumes were calculated utilizing the formula: tumor volume $(mm^3) = (a \times b^2/2)$ where 'b' is the smallest diameter and 'a' is the largest diameter. Mice with palpable tumor volumes of 31-74 $mm^3$ were randomized into 8-10/group and VLX9hum_08 or PBS (control) administration was initiated at this time. Mice were treated with 5 mg/kg of antibody 5×/week for 4 weeks by intraperitoneal injection. Tumor volumes and body weights were recorded twice weekly.

Figure 35:
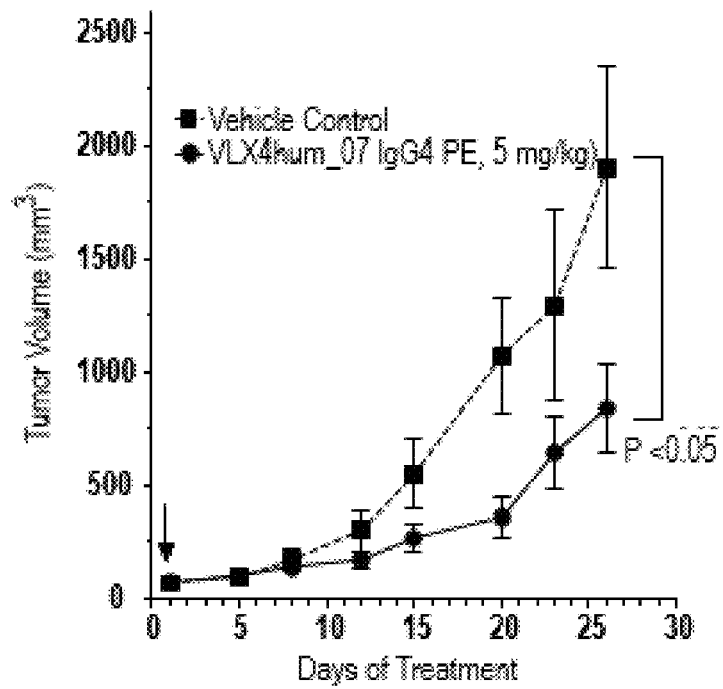
FIG. 35. VLX4 Humanized mAb Reduces Tumor Growth in Raji Xenograft Model. Female NSG mice were inoculated subcutaneously in the right flank with 0.1 mL of a 30% RPMI/70% Matrigel™ mixture containing a suspension of $5 \times 10^6$ Raji tumor cells. Five days following inoculation, tumor volumes were measured and mice with palpable tumor volumes of 31-74 $mm^3$ were randomized into 8-10/group. VLX4hum_07 IgG4PE or PBS (control) administration was initiated at this time. Mice were treated with 5 mg/kg of antibody 5×/week for 4 weeks by intraperitoneal injection. Tumor volumes and body weights were recorded twice weekly.

As shown in FIG. 35, treatment with the humanized VLX4hum_07 IgG4PE significantly reduced tumor growth of the Raji tumors (p<0.05, two-way ANOVA), demonstrating anti-tumor efficacy in vivo.

Figure 36:
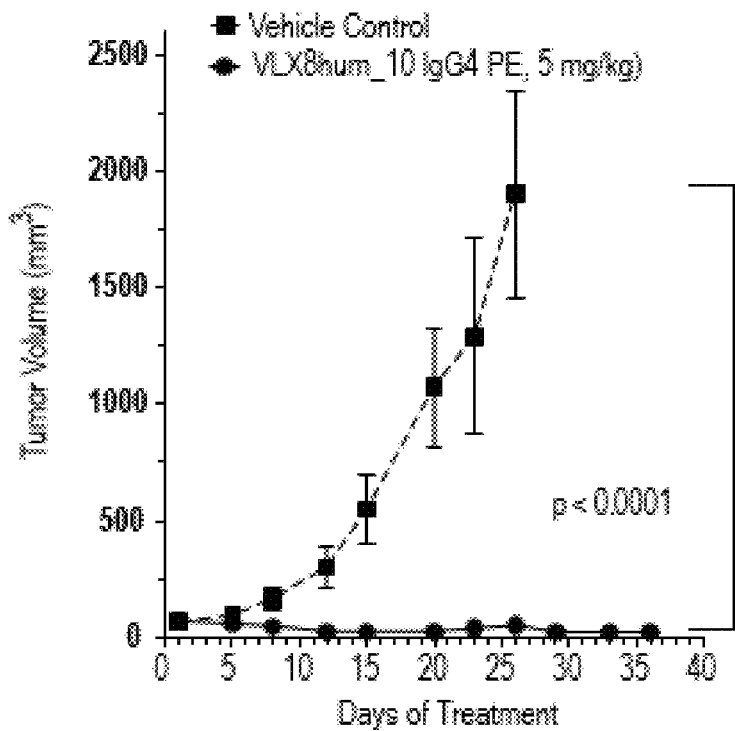
FIG. 36. VLX8 Humanized mAb Reduces Tumor Growth in Raji Xenograft Model. Female NSG mice were inoculated subcutaneously in the right flank with 0.1 mL of a 30% RPMI/70% Matrigel™ mixture containing a suspension of $5 \times 10^6$ Raji tumor cells. Five days following inoculation, tumor volumes were measured and mice with palpable tumor volumes of 31-74 $mm^3$ were randomized into 8-10/group. VLX8hum_10 IgG4PE or PBS (control) administration was initiated at this time. Mice were treated with 5 mg/kg of antibody 5×/week for 4 weeks by intraperitoneal injection. Tumor volumes and body weights were recorded twice weekly.

As shown in FIG. 36, treatment with the humanized anti-CD47 mAb, VLX8hum_10 IgG4PE significantly reduced (p<0.0001, two-way ANOVA) tumor growth of the Raji tumors, demonstrating anti-tumor efficacy in vivo.

Figure 37:
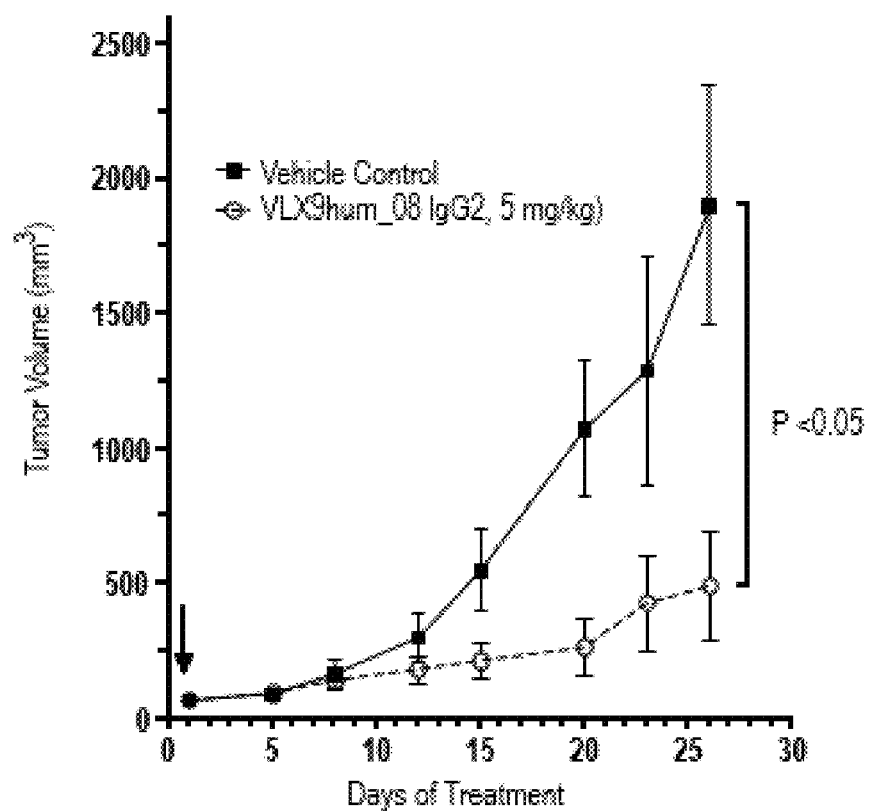
FIG. 37. VLX9 Humanized mAb Reduces Tumor Growth in Raji Xenograft Model. Female NSG mice were inoculated subcutaneously in the right flank with 0.1 mL of a 30% RPMI/70% Matrigel™ mixture containing a suspension of $5 \times 10^6$ Raji tumor cells. Five days following inoculation, tumor volumes were measured and mice with palpable tumor volumes of 31-74 $mm^3$ were randomized into 8-10/group. VLX9hum_08 IgG2 or PBS (control) administration was initiated at this time. Mice were treated with 5 mg/kg of antibody 5×/week for 4 weeks by intraperitoneal injection. Tumor volumes and body weights were recorded twice weekly.

As shown in FIG. 37, treatment with the humanized anti-CD47 mAb, VLX9hum_08 IgG2 significantly reduced (p<0.05, two-way ANOVA) tumor growth of the Raji tumors, demonstrating anti-tumor efficacy in vivo.

Example 14

Effect on Circulating Red Blood Cell Parameters

The purpose of this experiment is to demonstrate that VLX9 humanized antibodies that do not bind to human RBC in vitro (Table 2), exemplified by hum1017_08 IgG2, do not cause a reduction in either hemoglobin (Hg) or circulating RBCs following administration to cynomolgus monkeys.

Figure 38A:
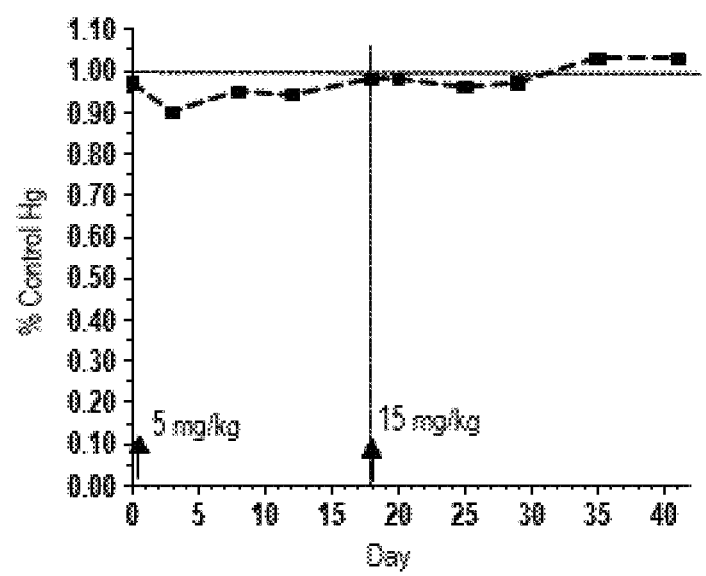
FIG. 38A. Hemoglobin Levels in Blood Following Administration of a Humanized VLX9 mAb to Cynomolgus Monkeys by Intravenous Infusion. VLX9hum_08 IgG2 or vehicle were administered as a one hour intravenous infusion a dose of 5 mg/kg on day 1 and a dose of 15 mg/kg on day 18. Hemoglobin levels were monitored throughout the study and normalized to control values.
Figure 38B:
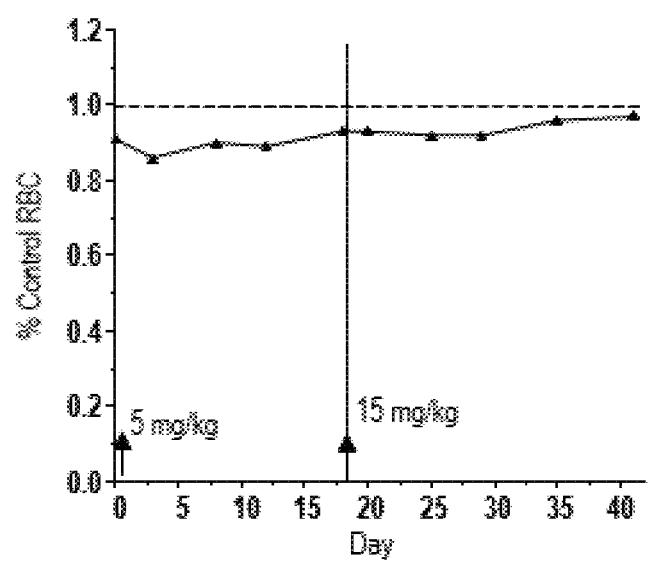
FIG. 38B. RBC Levels in Blood Following Administration of Humanized VLX9 mAbs to Cynomolgus Monkeys by Intravenous Infusion. VLX9hum_08 IgG2 or vehicle was administered as a one hour intraveneous infusion a dose of 5 mg/kg on day 1 and a dose of 15 mg/kg on day 18. RBC levels were monitored throughout the study and normalized to control values.

Female Chinese cynomolgus monkeys (Charles River Laboratories, Houston, Tex.) 2.5-3 kg were used in accordance with the Institutional Animal Care and Use guidelines. VLX9hum_08 IgG2 or vehicle (PBS) was administered as a 1 hour intravenous infusion on day 1 at a dose of 5 mg/kg and on day 18 at a dose of 15 mg/kg (3 animals/group). Hematological parameters were measured throughout the study on days −7, −3 (not shown), pre-dose, 3, 8, 12, 18 (pre-dose), 20, 25, 29, 35 and 41 and compared/normalized to the means values of control animals. The pre-treatment RBC and Hg values on day 0 in the VLX9hum_08 IgG2 group were lower than the control group. Following treatment with either dose of VLX9hum_08 IgG2, there were minimal changes (<10%) in Hg (FIG. 38A) or RBC counts (FIG. 38B) compared to the control group demonstrating that VLX9hum_08 IgG2 causes minimal reductions in RBC hematological parameters when administered to cynomolgus monkeys.

Example 15

Antibodies to CD47 Regulate Nitric Oxide Signaling

TSP1 binding to CD47 activates the heterotrimeric G protein Gi, which leads to suppression of intracellular cyclic AMP (cAMP) levels. In addition, the TSP1/CD47 pathway opposes the beneficial effects of the nitric oxide (NO) pathway in all vascular cells. The NO pathway consists of any of three nitric oxide synthase enzymes (NOS I, NOS II and NOS III) that generate bioactive gas NO using arginine as a substrate. NO can act within the cell in which it is produced or in neighboring cells, to activate the enzyme soluble guanylyl cyclase that produces the messenger molecule cyclic GMP (cGMP). The proper functioning of the NO/cGMP pathway is essential for protecting the cardiovascular system against stresses including, but not limited to, those resulting from wounding, inflammation, hypertension, metabolic syndrome, ischemia, and ischemia-reperfusion injury (IRI). In the context of these cellular stresses, the inhibition of the NO/cGMP pathway by the TSP1/CD47 system exacerbates the effects of stress. This is a particular problem in the cardiovascular system where both cGMP and cAMP play important protective roles. There are many cases in which ischemia and reperfusion injury cause or contribute to disease, trauma, and poor outcomes of surgical procedures.

The purpose of these experiment will be to demonstrate that humanized anti-CD47 mAbs of the present disclosure exhibit the ability to reverse TSP1-mediated inhibition of NO-stimulated cGMP synthesis as, for example, described previously using mouse monoclonal antibodies to CD47 as disclosed by Isenberg et al. (2006) J. Biol. Chem. 281: 26069-80, or alternatively other downstream markers of or effects resulting from NO signaling, for example smooth muscle cell relaxation or platelet aggregation as described previously by Miller et al. (2010) Br J. Pharmacol. 159: 1542-1547.

The method employed that will be to measure cGMP as described by the manufacturer (CatchPoint Cyclic-GMP Fluorescent Assay Kit, Molecular Devices, Sunnyvale, Calif.). Jurkat JE6.1 cells (ATCC, Manassas, Va.; Catalog #TIB-152) or other cells types that retain the NO/cGMP signaling pathway when grown in culture and exhibit a robust and reproducible inhibitory response to TSP1 ligation of CD47 will be used. Cells will be grown in Iscove's modified Dulbeccco's medium containing 5% (v/v) heat inactivated fetal bovine serum (BioWest; Catalogue #S01520), 100 units/mL penicillin, 100 μg mL streptomycin (Sigma; Catalogue #P4222) at densities less than 1×106 cells/mL. For the cGMP assay, cells will be plated in 96 well tissue culture plates at a density of 1×10$^5$ cells/ml in Iscoves modified Dulbecco's medium containing 5% (v/v) heat inactivated fetal bovine serum (BioWest; Catalog #S01520), 100 units/mL penicillin, 100 μg/mL streptomycin (Sigma; #P4222) for 24 hours and then transferred to serum free medium overnight.

The humanized antibodies as disclosed herein, purified from transient transfections in CHO cells as described above in Example 3, as well as the control chimeric antibody, will then be added at a final concentration of 20 ng/ml, followed 15 minutes later by 0 or 1 μg/ml human TSP1 (Athens Research and Technology, Athens, Ga., Catalogue #16-20-201319). After an additional 15 minutes, the NO donor, diethylamine (DEA) NONOate (Cayman Chemical, Ann Arbor, Mich., Catalog #82100), will be added to half the wells at a final concentration of 1 μM. Five minutes later, the cells will be lysed with buffer supplied in the cGMP kit, and aliquots of each well assayed for cGMP content.

It is anticipated that some of the chimeric or humanized antibodies will reverse TSP1 inhibition of cGMP. Reversal will be complete (>80%) or intermediate (20%-80%). This reversal of TSP1 inhibition of cGMP will demonstrate that they have the ability to increase NO signaling and suggest utility in protecting the cardiovascular system against stresses including, but not limited to, those resulting from wounding, inflammation, hypertension, metabolic syndrome, ischemia, and ischemia-reperfusion injury (IRI). Additional assay systems, for example smooth muscle cell contraction, will also be expected to show that some of the chimeric or humanized antibody clones reverse the inhibitory actions of TSP on downstream effects resulting from the activation of NO signaling.

What is claimed is:

1. A method of treating cancer in a human subject, the method comprising: administering to the human subject a monoclonal antibody or an antigen binding fragment thereof,
wherein the monoclonal antibody or an antigen binding fragment thereof
a) binds to human CD47 on the surface of a tumor cell;
b) blocks SIRPα binding to human CD47;
c) increases phagocytosis of human tumor cells; and
d) induces death of human tumor cells; and
wherein the monoclonal antibody or antigen binding fragment thereof comprises a combination of a heavy chain variable domain (VH) and a light chain variable domain (VL) selected from the group consisting of:
(i) a VH domain comprising the amino acid sequence of SEQ ID NO: 38 and a VL domain comprising the amino acid sequence of SEQ ID NO: 51;
(ii) a VH domain comprising the amino acid sequence of SEQ ID NO: 39 and a VL domain comprising the amino acid sequence of SEQ ID NO: 51;
(iii) a VH domain comprising the amino acid sequence of SEQ ID NO: 40 and a VL domain comprising the amino acid sequence of SEQ ID NO: 51;
(iv) a VH domain comprising the amino acid sequence of SEQ ID NO: 36 and a VL domain comprising the amino acid sequence of SEQ ID NO: 52;
(v) a VH domain comprising the amino acid sequence of SEQ ID NO: 38 and a VL domain comprising the amino acid sequence of SEQ ID NO: 52;
(vi) a VH domain comprising the amino acid sequence of SEQ ID NO: 39 and a VL domain comprising the amino acid sequence of SEQ ID NO: 52; and
(vii) a VH domain comprising the amino acid sequence of SEQ ID NO: 40 and a VL domain comprising the amino acid sequence of SEQ ID NO: 52.

2. The method of claim 1, wherein the monoclonal antibody or antigen binding fragment thereof binds a normal cell with an apparent $K_d$ of at least 8-fold greater compared to the binding of the monoclonal antibody or antigen binding fragment thereof to a human tumor cell, wherein the normal cell is an endothelial cell, a skeletal muscle cell, an epithelial cell, a T cell, a red blood cell, a peripheral blood mononuclear cell, an aortic endothelial cell, a skeletal muscle cell, a microvascular endothelial cell, a renal tubular epithelial cell, a peripheral blood CD3+ cell, or a peripheral blood mononuclear cell.

3. The method of claim 2, wherein the monoclonal antibody or antigen binding fragment thereof has minimal binding to human red blood cells (hRBCs).

4. The method of claim 1, wherein the monoclonal antibody or antigen binding fragment thereof causes no detectable agglutination of hRBCs.

5. The method of claim 1, wherein the monoclonal antibody or antigen binding fragment thereof induces characteristics of immunogenic cell death including one or more of the following:
(i) increased cell surface calreticulin expression on the human tumor cells;

(ii) increased adenosine triphosphate (ATP) release by human tumor cells;
(iii) increased high mobility group box 1 (HMGB1) release by human tumor cells;
(iv) increased annexin Al release by human tumor cells;
(v) increased type I interferon release by human tumor cells;
(vi) increased C-X-C Motif Chemokine Ligand 10 (CXCL10) release by human tumor cells;
(vii) increased cell surface protein protein disulfide-isomerase A3 (PDIA3) expression on human tumor cells;
(viii) increased cell surface heat shock protein 70 (HSP70) expression on human tumor cells; or
(ix) increased cell surface heat shock protein 90 (HSP90) expression on human tumor cells.

6. The method of claim 1, wherein the monoclonal antibody or antigen binding fragment thereof further comprises pH-dependent binding to human CD47 present on a human tumor cell.

7. The method of claim 6, wherein the monoclonal antibody or antigen binding fragment thereof possesses a greater affinity for CD47 at an acidic pH compared to physiological pH.

8. The method of claim 1, wherein the monoclonal antibody or antigen binding fragment thereof is a chimeric or humanized antibody.

9. The method of claim 1, wherein the monoclonal antibody or antigen binding fragment thereof comprises at least one heavy chain and at least one light chain selected from the group consisting of:
(i) a heavy chain comprising the amino acid sequence of SEQ ID NO: 82 and a light chain comprising the amino acid sequence SEQ ID NO: 74;
(ii) a heavy chain comprising the amino acid sequence of SEQ ID NO: 83 and a light chain comprising the amino acid sequence SEQ ID NO: 74;
(iii) a heavy chain comprising the amino acid sequence of SEQ ID NO: 89 and a light chain comprising the amino acid sequence SEQ ID NO: 74;
(iv) a heavy chain comprising the amino acid sequence of SEQ ID NO: 81 and a light chain comprising the amino acid sequence SEQ ID NO: 71;
(v) a heavy chain comprising the amino acid sequence of SEQ ID NO: 82 and a light chain comprising the amino acid sequence SEQ ID NO: 71;
(vi) a heavy chain comprising the amino acid sequence of SEQ ID NO: 83 and a light chain comprising the amino acid sequence SEQ ID NO: 71; and
(vii) a heavy chain comprising the amino acid sequence of SEQ ID NO: 89 and a light chain comprising the amino acid sequence SEQ ID NO: 71.

10. The method of claim 1, wherein the monoclonal antibody or antigen binding fragment thereof causes reversal of NO pathway inhibition.

11. The method of claim 1, wherein the monoclonal antibody or antigen binding fragment thereof displays one or more effector functions selected from the group consisting of antibody-dependent cellular cytotoxicity (ADCC), complement-dependent cytotoxicity (CDC), antibody-dependent cellular phagocytosis (ADCP), and C1q binding against CD47-expressing human tumor cells.

12. The method of claim 1, wherein the monoclonal antibody or antigen binding fragment thereof is formulated as a pharmaceutical composition comprising a pharmaceutically or physiologically acceptable carrier, diluent, or excipient.

13. The method of claim 1, wherein the monoclonal antibody or antigen binding fragment thereof is administered intravenously or subcutaneously.

14. The method of claim 1, wherein said cancer is chosen from the group consisting of leukemia, lymphoma, ovarian cancer, breast cancer, endometrial cancer, colon cancer, rectal cancer, bladder cancer, urothelial cancer, lung cancer, bronchial cancer, bone cancer, prostate cancer, pancreatic cancer, gastric cancer, hepatocellular carcinoma, gall bladder cancer, bile duct cancer, esophageal cancer, renal cell carcinoma, thyroid cancer, head and neck cancer, testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, cancer of uterus, glioblastoma, medulloblastoma, astrocytoma, glioma, meningioma, gastrinoma, neuroblastoma, melanoma, and sarcoma.

15. The method of claim 14,
wherein the lung cancer is non-small cell lung cancer, adenocarcinoma of the lung, or squamous cell carcinoma of the lung,
wherein the leukemia is selected from the group consisting of systemic mastocytosis, acute lymphocytic leukemia (ALL), T cell—ALL, acute myeloid leukemia (AML), myelogenous leukemia, chronic lymphocytic leukemia (CLL), multiple myeloma (MM), chronic myeloid leukemia (CIVIL), myeloproliferative neoplasm, myelodysplastic syndrome, monocytic cell leukemia, and plasma cell leukemia;
wherein the lymphoma is selected from the group consisting of histiocytic lymphoma, T cell lymphoma, B cell lymphoma, Hodgkin's lymphoma, non-Hodgkin's lymphoma, low grade follicular non-Hodgkin's lymphoma, follicular center cell lymphoma (FCC), mantle cell lymphoma (MCL), diffuse large cell lymphoma (DLCL), small lymphocytic (SL) NHL, intermediate grade follicular NHL, intermediate grade diffuse NHL, high grade immunoblastic NHL, high grade lymphoblastic NHL, high grade small non-cleaved cell NHL, bulky disease NHL, and Waldenstrom's Macroglobulinemia; and
wherein the sarcoma is selected from the group consisting of osteosarcoma, Ewing's sarcoma, leiomyosarcoma, synovial sarcoma, alveolar soft part sarcoma, angiosarcoma, liposarcoma, fibrosarcoma, rhabdomyosarcoma, and chrondrosarcoma.

16. The method of claim 1, wherein the monoclonal antibody further comprises an IgG isotype selected from the group consisting of IgG1, IgG1-N297Q, IgG2, IgG3, IgG4, IgG4 S228P, and IgG4 PE (S228P/L235E).

17. The method of claim 16, wherein the Fc domain of the IgG isotype comprises the amino acid sequence of SEQ ID NO: 53, 54, 55, 56, 57, 58, 59, or 99.

* * * * *

UNITED STATES PATENT AND TRADEMARK OFFICE
CERTIFICATE OF CORRECTION

PATENT NO. : 11,692,035 B2
APPLICATION NO. : 16/703484
DATED : July 4, 2023
INVENTOR(S) : Pamela T. Manning et al.

It is certified that error appears in the above-identified patent and that said Letters Patent is hereby corrected as shown below:

In the Claims

Column 226, Line 34 Claim 15:
"The method of claim 14, wherein the lung cancer is non-small cell lung cancer, adenocarcinoma of the lung, or squamous cell carcinoma of the lung, wherein the leukemia is selected from the group consisting of systemic mastocytosis, acute lymphocytic leukemia (ALL), T cell–ALL, acute myeloid leukemia (AML), myelogenous leukemia, chronic lymphocytic leukemia (CLL), multiple myeloma (MM), chronic myeloid leukemia (CIVIL), myeloproliferative neoplasm, myelodysplastic syndrome, monocytic cell leukemia, and plasma cell leukemia; wherein the lymphoma is selected from the group consisting of histiocytic lymphoma, T cell lymphoma, B cell lymphoma, Hodgkin's lymphoma, non-Hodgkin's lymphoma, low grade follicular non-Hodgkin's lymphoma, follicular center cell lymphoma (FCC), mantle cell lymphoma (MCL), diffuse large cell lymphoma (DLCL), small lymphocytic (SL) NHL, intermediate grade follicular NHL, intermediate grade diffuse NHL, high grade immunoblastic NHL, high grade lymphoblastic NHL, high grade small non-cleaved cell NHL, bulky disease NHL, and Waldenstrom's Macroglobulinemia; and wherein the sarcoma is selected from the group consisting of osteosarcoma, Ewing' sarcoma, leiomyosarcoma, synovial sarcoma, alveolar soft part sarcoma, angiosarcoma, liposarcoma, fibrosarcoma, rhabdomyosarcoma, and chrondrosarcoma."

Should read:
--The method of claim 14, wherein the lung cancer is non-small cell lung cancer, adenocarcinoma of the lung, or squamous cell carcinoma of the lung, wherein the leukemia is selected from the group consisting of systemic mastocytosis, acute lymphocytic leukemia (ALL), T cell–ALL, acute myeloid leukemia (AML), myelogenous leukemia, chronic lymphocytic leukemia (CLL), multiple myeloma (MM), chronic myeloid leukemia (CML), myeloproliferative neoplasm, myelodysplastic syndrome, monocytic cell leukemia, and plasma cell leukemia; wherein the lymphoma is selected from the group consisting of histiocytic lymphoma, T cell lymphoma, B cell lymphoma, Hodgkin's lymphoma, non-Hodgkin's lymphoma, low grade follicular non-Hodgkin's lymphoma, follicular center cell lymphoma (FCC), mantle cell lymphoma (MCL), diffuse large cell lymphoma (DLCL), small lymphocytic (SL) NHL, intermediate grade follicular NHL, intermediate grade diffuse NHL, high grade immunoblastic NHL, high grade lymphoblastic NHL, high grade small non-cleaved cell NHL, bulky disease NHL, Signed and Sealed this
Fifteenth Day of August, 2023

*Katherine Kelly Vidal*

Katherine Kelly Vidal
*Director of the United States Patent and Trademark Office* and Waldenstrom's Macroglobulinemia; and wherein the sarcoma is selected from the group consisting of osteosarcoma, Ewing' sarcoma, leiomyosarcoma, synovial sarcoma, alveolar soft part sarcoma, angiosarcoma, liposarcoma, fibrosarcoma, rhabdomyosarcoma, and chrondrosarcoma.--

SEQUENCE LISTING

```
<160> NUMBER OF SEQ ID NOS: 101

<210> SEQ ID NO 1
<211> LENGTH: 10
<212> TYPE: PRT
<213> ORGANISM: Homo sapiens

<400> SEQUENCE: 1

Gly Tyr Thr Phe Thr Asn Tyr Val Ile His
1               5                   10

<210> SEQ ID NO 2
<211> LENGTH: 10
<212> TYPE: PRT
<213> ORGANISM: Homo sapiens

<400> SEQUENCE: 2

Gly Tyr Ser Phe Thr Asn Tyr Tyr Ile His
1               5                   10

<210> SEQ ID NO 3
<211> LENGTH: 10
<212> TYPE: PRT
<213> ORGANISM: Homo sapiens

<400> SEQUENCE: 3

Gly Tyr Thr Phe Thr Asn Tyr Trp Ile His
1               5                   10

<210> SEQ ID NO 4
<211> LENGTH: 17
<212> TYPE: PRT
<213> ORGANISM: Homo sapiens
```

```
<400> SEQUENCE: 4

Tyr Ile Tyr Pro Tyr Asn Asp Gly Ile Leu Tyr Asn Glu Lys Phe Lys
1               5                   10                  15
Gly

<210> SEQ ID NO 5
<211> LENGTH: 17
<212> TYPE: PRT
<213> ORGANISM: Homo sapiens

<400> SEQUENCE: 5

Tyr Ile Asp Pro Leu Asn Gly Asp Thr Thr Tyr Asn Gln Lys Phe Lys
1               5                   10                  15
Gly

<210> SEQ ID NO 6
<211> LENGTH: 17
<212> TYPE: PRT
<213> ORGANISM: Homo sapiens

<400> SEQUENCE: 6

Tyr Thr Asp Pro Arg Thr Asp Tyr Thr Glu Tyr Asn Gln Lys Phe Lys
1               5                   10                  15
Asp

<210> SEQ ID NO 7
<211> LENGTH: 8
<212> TYPE: PRT
<213> ORGANISM: Homo sapiens

<400> SEQUENCE: 7

Gly Gly Tyr Tyr Val Pro Asp Tyr
1               5

<210> SEQ ID NO 8
<211> LENGTH: 8
<212> TYPE: PRT
<213> ORGANISM: Homo sapiens

<400> SEQUENCE: 8

Gly Gly Tyr Tyr Val Tyr Asp Tyr
1               5

<210> SEQ ID NO 9
<211> LENGTH: 8
<212> TYPE: PRT
<213> ORGANISM: Homo sapiens

<400> SEQUENCE: 9

Gly Gly Lys Arg Ala Met Asp Tyr
1               5

<210> SEQ ID NO 10
<211> LENGTH: 8
<212> TYPE: PRT
<213> ORGANISM: Homo sapiens

<400> SEQUENCE: 10

Gly Gly Arg Val Gly Leu Gly Tyr
1               5
```

-continued

```
<210> SEQ ID NO 11
<211> LENGTH: 16
<212> TYPE: PRT
<213> ORGANISM: Homo sapiens

<400> SEQUENCE: 11

Arg Ser Arg Gln Ser Ile Val His Thr Asn Gly Asn Thr Tyr Leu Gly
1               5                   10                  15

<210> SEQ ID NO 12
<211> LENGTH: 11
<212> TYPE: PRT
<213> ORGANISM: Homo sapiens

<400> SEQUENCE: 12

Arg Ala Ser Gln Asp Ile Ser Asn Tyr Leu Asn
1               5                   10

<210> SEQ ID NO 13
<211> LENGTH: 11
<212> TYPE: PRT
<213> ORGANISM: Homo sapiens

<400> SEQUENCE: 13

Arg Ala Ser Gln Ser Ile Ser Asn Tyr Leu Asn
1               5                   10

<210> SEQ ID NO 14
<211> LENGTH: 16
<212> TYPE: PRT
<213> ORGANISM: Homo sapiens

<400> SEQUENCE: 14

Arg Ser Ser Gln Asn Ile Val Gln Ser Asn Gly Asn Thr Tyr Leu Glu
1               5                   10                  15

<210> SEQ ID NO 15
<211> LENGTH: 7
<212> TYPE: PRT
<213> ORGANISM: Homo sapiens

<400> SEQUENCE: 15

Lys Val Ser Asn Arg Phe Ser
1               5

<210> SEQ ID NO 16
<211> LENGTH: 7
<212> TYPE: PRT
<213> ORGANISM: Homo sapiens

<400> SEQUENCE: 16

Tyr Thr Ser Arg Leu Tyr Ser
1               5

<210> SEQ ID NO 17
<211> LENGTH: 7
<212> TYPE: PRT
<213> ORGANISM: Homo sapiens

<400> SEQUENCE: 17

Lys Val Phe His Arg Phe Ser
1               5

<210> SEQ ID NO 18
<211> LENGTH: 9
```

```
<212> TYPE: PRT
<213> ORGANISM: Homo sapiens

<400> SEQUENCE: 18

Phe Gln Gly Ser His Val Pro Tyr Thr
1               5

<210> SEQ ID NO 19
<211> LENGTH: 9
<212> TYPE: PRT
<213> ORGANISM: Homo sapiens

<400> SEQUENCE: 19

Gln Gln Gly Asn Thr Leu Pro Trp Thr
1               5

<210> SEQ ID NO 20
<211> LENGTH: 9
<212> TYPE: PRT
<213> ORGANISM: Homo sapiens

<400> SEQUENCE: 20

Phe Gln Gly Ser His Val Pro Trp Thr
1               5

<210> SEQ ID NO 21
<211> LENGTH: 117
<212> TYPE: PRT
<213> ORGANISM: Homo sapiens

<400> SEQUENCE: 21

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Arg Arg Pro Gly Gln Gly Leu Glu Trp Ile
        35                  40                  45

Gly Tyr Ile Tyr Pro Tyr Asn Asp Gly Ile Leu Tyr Asn Glu Lys Phe
    50                  55                  60

Lys Gly Lys Ala Thr Val Thr Ser Asp Lys Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Thr Arg Gly Gly Tyr Tyr Val Pro Asp Tyr Trp Gly Gln Gly Thr Thr
            100                 105                 110

Leu Thr Val Ser Ser
        115

<210> SEQ ID NO 22
<211> LENGTH: 117
<212> TYPE: PRT
<213> ORGANISM: Homo sapiens

<400> SEQUENCE: 22

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Arg Arg Pro Gly Gln Gly Leu Glu Trp Ile
        35                  40                  45
```

Gly Tyr Ile Tyr Pro Tyr Asn Asp Gly Ile Leu Tyr Asn Glu Lys Phe
        50                  55                  60

Lys Gly Lys Ala Thr Val Thr Ser Asp Lys Ser Ser Thr Ala Tyr
65                  70                  75                  80

Met Asp Leu Ser Ser Leu Thr Ser Glu Asp Ser Ala Val Tyr Tyr Cys
                85                  90                  95

Thr Arg Gly Gly Tyr Tyr Val Pro Asp Tyr Trp Gly Gln Gly Thr Leu
                100                 105                 110

Val Thr Val Ser Ser
            115

<210> SEQ ID NO 23
<211> LENGTH: 117
<212> TYPE: PRT
<213> ORGANISM: Homo sapiens

<400> SEQUENCE: 23

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Thr Phe Thr Asn Tyr
                20                  25                  30

Val Ile His Trp Leu Arg Gln Ala Pro Gly Gln Gly Leu Glu Trp Met
            35                  40                  45

Gly Tyr Ile Tyr Pro Tyr Asn Asp Gly Ile Leu Tyr Asn Glu Lys Phe
        50                  55                  60

Lys Gly Arg Val Thr Met Thr Ser Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Gly Tyr Tyr Val Pro Asp Tyr Trp Gly Gln Ala Thr Leu
                100                 105                 110

Val Thr Val Ser Ser
            115

<210> SEQ ID NO 24
<211> LENGTH: 117
<212> TYPE: PRT
<213> ORGANISM: Homo sapiens

<400> SEQUENCE: 24

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Thr Phe Thr Asn Tyr
                20                  25                  30

Val Ile His Trp Leu Arg Gln Ala Pro Gly Gln Gly Leu Glu Trp Met
            35                  40                  45

Gly Tyr Ile Tyr Pro Tyr Asn Asp Gly Ile Leu Tyr Asn Glu Lys Phe
        50                  55                  60

Lys Gly Arg Val Thr Met Thr Ser Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Gly Tyr Tyr Val Tyr Asp Tyr Trp Gly Gln Ala Thr Leu
                100                 105                 110

Val Thr Val Ser Ser
            115

<210> SEQ ID NO 25
<211> LENGTH: 117
<212> TYPE: PRT
<213> ORGANISM: Homo sapiens

<400> SEQUENCE: 25

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asn Tyr
            20                  25                  30

Val Ile His Trp Val Gln Gln Ala Pro Gly Lys Gly Leu Glu Trp Met
        35                  40                  45

Gly Tyr Ile Tyr Pro Tyr Asn Asp Gly Ile Leu Tyr Asn Glu Lys Phe
    50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Tyr Tyr Val Pro Asp Tyr Trp Gly Gln Gly Thr Thr
            100                 105                 110

Val Thr Val Ser Ser
        115

<210> SEQ ID NO 26
<211> LENGTH: 117
<212> TYPE: PRT
<213> ORGANISM: Homo sapiens

<400> SEQUENCE: 26

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Val Ile His Trp Val Arg Gln Met Pro Gly Lys Gly Leu Glu Trp Met
        35                  40                  45

Gly Tyr Ile Tyr Pro Tyr Asn Asp Gly Ile Leu Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Tyr Val Pro Asp Tyr Trp Gly Gln Gly Thr Thr
            100                 105                 110

Val Thr Val Ser Ser
        115

<210> SEQ ID NO 27
<211> LENGTH: 117
<212> TYPE: PRT
<213> ORGANISM: Homo sapiens

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Ile His Trp Val Arg Gln Ala Pro Gly Gln Gly Leu Glu Trp Met

```
            35                  40                  45
Gly Tyr Ile Tyr Pro Tyr Asn Asp Gly Ile Leu Tyr Asn Glu Lys Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Gly Tyr Tyr Val Pro Asp Tyr Trp Gly Gln Gly Thr Thr
                100                 105                 110

Val Thr Val Ser Ser
            115

<210> SEQ ID NO 28
<211> LENGTH: 117
<212> TYPE: PRT
<213> ORGANISM: Homo sapiens

<400> SEQUENCE: 28

Glu Val Gln Leu Gln Gln Ser Gly Pro Glu Leu Met Lys Pro Gly Ala
 1               5                  10                  15

Ser Val Lys Ile Ser Cys Lys Ala Ser Gly Tyr Ser Phe Thr Asn Tyr
                 20                  25                  30

Tyr Ile His Trp Val Asn Gln Ser His Gly Lys Ser Leu Glu Trp Ile
             35                  40                  45

Gly Tyr Ile Asp Pro Leu Asn Gly Asp Thr Thr Tyr Asn Gln Lys Phe
 50                  55                  60

Lys Gly Lys Ala Thr Leu Thr Val Asp Lys Ser Ser Thr Ala Tyr
 65                  70                  75                  80

Met Arg Leu Ser Ser Leu Thr Ser Ala Asp Ser Ala Val Tyr Tyr Cys
                 85                  90                  95

Ala Arg Gly Gly Lys Arg Ala Met Asp Tyr Trp Gly Gln Gly Thr Ser
                100                 105                 110

Val Thr Val Ser Ser
            115

<210> SEQ ID NO 29
<211> LENGTH: 117
<212> TYPE: PRT
<213> ORGANISM: Homo sapiens

<400> SEQUENCE: 29

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Asn Tyr
                 20                  25                  30

Tyr Ile His Trp Val Arg Gln Ala Pro Gly Gln Gly Leu Glu Trp Met
             35                  40                  45

Gly Tyr Ile Asp Pro Leu Asn Gly Asp Thr Thr Tyr Asn Gln Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Lys Arg Ala Met Asp Tyr Trp Gly Gln Gly Thr Leu
                100                 105                 110

Val Thr Val Ser Ser
```

<210> SEQ ID NO 30
<211> LENGTH: 117
<212> TYPE: PRT
<213> ORGANISM: Homo sapiens

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser
        115

<210> SEQ ID NO 31
<211> LENGTH: 117
<212> TYPE: PRT
<213> ORGANISM: Homo sapiens

<400> SEQUENCE: 31

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile His Trp Val Arg Gln Met Pro Gly Lys Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser
        115

<210> SEQ ID NO 32
<211> LENGTH: 117
<212> TYPE: PRT
<213> ORGANISM: Homo sapiens

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
            35                  40                  45

Gly Tyr Ile Asp Pro Leu Asn Gly Asp Thr Thr Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Lys Arg Ala Met Asp Tyr Trp Gly Gln Gly Thr Leu
                100                 105                 110

Val Thr Val Ser Ser
        115

<210> SEQ ID NO 33
<211> LENGTH: 117
<212> TYPE: PRT
<213> ORGANISM: Homo sapiens

<400> SEQUENCE: 33

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
                 20                  25                  30

Tyr Ile His Trp Val Arg Gln Met Pro Gly Lys Gly Leu Glu Trp Met
            35                  40                  45

Gly Tyr Ile Asp Pro Leu Asn Gly Asp Thr Thr Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Lys Arg Ala Met Asp Tyr Trp Gly Arg Gly Thr Leu
                100                 105                 110

Val Thr Val Ser Ser
        115

<210> SEQ ID NO 34
<211> LENGTH: 117
<212> TYPE: PRT
<213> ORGANISM: Homo sapiens

<400> SEQUENCE: 34

Gln Val Gln Leu Val Gln Ser Gly Ala Glu Val Lys Lys Pro Gly Ala
 1               5                  10                  15

Ser Val Gln Val Ser Cys Lys Ala Ser Gly Tyr Ser Phe Thr Asn Tyr
                 20                  25                  30

Tyr Ile His Trp Leu Arg Gln Ala Pro Gly Gln Gly Leu Glu Trp Met
            35                  40                  45

Gly Tyr Ile Asp Pro Leu Asn Gly Asp Thr Thr Tyr Asn Gln Lys Phe
 50                  55                  60

Lys Gly Arg Val Thr Met Thr Ser Asp Thr Ser Ile Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Gly Gly Lys Arg Ala Met Asp Tyr Trp Gly Gln Ala Thr Leu
                100                 105                 110

Val Thr Val Ser Ser
        115

<210> SEQ ID NO 35
<211> LENGTH: 117
<212> TYPE: PRT
<213> ORGANISM: Homo sapiens

<400> SEQUENCE: 35

Gln Val Gln Leu Gln Gln Phe Gly Ala Glu Leu Ala Lys Pro Gly Ala
1               5                   10                  15

Ser Val Gln Met Ser Cys Lys Ala Ser Gly Tyr Thr Phe Thr Asn Tyr
            20                  25                  30

Trp Ile His Trp Val Lys Gln Arg Pro Gly Gln Gly Leu Glu Trp Ile
        35                  40                  45

Gly Tyr Thr Asp Pro Arg Thr Asp Tyr Thr Glu Tyr Asn Gln Lys Phe
    50                  55                  60

Lys Asp Lys Ala Thr Leu Ala Ala Asp Arg Ser Ser Thr Ala Tyr
65                  70                  75                  80

Met Arg Leu Ser Ser Leu Thr Ser Glu Asp Ser Ala Val Tyr Tyr Cys
                85                  90                  95

Ala Gly Gly Gly Arg Val Gly Leu Gly Tyr Trp Gly His Gly Ser Ser
            100                 105                 110

Val Thr Val Ser Ser
        115

<210> SEQ ID NO 36
<211> LENGTH: 117
<212> TYPE: PRT
<213> ORGANISM: Homo sapiens

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
        35                  40                  45

Gly Tyr Thr Asp Pro Arg Thr Asp Tyr Thr Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Val Gly Leu Gly Tyr Trp Gly Gln Gly Thr Leu
            100                 105                 110

Val Thr Val Ser Ser
        115

<210> SEQ ID NO 37
<211> LENGTH: 117
<212> TYPE: PRT
<213> ORGANISM: Homo sapiens

<400> SEQUENCE: 37

Gln Val Gln Leu Val Gln Ser Gly Ala Glu Val Lys Lys Pro Gly Ser
1               5                   10                  15

```
Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
            35                  40                  45

Gly Tyr Thr Asp Pro Arg Thr Asp Tyr Thr Glu Tyr Asn Gln Lys Phe
    50                  55                  60

Lys Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gly Arg Val Gly Leu Gly Tyr Trp Gly Gln Gly Thr Leu
            100                 105                 110

Val Thr Val Ser Ser
            115

<210> SEQ ID NO 38
<211> LENGTH: 117
<212> TYPE: PRT
<213> ORGANISM: Homo sapiens

<400> SEQUENCE: 38

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Trp Ile His Trp Val Arg Gln Met Pro Gly Lys Gly Leu Glu Trp Met
            35                  40                  45

Gly Tyr Thr Asp Pro Arg Thr Asp Tyr Thr Glu Tyr Asn Gln Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Gly Gly Arg Val Gly Leu Gly Tyr Trp Gly Gln Gly Thr Leu
            100                 105                 110

Val Thr Val Ser Ser
            115

<210> SEQ ID NO 39
<211> LENGTH: 117
<212> TYPE: PRT
<213> ORGANISM: Homo sapiens

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
            35                  40                  45

Gly Tyr Thr Asp Pro Arg Thr Asp Tyr Thr Glu Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95
```

```
Ala Arg Gly Gly Arg Val Gly Leu Gly Tyr Trp Gly Gln Gly Thr Leu
            100                 105                 110

Val Thr Val Ser Ser
        115

<210> SEQ ID NO 40
<211> LENGTH: 117
<212> TYPE: PRT
<213> ORGANISM: Homo sapiens

<400> SEQUENCE: 40

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Trp Ile His Trp Val Arg Gln Met Pro Gly Lys Gly Leu Glu Trp Met
        35                  40                  45

Gly Tyr Thr Asp Pro Arg Thr Asp Tyr Thr Glu Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Arg Val Gly Leu Gly Tyr Trp Gly Gln Gly Thr Leu
            100                 105                 110

Val Thr Val Ser Ser
        115

<210> SEQ ID NO 41
<211> LENGTH: 112
<212> TYPE: PRT
<213> ORGANISM: Homo sapiens

<400> SEQUENCE: 41

Asp Val Leu Met Thr Gln Thr Pro Leu Ser Leu Pro Val Asn Leu Gly
1               5                   10                  15

Asp Gln Ala Ser Ile Ser Cys Arg Ser Arg Gln Ser Ile Val His Thr
            20                  25                  30

Asn Gly Asn Thr Tyr Leu Gly Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 42
<211> LENGTH: 112
<212> TYPE: PRT
<213> ORGANISM: Homo sapiens

<400> SEQUENCE: 42

Asp Val Leu Met Thr Gln Thr Pro Leu Ser Leu Pro Val Asn Leu Gly
1               5                   10                  15

Asp Gln Ala Ser Ile Ser Cys Arg Ser Arg Gln Ser Ile Val His Thr
```

```
            20                  25                  30
Asn Gly Asn Thr Tyr Leu Gly Trp Phe Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Thr Ile
 65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gln Gly Thr Lys Val Glu Ile Lys
            100                 105                 110

<210> SEQ ID NO 43
<211> LENGTH: 112
<212> TYPE: PRT
<213> ORGANISM: Homo sapiens

<400> SEQUENCE: 43

Asp Ile Val Met Thr Gln Ser Pro Leu Ser Leu Pro Val Thr Pro Gly
 1               5                  10                  15

Glu Pro Ala Ser Ile Ser Cys Arg Ser Arg Gln Ser Ile Val His Thr
            20                  25                  30

Asn Gly Asn Thr Tyr Leu Gly Trp Tyr Leu Gln Lys Pro Gly Gln Ser
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Asp Asp Val Gly Ile Tyr Tyr Cys Phe Gln Gly
                85                  90                  95

Ser His Val Pro Tyr Thr Phe Gly Gln Gly Thr Lys Leu Glu Ile Lys
            100                 105                 110

<210> SEQ ID NO 44
<211> LENGTH: 112
<212> TYPE: PRT
<213> ORGANISM: Homo sapiens

<400> SEQUENCE: 44

Asp Val Val Met Thr Gln Ser Pro Leu Ser Leu Pro Val Thr Leu Gly
 1               5                  10                  15

Gln Pro Ala Ser Ile Ser Cys Arg Ser Arg Gln Ser Ile Val His Thr
            20                  25                  30

Asn Gly Asn Thr Tyr Leu Gly Trp Phe Gln Gln Arg Pro Gly Gln Ser
            35                  40                  45

Pro Arg Arg Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
            100                 105                 110

<210> SEQ ID NO 45
<211> LENGTH: 112
<212> TYPE: PRT
```

<213> ORGANISM: Homo sapiens

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Arg Ser Arg Gln Ser Ile Val His Thr
            20                  25                  30

Asn Gly Asn Thr Tyr Leu Gly Trp Tyr Gln Gln Lys Pro Gly Gln Pro
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Phe Gln Gly
                85                  90                  95

Ser His Val Pro Tyr Thr Phe Gly Gln Gly Thr Lys Leu Glu Ile Lys
                100                 105                 110

<210> SEQ ID NO 46
<211> LENGTH: 107
<212> TYPE: PRT
<213> ORGANISM: Homo sapiens

<400> SEQUENCE: 46

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Tyr Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
                100                 105

<210> SEQ ID NO 47
<211> LENGTH: 107
<212> TYPE: PRT
<213> ORGANISM: Homo sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Tyr Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

```
Thr Phe Gly Gln Gly Thr Lys Val Glu Ile Lys
            100                 105

<210> SEQ ID NO 48
<211> LENGTH: 107
<212> TYPE: PRT
<213> ORGANISM: Homo sapiens

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 49
<211> LENGTH: 107
<212> TYPE: PRT
<213> ORGANISM: Homo sapiens

<400> SEQUENCE: 49

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Asp Ile Ser Asn Tyr
            20                  25                  30

Leu Asn Trp Tyr Leu Gln Lys Pro Gly Gln Ser Pro Arg Leu Leu Ile
        35                  40                  45

Tyr Tyr Thr Ser Arg Leu Tyr Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Asp Asp Val Gly Ile Tyr Tyr Cys Gln Gln Gly Asn Thr Leu Pro Trp
                85                  90                  95

Thr Phe Gly Gln Gly Thr Lys Leu Glu Ile Lys
            100                 105

<210> SEQ ID NO 50
<211> LENGTH: 112
<212> TYPE: PRT
<213> ORGANISM: Homo sapiens

<400> SEQUENCE: 50

Asp Val Phe Met Thr Gln Thr Pro Leu Ser Leu Pro Val Ser Leu Gly
1               5                   10                  15

Asp Gln Ala Ser Ile Ser Cys Arg Ser Ser Gln Asn Ile Val Gln Ser
            20                  25                  30

Asn Gly Asn Thr Tyr Leu Glu Trp Tyr Leu Gln Lys Pro Gly Gln Ser
        35                  40                  45
```

```
Pro Lys Leu Leu Ile Tyr Lys Val Phe His Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Val Glu Ile Lys
                100                 105                 110
```

<210> SEQ ID NO 51
<211> LENGTH: 112
<212> TYPE: PRT
<213> ORGANISM: Homo sapiens

<400> SEQUENCE: 51

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Asn Ile Val Gln Ser
                 20                  25                  30

Asn Gly Asn Thr Tyr Leu Glu Trp Phe Gln Gln Arg Pro Gly Gln Ser
             35                  40                  45

Pro Arg Arg Leu Ile Tyr Lys Val Phe His Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Tyr Thr Phe Gly Gln Gly Thr Lys Leu Glu Ile Lys
                100                 105                 110
```

<210> SEQ ID NO 52
<211> LENGTH: 112
<212> TYPE: PRT
<213> ORGANISM: Homo sapiens

<400> SEQUENCE: 52

```
Asp Ile Val Met Thr Gln Ser Pro Asp Ser Leu Ala Val Ser Leu Gly
 1               5                  10                  15

Glu Arg Ala Thr Ile Asn Cys Arg Ser Ser Gln Asn Ile Val Gln Ser
                 20                  25                  30

Asn Gly Asn Thr Tyr Leu Glu Trp Tyr Gln Gln Lys Pro Gly Gln Pro
             35                  40                  45

Pro Lys Leu Leu Ile Tyr Lys Val Phe His Arg Phe Ser Gly Val Pro
         50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Phe Gln Gly
                 85                  90                  95

Ser His Val Pro Tyr Thr Phe Gly Gln Gly Thr Lys Leu Glu Ile Lys
                100                 105                 110
```

<210> SEQ ID NO 53
<211> LENGTH: 330
<212> TYPE: PRT
<213> ORGANISM: Homo sapiens

<400> SEQUENCE: 53

```
Ala Ser Thr Lys Gly Pro Ser Val Phe Pro Leu Ala Pro Ser Ser Lys
```

```
                1               5                  10                 15
            Ser Thr Ser Gly Gly Thr Ala Ala Leu Gly Cys Leu Val Lys Asp Tyr
                           20                  25                 30

Phe Pro Glu Pro Val Thr Val Ser Trp Asn Ser Gly Ala Leu Thr Ser
                           35                  40                 45

Gly Val His Thr Phe Pro Ala Val Leu Gln Ser Ser Gly Leu Tyr Ser
                50                      55                 60

Leu Ser Ser Val Val Thr Val Pro Ser Ser Leu Gly Thr Gln Thr
             65                      70                  75                 80

Tyr Ile Cys Asn Val Asn His Lys Pro Ser Asn Thr Lys Val Asp Lys
                                85                  90                 95

Lys Val Glu Pro Lys Ser Cys Asp Lys Thr His Thr Cys Pro Pro Cys
                           100                 105                110

Pro Ala Pro Glu Leu Leu Gly Gly Pro Ser Val Phe Leu Phe Pro Pro
                           115                 120                125

Lys Pro Lys Asp Thr Leu Met Ile Ser Arg Thr Pro Glu Val Thr Cys
             130                     135                 140

Val Val Val Asp Val Ser His Glu Asp Pro Glu Val Lys Phe Asn Trp
             145                     150                 155                160

Tyr Val Asp Gly Val Glu Val His Asn Ala Lys Thr Lys Pro Arg Glu
                                165                 170                175

Glu Gln Tyr Asn Ser Thr Tyr Arg Val Val Ser Val Leu Thr Val Leu
                           180                 185                 190

His Gln Asp Trp Leu Asn Gly Lys Glu Tyr Lys Cys Lys Val Ser Asn
                           195                 200                 205

Lys Ala Leu Pro Ala Pro Ile Glu Lys Thr Ile Ser Lys Ala Lys Gly
                       210                 215                 220

Gln Pro Arg Glu Pro Gln Val Tyr Thr Leu Pro Pro Ser Arg Asp Glu
            225                     230                 235                240

Leu Thr Lys Asn Gln Val Ser Leu Thr Cys Leu Val Lys Gly Phe Tyr
                           245                 250                 255

Pro Ser Asp Ile Ala Val Glu Trp Glu Ser Asn Gly Gln Pro Glu Asn
                           260                 265                 270

Asn Tyr Lys Thr Thr Pro Pro Val Leu Asp Ser Asp Gly Ser Phe Phe
                           275                 280                 285

Leu Tyr Ser Lys Leu Thr Val Asp Lys Ser Arg Trp Gln Gln Gly Asn
                       290                 295                 300

Val Phe Ser Cys Ser Val Met His Glu Ala Leu His Asn His Tyr Thr
            305                     310                 315                320

Gln Lys Ser Leu Ser Leu Ser Pro Gly Lys
                           325                 330

<210> SEQ ID NO 54
<211> LENGTH: 330
<212> TYPE: PRT
<213> ORGANISM: Homo sapiens

<400> SEQUENCE: 54

Ala Ser Thr Lys Gly Pro Ser Val Phe Pro Leu Ala Pro Ser Ser Lys
             1               5                  10                 15

Ser Thr Ser Gly Gly Thr Ala Ala Leu Gly Cys Leu Val Lys Asp Tyr
                           20                  25                 30

Phe Pro Glu Pro Val Thr Val Ser Trp Asn Ser Gly Ala Leu Thr Ser
                           35                  40                 45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 55
<211> LENGTH: 326
<212> TYPE: PRT
<213> ORGANISM: Homo sapiens

<400> SEQUENCE: 55

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95
```

```
Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 56
<211> LENGTH: 326
<212> TYPE: PRT
<213> ORGANISM: Homo sapiens

<400> SEQUENCE: 56

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
```

```
                130                 135                 140
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
                210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
                290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 57
<211> LENGTH: 377
<212> TYPE: PRT
<213> ORGANISM: Homo sapiens

<400> SEQUENCE: 57

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
                115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175
```

```
Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 58
<211> LENGTH: 326
<212> TYPE: PRT
<213> ORGANISM: Homo sapiens

<400> SEQUENCE: 58

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 59
<211> LENGTH: 326
<212> TYPE: PRT
<213> ORGANISM: Homo sapiens

<400> SEQUENCE: 59

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
```

```
            210                 215                 220
Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 60
<211> LENGTH: 327
<212> TYPE: PRT
<213> ORGANISM: Homo sapiens

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 61
<211> LENGTH: 107
<212> TYPE: PRT
<213> ORGANISM: Homo sapiens

<400> SEQUENCE: 61

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 62
<211> LENGTH: 329
<212> TYPE: PRT
<213> ORGANISM: Rattus norvegicus

<400> SEQUENCE: 62

Ala Arg Thr Thr Ala Pro Ser Val Tyr Pro Leu Val Pro Gly Cys Ser
1               5                   10                  15

Gly Thr Ser Gly Ser Leu Val Thr Leu Gly Cys Leu Val Lys Gly Tyr
            20                  25                  30

Phe Pro Glu Pro Val Thr Val Lys Trp Asn Ser Gly Ala Leu Ser Ser
        35                  40                  45

Gly Val His Thr Phe Pro Ala Val Leu Gln Ser Gly Leu Tyr Thr Leu
    50                  55                  60

Ser Ser Ser Val Thr Val Pro Ser Ser Thr Trp Ser Ser Gln Thr Val
65                  70                  75                  80

Thr Cys Ser Val Ala His Pro Ala Thr Lys Ser Asn Leu Ile Lys Arg
                85                  90                  95

Ile Glu Pro Arg Arg Pro Lys Pro Arg Pro Pro Thr Asp Ile Cys Ser
            100                 105                 110

Cys Asp Asp Asn Leu Gly Arg Pro Ser Val Phe Ile Phe Pro Pro Lys
        115                 120                 125

Pro Lys Asp Ile Leu Met Ile Thr Leu Thr Pro Lys Val Thr Cys Val
    130                 135                 140
```

```
Val Val Asp Val Ser Glu Glu Pro Asp Val Gln Phe Ser Trp Phe
145                 150                 155                 160

Val Asp Asn Val Arg Val Phe Thr Ala Gln Thr Gln Pro His Glu Glu
                165                 170                 175

Gln Leu Asn Gly Thr Phe Arg Val Val Ser Thr Leu His Ile Gln His
                180                 185                 190

Gln Asp Trp Met Ser Gly Lys Glu Phe Lys Cys Lys Val Asn Asn Lys
            195                 200                 205

Asp Leu Pro Ser Pro Ile Glu Lys Thr Ile Ser Lys Pro Arg Gly Lys
        210                 215                 220

Ala Arg Thr Pro Gln Val Tyr Thr Ile Pro Pro Arg Glu Gln Met
225                 230                 235                 240

Ser Lys Asn Lys Val Ser Leu Thr Cys Met Val Thr Ser Phe Tyr Pro
                245                 250                 255

Ala Ser Ile Ser Val Glu Trp Glu Arg Asn Gly Glu Leu Glu Gln Asp
                260                 265                 270

Tyr Lys Asn Thr Leu Pro Val Leu Asp Ser Asp Glu Ser Tyr Phe Leu
            275                 280                 285

Tyr Ser Lys Leu Ser Val Asp Thr Asp Ser Trp Met Arg Gly Asp Ile
        290                 295                 300

Tyr Thr Cys Ser Val Val His Glu Ala Leu His Asn His His Thr Gln
305                 310                 315                 320

Lys Asn Leu Ser Arg Ser Pro Gly Lys
                325

<210> SEQ ID NO 63
<211> LENGTH: 107
<212> TYPE: PRT
<213> ORGANISM: Rattus norvegicus

<400> SEQUENCE: 63

Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
                20                  25                  30

Tyr Pro Arg Asp Ile Ser Val Lys Trp Lys Ile Asp Gly Ser Glu Gln
            35                  40                  45

Arg Asp Gly Val Leu Asp Ser Val Thr Asp Gln Asp Ser Lys Asp Ser
        50                  55                  60

Thr Tyr Ser Met Ser Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                85                  90                  95

Pro Val Val Lys Ser Phe Asn Arg Asn Glu Cys
                100                 105

<210> SEQ ID NO 64
<211> LENGTH: 323
<212> TYPE: PRT
<213> ORGANISM: Oryctolagus cuniculus

<400> SEQUENCE: 64

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
                20                  25                  30
```

```
Leu Pro Glu Pro Val Thr Val Thr Trp Asn Ser Gly Thr Leu Thr Asn
            35                  40                  45

Gly Val Arg Thr Phe Pro Ser Val Arg Gln Ser Ser Gly Leu Tyr Ser
 50                  55                  60

Leu Ser Ser Val Val Ser Val Thr Ser Ser Ser Gln Pro Val Thr Cys
 65                  70                  75                  80

Asn Val Ala His Pro Ala Thr Asn Thr Lys Val Asp Lys Thr Val Ala
                 85                  90                  95

Pro Ser Thr Cys Ser Lys Pro Thr Cys Pro Pro Glu Leu Leu Gly
                100                 105                 110

Gly Pro Ser Val Phe Ile Phe Pro Pro Lys Pro Lys Asp Thr Leu Met
                115                 120                 125

Ile Ser Arg Thr Pro Glu Val Thr Cys Val Val Val Asp Val Ser Gln
130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
                180                 185                 190

Lys Glu Phe Lys Cys Lys Val His Asn Lys Ala Leu Pro Ala Pro Ile
                195                 200                 205

Glu Lys Thr Ile Ser Lys Ala Arg Gly Gln Pro Leu Glu Pro Lys Val
                210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
                260                 265                 270

Val Leu Asp Ser Asp Gly Ser Tyr Phe Leu Tyr Ser Lys Leu Ser Val
                275                 280                 285

Pro Thr Ser Glu Trp Gln Arg Gly Asp Val Phe Thr Cys Ser Val Met
                290                 295                 300

His Glu Ala Leu His Asn His Tyr Thr Gln Lys Ser Ile Ser Arg Ser
305                 310                 315                 320

Pro Gly Lys

<210> SEQ ID NO 65
<211> LENGTH: 104
<212> TYPE: PRT
<213> ORGANISM: Oryctolagus cuniculus

<400> SEQUENCE: 65

Arg Asp Pro Val Ala Pro Thr Val Leu Ile Phe Pro Pro Ala Ala Asp
1               5                  10                  15

Gln Val Ala Thr Gly Thr Val Thr Ile Val Cys Val Ala Asn Lys Tyr
                20                  25                  30

Phe Pro Asp Val Thr Val Thr Trp Glu Val Asp Gly Thr Thr Gln Thr
                35                  40                  45

Thr Gly Ile Glu Asn Ser Lys Thr Pro Gln Asn Ser Ala Asp Cys Thr
 50                  55                  60

Tyr Asn Leu Ser Ser Thr Leu Thr Leu Thr Ser Thr Gln Tyr Asn Ser
65                  70                  75                  80
```

```
His Lys Glu Tyr Thr Cys Lys Val Thr Gln Gly Thr Thr Ser Val Val
                 85                  90                  95

Gln Ser Phe Asn Arg Gly Asp Cys
            100
```

<210> SEQ ID NO 66
<211> LENGTH: 293
<212> TYPE: PRT
<213> ORGANISM: Oryctolagus cuniculus

<400> SEQUENCE: 66

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Glu
    290
```

<210> SEQ ID NO 67
<211> LENGTH: 219
<212> TYPE: PRT
<213> ORGANISM: Homo sapiens

<400> SEQUENCE: 67

Asp Val Leu Met Thr Gln Thr Pro Leu Ser Leu Pro Val Asn Leu Gly
1               5                   10                  15

Asp Gln Ala Ser Ile Ser Cys Arg Ser Arg Gln Ser Ile Val His Thr
            20                  25                  30

Asn Gly Asn Thr Tyr Leu Gly Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65              70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 68
<211> LENGTH: 219
<212> TYPE: PRT
<213> ORGANISM: Homo sapiens

<400> SEQUENCE: 68

Asp Val Leu Met Thr Gln Thr Pro Leu Ser Leu Pro Val Asn Leu Gly
1               5                   10                  15

Asp Gln Ala Ser Ile Ser Cys Arg Ser Arg Gln Ser Ile Val His Thr
            20                  25                  30

Asn Gly Asn Thr Tyr Leu Gly Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65              70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 69
<211> LENGTH: 219
<212> TYPE: PRT
<213> ORGANISM: Homo sapiens

<400> SEQUENCE: 69

```
Asp Ile Val Met Thr Gln Ser Pro Leu Ser Leu Pro Val Thr Pro Gly
1               5                   10                  15

Glu Pro Ala Ser Ile Ser Cys Arg Ser Arg Gln Ser Ile Val His Thr
            20                  25                  30

Asn Gly Asn Thr Tyr Leu Gly Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Phe Gln Gly
                85                  90                  95

Ser His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 70
<211> LENGTH: 214
<212> TYPE: PRT
<213> ORGANISM: Homo sapiens

<400> SEQUENCE: 70

```
Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Asp Ile Ser Asn Tyr
            20                  25                  30

Leu Asn Trp Tyr Leu Gln Lys Pro Gly Gln Ser Pro Arg Leu Leu Ile
        35                  40                  45
```

```
Tyr Tyr Thr Ser Arg Leu Tyr Ser Gly Val Pro Asp Arg Phe Ser Gly
         50                  55                  60

Ser Gly Ser Gly Thr Asp Phe Thr Leu Lys Ile Ser Arg Val Glu Ala
 65                  70                  75                  80

Asp Asp Val Gly Ile Tyr Tyr Cys Gln Gln Gly Asn Thr Leu Pro Trp
                 85                  90                  95

Thr Phe Gly Gln Gly Thr Lys Leu Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
    210

<210> SEQ ID NO 71
<211> LENGTH: 219
<212> TYPE: PRT
<213> ORGANISM: Homo sapiens

<400> SEQUENCE: 71

Asp Ile Val Met Thr Gln Ser Pro Asp Ser Leu Ala Val Ser Leu Gly
 1               5                  10                  15

Glu Arg Ala Thr Ile Asn Cys Arg Ser Ser Gln Asn Ile Val Gln Ser
             20                  25                  30

Asn Gly Asn Thr Tyr Leu Glu Trp Tyr Gln Gln Lys Pro Gly Gln Pro
         35                  40                  45

Pro Lys Leu Leu Ile Tyr Lys Val Phe His Arg Phe Ser Gly Val Pro
 50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Phe Gln Gly
                 85                  90                  95

Ser His Val Pro Tyr Thr Phe Gly Gln Gly Thr Lys Leu Glu Ile Lys
             100                 105                 110

Arg Thr Val Ala Ala Pro Ser Val Phe Ile Phe Pro Pro Ser Asp Glu
         115                 120                 125

Gln Leu Lys Ser Gly Thr Ala Ser Val Val Cys Leu Leu Asn Asn Phe
     130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
             180                 185                 190

Lys His Lys Val Tyr Ala Cys Glu Val Thr His Gln Gly Leu Ser Ser
```

```
            195                 200                 205
Pro Val Thr Lys Ser Phe Asn Arg Gly Glu Cys
    210                 215

<210> SEQ ID NO 72
<211> LENGTH: 214
<212> TYPE: PRT
<213> ORGANISM: Homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 73
<211> LENGTH: 219
<212> TYPE: PRT
<213> ORGANISM: Homo sapiens

<400> SEQUENCE: 73

Asp Val Val Met Thr Gln Ser Pro Leu Ser Leu Pro Val Thr Leu Gly
1               5                   10                  15

Gln Pro Ala Ser Ile Ser Cys Arg Ser Arg Gln Ser Ile Val His Thr
            20                  25                  30

Asn Gly Asn Thr Tyr Leu Gly Trp Phe Gln Gln Arg Pro Gly Gln Ser
        35                  40                  45

Pro Arg Arg Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
```

```
                85                  90                  95
Ser His Val Pro Tyr Thr Phe Gly Gln Gly Thr Lys Leu Glu Ile Lys
            100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
        130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
            195                 200                 205
Pro Val Thr Lys Ser Phe Asn Arg Gly Glu Cys
        210                 215

<210> SEQ ID NO 74
<211> LENGTH: 219
<212> TYPE: PRT
<213> ORGANISM: Homo sapiens

<400> SEQUENCE: 74

Asp Val Val Met Thr Gln Ser Pro Leu Ser Leu Pro Val Thr Leu Gly
1               5                   10                  15
Gln Pro Ala Ser Ile Ser Cys Arg Ser Ser Gln Asn Ile Val Gln Ser
            20                  25                  30
Asn Gly Asn Thr Tyr Leu Glu Trp Phe Gln Gln Arg Pro Gly Gln Ser
        35                  40                  45
Pro Arg Arg Leu Ile Tyr Lys Val Phe His Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Val Pro Tyr Thr Phe Gly Gln Gly Thr Lys Leu Glu Ile Lys
            100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
        130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
            195                 200                 205
Pro Val Thr Lys Ser Phe Asn Arg Gly Glu Cys
        210                 215

<210> SEQ ID NO 75
<211> LENGTH: 214
```

<212> TYPE: PRT
<213> ORGANISM: Homo sapiens

<400> SEQUENCE: 75

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Tyr Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Trp
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210
```

<210> SEQ ID NO 76
<211> LENGTH: 214
<212> TYPE: PRT
<213> ORGANISM: Mus musculus

<400> SEQUENCE: 76

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Tyr Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
            85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 77
<211> LENGTH: 219
<212> TYPE: PRT
<213> ORGANISM: Mus musculus

<400> SEQUENCE: 77

Asp Val Phe Met Thr Gln Thr Pro Leu Ser Leu Pro Val Ser Leu Gly
1               5                   10                  15
Asp Gln Ala Ser Ile Ser Cys Arg Ser Ser Gln Asn Ile Val Gln Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Phe His Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Trp Thr Phe Gly Gly Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 78
<211> LENGTH: 444
<212> TYPE: PRT
<213> ORGANISM: Mus musculus

<400> SEQUENCE: 78

Glu Val Gln Leu Gln Gln Ser Gly Pro Glu Leu Val Lys Pro Gly Ala
1               5                   10                  15
```

```
Ser Val Lys Met Ser Cys Lys Ala Ser Gly Tyr Thr Phe Thr Asn Tyr
            20                  25                  30

Val Ile His Trp Val Lys Arg Arg Pro Gly Gln Gly Leu Glu Trp Ile
        35                  40                  45

Gly Tyr Ile Tyr Pro Tyr Asn Asp Gly Ile Leu Tyr Asn Glu Lys Phe
    50                  55                  60

Lys Gly Lys Ala Thr Val Thr Ser Asp Lys Ser Ser Thr Ala Tyr
65                  70                  75                  80

Met Asp Leu Ser Ser Leu Thr Ser Glu Asp Ser Ala Val Tyr Tyr Cys
                85                  90                  95

Thr Arg Gly Gly Tyr Tyr Val Pro Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Lys Thr Tyr Thr Cys Asn Val Asp His Lys Pro Ser Asn
    195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
        420                 425                 430

Tyr Thr Gln Lys Ser Leu Ser Leu Ser Leu Gly Lys
```

<210> SEQ ID NO 79
<211> LENGTH: 444
<212> TYPE: PRT
<213> ORGANISM: Homo sapiens

<400> SEQUENCE: 79

```
Gln Val Gln Leu Val Gln Ser Gly Ala Glu Val Lys Lys Pro Gly Ala
1               5                   10                  15

Ser Val Gln Val Ser Cys Lys Ala Ser Gly Tyr Thr Phe Thr Asn Tyr
            20                  25                  30

Val Ile His Trp Leu Arg Gln Ala Pro Gly Gln Gly Leu Glu Trp Met
        35                  40                  45

Gly Tyr Ile Tyr Pro Tyr Asn Asp Gly Ile Leu Tyr Asn Glu Lys Phe
    50                  55                  60

Lys Gly Arg Val Thr Met Thr Ser Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Gly Tyr Tyr Val Pro Asp Tyr Trp Gly Gln Ala Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365
```

-continued

```
Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 80
<211> LENGTH: 444
<212> TYPE: PRT
<213> ORGANISM: Homo sapiens

<400> SEQUENCE: 80

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Ser Phe Thr Asn Tyr
                20                  25                  30

Tyr Ile His Trp Leu Arg Gln Ala Pro Gly Gln Gly Leu Glu Trp Met
            35                  40                  45

Gly Tyr Ile Asp Pro Leu Asn Gly Asp Thr Thr Tyr Asn Gln Lys Phe
    50                  55                  60

Lys Gly Arg Val Thr Met Thr Ser Asp Thr Ser Ile Ser Thr Ala Tyr
65                  70                  75                  80

Met Glu Leu Ser Ser Leu Arg Ser Asp Thr Ala Val Tyr Tyr Cys
                85                  90                  95

Ala Arg Gly Gly Lys Arg Ala Met Asp Tyr Trp Gly Gln Ala Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300
```

```
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440

<210> SEQ ID NO 81
<211> LENGTH: 443
<212> TYPE: PRT
<213> ORGANISM: Homo sapiens

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Ile His Trp Val Arg Gln Ala Pro Gly Gln Gly Leu Glu Trp Met
            35                  40                  45

Gly Tyr Thr Asp Pro Arg Thr Asp Tyr Thr Glu Tyr Asn Gln Lys Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Val Gly Leu Gly Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
```

```
                225                 230                 235                 240
Pro Lys Pro Lys Asp Thr Leu Met Ile Ser Arg Thr Pro Glu Val Thr
                    245                 250                 255
Cys Val Val Asp Val Ser His Glu Asp Pro Glu Val Gln Phe Asn
                260                 265                 270
Trp Tyr Val Asp Gly Val Glu Val His Asn Ala Lys Thr Lys Pro Arg
                    275                 280                 285
Glu Glu Gln Phe Asn Ser Thr Phe Arg Val Val Ser Val Leu Thr Val
                290                 295                 300
Val His Gln Asp Trp Leu Asn Gly Lys Glu Tyr Lys Cys Lys Val Ser
305                 310                 315                 320
Asn Lys Gly Leu Pro Ala Pro Ile Glu Lys Thr Ile Ser Lys Thr Lys
                    325                 330                 335
Gly Gln Pro Arg Glu Pro Gln Val Tyr Thr Leu Pro Pro Ser Arg Glu
                340                 345                 350
Glu Met Thr Lys Asn Gln Val Ser Leu Thr Cys Leu Val Lys Gly Phe
                355                 360                 365
Tyr Pro Ser Asp Ile Ala Val Glu Trp Glu Ser Asn Gly Gln Pro Glu
                370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                    405                 410                 415
Asn Val Phe Ser Cys Ser Val Met His Glu Ala Leu His Asn His Tyr
                420                 425                 430
Thr Gln Lys Ser Leu Ser Leu Ser Pro Gly Lys
                435                 440

<210> SEQ ID NO 82
<211> LENGTH: 443
<212> TYPE: PRT
<213> ORGANISM: Homo sapiens

<400> SEQUENCE: 82

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Thr Phe Thr Asn Tyr
                20                  25                  30
Trp Ile His Trp Val Arg Gln Met Pro Gly Lys Gly Leu Glu Trp Met
            35                  40                  45
Gly Tyr Thr Asp Pro Arg Thr Asp Tyr Thr Glu Tyr Asn Gln Lys Phe
        50                  55                  60
Lys Asp Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Gly Gly Arg Val Gly Leu Gly Tyr Trp Gly Gln Gly Thr Leu
                100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
        130                 135                 140
Leu Val Lys Asp Tyr Phe Pro Glu Pro Val Thr Val Ser Trp Asn Ser
145                 150                 155                 160
```

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Phe Arg Val Val Ser Val Leu Thr Val
            290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
            325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 83
<211> LENGTH: 443
<212> TYPE: PRT
<213> ORGANISM: Homo sapiens

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
            35                  40                  45

Gly Tyr Thr Asp Pro Arg Thr Asp Tyr Thr Glu Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gly Arg Val Gly Leu Gly Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 84
<211> LENGTH: 444
<212> TYPE: PRT
<213> ORGANISM: Homo sapiens

<400> SEQUENCE: 84

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Thr Phe Thr Asn Tyr

```
                 20                  25                  30
Val Ile His Trp Leu Arg Gln Ala Pro Gly Gln Gly Leu Glu Trp Met
             35                  40                  45
Gly Tyr Ile Tyr Pro Tyr Asn Asp Gly Ile Leu Tyr Asn Glu Lys Phe
 50                  55                  60
Lys Gly Arg Val Thr Met Thr Ser Asp Thr Ser Ile Ser Thr Ala Tyr
 65                  70                  75                  80
Met Glu Leu Ser Ser Leu Arg Ser Asp Asp Thr Ala Val Tyr Tyr Cys
             85                  90                  95
Ala Arg Gly Gly Tyr Tyr Val Tyr Asp Tyr Trp Gly Gln Ala Thr Leu
            100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
            165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
            195                 200                 205
Thr Lys Val Asp Lys Arg Val Glu Ser Lys Tyr Gly Pro Pro Cys Pro
            210                 215                 220
Pro Cys Pro Ala Pro Glu Phe Glu Gly Gly Pro Ser Val Phe Leu Phe
225                 230                 235                 240
Pro Pro Lys Pro Lys Asp Thr Leu Met Ile Ser Arg Thr Pro Glu Val
            245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
            275                 280                 285
Arg Glu Glu Gln Phe Asn Ser Thr Tyr Arg Val Val Ser Val Leu Thr
            290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
            325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
            355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
            405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly Lys
            435                 440
```

<210> SEQ ID NO 85
<211> LENGTH: 443
<212> TYPE: PRT
<213> ORGANISM: Homo sapiens

<400> SEQUENCE: 85

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Tyr | Thr | Phe | Thr | Asn | Tyr |
| | | | 20 | | | | | 25 | | | | | 30 | | |
| Trp | Ile | His | Trp | Val | Arg | Gln | Ala | Pro | Gly | Gln | Gly | Leu | Glu | Trp | Met |
| | | 35 | | | | | 40 | | | | | 45 | | | |
| Gly | Tyr | Thr | Asp | Pro | Arg | Thr | Asp | Tyr | Thr | Glu | Tyr | Asn | Gln | Lys | Phe |
| | 50 | | | | | 55 | | | | | 60 | | | | |
| Lys | Asp | Arg | Val | Thr | Ile | Thr | Ala | Asp | Glu | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Gly | Gly | Arg | Val | Gly | Leu | Gly | Tyr | Trp | Gly | Gln | Gly | Thr | Leu |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Cys | Ser | Arg | Ser | Thr | Ser | Glu | Ser | Thr | Ala | Ala | Leu | Gly | Cys |
| | 130 | | | | | 135 | | | | | 140 | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Asn |
| | | | 180 | | | | | 185 | | | | | 190 | | |
| Phe | Gly | Thr | Gln | Thr | Tyr | Thr | Cys | Asn | Val | Asp | His | Lys | Pro | Ser | Asn |
| | | 195 | | | | | 200 | | | | | 205 | | | |
| Thr | Lys | Val | Asp | Lys | Thr | Val | Glu | Arg | Lys | Cys | Cys | Val | Glu | Cys | Pro |
| | 210 | | | | | 215 | | | | | 220 | | | | |
| Pro | Cys | Pro | Ala | Pro | Pro | Val | Ala | Gly | Pro | Ser | Val | Phe | Leu | Phe | Pro |
| 225 | | | | | 230 | | | | | 235 | | | | | 240 |
| Pro | Lys | Pro | Lys | Asp | Thr | Leu | Met | Ile | Ser | Arg | Thr | Pro | Glu | Val | Thr |
| | | | | 245 | | | | | 250 | | | | | 255 | |
| Cys | Val | Val | Asp | Val | Ser | His | Glu | Asp | Pro | Glu | Val | Gln | Phe | Asn |
| | | | 260 | | | | | 265 | | | | | 270 | | |
| Trp | Tyr | Val | Asp | Gly | Val | Glu | Val | His | Asn | Ala | Lys | Thr | Lys | Pro | Arg |
| | | 275 | | | | | 280 | | | | | 285 | | | |
| Glu | Glu | Gln | Phe | Asn | Ser | Thr | Phe | Arg | Val | Val | Ser | Val | Leu | Thr | Val |
| | 290 | | | | | 295 | | | | | 300 | | | | |
| Val | His | Gln | Asp | Trp | Leu | Asn | Gly | Lys | Glu | Tyr | Lys | Cys | Lys | Val | Ser |
| 305 | | | | | 310 | | | | | 315 | | | | | 320 |
| Asn | Lys | Gly | Leu | Pro | Ala | Pro | Ile | Glu | Lys | Thr | Ile | Ser | Lys | Thr | Lys |
| | | | | 325 | | | | | 330 | | | | | 335 | |
| Gly | Gln | Pro | Arg | Glu | Pro | Gln | Val | Tyr | Thr | Leu | Pro | Pro | Ser | Arg | Glu |
| | | | 340 | | | | | 345 | | | | | 350 | | |
| Glu | Met | Thr | Lys | Asn | Gln | Val | Ser | Leu | Thr | Cys | Leu | Val | Lys | Gly | Phe |
| | | 355 | | | | | 360 | | | | | 365 | | | |
| Tyr | Pro | Ser | Asp | Ile | Ala | Val | Glu | Trp | Glu | Ser | Asn | Gly | Gln | Pro | Glu |

```
                370                 375                 380
Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 86
<211> LENGTH: 444
<212> TYPE: PRT
<213> ORGANISM: Homo sapiens

<400> SEQUENCE: 86

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Tyr Ile His Trp Val Arg Gln Met Pro Gly Lys Gly Leu Glu Trp Met
            35                  40                  45

Gly Tyr Ile Asp Pro Leu Asn Gly Asp Thr Thr Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Lys Arg Ala Met Asp Tyr Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300
```

```
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440

<210> SEQ ID NO 87
<211> LENGTH: 444
<212> TYPE: PRT
<213> ORGANISM: Homo sapiens

<400> SEQUENCE: 87

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
                20                  25                  30

Val Ile His Trp Val Arg Gln Met Pro Gly Lys Gly Leu Glu Trp Met
            35                  40                  45

Gly Tyr Ile Tyr Pro Tyr Asn Asp Gly Ile Leu Tyr Asn Glu Lys Phe
        50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Tyr Val Pro Asp Tyr Trp Gly Gln Gly Thr Thr
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
        210                 215                 220

Pro Cys Pro Ala Pro Glu Phe Glu Gly Gly Pro Ser Val Phe Leu Phe
225                 230                 235                 240
```

```
Pro Pro Lys Pro Lys Asp Thr Leu Met Ile Ser Arg Thr Pro Glu Val
            245                 250                 255

Thr Cys Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 88
<211> LENGTH: 444
<212> TYPE: PRT
<213> ORGANISM: Homo sapiens

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Val Ile His Trp Val Arg Gln Ala Pro Gly Gln Gly Leu Glu Trp Met
        35                  40                  45

Gly Tyr Ile Tyr Pro Tyr Asn Asp Gly Ile Leu Tyr Asn Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Tyr Val Pro Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
```

```
                        165                 170                 175
Ser Gly Leu Tyr Ser Leu Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 89
<211> LENGTH: 443
<212> TYPE: PRT
<213> ORGANISM: Homo sapiens

<400> SEQUENCE: 89

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Trp Ile His Trp Val Arg Gln Met Pro Gly Lys Gly Leu Glu Trp Met
        35                  40                  45

Gly Tyr Thr Asp Pro Arg Thr Asp Tyr Thr Glu Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

Ala Arg Gly Gly Arg Val Gly Leu Gly Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 90
<211> LENGTH: 444
<212> TYPE: PRT
<213> ORGANISM: Homo sapiens

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

```
Tyr Ile His Trp Val Arg Gln Ala Pro Gly Gln Gly Leu Glu Trp Met
         35                  40                  45
Gly Tyr Ile Asp Pro Leu Asn Gly Asp Thr Thr Tyr Asn Gln Lys Phe
 50                  55                  60
Lys Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Gly Gly Lys Arg Ala Met Asp Tyr Trp Gly Gln Gly Thr Leu
                100                 105                 110
Val Thr Val Ser Ser Ala Ser Thr Lys Gly Pro Ser Val Phe Pro Leu
                115                 120                 125
Ala Pro Cys Ser Arg Ser Thr Ser Glu Ser Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
    210                 215                 220
Pro Cys Pro Ala Pro Glu Phe Glu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly Lys
        435                 440
```

<210> SEQ ID NO 91
<211> LENGTH: 444
<212> TYPE: PRT
<213> ORGANISM: Homo sapiens

<400> SEQUENCE: 91

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380
```

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 92
<211> LENGTH: 444
<212> TYPE: PRT
<213> ORGANISM: Homo sapiens

<400> SEQUENCE: 92

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile His Trp Val Arg Gln Met Pro Gly Lys Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val

```
                305                 310                 315                 320
Ser Asn Lys Gly Leu Pro Ser Ser Ile Glu Lys Thr Ile Ser Lys Ala
                        325                 330                 335

Lys Gly Gln Pro Arg Glu Pro Gln Val Tyr Thr Leu Pro Pro Ser Gln
                        340                 345                 350

Glu Glu Met Thr Lys Asn Gln Val Ser Leu Thr Cys Leu Val Lys Gly
                        355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
                435                 440
```

<210> SEQ ID NO 93
<211> LENGTH: 444
<212> TYPE: PRT
<213> ORGANISM: Homo sapiens

<400> SEQUENCE: 93

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asn Tyr
                20                  25                  30

Tyr Ile His Trp Val Arg Gln Ala Pro Gly Gln Gly Leu Glu Trp Met
            35                  40                  45

Gly Tyr Ile Asp Pro Leu Asn Gly Asp Thr Thr Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Glu Gly Gly Pro Ser Val Phe Leu Phe
225                 230                 235                 240
```

```
Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 94
<211> LENGTH: 444
<212> TYPE: PRT
<213> ORGANISM: Homo sapiens

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
        420                 425                 430

Tyr Thr Gln Lys Ser Leu Ser Leu Ser Leu Gly Lys
    435                 440

<210> SEQ ID NO 95
<211> LENGTH: 444
<212> TYPE: PRT
<213> ORGANISM: Mus musculus

<400> SEQUENCE: 95

Glu Val Gln Leu Gln Gln Ser Gly Pro Glu Leu Met Lys Pro Gly Ala
1               5                   10                  15

Ser Val Lys Ile Ser Cys Lys Ala Ser Gly Tyr Ser Phe Thr Asn Tyr
            20                  25                  30

Tyr Ile His Trp Val Asn Gln Ser His Gly Lys Ser Leu Glu Trp Ile
        35                  40                  45

Gly Tyr Ile Asp Pro Leu Asn Gly Asp Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Arg Leu Ser Ser Leu Thr Ser Ala Asp Ser Ala Val Tyr Tyr Cys
            85                  90                  95

Ala Arg Gly Gly Lys Arg Ala Met Asp Tyr Trp Gly Gln Gly Thr Ser

```
            100                 105                 110
Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 96
<211> LENGTH: 443
<212> TYPE: PRT
<213> ORGANISM: Mus musculus

<400> SEQUENCE: 96

Gln Val Gln Leu Gln Gln Phe Gly Ala Glu Leu Ala Lys Pro Gly Ala
1               5                   10                  15

Ser Val Gln Met Ser Cys Lys Ala Ser Gly Tyr Thr Phe Thr Asn Tyr
            20                  25                  30
```

```
Trp Ile His Trp Val Lys Gln Arg Pro Gly Gln Gly Leu Glu Trp Ile
             35                  40                  45
Gly Tyr Thr Asp Pro Arg Thr Asp Tyr Thr Glu Tyr Asn Gln Lys Phe
 50                  55                  60
Lys Asp Lys Ala Thr Leu Ala Ala Asp Arg Ser Ser Ser Thr Ala Tyr
 65                  70                  75                  80
Met Arg Leu Ser Ser Leu Thr Ser Glu Asp Ser Ala Val Tyr Tyr Cys
                 85                  90                  95
Ala Gly Gly Gly Arg Val Gly Leu Gly Tyr Trp Gly His Gly Ser Ser
                100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Asn
            180                 185                 190
Phe Gly Thr Gln Thr Tyr Thr Cys Asn Val Asp His Lys Pro Ser Asn
        195                 200                 205
Thr Lys Val Asp Lys Thr Val Glu Arg Lys Cys Cys Val Glu Cys Pro
210                 215                 220
Pro Cys Pro Ala Pro Pro Val Ala Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Gln Phe Asn
            260                 265                 270
Trp Tyr Val Asp Gly Val Glu Val His Asn Ala Lys Thr Lys Pro Arg
        275                 280                 285
Glu Glu Gln Phe Asn Ser Thr Phe Arg Val Val Ser Val Leu Thr Val
290                 295                 300
Val His Gln Asp Trp Leu Asn Gly Lys Glu Tyr Lys Cys Lys Val Ser
305                 310                 315                 320
Asn Lys Gly Leu Pro Ala Pro Ile Glu Lys Thr Ile Ser Lys Thr Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
        435                 440
```

<210> SEQ ID NO 97
<211> LENGTH: 443
<212> TYPE: PRT
<213> ORGANISM: Homo sapiens

<400> SEQUENCE: 97

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380
```

```
Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 98
<211> LENGTH: 443
<212> TYPE: PRT
<213> ORGANISM: Homo sapiens

<400> SEQUENCE: 98

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320
```

Asn Lys Gly Leu Pro Ala Pro Ile Glu Lys Thr Ile Ser Lys Thr Lys
            325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 99
<211> LENGTH: 443
<212> TYPE: PRT
<213> ORGANISM: Homo sapiens

<400> SEQUENCE: 99

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile His Trp Val Arg Gln Met Pro Gly Lys Gly Leu Glu Trp Met
            35                  40                  45

Gly Tyr Ile Asp Pro Leu Asn Gly Asp Thr Thr Tyr Asn Gln Lys Phe
        50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
            210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr

```
              245                 250                 255
    Cys Val Val Asp Val Ser His Glu Asp Pro Glu Val Gln Phe Asn
                260                 265                 270

Trp Tyr Val Asp Gly Val Glu Val His Asn Ala Lys Thr Lys Pro Arg
                    275                 280                 285

Glu Glu Gln Phe Asn Ser Thr Phe Arg Val Val Ser Val Leu Thr Val
                290                 295                 300

Val His Gln Asp Trp Leu Asn Gly Lys Glu Tyr Lys Cys Lys Val Ser
    305                 310                 315                 320

Asn Lys Gly Leu Pro Ala Pro Ile Glu Lys Thr Ile Ser Lys Thr Lys
                    325                 330                 335

Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
                    355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Met Leu Asp Ser Asp Gly Ser Phe
    385                 390                 395                 400

Phe Leu Tyr Ser Lys Leu Thr Val Asp Lys Ser Arg Trp Gln Gln Gly
                    405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 100
<211> LENGTH: 443
<212> TYPE: PRT
<213> ORGANISM: Homo sapiens

<400> SEQUENCE: 100

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asn Tyr
                20                  25                  30

Tyr Ile His Trp Val Arg Gln Ala Pro Gly Gln Gly Leu Glu Trp Met
            35                  40                  45

Gly Tyr Ile Asp Pro Leu Asn Gly Asp Thr Thr Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

Ser Gly Leu Tyr Ser Leu Ser Ser Val Val Thr Val Pro Ser Ser Asn
                180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
        210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 101
<211> LENGTH: 326
<212> TYPE: PRT
<213> ORGANISM: Homo sapiens

<400> SEQUENCE: 101

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

```
Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325
```